US012643882B2

(12) United States Patent
Beshore et al.

(10) Patent No.: US 12,643,882 B2
(45) Date of Patent: Jun. 2, 2026

(54) INHIBITORS OF HUMAN RESPIRATORY SYNCYTIAL VIRUS AND METAPNEUMOVIRUS

(71) Applicant: Merck Sharp & Dohme LLC, Rahway, NJ (US)

(72) Inventors: Douglas C. Beshore, Lower Gwynedd, PA (US); Brett R. Ambler, Blue Bell, PA (US); Kira A. Armacost, Doylestown, PA (US); Christopher James Bungard, Lansdale, PA (US); Danielle M. Hurzy, Garnet Valleu, PA (US); Peter J. Manley, Harleysville, PA (US); Kelly Ann S. Schlegel, Fleetwood, PA (US); Linda M. Suen-Lai, Malvern, PA (US); Mahdieh Yazdani, Blue Bell, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 492 days.

(21) Appl. No.: 18/315,797

(22) Filed: May 11, 2023

(65) Prior Publication Data

US 2023/0365531 A1 Nov. 16, 2023

Related U.S. Application Data

(60) Provisional application No. 63/497,595, filed on Apr. 21, 2023, provisional application No. 63/341,860, filed on May 13, 2022.

(51) Int. Cl.

| | |
|---|---|
| ***C07D 401/14*** | (2006.01) |
| ***A61P 31/14*** | (2006.01) |
| ***C07D 413/14*** | (2006.01) |
| ***C07D 417/14*** | (2006.01) |

(52) U.S. Cl.

CPC ............ *C07D 401/14* (2013.01); *A61P 31/14* (2018.01); *C07D 413/14* (2013.01); *C07D 417/14* (2013.01); *C07B 2200/07* (2013.01)

(58) Field of Classification Search

CPC .. C07D 401/14; C07D 413/14; C07D 417/14; A61P 31/14; C07B 2200/07

See application file for complete search history.

(56) References Cited

FOREIGN PATENT DOCUMENTS

| | | | |
|---|---|---|---|
| WO | WO-2008023239 A1 * | 2/2008 | ................ A61P 3/10 |
| WO | 2016149271 A1 | 9/2016 | |

OTHER PUBLICATIONS

Aitipamula, S., et al, "Polymorphs, Salts, and Cocrystals: What's in a Name", Crystal Growth and Design, 2012, pp. 2147-2152, vol. 12.

Biacchesi, Stéphane et al., Frequent Frameshift and Point Mutations in the SH Gene of Human Metapneumovirus Passaged In Vitro, Journal of Virology, 2007, 6057-6067, 81(11).

Fearns, Rachel et al., New antiviral approaches for respiratory syncytial virus and other mononegaviruses: Inhibiting the RNA polymerase, Antiviral Research, 2016, 63-76, 134.

Kesisoglou, F., et al., "Nanosizing—Oral Formulation Developement and Biopharmaceutical Evaluation", Adv. Drug Delivery, 2007, pp. 631-644, vol. 59, No. 7.

Kim, Hyun Wha et al., Respiratory Syncytial Virus Disease in Infants Despite Prior Administration of Antigenic Inactivated Vaccine, American Journal of Epidemiology, 1969, 422-434, 89(4).

Serajuddin, A., et al.,, "Solid Dispersion of Poorly Water-Soluble Drugs: Early Promises, Subsequent Problems, and Recent Breakthroughs", J. Pharm Sci., 1999, pp. 1058-1066, vol. 88, No. 10.

Wen, Zhiyun et al., Development and application of a higher throughput RSV plaque assay by immunofluorescent imaging, Journal of Virological Methods, 2019, 88-95, 263.

* cited by examiner

*Primary Examiner* — James H Alstrum-Acevedo
*Assistant Examiner* — Justin Christopher Sanchez
(74) *Attorney, Agent, or Firm* — Eric Greenwald; John C. Todaro

(57) ABSTRACT

The present disclosure is directed to compounds of Formula I:

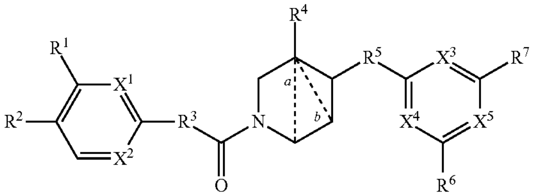

and their use as anti-viral agents for inhibition of the replication of hRSV and hMPV and treatment and prophylaxis of hRSV and hMPV infection.

22 Claims, No Drawings

INHIBITORS OF HUMAN RESPIRATORY SYNCYTIAL VIRUS AND METAPNEUMOVIRUS

FIELD OF THE INVENTION

The present invention relates to therapeutic compounds useful for the inhibition of respiratory syncytial virus replication and metapneumovirus replication. The therapeutic compounds may be used in the treatment or prevention of respiratory syncytial virus infection and metapneumovirus infection.

BACKGROUND OF THE INVENTION

Paramyxoviruses are enveloped negative-strand RNA viruses that are significant human and animal pathogens. Human Respiratory Syncytial Virus (hRSV, RSV) belongs to the family Paramyxoviridae, subfamily Pneumovirinae. Two subtypes, type A and type B, have been identified and are a major cause of severe and sometimes even fatal respiratory infections in children less than 6 months of age. Adults with underlying diseases, such as COPD, asthma, cancer, immunocompromised status, including HIV or post transplantation, are also at risk of developing severe RSV infections. Fifteen percent of annual hospitalizations in adults over 50 years of age are due to acute respiratory infections caused by RSV. In the United States, RSV causes more than 100,000 hospitalizations annually and is estimated to cause 160,000 deaths globally each year. Other viral family members, including human metapneumovirus (hMPV) and human Parainfluenza Virus (hPIV), are also responsible for acute respiratory illness similar to hRSV.

The RSV genome is a single-stranded negative-sense RNA molecule of approximately 15 kb, which encodes for 11 proteins. Two of these proteins are the main surface glycoproteins of the virion. These are the attachment (G) protein, which mediates virus binding to cells, and the fusion (F) protein, which promotes both fusion of the viral and cell membranes at the initial stages of the infectious cycle and fusion of the membrane of infected cells with those of adjacent cells to form characteristic syncytia. Four of the polypeptides, together with the viral RNA genome, form the RSV ribonucleoprotein (RNP) complex. These proteins are the nucleocapsid (N) protein, phosphoprotein (P), RNA polymerase (L) protein, and transcription factor M2-1, which are also each required for the transcription and replication of the viral genome and the subject of drug discovery research.

After hRSV, hMPV is the second most common cause of lower respiratory infection in young children. hMPV is responsible for 5-40% of respiratory tract infections in hospitalized and outpatient children. In healthy adults, hMPV generally results in mild respiratory tract infections; However, adults 70 years old and older, immunocompromised individuals and, people with comorbidities such as asthma and chronic obstructive pulmonary disease (COPD) are at higher risk for more serious disease and hospitalization as a result of hMPV infection. The hMPV genome is approximately 13 kb and the organization is similar to hRSV. hMPV genome RNA replication and mRNA transcription relies on the hMPV L-protein polymerase, which is highly homologous with the hRSV L-protein polymerase.

Currently there are few options available for prophylaxis and treatment of RSV infections. There is no marketed vaccine for RSV. A clinical trial with a formalin-inactivated virus was associated with increased disease severity in infants upon infection with RSV (see Kim et al., *American Journal of Epidemiology,* 89:422-434 (1969)). The monoclonal antibody palivizumab (Synagis®) is approved for prophylactic use but has limited efficacy and its use is limited to high-risk infants as a result of high cost. Ribavarin (ViraZole®), a guanosine nucleoside analog broad-spectrum antiviral is approved as an inhaled treatment for RSV infection in infants, but clear efficacy data is lacking (Fearns et al., 2016 *Antiviral Research,* 134:63-76). In addition, the teratogenic potential of ribavirin raises significant risks for caregivers. The standard of care currently for RSV-infected patients is palliative and includes supplemental oxygen and intravenous fluids.

There continues to be a need for anti-viral agents with pharmacokinetic properties suitable for a significant number of patients in the affected population. The present invention provides novel replication inhibitors of hRSV and hMPV useful for the inhibition of respiratory syncytial virus replication and metapneumovirus replication for addressing this need.

SUMMARY OF THE INVENTION

The present disclosure is directed to compounds of Formula I and embodiments thereof for use as anti-viral agents for inhibition of the replication of hRSV and hMPV and the treatment and/or prophylaxis of hRSV and hMPV infection. Compositions and methods of use comprising the compounds of this disclosure are also provided.

DETAILED DESCRIPTION OF THE INVENTION

The present disclosure is directed to compounds of Formula I (I)

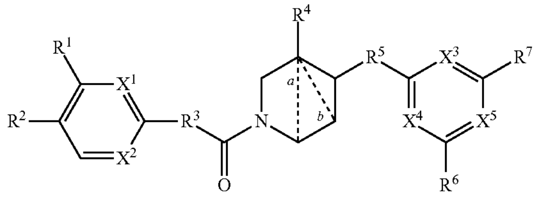

or a pharmaceutically acceptable salt thereof, wherein:

$X^1$ and $X^2$ are each independently selected from —CH and N;

$R^1$ and $R^2$ are each independently selected from H, halo and $C_{1-6}$ alkyl;

$R^3$ is a 5-member aromatic heterocyclyl ring comprised of:

(1) three carbon atoms and (i) two of N, (ii) N and NH, or (iii) N and one of S or O, or (2) two carbon atoms and (i) three of N, (ii) two of N and one of NH, or (iii) two of N and one of S or O, wherein the heterocyclyl ring is unsubstituted or substituted with 1, 2 or 3 substituents, as valence will allow, independently selected at each occurrence from:

(a) halo, (b) —$NH_2$, (c) —$C_{3-6}$ cycloalkyl, (d) —$C_{1-6}$alkyl unsubstituted or substituted with 1 to 6 substituents independently selected at each occurrence from halo, dihalo, —OH, —$NH_2$, and triazole, and (e) —$OC_{1-6}$alkyl unsubstituted or substituted with 1 to 6 substituents independently selected at each occurrence from halo, —OH and —$NH_2$;

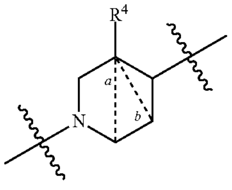

represents a bicyclic ring that is:

(i)

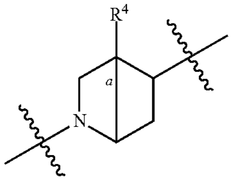

or 2-azabicyclo[2.2.0]hexane (ii)

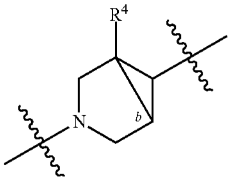

;

3-azabicyclo[3.1.0]hexane $R^4$ is —H, halo or —$C_{1-6}$alkyl;

$R^5$ is —O— or —NH—;

one of $X^3$, $X^4$ and $X^5$ is N and the others are each CH; or one of $X^3$ and $X^4$ is N, and $X^5$ is a $C_1$alkyl unsubstituted or substituted with a halo;

$R^6$ is selected from —$C_{1-6}$alkyl unsubstituted or substituted with 1 to 6 substituents independently selected at each occurrence from halo, —OH and —$NH_2$ and

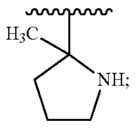 [SMILES: *C1(C)CCCN1]

and $R^7$ is selected from:

(1) phenyl unsubstituted or substituted with 1 to 5 substituents independently selected at each occurrence from:

(a) halo, (b) —CN, (c) —$C_{1-6}$alkyl unsubstituted or substituted with 1 to 6 substituents independently selected at each occurrence from halo and —OH;

(d) —$OC_{1-6}$alkyl, unsubstituted or substituted with 1 to 6 substituents independently selected at each occurrence from halo and —OH, and (e) —$C_{3-6}$cycloalkyl unsubstituted or substituted with 1 to 5 substituents independently selected at each occurrence from halo, —OH, —$C_{1-3}$alkyl and —$OC_{1-3}$alkyl;

(2) pyridinyl, unsubstituted or substituted with 1, 2 or 3 substituents independently selected at each occurrence from (i) halo (e.g., F, Cl), (ii) CN, (iii) —$C_{1-3}$alkyl unsubstituted, and (iv) —$CH_2F$, —$CHF_2$, —$CF_3$ and —$C(CH_3)F_2$;

(3) piperidinyl, substituted with 1, 2, or 3 substituents independently selected from —H, —$C_{1-3}$alkyl and —$CF_3$;

(4)

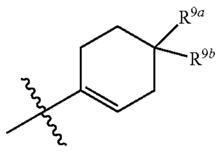

and

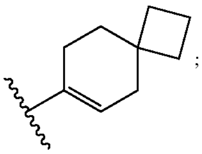

;

and;

wherein $R^{9a}$ and $R^{9b}$ are each selected from —H, —$C_{1-3}$alkyl and —$CF_3$;

(5) A bicyclic ring system selected from:

(a)

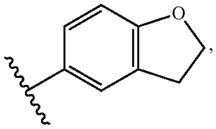

, (b)

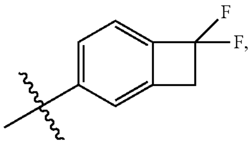

, (c)

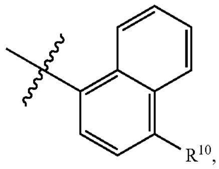

, (d)

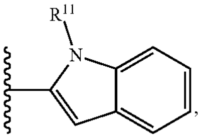

, (e)

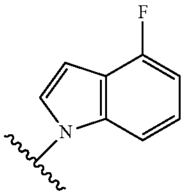

and

-continued (f)

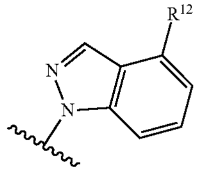

wherein $R^{10}$, $R^{11}$ and $R^{12}$ are independently selected at each occurrence from —H, —$C_{1-3}$alkyl, —$CF_3$ and 1, 2 or 3 of halo;

(6)

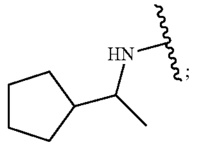 [SMILES: *NC(C)C1CCCC1]

and

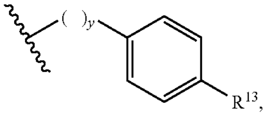

(7), wherein $R^{13}$ is independently selected from —H and halo, and y is 1, 2 or 3.

In some embodiments, $X^1$ and $X^2$ are each independently selected from —CH and N;

$R^1$ and $R^2$ are each independently selected from H, halo and $C_{1-6}$ alkyl;

$R^3$ is a 5-member aromatic heterocyclyl ring comprised of:

(1) three carbon atoms and (i) two of N, (ii) N and NH, or (iii) N and one of S or O, or (2) two carbon atoms and (i) three of N, (ii) two of N and one of NH, or (iii) two of N and one of S or O, wherein the heterocyclyl ring is unsubstituted or substituted with 1 or 2 substituents, as valence will allow, independently selected at each occurrence from:

(a) halo, (b) —$NH_2$, (c) —$C_{3-6}$cycloalkyl, (d) —$C_{1-6}$alkyl unsubstituted or substituted with 1 to 6 substituents independently selected at each occurrence from halo, —OH, and —$NH_2$, and (e) —$OC_{1-6}$alkyl unsubstituted or substituted with 1 to 6 substituents independently selected at each occurrence from halo, —OH and —$NH_2$;

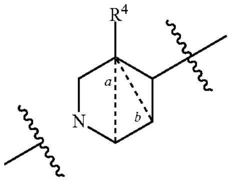

represents a bicyclic ring that is:

(i)

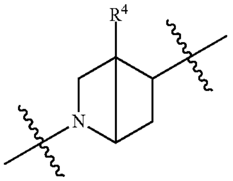

or 2-azabicyclo[2.2.0]hexane (ii)

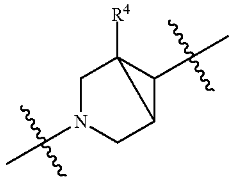

;

3-azabicyclo[3.1.0]hexane $R^4$ is —H, halo or —$C_{1-6}$alkyl;

$R^5$ is —O— or —NH—;

one of $X^3$, $X^4$ and $X^5$ is N, and the others are each CH;

$R^6$ is selected from —$C_{1-6}$alkyl unsubstituted or substituted with 1 to 6 substituents independently selected at each occurrence from halo, —OH and —$NH_2$ and $H_3C$

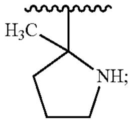 [SMILES: *C1(C)CCCN1]

and $R^7$ is selected from:

(1) phenyl unsubstituted or substituted with 1 to 5 substituents independently selected at each occurrence from:

(a) halo, (b) —CN, (c) —$C_{1-6}$alkyl unsubstituted or substituted with 1 to 6 substituents independently selected at each occurrence from halo and —OH;

(d) —$OC_{1-6}$alkyl unsubstituted or substituted with 1 to 6 substituents independently selected at each occurrence from halo and —OH, and (e) —$C_{3-6}$cycloalkyl unsubstituted or substituted with 1 to 5 substituents independently selected at each occurrence from halo, —OH, —$C_{1-3}$alkyl and —$OC_{1-3}$alkyl;

(2) pyridinyl, unsubstituted or substituted with 1, 2 or 3 substituents independently selected at each occurrence from (i) halo (e.g., F, Cl), (ii) CN, and (iii) —$CH_2F$, —$CHF_2$, —$CF_3$ and —$C(CH_3)F_2$;

(3)

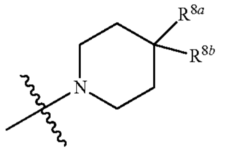

wherein $R^{8a}$ and $R^{8b}$ are each selected from —H, —$C_{1-3}$alkyl and —$CF_3$;

(4)

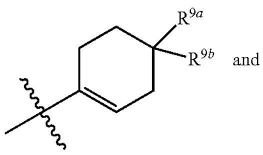 and 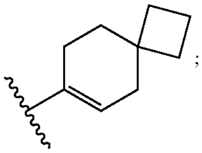 ;

and wherein $R^{9a}$ and $R^{9b}$ are each selected from —H, —$C_{1-3}$alkyl and —$CF_3$;

(5) A bicyclic ring system selected from:

(a)

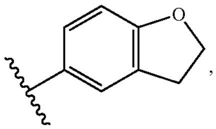

(b)

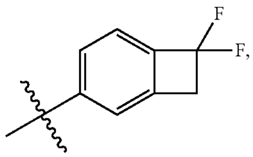

(c)

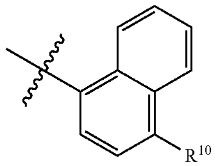

(d)

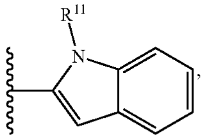

(e)

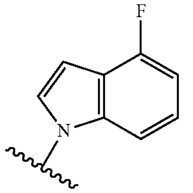 and (f)

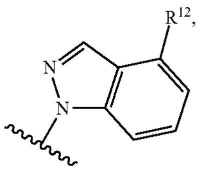

wherein $R^{10}$, $R^{11}$ and $R^{12}$ are independently selected at each occurrence from —H, —$C_{1-3}$alkyl, —$CF_3$, and 1, 2 or 3 of halo.

In Embodiment 1 of this disclosure are compounds of Formula I, or a pharmaceutically acceptable salt thereof, wherein: (i) $X^1$ and $X^2$ are each N, (ii) $X^1$ is N and $X^2$ is —CH, (iii) $X^1$ is —CH and $X^2$ is N, or (iv) $X^1$ and $X^2$ are each —CH. In a class thereof are compounds of Formula I, or a pharmaceutically acceptable salt thereof, wherein: (i) $X^1$ and $X^2$ are each N, (ii) $X^1$ is N and $X^2$ is —CH, or (iii) $X^1$ and $X^2$ are each —CH.

In Embodiment 2 of this disclosure are compounds of Formula I and Embodiment 1, or a pharmaceutically acceptable salt thereof, wherein $R^1$ and $R^2$ are each independently selected from —H, halo and $C_{1-3}$alkyl. In a first class thereof, $R^1$ and $R^2$ are each independently selected from —H, —F, —Cl and $C_{1-3}$alkyl. In a second class thereof, $R^1$ and $R^2$ are each independently selected from —H, —F, —Cl and —$CH_3$.

In Embodiment 3 of this disclosure are compounds of Formula I, and each of Embodiments 1 and 2, or a pharmaceutically acceptable salt thereof, wherein $R^3$ is selected from:

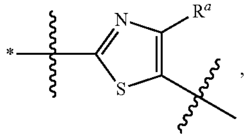 , 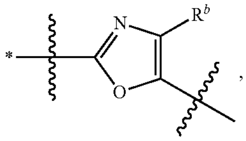 ,

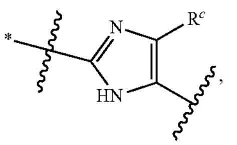 , 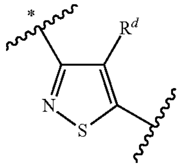

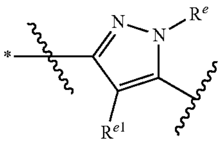 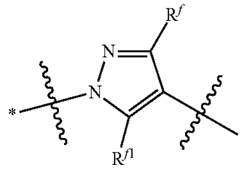 and

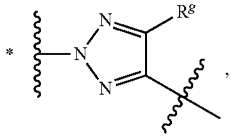 , wherein * is the point of attachment to

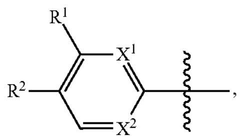 , and each of $R^a$, $R^b$, $R^c$, $R^d$, $R^e$, $R^{e1}$, $R^f$, $R^{f1}$ and $R^g$ is independently selected from: (a) —H, (b) halo, (c) —$NH_2$, (d) —$C_{3-6}$cycloalkyl, (e) —$C_{1-6}$alkyl unsubstituted or substituted with 1 to 6 substituents independently selected at each occurrence from halo, —OH and —$NH_2$, and (f) —$OC_{1-6}$alkyl unsubstituted or substituted with 1 to 6 substituents independently selected at each occurrence from halo, —OH and —$NH_2$.

In a class of Embodiment 3, each of $R^a$, $R^b$, $R^c$, $R^d$, $R^e$, $R^{e1}$, $R^f$, $R^{f1}$ and $R^g$ is independently selected from: (a) —H, (b) halo (e.g., —F and —Cl), (c) —$NH_2$, (d) —$C_{3-6}$cycloalkyl (e.g., cyclopropyl), (e) —$C_{1-3}$alkyl unsubstituted or substituted with 1, 2 or 3 substituents independently selected at each occurrence from halo (e.g., —F and —Cl), —OH, and —$NH_2$, and (f) —$OC_{1-3}$alkyl unsubstituted or substituted with 1, 2 or 3 substituents independently selected at each occurrence from halo (e.g., —F and —Cl), —OH, and —$NH_2$.

In a class of Embodiment 3, any of $R^a$, $R^b$, $R^c$, $R^d$, $R^e$, $R^{e1}$, $R^f$, $R^{f1}$ and $R^g$ is an unsubstituted —$OC_{1-6}$alkyl, or a —$C_{1-3}$ alkyl substituted with 1, 2 or 3 substituents independently selected at each occurrence from a dihalo (e.g., difluoro ($F_2$)) and a triazole (e.g., 2H-1,2,3-triazole). In some embodiments, $R^3$ is the above-illustrated pyrazole moiety substituted with $R^f$ and/or $R^{f1}$. In some sub-embodiments of this class, one of $R^f$ and $R^{f1}$ is an unsubstituted —$OC_{1-6}$alkyl or a —$C_{1-3}$alkyl substituted with a substituent selected from a dihalo and a triazole. In some embodiments, $R^f$ is an —$OC_{1-3}$alkyl (e.g., —$OCH_3$), and $R^{f1}$ is H. In some embodiments, $R^f$ is a —$C_{1-3}$alkyl substituted with a dihalo or a triazole, and $R^{f1}$ is H. In some embodiments, $R^f$ is methyl difluoro ($CH_2CHF_2$), and $R^{f1}$ is H. In particular embodiments, $R^f$ is methyl-2H-1,2,3-triazole ($CH_2$—$C_2H_2N_3$), and $R^{f1}$ is H.

In Embodiment 4A of this disclosure are compounds of Formula I, and each of Embodiments 1-3 and classes thereof, or a pharmaceutically acceptable salt thereof wherein:

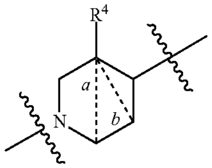

is

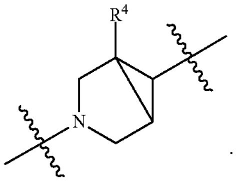

.

In Embodiment 4B of this disclosure are compounds of Formula I, and each of Embodiments 1-3, and classes thereof, or a pharmaceutically acceptable salt thereof wherein:

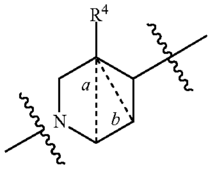

is

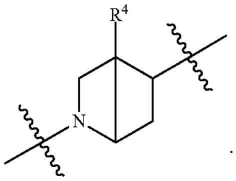

.

In Embodiment 5 of this disclosure, as well as Embodiments 1-3, 4A and 4B, and classes thereof, are compounds of Formula I, or a pharmaceutically acceptable salt thereof, wherein $R^4$ is selected from —H, halo and —$C_{1-3}$alkyl. In a first class thereof, $R^4$ is selected from —H, F, Cl or —$C_{1-3}$alkyl. In a second class thereof, $R^4$ is selected from —H, F, Cl or —$CH_3$.

In Embodiment 6A of this disclosure are compounds of Formula I, and each of Embodiments 1-5, and classes thereof, or a pharmaceutically acceptable salt thereof, wherein $R^5$ is —O—.

In Embodiment 6B of this disclosure are compounds of Formula I, and each of Embodiments 1-5, and classes thereof, or a pharmaceutically acceptable salt thereof, wherein $R^5$ is —NH—.

In Embodiment 7 of this disclosure are compounds of Formula I, and each of Embodiments 1-5, 6A and 6B, and classes thereof, or a pharmaceutically acceptable salt thereof, wherein $X^3$ is N, and $X^4$ and $X^5$ are each CH; or $X^4$ is N, and $X^3$ and $X^5$ are each CH; or $X^5$ is N and $X^3$ and $X^4$ are each CH; or $X^3$ is N, $X^4$ is CH, and $X^5$ is CF or CCl.

In a class of Embodiment 7, $X^5$ is a $C_1$alkyl unsubstituted or substituted with a halo. In sub-embodiments of this class, $X^5$ is a $C_1$alkyl substituted with a halo. In some embodiments, $X^5$ is CF or CCl. In some embodiments, $X^5$ is CF. In some embodiments, $X^5$ is CCl. In some embodiments, $X^3$ is N, $X^4$ is CH, and $X^5$ is CF or CCl.

In Embodiment 8 of this disclosure are compounds of Formula I, and each of Embodiments 1-7, and classes thereof, or a pharmaceutically acceptable salt thereof, wherein $R^6$ is —$C_{1-6}$alkyl unsubstituted or substituted with 1, 2 or 3 substituents independently selected at each occurrence from halo (e.g., F or Cl), —OH, —$NH_2$ and

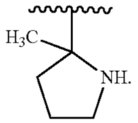

In some embodiments, $R^6$ is a —$C_{1-6}$alkyl substituted with —$NH_2$, e.g., a C3 alkyl substituted with —$NH_2$.

In a further class thereof, $R^6$ is selected from —$C_{1-3}$alkyl unsubstituted or substituted with 1, 2 or 3 substituents independently selected at each occurrence from F, Cl, —$C(CH_3)_2NH_2$, —$C(CH_3)(NH_2)CH_2OH$, and

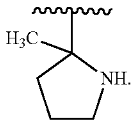

In Embodiment 9 of this disclosure are compounds of Formula I, and each of Embodiments 1-8 and classes thereof, or a pharmaceutically acceptable salt thereof, wherein $R^7$ is selected from:

(1) phenyl unsubstituted or substituted with 1, 2 or 3 substituents independently selected at each occurrence from:

(a) halo (e.g., —F, —Cl), (b) —CN, (c) —$C_{1-3}$alkyl (e.g., methyl), unsubstituted or substituted with 1, 2 or 3 substituents independently selected at each occurrence from (i) halo (e.g., —F and —Cl) and (ii) —OH, (d) —$OC_{1-3}$alkyl unsubstituted or substituted with 1, 2 or 3 substituents independently selected at each occurrence from (i) halo (e.g., F and Cl) and (ii) —OH, (e) —$C_{3-6}$cycloalkyl (e.g., cyclopropyl) unsubstituted or substituted with 1, 2 or 3 substituents independently selected at each occurrence from halo (e.g., F or Cl), —OH, —$C_{1-3}$alkyl and —$OC_{1-3}$alkyl;

(2) pyridinyl, unsubstituted or substituted with 1, 2 or 3 substituents independently selected at each occurrence from (i) halo (e.g., F or Cl), (ii) CN, (iii) —$C_{1-3}$alkyl unsubstituted or substituted with 1 to 3 of F or Cl (e.g., —$CH_2F$, —$CHF_2$, —$CF_3$ and —$C(CH_3)F_2$);

(3)

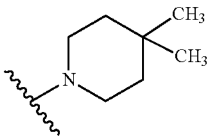

and

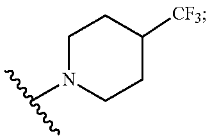

(4) unsubstituted or substituted cyclohexenyl selected from

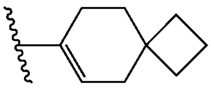

and

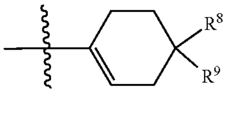

and $R^9$ wherein $R^8$ and $R^9$ are each independently selected from —H, —$CH_3$ and —$CF_3$; and (5) A bicyclic ring system selected from:

(a)

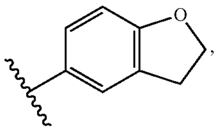

(b)

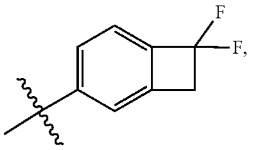

(c)

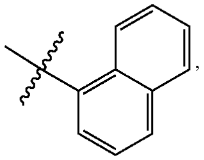

(d)

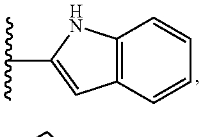

(e)

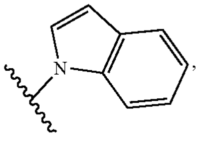

and (f)

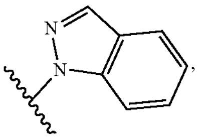

wherein each bicyclic ring system is unsubstituted or substituted with 1, 2 or 3 substituents independently selected at each occurrence from —$C_{1-3}$alkyl and 1, 2 or 3 of halo (e.g., F, Cl).

In some embodiments, $R^7$ is (3) a piperidinyl, substituted with 1, 2, or 3 substituents independently selected from —H, —$C_{1-3}$alkyl and —$CF_3$. In some embodiments, $R^7$ is a piperidinyl substituted with 1, 2, or 3 substituents independently selected from —$C_{1-3}$alkyl and —$CF_3$. In some embodiments, $R^7$ is a 4,4-dimethylpiperidinyl. In some embodiments, $R^7$ is a 4-(trifluoromethyl)piperidinyl. In some embodiments, $R^7$ is a 2,4,4-trimethylpiperidinyl. In some embodiments, $R^7$ is a 2-methyl-4-(trifluoromethyl) piperidinyl.

In some embodiments, $R^7$ is a phenyl substituted with a halo, (e.g., —F, —Cl).

In Embodiment 9, $R^7$ may be the following heterocyclohexenyl:

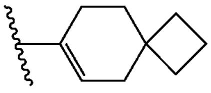 [SMILES: *C1=CCC2(CCC2)CC1]

In some embodiments, $R^7$ is:

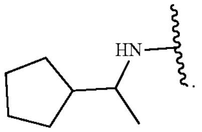 [SMILES: *NC(C)C1CCCC1]

In some embodiments, $R^7$ is

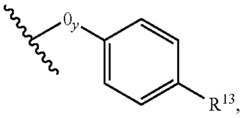

wherein $R^{13}$ is independently selected from —H and halo, and y is 1. In some embodiments, $R^7$ is methyl phenylfluoride:

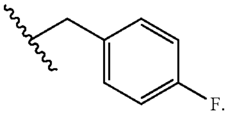 [SMILES: *Cc1ccc(F)cc1]

Reference to the compounds of Formula I herein encompasses the compounds of Formula I, Ia, Ib and Ic, and all embodiments, classes and sub-classes thereof and includes the compounds of the Examples herein. The compounds of Formula I encompass neutral compounds or salts thereof when such salts are possible, including pharmaceutically acceptable salts.

The term "e.g." means "for example." When the terms "e.g.," or "for example" are used herein, the example(s) recited are intended to be illustrative and are not intended to be an exhaustive list of all relevant examples.

As used herein, "alkyl" refers to both branched- and straight-chain saturated aliphatic hydrocarbon groups having the specified number of carbon atoms in a specified range. For example the term "$C_{1-6}$alkyl" means linear or branched chain alkyl groups, including all possible isomers, having 1, 2, 3, 4, 5 or 6 carbon atoms, and includes each of the hexyl ("$C_6$alkyl") and pentyl ("$C_5$alkyl") isomers as well as n-, iso-, sec- and tert-butyl (butyl, i-butyl, s-butyl, t-butyl, collectively "$C_4$alkyl"; Bu=butyl), n- and i-propyl (propyl, i-propyl, collectively "$C_3$alkyl"; Pr=propyl), ethyl (Et) and methyl (Me). "$C_{1-3}$alkyl" has 1, 2 or 3 carbon atoms and includes each of n-propyl, i-propyl, ethyl and methyl.

"Cycloalkyl" refers to a cyclized alkyl ring having the indicated number of carbon atoms in a specified range. Thus, for example, "$C_{3-6}$cycloalkyl" includes each of cyclopropyl, cyclobutyl, cyclopentyl and cyclohexyl, and "$C_{3-4}$cycloalkyl" includes each of cyclopropyl and cyclobutyl.

"Halo" or "halogen" refers to chloro, fluoro, bromo or iodo. Chloro, fluoro and bromo are a class of halogens of interest, and more particularly fluoro and chloro.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present disclosure are limited to stable compounds embraced by Formula I and its embodiments. For example, certain moieties as defined in Formula I may be unsubstituted or substituted, and the latter is intended to encompass substitution patterns (i.e., number and kind of substituents) that are chemically possible for the moiety and that result in a stable compound.

This disclosure includes individual diastereomers, particularly epimers, i.e., compounds having the same chemical formula but which differ in the spatial arrangement around a single atom. This disclosure also includes mixtures of diastereomers, particularly mixtures of epimers, in all ratios. This disclosure encompasses compounds of Formula I having either the (R) or (S) stereo-configuration at an asymmetric center and at any additional asymmetric centers that may be present in a compound of Formula I, as well as stereo-isomeric mixtures thereof. Embodiments of this disclosure also include a mixture of enantiomers enriched with 51% or more of one of the enantiomers, including for example 60% or more, 70% or more, 80% or more, or 90% or more of one enantiomer. A single epimer is preferred. An individual or single enantiomer refers to an enantiomer obtained by chiral synthesis and/or using generally known separation and purification techniques, and which may be 100% of one enantiomer or may contain small amounts (e.g., 10% or less) of the opposite enantiomer. Thus, individual enantiomers are a subject of this disclosure in pure form, both as levorotatory and as dextrorotatory antipodes, in the form of racemates and in the form of mixtures of the two enantiomers in all ratios. In the case of a cis/trans isomerism this disclosure includes both the cis form and the trans form as well as mixtures of these forms in all ratios.

The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present disclosure includes all such isomers, as well as salts, solvates (which includes hydrates). and solvated salts of such racemates, enantiomers, diastereomers and tautomers and mixtures thereof.

As would be recognized by one of ordinary skill in the art, certain compounds of the present disclosure may be able to exist as tautomers. All tautomeric forms of such compounds, whether isolated individually or in mixtures, are within the scope of the present disclosure. For example, in instances where an oxo (═O) substituent is permitted on an aromatic heterocyclic ring (also referred to as a heteroaromatic ring) and keto-enol tautomerism is possible, it is understood that the substituent might in fact be present, in whole or in part, in the —OH form.

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of Formula I; for example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). When the compounds of Formula I contain one or more acidic groups or basic groups, the invention includes the corresponding pharmaceutically acceptable salts.

The compounds of Formula I, and pharmaceutically acceptable salts thereof, which contain one or more basic groups, i.e., groups which can be protonated, can be used according to the invention in the form of their acid addition salts with inorganic or organic acids as, for example but not limited to, salts with hydrogen chloride, hydrogen fluoride, hydrogen bromide, trifluoroacetic acid (trifluoroacetate), phosphoric acid, sulfuric acid, nitric acid, benzenesulfonic acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. In some embodiments, one or more $NH_2$ groups (e.g., a single $NH_2$ group, or two $NH_2$ groups) of any of the compounds of Formula I is protonated in a salt form. In some embodiments, one or more $NH_2$ groups (e.g., a single $NH_2$ group) of any of the compounds of Formula I is protonated in a salt form with trifluoroacetic acid (trifluoroacetate). In some embodiments, one or more $NH_2$ groups (e.g., a single $NH_2$ group) of any of the compounds of Formula I is protonated in a salt form with hydrogen chloride. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present disclosure also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

The present disclosure encompasses any composition comprised of a compound of Formula I or a compound that is a salt thereof, including for example but not limited to, a composition comprised of said compound associated together with one or more additional molecular and/or ionic component(s) which may be referred to as a "co-crystal." The term "co-crystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals). There is no proton transfer between the dissimilar components and the solid phase is neither a simple salt nor a solvate. A discussion of co-crystals can be found, e.g., in S. Aitipamula et al., *Crystal Growth and Design,* 2012, 12 (5), pp. 2147-2152.

Furthermore, compounds of the present disclosure may exist in amorphous form and/or one or more crystalline forms, and as such all amorphous and crystalline forms and mixtures thereof of the compounds of Formula I and salts thereof are intended to be included within the scope of the present disclosure. In addition, some of the compounds of the present disclosure may form solvates with water (i.e., a hydrate) or common organic solvents. Such solvates and hydrates, particularly the pharmaceutically acceptable solvates and hydrates, of the compounds of this disclosure are likewise encompassed within the scope of the compounds defined by Formula I and the pharmaceutically acceptable salts thereof, along with un-solvated and anhydrous forms of such compounds.

Accordingly, the compounds of Formula I or salts thereof including pharmaceutically acceptable salts thereof, embodiments thereof and specific compounds described and claimed herein, encompass all possible stereoisomers, tautomers, physical forms (e.g., amorphous and crystalline forms), co-crystal forms, solvate and hydrate forms, and any combination of the foregoing forms where such forms are possible.

Another embodiment of the present disclosure is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as, high performance liquid chromatography, and/or mass spectrometry or NMR techniques. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual stereoisomer.

The compounds of Formula I herein, and pharmaceutically acceptable salts thereof, are useful for the inhibition of respiratory syncytial virus replication and METAPNEUMOVIRUS replication. Thus, the compounds of Formula I and pharmaceutically acceptable salts thereof are useful for:

(i) a method for the treatment of respiratory syncytial virus infection in a human subject in need thereof which comprises administering to the human subject an effective amount of the compound according to Formula I, or a pharmaceutically acceptable salt thereof;

(ii) a method for the prophylaxis of respiratory syncytial virus infection in a human subject in need thereof which comprises administering to the human subject an effective amount of the compound according to Formula I, or a pharmaceutically acceptable salt thereof;

(iii) a method for the treatment of metapneumovirus infection in a human subject in need thereof which comprises administering to the human subject an effective amount of the compound according to Formula I, or a pharmaceutically acceptable salt thereof; and/or (iv) a method for the prophylaxis of metapneumovirus infection in a human subject in need thereof which comprises administering to the human subject an effective amount of the compound according to Formula I, or a pharmaceutically acceptable salt thereof.

Additional embodiments of the present disclosure include the following:

(a) a pharmaceutical composition comprising an effective amount of a compound of Formula I or a pharmaceutically acceptable salt thereof, and a pharmaceutically acceptable carrier, and (b) a pharmaceutical composition which comprises the product prepared by combining (e.g., mixing) an effective amount of a compound of Formula I or a pharmaceutically acceptable salt thereof, and a pharmaceutically acceptable carrier.

Additional embodiments of the present disclosure include each of the pharmaceutical compositions, methods and uses set forth in the preceding paragraphs, wherein the compound of Formula I or its salt employed therein in substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se.

The term "administration" and variants thereof (e.g., "administering" a compound) in reference to a compound of Formula I means providing the compound to the individual in need of treatment or prophylaxis and includes both self-administration and administration to the patient by another person or any other means.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

The term "subject" as used herein refers to an animal, such as a human, that is the object of treatment, observation or experiment. In various embodiments of the present disclosure, a "subject" encompasses a mammalian animal. In some embodiments, the subject encompasses a domesticated or companion animal, or an experimental animal model. In some embodiments, the subject is a rodent, such as a mouse or rat. In some embodiments, the subject is a primate. In some embodiments, the subject is a non-human primate, such as a macaque. In some embodiments, the subject is a human.

The term "human subject" or "patient" as used herein refers to a human (or "person") who has been the object of treatment, observation or experiment. Patients to be treated with an RSV inhibitor (RSV-i) and/or an MPV inhibitor (MPV-i) agent include but are not limited to, patients who have been infected with RSV and/or MPV. Patients to be treated with an RSV-i and/or an MPV-i agent also include, but are not limited to, those using an RSV-i and/or an MPV-i agent for prophylaxis of RSV and/or MPV infection or for post-exposure prophylaxis after being potentially exposed to RSV and/or MPV to prevent or reduce the severity of symptoms of virus-associated disease or condition; or prevent the patient from becoming infected.

"Prophylaxis" includes each of pre-exposure prophylaxis (PrEP), i.e., using a compound of Formula I or a pharmaceutically acceptable salt thereof to prevent hRSV and/or hMPV infection in a person who is not infected with hRSV and/or hMPV, and post-exposure prophylaxis (PEP), i.e., using a compound of Formula I or a pharmaceutically acceptable salt thereof after being exposed or potentially exposed to hRSV and/or hMPV to prevent or reduce the severity of symptoms of virus-associated disease or condition; or prevent the patient from becoming infected.

The term "effective amount" as used herein means the amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented.

When the active compound (i.e., active ingredient) is administered as the salt, references to the amount of active ingredient are to the free form (i.e., the non-salt form) of the compound.

In the methods of the present disclosure, the disclosed compounds, and salts thereof, can be administered by means that produce contact of the active agent with the agent's site of action. They can be administered by conventional means available for use in conjunction with pharmaceuticals, either as individual therapeutic agents or with other therapeutic agents the patient may be in need of. The compound can be administered itself, but typically is administered with a pharmaceutical carrier selected on the basis of the chosen route of administration and standard pharmaceutical practice. The compounds of the invention can, for example, be administered orally (e.g., via tablet or capsule), parenterally (including subcutaneous injection; intravenous, intramuscular or intrasternal injection; or infusion techniques), by inhalation spray, or rectally, in the form of a unit dosage of a pharmaceutical composition containing an effective amount of the compound and conventional non-toxic pharmaceutically acceptable carriers, adjuvants and vehicles. The compound could also be administered via an implantable drug delivery device adapted to provide an effective amount of the compound or a pharmaceutical composition of the compound over an extended period of time.

Formulations

Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Implantable compositions can be prepared according to methods known in the art wherein the carrier comprises the active chemical ingredient with polymers and suitable excipients, or utilizing an implantable device for drug delivery. Further description of methods suitable for use in preparing pharmaceutical compositions for use in the present disclosure and of ingredients suitable for use in said compositions is provided in Remington—The Science and Practice of Pharmacy, 22nd Edition, published by Pharmaceutical Press and Philadelphia College of Pharmacy at University of the Sciences, 2012, ISBN 978 0 85711-062-6 and prior editions.

Formulations of compounds of Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are known in the art. For example, solid dispersions can be prepared using excipients and processes as described in reviews (e.g., A. T. M. Serajuddin, *J Pharm Sci,* 88:10, pp. 1058-1066 (1999)). Nanoparticulate systems based on both attrition and direct synthesis have also been described in reviews such as Wu et al. (F. Kesisoglou, S. Panmai, Y. Wu, *Advanced Drug Delivery Reviews,* 59:7 pp. 631-644 (2007)).

The compounds of Formula I may be administered in a dosage range of, e.g., 1 to 20 mg/kg, or 1 to 10 mg/kg, or about 5 mg/kg of mammal (e.g., human) body weight per day, or at other time intervals as appropriate, in a single dose or in divided doses. The compounds of Formula I may be administered in a dosage range of 0.001 to 2000 mg per day in a single dose or in divided doses. Examples of dosage ranges are 0.01 to 1500 mg per day, or 0.1 to 1000 mg per day, administered orally or via other routes of administration in a single dose or in divided doses.

For oral (e.g., tablets or capsules) or other routes of administration, the dosage units may contain 100 mg to 1500 mg of the active ingredient, for example but not limited to 0.1 mg to about 1500 mg of the active ingredient, for example but not limited to 0.1, 0.25, 0.5, 1, 2, 2.5, 5, 10, 15, 20, 25, 40, 50, 75, 100, 125, 150, 175, 200, 225, 250, 500, 1000, 1250, or 1500 milligrams of the active ingredient for the symptomatic adjustment of the dosage to the patient to be treated. Furthermore, the compound may be formulated in oral formulations for immediate or modified release such as extended or controlled release. When the compound of Formula I is administered as a salt, reference to an amount of the compound in milligrams or grams is based on the free form (i.e., the non-salt form) of the compound.

Daily administration can be via any suitable route of administration but is preferably via oral administration and can be a single dose or more than one dose at staggered times (divided daily doses) within each 24-hour period. Each dose may be administered using one or multiple dosage units as appropriate.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, the effect of other drugs the patient is taking while using and RSP-i or an MPV-i compound described herein, the severity of the particular condition, and the host undergoing therapy. In some cases, depending on the potency of the compound or the individual response, it may be necessary to deviate upwards or downwards from the given dose. The amount and frequency of administration will be regulated according to the judgment of the attending clinician considering such factors.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals.

The following acronyms and abbreviations have the indicated meanings: Ad-BippyPhos is 5-[di(1-adamantyl)phosphino]-1',3',5'-triphenyl-1'H-[1,4']bipyrazole; (Ad-BippyPhos)$_2$PdCl$_2$ is bis[5-(di(1-adamantyl)phosphino)-1',3',5'-triphenyl-1'H-[1,4']bipyrazole]palladium(II) dichloride; BINAP is 2,2'-bis(diphenylphosphino)-1,1'-binaphthalene; CPME is cyclopentyl methyl ether; CV is column volume (s); d is day(s); DCM is dichloromethane; DEA is N,N-diethylamine; DIPEA is N,N-diisopropyl-N-ethylamine; DMA is N,N-dimethylacetamide; DME is dimethoxyethane; DMF is N,N-dimethylformamide; DMSO is dimethyl sulfoxide; Et is ethyl; Et$_2$O is diethyl ether; EtOAc is ethyl acetate; EtOH is ethanol; Ex. is example(s); h is hour(s); HATU is 1-[bis(dimethylamino)methylene]-1H-1,2,3-triazolo[4,5-b]pyridinium 3-oxid hexafluorophosphate; HCl is hydrochloric acid; IPA is 2-propanol; Int. is intermediate(s); MeCN is acetonitrile; MTBE is methyl tert-butyl ether; NH$_4$OH is ammonium hydroxide; NMP is 1-methyl-2-pyrrolidinone; Pd$_2$(dba)$_3$ is tris(dibenzylideneacetone)dipalladium(0); Pd(dppf)Cl$_2$ is [1,1'-bis(diphenylphosphino)ferrocene]dichloropalladium(II); Pd(dtbpf)Cl$_2$ is [1,1'-bis(di-tert-butylphosphino)ferrocene]dichloropalladium(II); Pd(OAc)$_2$ is palladium(II) acetate; Pd(PPh$_3$)$_4$ is tetrakis(triphenylphosphine)palladium(0); PhCF$_3$ is α,α,α-trifluorotoluene; PhMe is toluene; PyBOP is (benzotriazol-1-yloxy)tripyrrolidinophosphonium hexafluorophosphate; rpm is revolutions per minute; rt is room temperature; SFC is supercritical fluid chromatography; T3P is 2,4,6-tripropyl-1,3,5,2,4,6-trioxatriphosphorinane-2,4,6-trioxide; TBDPS is tert-butyldiphenylsilyl; TFA is trifluoroacetic acid; THF is tetrahydrofuran; XPhos Pd G2 is chloro(2-dicyclohexylphosphino-2',4',6'-triisopropyl-1,1'-biphenyl)[2-(2'-amino-1,1'-biphenyl)]palladium(II).

It is understood that a chiral center in a compound may exist in the "S" or "R" stereo-configuration, or as a mixture of both. Within a molecule, each bond drawn as a straight line from a chiral center encompasses each of the (R) and (S) stereoisomers as well as mixtures thereof unless otherwise noted. For compounds in the Examples that contain a chiral center, isomer mixtures may have been separated, providing one or both of an isomer 1 (the faster eluting isomer) and an isomer 2 (the slower eluting isomer), based on their observed elution order resulting from the separation as performed in the Example. Elution time and/or order of separated isomers may differ if performed under conditions different than those employed herein. Absolute stereochemistry (R or S) of the chiral center in each of isomer "1" and/or isomer "2" separated stereoisomers in the intermediates and Examples was not determined, and "1" and "2" only refer to elution order resulting from the purification conditions as performed.

General Procedures

The following reaction schemes and Examples illustrate methods which may be employed for the synthesis of the compounds of structural Formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural Formula I.

The compounds of the present disclosure can be prepared according to the procedures of the following Examples, using appropriate materials. The compounds illustrated in the examples are not, however, to be construed as forming the only genus that is considered as the invention. The Examples further illustrate details for the preparation of the compounds of the present disclosure. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature.

Reactions sensitive to moisture or air were performed under nitrogen or argon using anhydrous solvents and reagents. The progress of reactions was determined by either liquid chromatography-mass spectrometry (LC-MS) or analytical thin layer chromatography (TLC) usually performed with Merck KGaA glass-backed TLC plates, silica gel 60 F$_2$54. All temperatures are degrees Celsius unless otherwise noted. Mass spectra (MS) were measured either by electrospray ionization mass spectroscopy (ESI) or by atmospheric pressure chemical ionization mass spectroscopy (APCI).

In general, compounds of Formula (I) can be prepared by amide coupling of appropriately functionalized carboxylic acids of Formula (II) and amines of Formula (III). Acids of Formula (II) and amines of Formula (III) are commercially available or may be synthesized from appropriate intermediates. Other synthetic methods to prepare compounds of Formula (I) are presented for the exemplification of compounds. Further, compounds of Formula (I) can be prepared by reaction procedures generally known in the art.

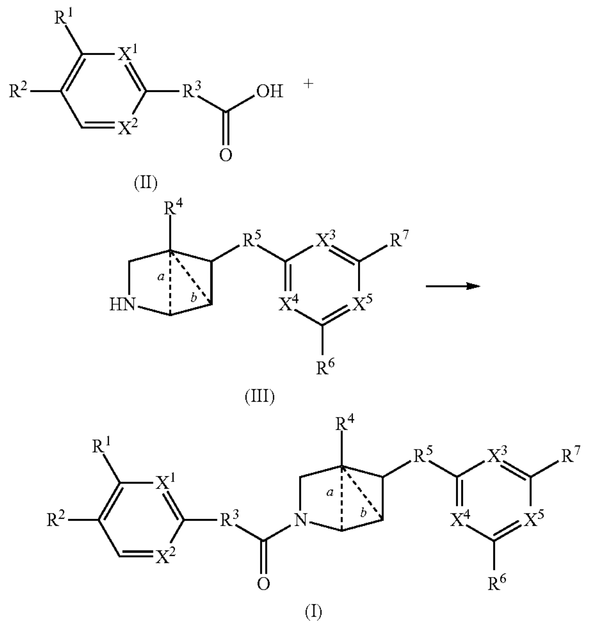

(II)

(III)

(I)

Analytical LC-MS was commonly performed on a Waters SQD single quadrupole mass spectrometer with electrospray ionization in positive ion detection mode (mass range set at 150-900 daltons, data collected in centroid mode and scan time set to 0.2 seconds) and a Waters Acquity UPLC system (binary solvent manager, sample manager, and TUV). The column used was a Waters Acquity BEH C18 1×50 mm, 1.7 μm, heated to 50° C. The mobile phases used were modified with either acidic or basic additives. The acidic mobile phase consisted of water (with 0.1% TFA modifier) for Solvent A and 100% MeCN for Solvent B. A two-minute run was established at a flow rate of 0.3 mL/min with initial conditions of 95% Solvent A and ramping up to 99% Solvent B at 1.60 minutes and holding at 99% Solvent B for 0.40 minutes. The injection volume was 0.5 μL using partial loop needle overfill injection mode. The TUV monitored wavelength 215 or 254 nm with a sampling rate of 20 points/second, normal filter constant and absorbance data mode. The basic mobile phase consisted of water (with 0.05% $NH_4OH$ modifier) for solvent A and 100% MeCN for solvent B. A two-minute run was established at a flow rate of 0.3 mL/min with Initial conditions of 99% Solvent A and ramping up to 99% Solvent B at 1.90 minutes and holding at 99% Solvent B for 0.10 minutes. A five-minute run was established at a flow rate of 0.3 mL/min with initial conditions of 95% Solvent A and ramping up to 99% Solvent B at 4.90 minutes and holding at 99% Solvent B for 0.10 minutes. For both methods, the injection volume was 5.0 μL using Partial Loop Needle Overfill Injection mode. The TUV monitored wavelength 215 nm with a sampling rate of 20 points/second, normal filter constant and absorbance data mode. Alternatively, a commonly used system consisted of a Waters ZQ™ platform with electrospray ionization in positive ion detection mode with an Agilent 1100 series HPLC with autosampler. The column was commonly a Waters Xterra MS C18, 3.0×50 mm, 5 μm or a Waters Acquity UPLC® BEH C18 1.0×50 mm, 1.7 μm. The flow rate was 1 mL/min, and the injection volume was 10 μL. UV detection was in the range 210-400 nm. The mobile phase consisted of solvent A (water with 0.05% TFA modifier) and solvent B (MeCN with 0.05% TFA modifier) with a gradient of 100% solvent A for 0.7 min changing to 100% solvent B over 3.75 min, maintained for 1.1 min, then reverting to 100% solvent A over 0.2 min.

Preparative reverse-phase chromatography was generally carried out on a Teledyne ISCO ACCQPrep HP125 or HP150 apparatus equipped with UV and ELSD detectors. The UV detector typically monitored wavelengths of 215 and 254 nm. The column was commonly one of the following: Waters XBridge Prep C18 OBD 5 μm 30×150 mm, Waters XBridge Prep C18 OBD 5 μm 30×250 mm, Waters XBridge Prep C18 OBD 5 μm 50×250 mm, Waters SunFire Prep C18 OBD 5 μm 30×150 mm, Waters SunFire Prep C18 OBD 10 μm 30×150 mm, Waters SunFire Prep C18 OBD 5 μm 50×250 mm, Waters SunFire Prep C18 OBD 10 μm 50×250 mm, or Phenomenex Luna Prep C18 5 μm 50×250 mm. The mobile phases consisted of mixtures of MeCN (with 0.1% TFA modifier) and water (with 0.1% TFA modifier). Alternatively, a commonly used system was a Waters Chromatography Workstation configured with an LCMS system consisting of: Waters ZQ™ single quad MS system with Electrospray Ionization, Waters 2525 Gradient Pump, Waters 2767 Injector/Collector, Waters 996 PDA Detector. MS conditions were: 150-750 amu, positive electrospray, collection triggered by MS. Columns used were commonly a Waters SunFire C18 5 μm 30×150 mm, a Boston Green ODS 5 μm 150×30 mm, or a YMC-Actus Triart C18 5 μm 150×30 mm column. The mobile phases consisted of mixtures of MeCN (10-100%) in water (with 0.1% TFA modifier). Flow rates were maintained at 50 mL/min, and the UV detection range was 210-400 nm. An additional preparative HPLC system used was a Gilson Workstation consisting of: Gilson GX-281 Injector/Collector, Gilson UV/VIS-155 Detector, Gilson 333 and 334 Pumps, and either a Phenomenex Gemini-NX C18 5 μm 50×250 mm column, a Waters XBridge Prep C18 OBD 5 μm 30×250 mm, or a Welch Xtimate C18 5 μm 150×25 mm. The mobile phases consisted of mixtures of acetonitrile (0-75%) in water containing 5 mM $(NH_4)HCO_3$. Flow rates were maintained at 50 mL/min for the Waters XBridge column, 90 mL/min for the Phenomenex Gemini column, and 25 L/min for the Welch Xtimate column. The UV detection range was 210-400 nm. Mobile phase gradients were optimized for the individual compounds.

Silica gel chromatography was usually performed using an ISCO CombiFlash Rf apparatus, a Biotage® Flash Chromatography apparatus (Dyax Corp.), or an ISCO CombiFlash® Companion XL apparatus on silica gel (60 Å pore size) in pre-packed RediSep Rf, RediSep Rf Gold, or SepaFlash columns. Mobile phases generally consisted of mixtures of hexanes, petroleum ether, or DCM with EtOAc, 3:1 EtOAc:EtOH, or MeOH. Mobile phase gradients were optimized for the individual compounds.

Chiral chromatography was commonly performed by supercritical fluid chromatography with a column chosen from one of the following: ChiralPak AD, ChiralPak AD-3, ChiralPak AD-H, ChiralPak AS, ChiralPak AS-3, ChiralPak AS-H, ChiralPak IB-N, ChiralPak OD-H, ChiralPak OJ-3, ChiralPak OJ-H, Phenomenex-Cellulose-2, or (S,S)Whelk-O1. Mobile phases consisted of mixtures of $CO_2$ or hexane with MeOH, EtOH, or IPA using 0.05-0.1% DEA or $NH_4OH$ modifier. Mobile phase gradients were optimized for the individual compounds. Pressure was typically maintained at 100 bar, and flow rates ranged from 50-200 mL/min. UV monitoring was generally carried out at 220 or 205 nM.

$^1H$ NMR data were typically acquired using a Bruker NEO 500 MHz NMR spectrometer equipped with a room temperature 5 mm BBF iProbe, a Bruker Avance NEO 400

MHz NMR spectrometer equipped with a Bruker PI HR-BBO400S1-BBF/H/D-5.0-Z SP probe, or a Bruker Avance III 500 MHz NMR spectrometer equipped with a Bruker 5 mm PABBO probe. Chemical shift values are reported in delta (δ) units, parts per million (ppm). Chemical shifts for $^{1}$H NMR spectra are given relative to signals for residual non-deuterated solvent ($CDCl_3$ referenced at δ 7.26 ppm; DMSO-$d^6$ referenced at δ 2.50 ppm and $CD_3OD$ referenced at δ 3.31 ppm). Multiplets are reported by the following abbreviations: s=singlet, d=doublet, t=triplet, q=quartet, dd=doublet of doublets, m=multiplet or overlap of non-equivalent resonances. Coupling constants (J) are reported in Hertz (Hz). When compounds appear as mixtures of rotamers by NMR, spectral data corresponding to the major species observed in solution are reported.

Scheme

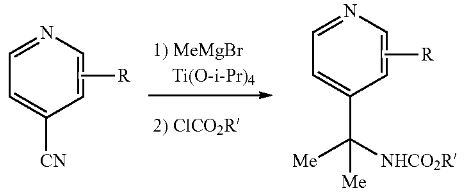

Intermediate A-1 benzyl (2-(2,6-dichloropyridin-4-yl)propan-2-yl)carbamate

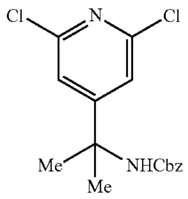 [SMILES: CC(C)(NC(=O)OCc1ccccc1)c1cc(Cl)nc(Cl)c1]

Step 1: 2-(2,6-dichloropyridin-4-yl)propan-2-amine

A solution of methylmagnesium bromide (3.0 M in $Et_2O$, 1.7 L, 5.2 mol) was added dropwise over 1 h to a 0° C. mixture of 2,6-dichloroisonicotinonitrile (0.30 kg, 1.7 mol) in PhMe (1.5 L). The mixture was warmed up to 25° C. and stirred for 1 h. The mixture was cooled to 0° C. and titanium(IV) isopropoxide (490 g, 1.7 mol) was added dropwise over 30 min. The mixture was heated to 100° C. and stirred for 1 h. The mixture was cooled to 5-10° C. and then treated with a solution of sodium carbonate (saturated aqueous, 5 L) at 5-10° C. The mixture was filtered, and the filter cake was washed with EtOAc (800 mL×3). The filtrate was separated, and the organic phase was concentrated to afford the title compound.

Step 2: benzyl (2-(2,6-dichloropyridin-4-yl)propan-2-yl)carbamate

Benzyl chloroformate (250 g, 1.5 mol) was added dropwise over 30 min to a 0° C. mixture of 2-(2,6-dichloropyridin-4-yl)propan-2-amine (270 g, 1.3 mol), DIPEA (190 g, 1.5 mol), and DCM (2.7 L). The mixture was warmed up to 25° C. and stirred for 12 h. The mixture was washed with HCl (1 N, 800 mL×3), dried with anhydrous sodium sulfate, filtered, and concentrated. The material was triturated (MTBE/EtOAc=10:1, 800 mL) at 25° C. for 12 h. The mixture was filtered and concentrated under reduced pressure to afford the title compound.

Utilizing the procedures described in the preparation of Intermediate A-1, the below compound was prepared, substituting the appropriate reagents for 2,6-dichloroisonicotinonitrile and benzyl chloroformate.

| Int. | Structure | Name |
|---|---|---|
| A-2 | 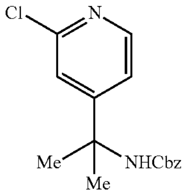 [SMILES: CC(C)(NC(=O)OCc1ccccc1)c1ccnc(Cl)c1] | benzyl (2-(2-chloropyridin-4-yl)propan-2-yl)carbamate |

Scheme

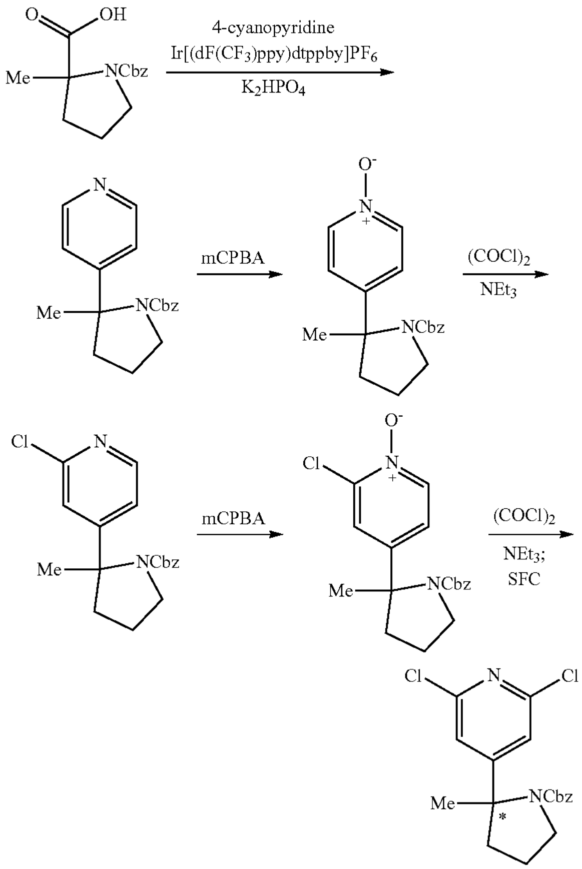

Intermediates A-3-ent-1 benzyl ent-2-(2,6-dichloropyridin-4-yl)-2-methylpyrrolidine-1-carboxylate (Enantiomer 1)

and

Intermediates A-3-ent-2 benzyl ent-2-(2,6-dichloropyridin-4-yl)-2-methylpyrrolidine-1-carboxylate (Enantiomer 2)

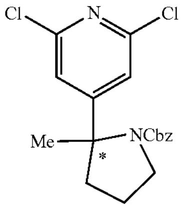 [SMILES: CC1(c2cc(Cl)nc(Cl)c2)CCCN1C(=O)OCc1ccccc1]

Step 1: benzyl rac-2-methyl-2-(pyridin-4-yl)pyrrolidine-1-carboxylate

Five reactions were carried out in parallel. A mixture of 1-((benzyloxy)carbonyl)-2-methylpyrrolidine-2-carboxylic acid (130 g, 470 mmol), isonicotinonitrile (25 g, 240 mmol), dipotassium hydrogen phosphate (120 g, 710 mmol), and DMSO (5.0 L) was degassed and purged with $N_2$ (3×). (4,4'-Di-tert-butyl-2,2'-bipyridine)bis[3,5-difluoro-2-[5-(trifluoromethyl)-2-pyridinyl]phenyl]iridium(III) hexafluorophosphate (2.7 g, 2.4 mmol) was added to the suspension under $N_2$. The suspension was stirred for 7 h under 1200 W blue LEDs (460-465 nm). The five batches were combined, and the suspension was poured into a below 0° C. solution of sodium bicarbonate (saturated aqueous, 20 L). The mixture was extracted with EtOAc (8 L×2). The combined organic mixture was washed with brine (3 L), dried with anhydrous sodium sulfate, filtered, and concentrated under reduce pressure. The residue was subjected to silica gel chromatography (5-100% EtOAc/petroleum ether) to afford the title compound.

Step 2: rac-4-(1-((benzyloxy)carbonyl)-2-methylpyrrolidin-2-yl)pyridine 1-oxide

Under an atmosphere of nitrogen, a solution of benzyl rac-2-methyl-2-(pyridin-4-yl)pyrrolidine-1-carboxylate (220 g, 740 mmol) in DCM (1.5 L) was cooled to 15-20° C. 3-chloroperoxybenzoic acid (320 g, 1.5 mol, 80% purity) was added to the reaction at 15-20° C. over 20 batches. The mixture was degassed and purged with $N_2$ (3×) and stirred at 20° C. for 2 h. The reaction mixture was washed with sodium sulfite (saturated aqueous, 250 mL×4) and sodium bicarbonate (saturated aqueous, 250 mL×5), extracted with EtOAc (200 mL×2). The combined organic mixture was washed with brine (300 mL), dried with anhydrous sodium sulfate, filtered, and concentrated under reduce pressure to afford the title compound.

Step 3: benzyl rac-2-(2-chloropyridin-4-yl)-2-methylpyrrolidine-1-carboxylate

A mixture of rac-4-(1-((benzyloxy)carbonyl)-2-methylpyrrolidin-2-yl)pyridine 1-oxide (190 g, 610 mmol) and DCM (1.3 L) was degassed and purged with $N_2$ (3×) and cooled to 0° C. Triethylamine (340 mL, 2.4 mol) was added dropwise to the reaction at −5-0° C. Oxalyl dichloride (110 mL, 1.2 mol) was added dropwise to the reaction at −5-0° C. The reaction was stirred at 0° C. for 1 h. The reaction mixture was quenched by sodium bicarbonate (saturated aqueous, 1 L) and extracted with DCM (500 mL×2). The combined organic extracts were washed with brine (500 mL), dried with anhydrous sodium sulfate, filtered, and concentrated under reduced pressure. The residue was subjected to silica gel chromatography (5-100% EtOAc/petroleum ether) to afford the title compound.

Step 4: rac-4-(1-((benzyloxy)carbonyl)-2-methylpyrrolidin-2-yl)-2-chloropyridine 1-oxide A mixture of benzyl rac-2-(2-chloropyridin-4-yl)-2-methylpyrrolidine-1-carboxylate (140 g, 410 mmol) and DCM (960 mL) was degassed and purged with $N_2$ (3×), then cooled to 10-15° C. 3-chloroperoxybenzoic acid (170 g, 820 mmol, 85% purity) was added to the reaction at 15-20° C. under $N_2$. The reaction was stirred at 20° C. for 12 h. The mixture was poured into sodium sulfite (saturated aqueous, 800 L×2) at 0-5° C. and extracted with DCM (500 mL×3). The combined organic mixture was washed with brine (500 mL), dried with anhydrous sodium sulfate, filtered, and concentrated under reduced pressure to afford the title compound.

Step 5: benzyl ent-2-(2,6-dichloropyridin-4-yl)-2-methylpyrrolidine-1-carboxylate (Enantiomers 1 and 2)

Thirteen reactions were carried out in parallel. A mixture of rac-4-(1-((benzyloxy)carbonyl)-2-methylpyrrolidin-2-yl)-2-chloropyridine 1-oxide (0.010 kg, 29 mmol), DCM (70 mL) and triethylamine (24 mL, 170 mmol) was degassed and purged with $N_2$ (3×), then cooled to −5-0° C. Oxalyl dichloride (7.6 mL, 87 mmol) was added dropwise to the reaction at −5-0° C. The mixture was stirred at 0° C. for 30 min. The reaction was warmed to 20° C. and stirred for 1 h. The thirteen reactions were combined, treated with sodium bicarbonate (saturated aqueous, 5 L) and the mixture was extracted with DCM (3 L×3). The combined organic mixture was washed with brine (2 L), dried with anhydrous sodium sulfate, filtered, and concentrated under reduce pressure. The residue was purified by silica gel chromatography (5-100% EtOAc/petroleum ether) to afford racemic title compound. The mixture of two stereoisomers was subjected to chiral SFC ((S,S)Whelk-O1, 40% IPA/$CO_2$) to afford the title compounds, Int. A-3-ent-1 (faster eluting enantiomer) and Int. A-3-ent-2 (slower eluting enantiomer).

Scheme

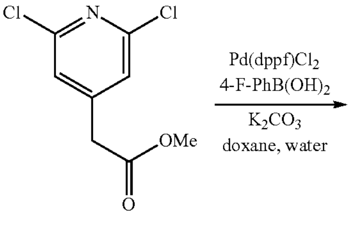

-continued

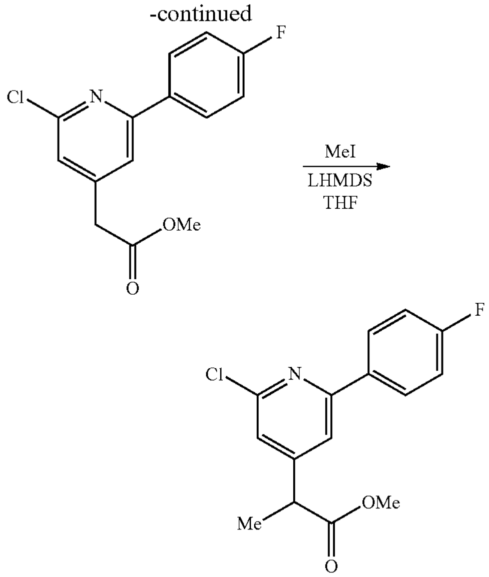

Intermediate B methyl 2-(2-chloro-6-(4-fluorophenyl)pyridin-4-yl) propanoate

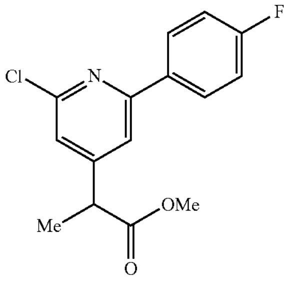 [SMILES: COC(=O)C(C)c1cc(Cl)nc(-c2ccc(F)cc2)c1]

Step 1: methyl 2-(2-chloro-6-(4-fluorophenyl)pyridin-4-yl)acetate

Under an atmosphere of nitrogen, a mixture of methyl 2-(2,6-dichloropyridin-4-yl)acetate (0.030 kg, 0.14 mol), (4-fluorophenyl)boronic acid (19 g, 0.14 mol), Pd(dppf)$Cl_2$ (5.0 g, 6.8 mmol), potassium carbonate (38 g, 0.27 mol), 1,4-dioxane (0.40 L), and water (0.040 L) was stirred at 100° C. for 2 h. The mixture was cooled to rt, filtered, and concentrated under reduced pressure. The residue was subjected to silica gel chromatography (0-8% EtOAc/petroleum ether) to afford the title compound.

Step 2: methyl 2-(2-chloro-6-(4-fluorophenyl)pyridin-4-yl)propanoate

Under an atmosphere of nitrogen, to a −78° C. solution of methyl 2-(2-chloro-6-(4-fluorophenyl)pyridin-4-yl)acetate (14 g, 0.050 mol) in THF (0.15 L) was added a solution of lithium bis(trimethylsilyl)amide (1.0 M in THF, 0.060 L, 0.060 mol). The mixture was stirred for 30 min and iodomethane (6.3 mL, 0.10 mol) was added dropwise. The mixture was warmed to room temperature and stirred for 2 h. Water (100 mL) was added and the mixture was extracted with EtOAc (100 mL×3). The combined organic extracts were washed with brine (100 mL), dried over anhydrous sodium sulfate, and concentrated under reduced pressure. The residue was subjected to silica gel chromatography (0-5% EtOAc/petroleum ether) to afford the title compound.

Utilizing the procedures described in the synthesis of Intermediate A-1, the below compounds were prepared substituting the appropriate reagents for 2,6-dichloroisonicotinonitrile and benzyl chloroformate.

| Int. | Structure | Name |
|---|---|---|
| C-1 | 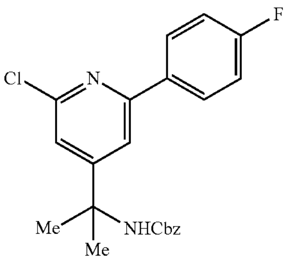 [SMILES: CC(C)(NC(=O)OCc1ccccc1)c1cc(Cl)nc(-c2ccc(F)cc2)c1] | benzyl (2-(2-chloro-6-(4-fluorophenyl)pyridin-4-yl)propan-2-yl)carbamate |
| C-2 | 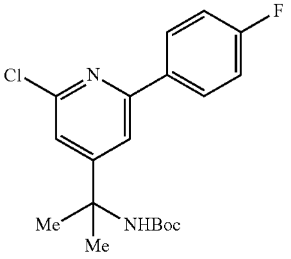 [SMILES: CC(C)(C)OC(=O)NC(C)(C)c1cc(Cl)nc(-c2ccc(F)cc2)c1] | tert-butyl (2-(2-chloro-6-(4-fluorophenyl)pyridin-4-yl)propan-2-yl)carbamate |

Scheme

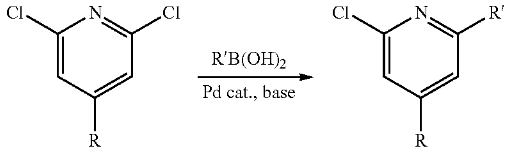

Intermediate C-3 benzyl (2-(2-chloro-6-(4-(trifluoromethyl)phenyl) pyridin-4-yl)propan-2-yl)carbamate

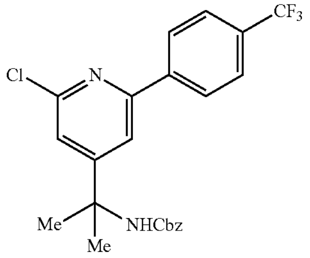 [SMILES: CC(C)(NC(=O)OCc1ccccc1)c1cc(Cl)nc(-c2ccc(C(F)(F)F)cc2)c1]

To a mixture of benzyl (2-(2,6-dichloropyridin-4-yl)propan-2-yl)carbamate (Int. A-1, 2.0 g, 5.9 mmol) and (4-(trifluoromethyl)phenyl)boronic acid (1.0 g, 5.3 mmol) in water (4.0 mL) and 1,4-dioxane (0.020 L) was added potassium carbonate (1.6 g, 12 mmol). The resulting mixture was degassed (evacuated and backfilled with nitrogen×3) then $Pd(dppf)Cl_2$ (0.43 g, 0.59 mmol) was added. The mixture was heated at 100° C. for 2 h. The mixture was cooled to room temperature, filtered, and concentrated under reduced pressure. The residue was subjected to silica gel chromatography (0-10% EtOAc/petroleum ether) to afford the title compound.

Utilizing the procedures described in the synthesis of Intermediate C-3, the below compounds were prepared substituting the appropriate reagents for benzyl (2-(2,6-dichloropyridin-4-yl)propan-2-yl)carbamate and (4-(trifluoromethyl)phenyl)boronic acid.

| Int. | Structure | Name | Comments |
|---|---|---|---|
| C-4 | 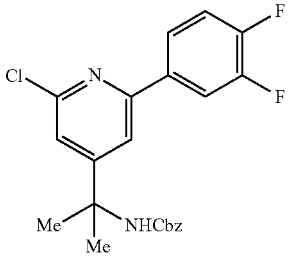 [SMILES: CC(C)(NC(=O)OCc1ccccc1)c1cc(Cl)nc(-c2ccc(F)c(F)c2)c1] | benzyl (2-(2-chloro-6-(3,4-difluorophenyl)pyridin-4-yl)propan-2-yl)carbamate | — |
| C-5 | 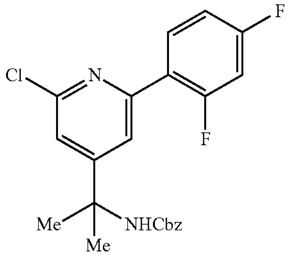 [SMILES: CC(C)(NC(=O)OCc1ccccc1)c1cc(Cl)nc(-c2ccc(F)cc2F)c1] | benzyl (2-(2-chloro-6-(2,4-difluorophenyl)pyridin-4-yl)propan-2-yl)carbamate | — |
| C-6-ent-1 | 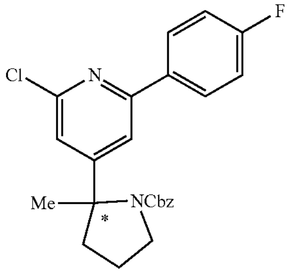 [SMILES: CC1(c2cc(Cl)nc(-c3ccc(F)cc3)c2)CCCN1C(=O)OCc1ccccc1] | benzyl ent-2-(2-chloro-6-(4-fluorophenyl)pyridin-4-yl)-2-methylpyrrolidine-1-carboxylate (enantiomer 1) | Int. A-3-ent-1 (3.0 mmol), (4-fluorophenyl)boronic acid (2.7 mmol), $Pd(dppf)Cl_2$ (0.30 mmol), potassium carbonate (6.0 mmol), 1,4-dioxane (0.010 L), water (2.0 mL), 100° C., 1.5 h |

Scheme

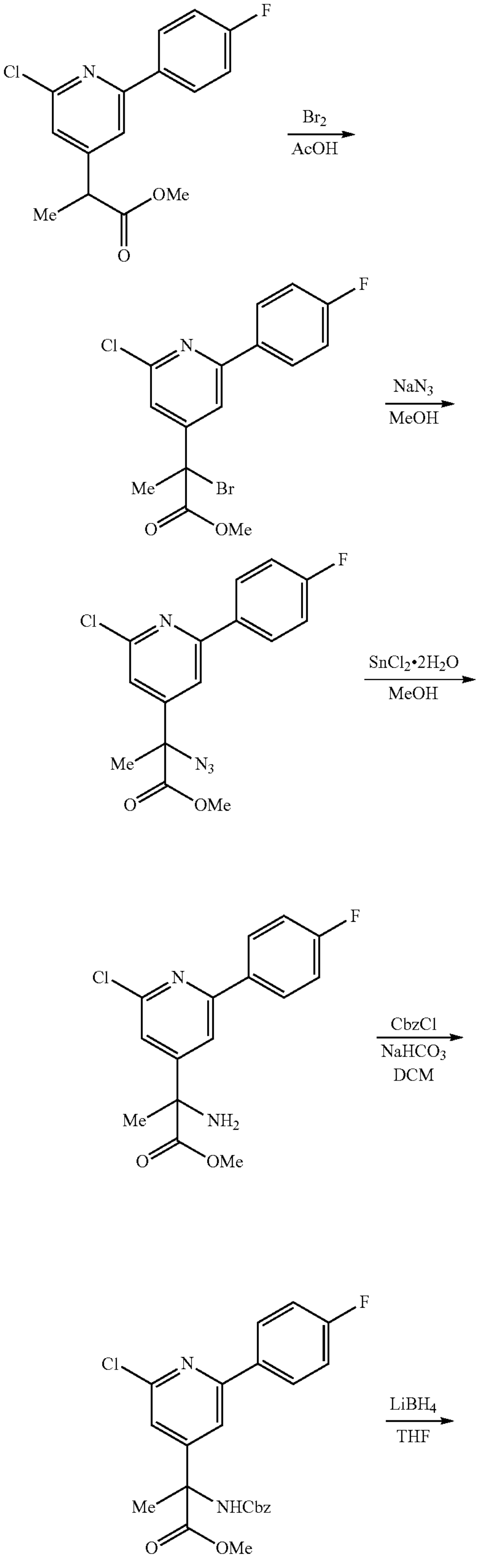

-continued

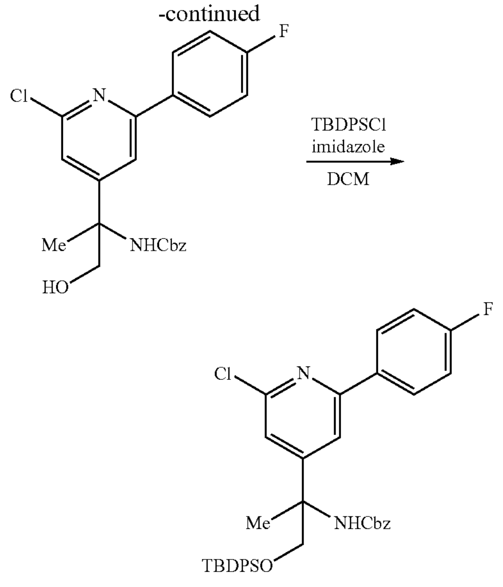

Intermediate C-7 benzyl rac-(1-((tert-butyldiphenylsilyl)oxy)-2-(2-chloro-6-(4-fluorophenyl)pyridin-4-yl)propan-2-yl) carbamate

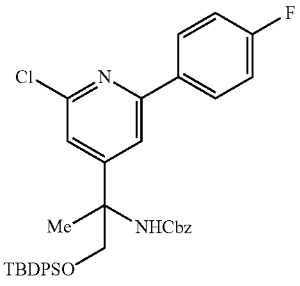

Step 1: methyl rac-2-bromo-2-(2-chloro-6-(4-fluorophenyl)pyridin-4-yl)propanoate To a solution of methyl 2-(2-chloro-6-(4-fluorophenyl) pyridin-4-yl)propanoate (Int. B, 2.0 g, 6.8 mmol) in acetic acid (0.020 L) was added bromine (0.39 mL, 7.5 mmol). The mixture was then stirred at 100° C. for 8 h. The mixture was cooled to room temperature and concentrated under reduced pressure. EtOAc (40 mL) was added and the mixture was washed with sodium thiosulfate (saturated aqueous, 20 mL), sodium bicarbonate (saturated aqueous, 20 mL) and brine (20 mL×3). The organic solution was dried over anhydrous sodium sulfate, filtered, and concentrated under reduced pressure. The residue was subjected to silica gel chromatography (0-20% EtOAc/petroleum ether) to afford the title compound.

Step 2: methyl rac-2-azido-2-(2-chloro-6-(4-fluorophenyl)pyridin-4-yl)propanoate To a solution of methyl 2-bromo-2-(2-chloro-6-(4-fluorophenyl)pyridin-4-yl)propanoate (1.6 g, 4.3 mmol) in MeOH (0.020 L) was added sodium azide (1.3 g, 0.020 mol). The mixture was stirred at 60° C. for 5 h. Water (20 mL) was added, and the mixture was basified (pH=9) with sodium bicarbonate. The mixture was extracted with EtOAc (30 mL×3) and the combined organic extracts were washed with brine (20 mL×3), dried over anhydrous sodium sulfate, filtered, and concentrated under reduced pressure to afford the title compound.

Step 3: methyl rac-2-amino-2-(2-chloro-6-(4-fluorophenyl)pyridin-4-yl)propanoate To a solution of methyl rac-2-azido-2-(2-chloro-6-(4-fluorophenyl)pyridin-4-yl)propanoate (1.4 g, 4.2 mmol) in MeOH (0.020 L) was added tin(II) chloride dihydrate (2.8 g, 13 mmol). The mixture was stirred at rt for 2 h. Water (10 mL) was added and the mixture was extracted with EtOAc (20 mL×3). The combined organic extracts were dried over anhydrous sodium sulfate, filtered, and concentrated under reduced pressure to afford the title compound.

Step 4: methyl rac-2-(((benzyloxy)carbonyl)amino)-2-(2-chloro-6-(4-fluorophenyl)pyridin-4-yl)propanoate To a solution of methyl rac-2-amino-2-(2-chloro-6-(4-fluorophenyl)pyridin-4-yl)propanoate (1.2 g, 3.1 mmol) in DCM (12 mL) was added sodium bicarbonate (1.0 g, 12 mmol) and benzyl chloroformate (2.2 mL, 16 mmol). The mixture was stirred at rt for 1 h. Water (10 mL) was added, and the mixture was extracted with EtOAc (30 mL×3). The combined organic extracts were dried over anhydrous sodium sulfate, filtered, and concentrated under reduced pressure. The residue was subjected to prep-TLC (25% EtOAc/petroleum ether, Rf=0.45) to afford the title compound.

Step 5: benzyl rac-(2-(2-chloro-6-(4-fluorophenyl)pyridin-4-yl)-1-hydroxypropan-2-yl)carbamate To a mixture of methyl rac-2-(((benzyloxy)carbonyl)amino)-2-(2-chloro-6-(4-fluorophenyl)pyridin-4-yl)propanoate (1.2 g, 2.7 mmol) in THF (15 mL) was added lithium borohydride (0.35 g, 16 mmol). The reaction mixture was stirred at rt for 1 h. A solution of ammonium chloride (saturated aqueous, 30 mL) was added and the mixture was extracted with EtOAc (20 mL×3). The combined organic extracts were dried over anhydrous sodium sulfate, filtered, and concentrated under reduced pressure. The residue was subjected to silica gel chromatography (30-50% EtOAc/petroleum ether) to afford the title compound.

Step 6: benzyl rac-(1-((tert-butyldiphenylsilyl)oxy)-2-(2-chloro-6-(4-fluorophenyl)pyridin-4-yl)propan-2-yl)carbamate To a solution of benzyl rac-(2-(2-chloro-6-(4-fluorophenyl)pyridin-4-yl)-1-hydroxypropan-2-yl)carbamate (0.50 g, 1.2 mmol) in DCM (0.010 L) was added imidazole (0.16 g, 2.4 mmol) and tert-butyl(chloro)diphenylsilane (0.66 g, 2.4 mmol). The mixture was stirred at rt for 12 h. Water (20 mL) was added and the mixture was extracted with DCM (30 mL×3). The combined organic extracts were dried over anhydrous sodium sulfate, filtered, and concentrated under reduced pressure. The residue was subjected to silica gel chromatography (0-20% EtOAc/petroleum ether) to afford the title compound.

Scheme

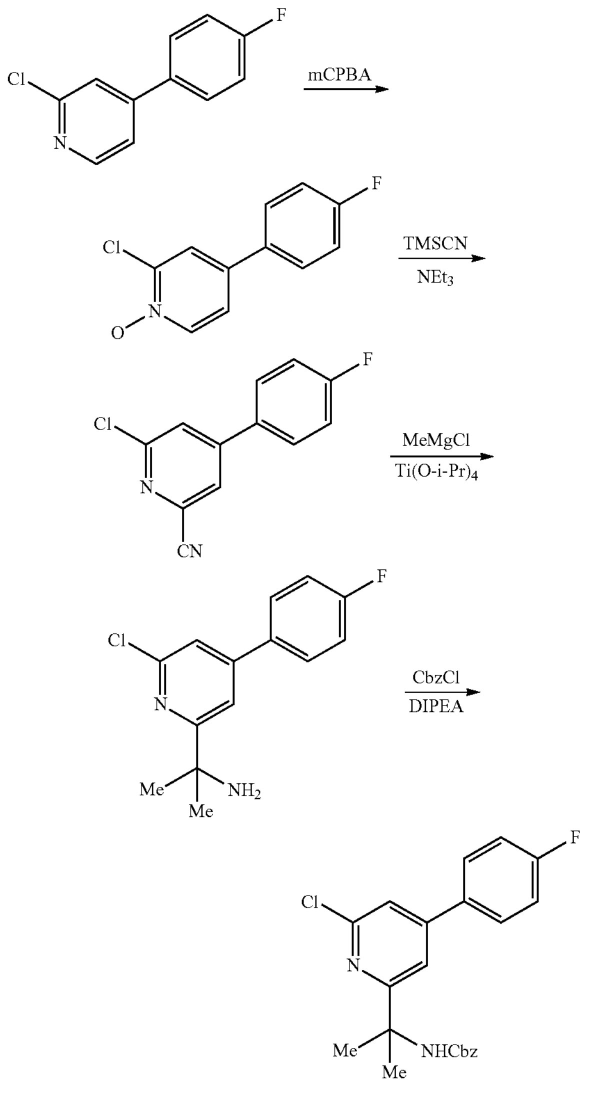

Intermediate C-8 benzyl (2-(6-chloro-4-(4-fluorophenyl)pyridin-2-yl)propan-2-yl)carbamate

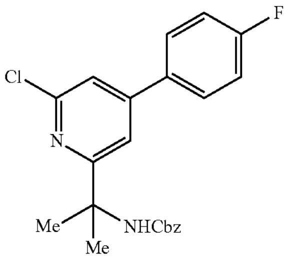 [SMILES: CC(C)(NC(=O)OCc1ccccc1)c1cc(-c2ccc(F)cc2)cc(Cl)n1]

Step 1: 2-chloro-4-(4-fluorophenyl)pyridine 1-oxide

To a solution of 2-chloro-4-(4-fluorophenyl)pyridine (5.8 g, 28 mmol) in DCM (0.10 mL) was added 3-chloroperoxybenzoic acid (15 g, 84 mmol). The mixture was heated under an atmosphere of nitrogen at 50° C. for 12 h. sodium bicarbonate (saturated aqueous, 100 mL) and sodium sulfite (saturated aqueous, 100 mL) were added, and the mixture was extracted by EtOAc (50 mL×4). The combined organic extracts were washed with brine (100 mL), dried over anhydrous sodium sulfate, filtered, and concentrated under reduced pressure. The residue was subjected to silica gel chromatography (0-70% EtOAc/petroleum ether) to afford the title compound.

Step 2: 6-chloro-4-(4-fluorophenyl)picolinonitrile

A solution of 2-chloro-4-(4-fluorophenyl)pyridine 1-oxide (4.3 g, 19 mmol), trimethylsilyl cyanide (11 g, 0.12 mol) and triethylamine (5.4 mL, 39 mmol) was heated under an atmosphere of nitrogen at 100° C. for 12 h. The mixture was concentrated under reduced pressure. The residue was subjected to silica gel chromatography (0-40% EtOAc/petroleum ether) to afford the title compound.

Step 3: 2-(6-chloro-4-(4-fluorophenyl)pyridin-2-yl) propan-2-amine

To a solution of 6-chloro-4-(4-fluorophenyl)picolinonitrile (2.7 g, 12 mmol) in THF (0.080 L) was slowly added methylmagnesium bromide (3.0 M in $Et_2O$, 19 mL, 58 mmol) at 0° C. The mixture was warmed to 25° C. and stirred for 30 min. Titanium isopropoxide (3.4 mL, 12 mmol) was added and the mixture was stirred at 80° C. for 12 h. The mixture was cooled to room temperature, treated with ammonium chloride (saturated aqueous, 50 mL), and extracted with EtOAc (50 mL×3). The combined organic extracts were washed with brine (50 mL), dried over anhydrous sodium sulfate, filtered, and concentrated to afford the title compound.

Step 4: benzyl (2-(6-chloro-4-(4-fluorophenyl)pyridin-2-yl)propan-2-yl)carbamate To a mixture of 2-(6-chloro-4-(4-fluorophenyl)pyridin-2-yl)propan-2-amine (2.0 g, 7.6 mmol) and DIPEA (4.0 mL, 23 mmol) in DCM (0.040 L) was added benzyl chloroformate (2.2 mL, 15 mmol) at 0° C. The resulting mixture was stirred at rt for 12 h. The mixture was concentrated under reduced pressure and the residue was subjected to silica gel chromatography (0-20% EtOAc/petroleum ether) to afford the title compound.

Scheme

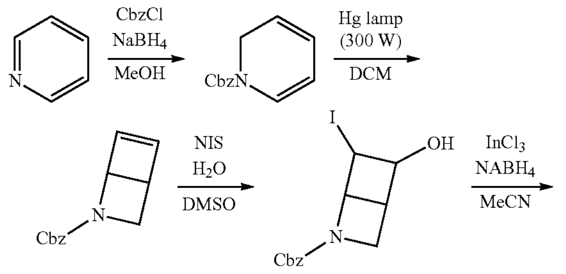

-continued

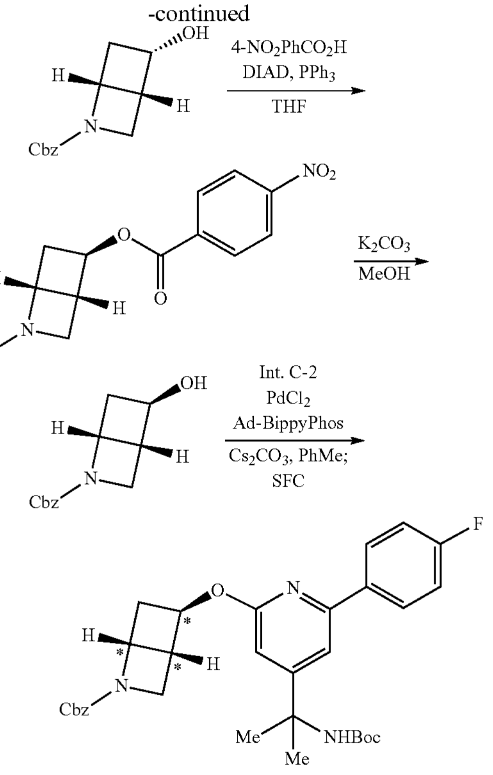

Intermediate D-ent-1 benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (Enantiomer 1)

and

Intermediate D-ent-¬2 benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (Enantiomer 2)

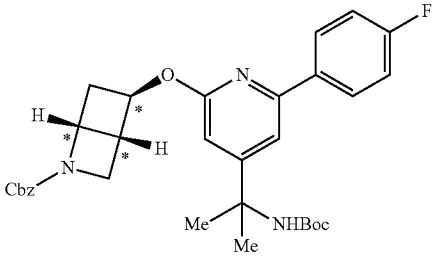 [SMILES: CC(C)(C)OC(=O)NC(C)(C)c1cc(O[C@@H]2C[C@@H]3[C@H]2CN3C(=O)OCc2ccccc2)nc(-c2ccc(F)cc2)c1]

Step 1: benzyl pyridine-1(2H)-carboxylate

To a −78° C. solution of anhydrous pyridine (12 g, 0.15 mol) in anhydrous MeOH (0.10 L) under argon was added sodium borohydride (5.7 g, 0.15 mol). Benzyl chloroformate (21 mL, 0.15 mol) was added dropwise and the mixture was stirred for 3 h. MTBE (100 mL) and water (100 mL) were added, and mixture was warmed to room temperature. The mixture was extracted with MTBE (100 mL×2) and the combined extracts were washed with water (100 mL×2) and brine (100 mL). The organic solution was dried over anhydrous magnesium sulfate, filtered, and concentrated under reduced pressure to afford the title compound.

Step 2: benzyl 2-azabicyclo[2.2.0]hex-5-ene-2-carboxylate

Under an atmosphere of nitrogen, a solution of benzyl pyridine-1(2H)-carboxylate (6.0 g, 25 mmol) in DCM (0.75 L) was irradiated (300 W, Photo-reactor, Hg lamp) for 6 h. The mixture was concentrated under reduced pressure and subjected to silica gel chromatography (0-17% EtOAc/petroleum ether) to afford the title compound.

Step 3: benzyl 5-hydroxy-6-iodo-2-azabicyclo[2.2.0]hexane-2-carboxylate

To a −5° C. solution of benzyl 2-azabicyclo[2.2.0]hex-5-ene-2-carboxylate (4.8 g, 22 mmol) in DMSO (72 mL) and water (72 mL) was added N-iodosuccinimide (15 g, 67 mmol) portion wise. The mixture was warmed to room temperature and stirred for 12 h. Water (100 mL) was added, and the mixture was extracted with EtOAc (50 mL×3). The combined organic extracts were washed with water (100 mL) and brine (100 mL), dried over anhydrous sodium sulfate, filtered, and concentrated under reduced pressure. The residue was subjected to silica gel chromatography (0-25% EtOAc/petroleum ether) to afford the title compound.

Step 4: benzyl rac-(1R,4R,5S)-5-hydroxy-2-azabicyclo[2.2.0]hexane-2-carboxylate

A mixture of freshly dried indium(III) chloride (4.4 g, 0.020 mol) and sodium borohydride (1.5 g, 0.040 mol) in MeCN (41 mL) was stirred at −78° C. for 10 min. The mixture was warmed to room temperature and benzyl 5-hydroxy-6-iodo-2-azabicyclo[2.2.0]hexane-2-carboxylate (5.5 g, 15 mmol) in MeCN (82 mL) was added dropwise. The mixture was stirred at rt for 2 h. The mixture was poured into water (60 mL) and extracted with EtOAc (40 mL×3). The combined organic extracts were washed with brine (50 mL), dried over anhydrous sodium sulfate, filtered, and concentrated under reduced pressure. The residue was subjected to silica gel chromatography (0-50% EtOAc/petroleum ether) to afford the title compound.

Step 5: benzyl rac-(1R,4R,5R)-5-((4-nitrobenzoyl)oxy)-2-azabicyclo[2.2.0]hexane-2-carboxylate To a 0° C. solution of benzyl rac-(1R,4R,5S)-5-hydroxy-2-azabicyclo[2.2.0]hexane-2-carboxylate (2.6 g, 11 mmol) and 4-nitrobenzoic acid (2.8 g, 17 mmol) in THF (0.080 L) was added triphenylphosphine (4.4 g, 17 mmol). Diisopropyl azodicarboxylate (4.6 g, 0.020 mol) was added and the mixture was stirred at rt for 12 h. The mixture was concentrated under reduced pressure and the residue was subjected to silica gel chromatography (0-17% EtOAc/petroleum ether) to afford the title compound.

Step 6: benzyl rac-(1R,4R,5R)-5-hydroxy-2-azabicyclo[2.2.0]hexane-2-carboxylate

To a solution of benzyl rac-(1R,4R,5R)-5-((4-nitrobenzoyl)oxy)-2-azabicyclo[2.2.0]hexane-2-carboxylate (5.5 g, 11 mmol) in MeOH (0.10 L) was added potassium carbonate (6.0 g, 43 mmol). The mixture was stirred at rt for 2 h. Water (100 mL) was added, and the mixture was extracted with EtOAc (50 mL×3). The combined organic extracts were washed with brine (20 mL×3), dried over anhydrous sodium sulfate, filtered, and concentrated under reduced pressure. The residue was subjected to silica gel chromatography (0-30% EtOAc/petroleum ether) to afford the title compound.

Step 7: benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (Enantiomers 1 and 2)

Under an atmosphere of nitrogen, a mixture of tert-butyl (2-(2-chloro-6-(4-fluorophenyl)pyridin-4-yl)propan-2-yl) carbamate (Int. C-2, 5.2 g, 14 mmol), benzyl rac-(1R,4R,5R)-5-hydroxy-2-azabicyclo[2.2.0]hexane-2-carboxylate (2.2 g, 9.4 mmol), $(Ad\text{-}BippyPhos)_2PdCl_2$ (0.99 g, 0.66 mmol), cesium carbonate (9.2 g, 28 mmol), and PhMe (0.18 L) were stirred at 90° C. for 24 h. The mixture was cooled to room temperature, filtered through a thin pad of silica gel (eluting with EtOAc), and concentrated under reduced pressure. The residue was subjected to silica gel chromatography (0-15% EtOAc/petroleum ether). The mixture of two stereoisomers was subjected to chiral SFC (ChiralPak AD-3, 5-40% IPA (with 0.05% DEA modifier)/$CO_2$) to afford benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (enantiomer 1, faster eluting, Int. D-ent-1) and benzyl rel-(1R,4R,5R)-5-((4-(2-((tert-butoxycarbonyl)amino)propan-2-yl)-6-(4-fluorophenyl)pyridin-2-yl)oxy)-2-azabicyclo[2.2.0]hexane-2-carboxylate (enantiomer 2, slower eluting, Int. D-ent-2).

Scheme

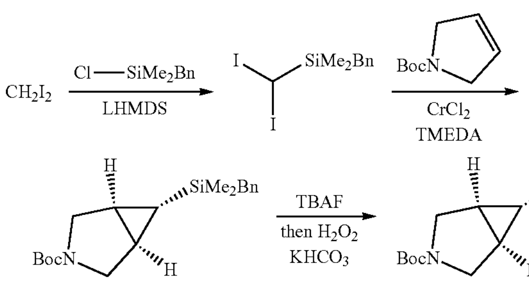

Intermediate E tert-butyl (1R,5S,6s)-6-hydroxy-3-azabicyclo[3.1.0]hexane-3-carboxylate

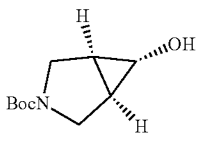

Step 1: benzyl(diiodomethyl)dimethylsilane

Ten reactions were carried out in parallel. Lithium bis(trimethylsilyl)amide solution (1.0 M, 1.5 L, 1.5 mol) in isopropyl ether (3.0 L) was charged into a 10 L vessel. Diiodomethane (130 mL, 1.6 mol) was added to the mixture at −65° C. The mixture was stirred at −65° C. for 0.25 h. Benzylchlorodimethylsilane (0.20 kg, 1.1 mol, 0.20 L) was added and mixture was stirred at −65° C. for 3 h, then stirred at 25° C. for 12. The reactions were combined and quenched with water (10 L). The mixture was extracted with MTBE (5 L×2). The organic extracts were combined, washed with brine, and dried over anhydrous sodium sulfate. The mixture was filtered and concentrated under reduced pressure. The residue was purified by silica gel chromatography (2-100% EtOAc/petroleum ether) to afford the title compound.

Step 2: tert-butyl (1R,5S,6s)-6-(benzyldimethylsilyl)-3-azabicyclo[3.1.0]hexane-3-carboxylate Fourteen reactions were carried out in parallel. Chromium (II) chloride (150 g, 1.2 mol) was charged to a 5 L vessel. THF (2.5 L) and N,N,N,N-tetramethylethylenediamine (360 mL, 2.4 mol) were added to the mixture at 25° C. over 30 min. Benzyl(diiodomethyl)dimethylsilane (240 g, 560 mmol) was added and the mixture was stirred at 25° C. for 30 min. tert-Butyl 2,5-dihydro-1H-pyrrole-1-carboxylate (0.050 kg, 0.30 mol) was added to the mixture at 25° C. The mixture was stirred at 50° C. for 18 h. The reactions were combined, treated with water (15 L), and extracted with MTBE (7 L×3). The organic extracts were combined, washed with brine, dried over anhydrous sodium sulfate, filtered, and concentrated. The residue was subjected to silica gel chromatography (1-100% EtOAc/petroleum ether) to afford the title compound.

Step 3: tert-butyl (1R,5S,6s)-6-hydroxy-3-azabicyclo[3.1.0]hexane-3-carboxylate Fourteen reactions were carried out in parallel. tert-Butyl (1R,5S,6s)-6-(benzyldimethylsilyl)-3-azabicyclo[3.1.0]hexane-3-carboxylate (0.070 kg, 210 mmol) in THF (2.1 L) was charged to a 10 L vessel. Tetrabutylammonium fluoride (1.0M in THF, 630 mL) was added and the mixture was stirred for 30 min at 25° C. MeOH (2.1 L) and potassium bicarbonate (0.20 kg, 2.1 mol) were added to the cooled reaction mixture at 0° C. Hydrogen peroxide (30 wt % in water, 0.10 L, 1.1 mol) was added and the mixture was stirred at 0° C. for 30 min and then at 25° C. for 16 h. The reactions were combined and the mixture was treated with sodium sulfite (saturated aqueous, 25 L) and extracted with EtOAc (7 L×2). The organic layers were combined, washed with brine, and dried over anhydrous sodium sulfate. The mixture was filtered and concentrated. The residue was subjected to silica gel chromatography (0-100% EtOAc/hexane) and re-crystallized from n-heptane:MTBE=20:1 (9 L) to afford the title compound.

Intermediate E-01 benzyl (1R,5S,6s)-6-hydroxy-3-azabicyclo[3.1.0]hexane-3-carboxylate

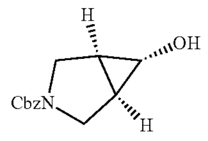 [SMILES: O=C(OCc1ccccc1)N1C[C@@H]2[C@@H](O)[C@@H]2C1]

Step 1: (1R,5S,6s)-3-azabicyclo[3.1.0]hexan-6-ol

To a solution of tert-butyl (1R,5S,6s)-6-hydroxy-3-azabicyclo[3.1.0]hexane-3-carboxylate (Int. E, 5.0 g, 25 mmol) in DCM (0.030 L) was added TFA (12 mL, 0.16 mol). The solution was stirred at 25° C. for 1 h and then concentrated under reduced pressure to afford the title compound.

Step 2: benzyl (1R,5S,6s)-6-hydroxy-3-azabicyclo[3.1.0]hexane-3-carboxylate

To a 0° C. solution of (1R,5S,6s)-3-azabicyclo[3.1.0]hexan-6-ol (2.4 g, 24 mmol) in THF (0.080 L) was added potassium carbonate (17 g, 0.12 mol) and benzyl chloroformate (5.2 mL, 36 mmol). The mixture was stirred at 25° C. for 12 h and then diluted with water (30 mL) and extracted with EtOAc (40 mL×3). The combined organic extracts were washed with brine (20 mL×2), dried over anhydrous sodium sulfate, filtered, and concentrated under reduced pressure. The residue was subjected to silica gel chromatography (0-40% EtOAc/petroleum ether) to afford the title compound.

Scheme

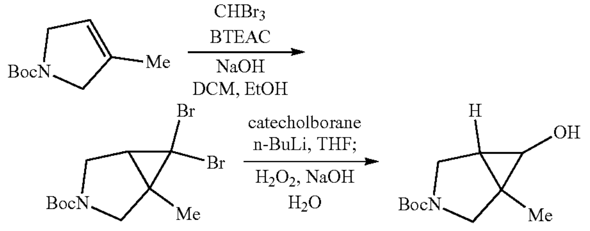

Intermediate F tert-butyl 6-hydroxy-1-methyl-3-azabicyclo[3.1.0]hexane-3-carboxylate

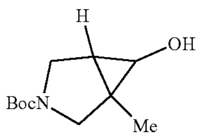

Step 1: tert-butyl 6,6-dibromo-1-methyl-3-azabicyclo[3.1.0]hexane-3-carboxylate

A mixture of tert-butyl 3-methyl-2,5-dihydro-1H-pyrrole-1-carboxylate (15 g, 82 mmol), bromoform (62 g, 0.25 mol) and N-benzyl-N,N,N-triethylammonium chloride (0.75 g, 3.3 mmol) in DCM (0.40 L) and EtOH (8.0 mL) was cooled to 0° C. under an atmosphere of nitrogen. A solution of sodium hydroxide (50 wt. % aqueous, 66 g, 0.82 mol) was added at 0° C. The mixture was warmed to 45° C. and stirred for 12 h. Water (150 mL) was added, and the mixture was extracted with DCM (80 mL×3). The combined organic extracts were washed with brine (50 mL), dried over anhydrous sodium sulfate, filtered, and concentrated under reduced pressure. The residue was subjected to silica gel chromatography (0-5% EtOAc/petroleum ether) to afford the title compound.

Step 2: tert-butyl 6-hydroxy-1-methyl-3-azabicyclo[3.1.0]hexane-3-carboxylate

A solution of tert-butyl 6,6-dibromo-1-methyl-3-azabicyclo[3.1.0]hexane-3-carboxylate (2.0 g, 5.6 mmol) in THF (0.040 L) was cooled to −78° C. A solution of n-butyllithium (2.5 M in hexane, 2.7 mL, 6.8 mmol) was added dropwise and the mixture was stirred for 15 min. A solution of catecholborane (1.0 M in THF, 11 mL, 11 mmol) was added and the mixture was warmed to 50° C. and stirred for 12 h. The mixture was cooled to 0° C. and hydrogen peroxide (30% (w/w) aqueous, 2.9 mL, 28 mmol) and sodium hydroxide (2.5 M aqueous, 9.0 mL, 23 mmol) were added. This mixture was warmed room temperature and stirred for 12 h. Sodium sulfite (saturated aqueous, 5 mL) and water (20 mL) were added, and the mixture was extracted with EtOAc (30 mL×3). The combined organic extracts were dried over anhydrous sodium sulfate, filtered, and concentrated under reduced pressure. The residue was subjected to silica gel chromatography (0-60% EtOAc/petroleum ether) to afford the title compound.

Scheme

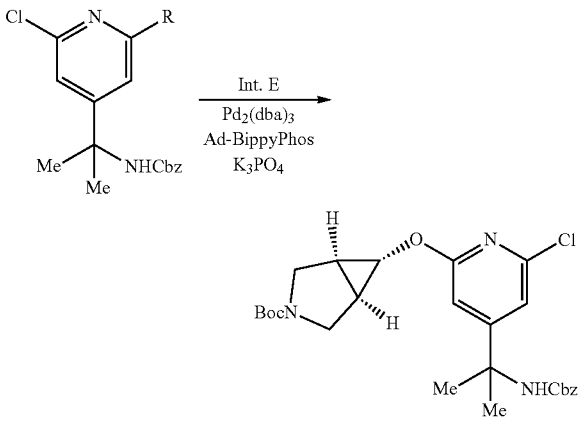

Intermediate G tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate

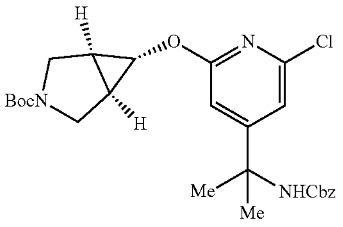 [SMILES: CC(C)(C)OC(=O)N1C[C@@H]2[C@H](C1)[C@H]2Oc1cc(C(C)(C)NC(=O)OCc2ccccc2)cc(Cl)n1]

A mixture of benzyl (2-(2,6-dichloropyridin-4-yl)propan-2-yl)carbamate (Int. A-1, 66 g, 65 mmol), tert-butyl (1R,5S,6s)-6-hydroxy-3-azabicyclo[3.1.0]hexane-3-carboxylate (Int. E, 0.030 kg, 0.050 mol), potassium phosphate tribasic (96 g, 150 mmol), Ad-BippyPhos (3.0 g, 1.5 mmol), and 1,4-dioxane (1.2 L) was purged and degassed with $N_2$ (5×) at 15° C. $Pd_2(dba)_3$ (1.7 g, 0.63 mmol) was added and the mixture was purged and degassed with $N_2$ (5×). The mixture was stirred at 70° C. for 16 h. The mixture was cooled to 15° C., washed with sodium bicarbonate (saturated aqueous, 1.0 L), and filtered. The filter cake was washed with EtOAc (1.5 L) and the organic phase was separated. The aqueous phase was extracted with EtOAc (500 mL×4), and the combined organic fractions were dried with anhydrous sodium sulfate, filtered, and concentrated. The residue was subjected to silica gel chromatography (1-17% EtOAc/petroleum ether). The mixture was subjected to reverse phase HPLC (40-70% MeCN/water) to afford the title compound.

Scheme

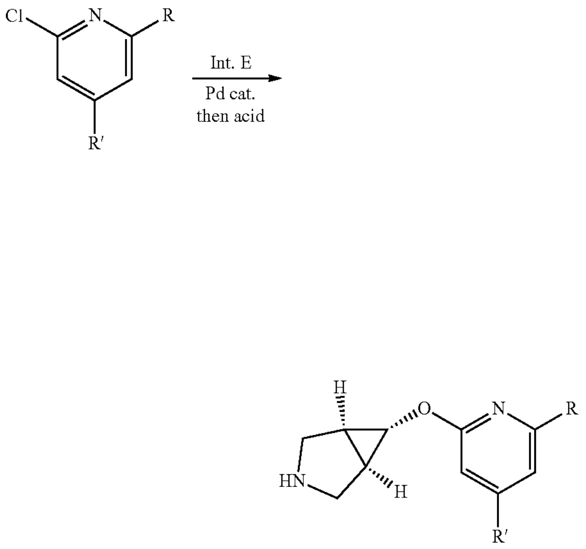

Intermediate H-01

2-(2-(((1R,5S,6s)-3-azabicyclo[3.1.0]hexan-6-yl)oxy)-6-(4-fluorophenyl)pyridin-4-yl)propan-2-amine

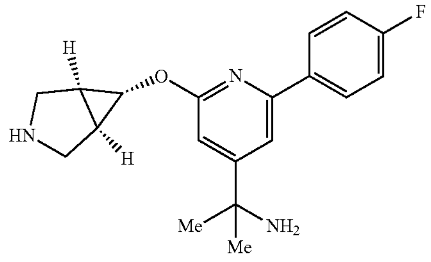 [SMILES: CC(C)(N)c1cc(O[C@H]2[C@@H]3CNC[C@@H]32)nc(-c2ccc(F)cc2)c1]

Step 1: tert-butyl (1R,5S,6s)-6-((4-(2-((tert-butoxycarbonyl)amino)propan-2-yl)-6-(4-fluorophenyl)pyridin-2-yl)oxy)-3-azabicyclo[3.1.0]hexane-3-carboxylate Under an atmosphere of nitrogen, a mixture of tert-butyl (2-(2-chloro-6-(4-fluorophenyl)pyridin-4-yl)propan-2-yl) carbamate (Int. C-2, 1.0 g, 2.7 mmol), tert-butyl (1R,5S,6s)-6-hydroxy-3-azabicyclo[3.1.0]hexane-3-carboxylate (Int. E, 0.60 g, 3.0 mmol), cesium carbonate (2.7 g, 8.2 mmol), Ad-BippyPhos (0.18 g, 0.27 mmol), $Pd_2(dba)_3$ (0.13 g, 0.14 mmol), and 1,4-dioxane (14 mL) was stirred at 85° C. for 2 h. The mixture was cooled to room temperature, filtered, and concentrated under reduced pressure. The residue was subjected to silica gel chromatography (0-50% EtOAc/hexanes) to afford the title compound.

Step 2: 2-(2-(((1R,5S,6s)-3-azabicyclo[3.1.0]hexan-6-yl)oxy)-6-(4-fluorophenyl)pyridin-4-yl)propan-2-amine To a 0° C. solution of tert-butyl (1R,5S,6s)-6-((4-(2-((tert-butoxycarbonyl)amino)propan-2-yl)-6-(4-fluorophenyl)pyridin-2-yl)oxy)-3-azabicyclo[3.1.0]hexane-3-carboxylate (1.3 g, 2.4 mmol) in DCM (0.020 L) was added a solution of HCl (4.0 M in 1,4-dioxane, 6.1 mL, 24 mmol). The mixture was warmed to room temperature and stirred for 1 h. The mixture was concentrated under reduced pressure, suspended in $Et_2O$, cooled to 0° C., and filtered. The filter cake was dried under reduced pressure to afford the title compound as a HCl salt.

Intermediate H-02 benzyl (2-(2-(((1R,5S,6s)-3-azabicyclo[3.1.0]hexan-6-yl)oxy)-6-(4-fluorophenyl)pyridin-4-yl)propan-2-yl)carbamate

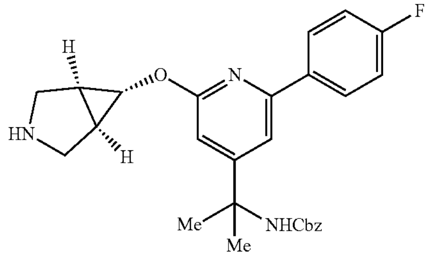 [SMILES: CC(C)(NC(=O)OCc1ccccc1)c1cc(O[C@H]2[C@@H]3CNC[C@@H]32)nc(-c2ccc(F)cc2)c1]

Step 1: tert-butyl (1R,5S,6s)-6-((4-(2-(((benzyloxy)carbonyl)amino)propan-2-yl)-6-(4-fluorophenyl)pyridin-2-yl)oxy)-3-azabicyclo[3.1.0]hexane-3-carboxylate Under an atmosphere of nitrogen, a mixture of benzyl (2-(2-chloro-6-(4-fluorophenyl)pyridin-4-yl)propan-2-yl) carbamate (Int. C-1, 1.0 g, 2.5 mmol), tert-butyl (1R,5S,6s)-6-hydroxy-3-azabicyclo[3.1.0]hexane-3-carboxylate (Int. E, 0.50 g, 2.5 mmol), potassium phosphate (1.6 g, 7.5 mmol), Ad-BippyPhos (0.17 g, 0.25 mmol), $Pd(OAc)_2$ (28 mg, 0.13 mmol), CPME (0.010 L), and $PhCF_3$ (0.010 L) was stirred at 90° C. for 16 h. The mixture was cooled to rt, filtered through a thin pad of silica gel (eluted with EtOAc), and concentrated under reduced pressure. The residue was subjected to silica gel chromatography (0-45% EtOAc/petroleum ether) to afford the title compound.

Step 2: benzyl (2-(2-(((1R,5S,6s)-3-azabicyclo[3.1.0]hexan-6-yl)oxy)-6-(4-fluorophenyl)pyridin-4-yl)propan-2-yl)carbamate To a mixture of tert-butyl (1R,5S,6s)-6-((4-(2-(((benzyloxy)carbonyl)amino)propan-2-yl)-6-(4-fluorophenyl)pyridin-2-yl)oxy)-3-azabicyclo[3.1.0]hexane-3-carboxylate (1.4 g, 2.5 mmol) in DCM (0.010 L) was added TFA (2.0 mL). The mixture was stirred at rt for 1 h and concentrated under reduced pressure. The residue was subjected to silica gel chromatography (0-10% MeOH/DCM) to afford the title compound.

Utilizing the procedures described in the synthesis of Intermediate H-02, the below compounds were prepared substituting the appropriate reagents for benzyl (2-(2-chloro-6-(4-fluorophenyl)pyridin-4-yl)propan-2-yl)carbamate.

| Int. | Structure | Name | Comments |
| --- | --- | --- | --- |
| H-03 | 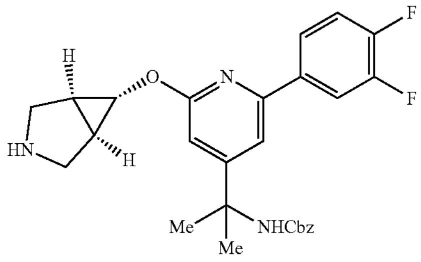 [SMILES: CC(C)(NC(=O)OCc1ccccc1)c1cc(O[C@H]2[C@@H]3CNC[C@@H]32)nc(-c2ccc(F)c(F)c2)c1] | benzyl (2-(2-(((1R,5S,6s)-3-azabicyclo[3.1.0]hexan-6-yl)oxy)-6-(3,4-difluorophenyl)pyridin-4-yl)propan-2-yl)carbamate | Step 1: Int. C-4 (2.6 mmol), Int. E (2.9 mmol), cesium carbonate (7.9 mmol), Ad-BippyPhos (0.26 mmol), $Pd(OAc)_2$ (0.13 mmol), PhMe (15 mL), 90° C., 12 h |

-continued

| Int. | Structure | Name | Comments |
|---|---|---|---|
| H-04-ent-1 | 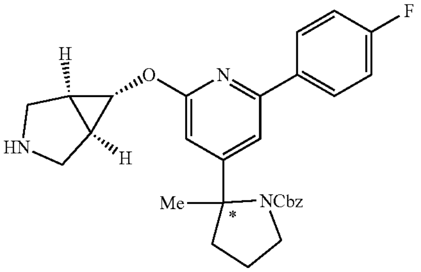 [SMILES: CC1(c2cc(O[C@H]3[C@@H]4CNC[C@@H]43)nc(-c3ccc(F)cc3)c2)CCCN1C(=O)OCc1ccccc1] | benzyl ent-2-(2-(((1R,5S,6s)-3-azabicyclo[3.1.0]hexan-6-yl)oxy)-6-(4-fluorophenyl)pyridin-4-yl)-2-methylpyrrolidine-1-carboxylate (enantiomer 1) | Step 1: Int. C-6-ent-1 (1.1 mmol), Int. E (1.1 mmol), $Pd_2(dba)_3$ (0.060 mmol), Ad-BippyPhos (0.11 mmol), cesium carbonate (3.4 mmol), PhMe (0.010 L), 90° C., 12 h<br>Form: TFA salt |
| H-05 | 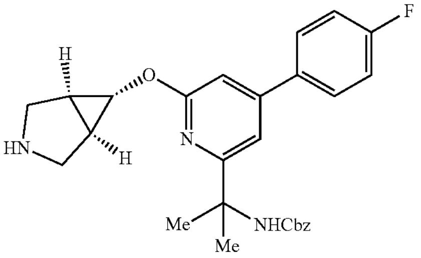 [SMILES: CC(C)(NC(=O)OCc1ccccc1)c1cc(-c2ccc(F)cc2)cc(O[C@H]2[C@@H]3CNC[C@@H]32)n1] | benzyl (2-(6-(((1R,5S,6s)-3-azabicyclo[3.1.0]hexan-6-yl)oxy)-4-(4-fluorophenyl)pyridin-2-yl)propan-2-yl)carbamate | — |

Scheme

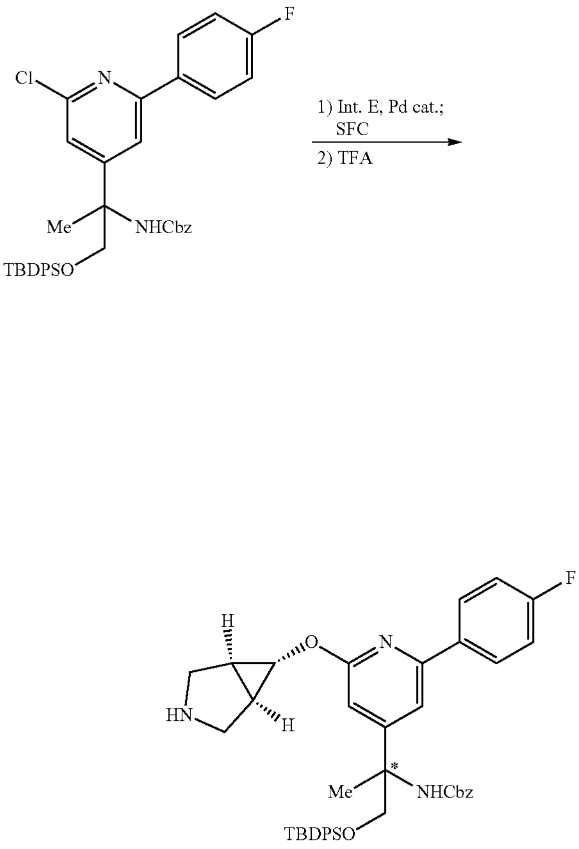

Intermediate H-06-ent-1 benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (Enantiomer 1)

and

Intermediate H-06-ent-2 benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (Enantiomer 2)

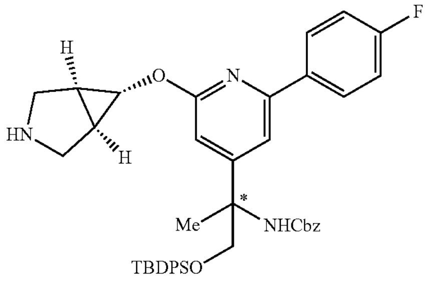

Step 1: tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo[3.1.0]hexane-3-carboxylate (Enantiomers 1 and 2)

Under an atmosphere of argon, a mixture of benzyl rac-(1-((tert-butyldiphenylsilyl)oxy)-2-(2-chloro-6-(4-fluorophenyl)pyridin-4-yl)propan-2-yl)carbamate (Int. C-7, 0.80 g, 1.2 mmol) and tert-butyl (1R,5S,6s)-6-hydroxy-3-azabicyclo[3.1.0]hexane-3-carboxylate (Int. E, 0.27 g, 1.3 mmol), Ad-BippyPhos (81 mg, 0.12 mmol), $Pd_2(dba)_3$ (56 mg, 0.061 mmol), cesium carbonate (1.2 g, 3.7 mmol), and PhMe (15 mL) was stirred at 90° C. for 12 h. The mixture was cooled to rt, filtered through a thin pad of silica gel (eluted w/EtOAc), and concentrated under reduced pressure. The residue was subjected to silica gel chromatography (0-25% EtOAc/petroleum ether). The mixture of two enantiomers was subjected to chiral SFC ((S,S)Whelk-01, 40% MeOH (with 0.05% DEA modifier)/$CO_2$) to afford the title compounds, tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo[3.1.0]hexane-3-carboxylate (enantiomer 1, faster eluting) and tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo[3.1.0]hexane-3-carboxylate (enantiomer 2, slower eluting).

Step 2-1: benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (Enantiomer 1)

To a solution of tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo[3.1.0]hexane-3-carboxylate (enantiomer 1, faster eluting, 0.31 g, 0.38 mmol) in DCM (5.0 mL) was added TFA (2.0 mL). The mixture was stirred at rt for 1 h. The mixture was concentrated under reduced pressure to afford the title compound (Int. H-06¬ent-1).

Step 2-2: benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (Enantiomer 2)

To a solution of tert-butyl ent-(1R,5S,6s)-6-((6-(4-fluorophenyl)-4-(5,9,9-trimethyl-3-oxo-1,8,8-triphenyl-2,7-dioxa-4-aza-8-siladecan-5-yl)pyridin-2-yl)oxy)-3-azabicyclo[3.1.0]hexane-3-carboxylate (enantiomer 2, slower eluting, 0.31 g, 0.38 mmol) in DCM (5.0 mL) was added TFA (2.0 mL). The mixture was stirred at rt for 1 h. The mixture was concentrated under reduced pressure to afford the title compound (Int. H-06-ent-2).

Scheme

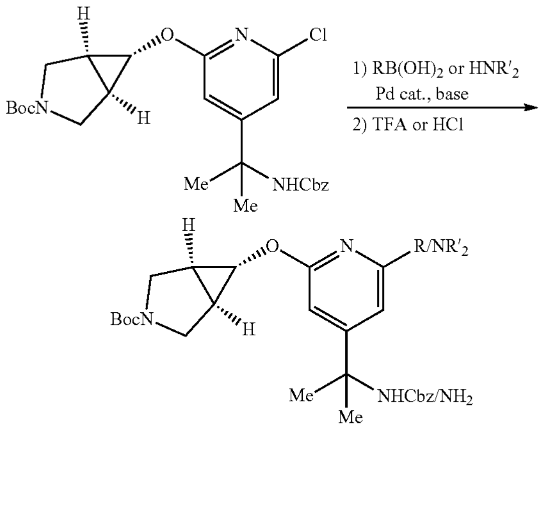

Intermediate H-07 benzyl (2-(2-(((1R,5S,6s)-3-azabicyclo[3.1.0]hexan-6-yl)oxy)-6-(2,4-difluorophenyl)pyridin-4-yl)propan-2-yl)carbamate

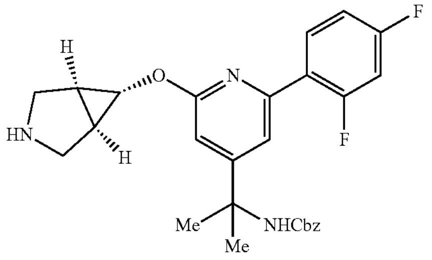 [SMILES: CC(C)(NC(=O)OCc1ccccc1)c1cc(O[C@H]2[C@@H]3CNC[C@@H]32)nc(-c2ccc(F)cc2F)c1]

Step 1: tert-butyl (1R,5S,6s)-6-((4-(2-(((benzyloxy)carbonyl)amino)propan-2-yl)-6-(2,4-difluorophenyl)pyridin-2-yl)oxy)-3-azabicyclo[3.1.0]hexane-3-carboxylate Under an atmosphere of nitrogen, a mixture of tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 0.50 g, 0.10 mmol), 2,4-difluorophenylboronic acid (0.19 g, 1.2 mmol), Xphos Pd G2 (78 mg, 0.10 mmol), potassium phosphate (1.0 M aqueous, 3.0 mL, 3.0 mmol), and 1,4-dioxane (5.0 mL) was stirred at 100° C. for 2 h. The mixture was cooled to room temperature, filtered, and concentrated under reduced pressure. The residue was subjected to silica gel chromatography (0-20% (3:1 EtOAc/EtOH)/hexanes) to afford the title compound.

Step 2: benzyl (2-(2-(((1R,5S,6s)-3-azabicyclo[3.1.0]hexan-6-yl)oxy)-6-(2,4-difluorophenyl)pyridine-4-yl)propan-2-yl)carbamate To a solution of tert-butyl (1R,5S,6s)-6-((4-(2-(((benzyloxy)carbonyl)amino)propan-2-yl)-6-(2,4-difluorophenyl)pyridin-2-yl)oxy)-3-azabicyclo[3.1.0]hexane-3-carboxylate (0.50 g, 0.86 mmol) in DCM (0.050 L) was added a solution of HCl (4.0 M in 1,4-dioxane, 1.0 mL, 4.3 mmol). The reaction mixture was stirred at rt for 1 h. The reaction was concentrated under reduced pressure to afford the title compound as a HCl salt.

Scheme

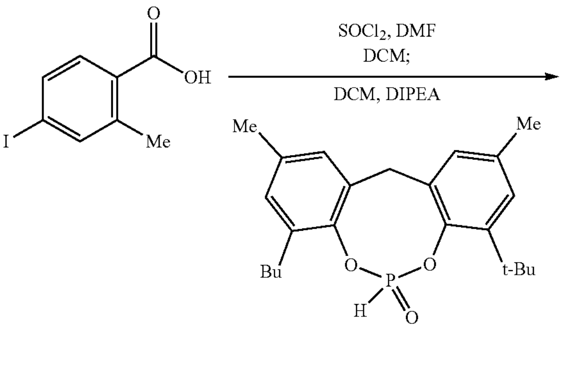

-continued

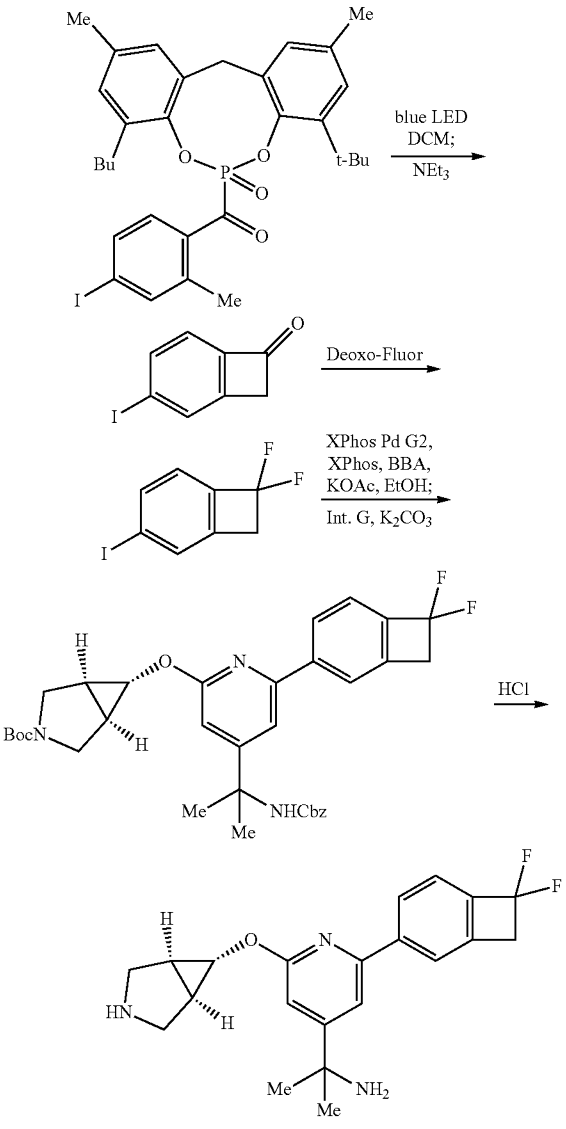

Intermediate H-08

2-(2-(((1R,5S,6s)-3-azabicyclo[3.1.0]hexan-6-yl)oxy)-6-(7,7-difluorobicyclo[4.2.0]octa-1(6),2,4-trien-3-yl)pyridin-4-yl)propan-2-amine

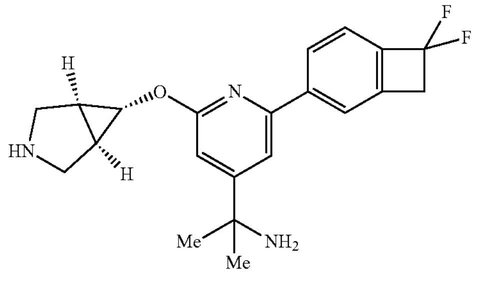 [SMILES: CC(C)(N)c1cc(O[C@H]2[C@@H]3CNC[C@@H]32)nc(-c2ccc3c(c2)CC3(F)F)c1]

Step 1: (4,8-di-tert-butyl-2,10-dimethyl-6-oxido-12H-dibenzo[d,g][1,3,2]dioxaphosphocin-6-yl)(4-iodo-2-methylphenyl)methanone To a solution of 4-iodo-2-methylbenzoic acid (4.1 g, 16 mmol) in DCM (31 mL) was added a solution of oxalyl chloride (2.0 M in DCM, 2.7 mL, 31 mmol), followed by DMF (2 drops). The mixture was heated at reflux for 1 h. The mixture was concentrated under reduced pressure. DCM (31 mL) and DIPEA (14 mL, 78 mmol) were added then a solution of 4,8-di-tert-butyl-2,10-dimethyl-12H-dibenzo[d,g][1,3,2]dioxaphosphocine 6-oxide (6.0 g, 16 mmol) in DCM (31 mL) was added dropwise over 1 h. The mixture was stirred at rt for 6 h. DCM (50 mL) was added, and the mixture was washed with HCl (1 N, 50 mL) and a solution of sodium bicarbonate (saturated aqueous, 50 mL). The organic fraction was dried over anhydrous magnesium sulfate, filtered, and concentrated under reduced pressure. The residue was subjected to silica gel chromatography (0-30% EtOAc/hexanes) to afford the title compound.

Step 2: 3-iodobicyclo[4.2.0]octa-1(6),2,4-trien-7-one

A solution of (4,8-di-tert-butyl-2,10-dimethyl-6-oxido-12H-dibenzo[d,g][1,3,2]dioxaphosphocin-6-yl)(4-iodo-2-methylphenyl)methanone (4.7 g, 7.4 mmol) in PhMe (15 mL) was irradiated in a PennOC Photoreactor® (wavelength: 420 nm; LED intensity: 100%; fan speed: 5000 rpm; stir: 1200 rpm) for 12 h. Triethylamine (1.0 mL, 7.4 mmol) was added, and the mixture was heated to 45° C. for 4 h. The mixture was subjected to silica gel chromatography (0-15% EtOAc/hexanes) to afford the title compound.

Step 3: 7,7-difluoro-3-iodobicyclo[4.2.0]octa-1(6),2,4-triene

A mixture of bis(2-methoxyethyl)aminosulfur trifluoride (0.93 mL, 5.0 mmol) and 3-iodobicyclo[4.2.0]octa-1(6),2,4-trien-7-one (250 mg, 1.0 mmol) was stirred at 50° C. for 16 h. A 0° C. solution of sodium bicarbonate (saturated aqueous, 30 mL) was added dropwise and the mixture was extracted with DCM (30 mL×3). The combined organic extracts were dried over anhydrous magnesium sulfate, filtered, and concentrated under reduced pressure. The residue was subjected to silica gel chromatography (hexanes) to afford the title compound.

Step 4: tert-Butyl (1R,5S,6s)-6-((4-(2-(((benzyloxy)carbonyl)amino)propan-2-yl)-6-(7,7-difluorobicyclo[4.2.0]octa-1(6),2,4-trien-3-yl)pyridin-2-yl)oxy)-3-azabicyclo[3.1.0]hexane-3-carboxylate Under an atmosphere of nitrogen, a mixture of 7,7-difluoro-3-iodobicyclo[4.2.0]octa-1(6),2,4-triene (0.20 g, 0.74 mmol), Xphos Pd G2 (58 mg, 0.074 mmol), Xphos (0.070 g, 0.15 mmol), tetrahydroxydiboron (0.20 g, 2.2 mmol), potassium acetate (0.22 g, 2.2 mmol), and EtOH (7.4 mL) was stirred at 80° C. for 2 h. A solution of potassium carbonate (1.8 M aqueous, 1.2 mL, 2.2 mmol) and tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 0.37 g, 0.74 mmol) were added and the mixture was stirred at 80° C. for 2 h. The mixture was cooled to room temperature, a solution of potassium phosphate monobasic (saturated aqueous, 20 mL) was added, and the mixture was extracted with EtOAc (20 mL×3). The combined organic extracts were dried over anhydrous magnesium sulfate, filtered, and concentrated under reduced pressure. The residue was subjected to silica gel chromatography (0-100% EtOAc/hexanes) to afford the title compound.

Step 5: 2-(2-(((1R,5S,6s)-3-Azabicyclo[3.1.0]hexan-6-yl)oxy)-6-(7,7-difluorobicyclo[4.2.0]octa-1(6),2,4-trien-3-yl)pyridin-4-yl)propan-2-amine A mixture of tert-butyl (1R,5S,6s)-6-((4-(2-(((benzyloxy)carbonyl)amino)propan-2-yl)-6-(7,7-difluorobicyclo[4.2.0]octa-1(6),2,4-trien-3-yl)pyridin-2-yl)oxy)-3-azabicyclo[3.1.0]hexane-3-carboxylate (0.41 g, 0.68 mmol) and HCl (37%, 6.7 mL) was stirred at 80° C. for 10 min. The mixture was cooled to rt, diluted with water (10 mL), and loaded onto a Flash SCX-2 cartridge (preconditioned with MeOH). The cartridge was washed with MeOH (2 CV) and eluted with a methanolic solution of $NH_3$ (2 N, 2 CV). The eluent was concentrated under reduced pressure. The residue was dissolved in DCM (0.010 L), then HCl (4.0 M in 1,4-dioxane, 1.7 mL, 6.8 mmol) was added. The mixture was stirred at rt for 15 min and concentrated under reduced pressure to afford the title compound as a HCl salt.

Scheme

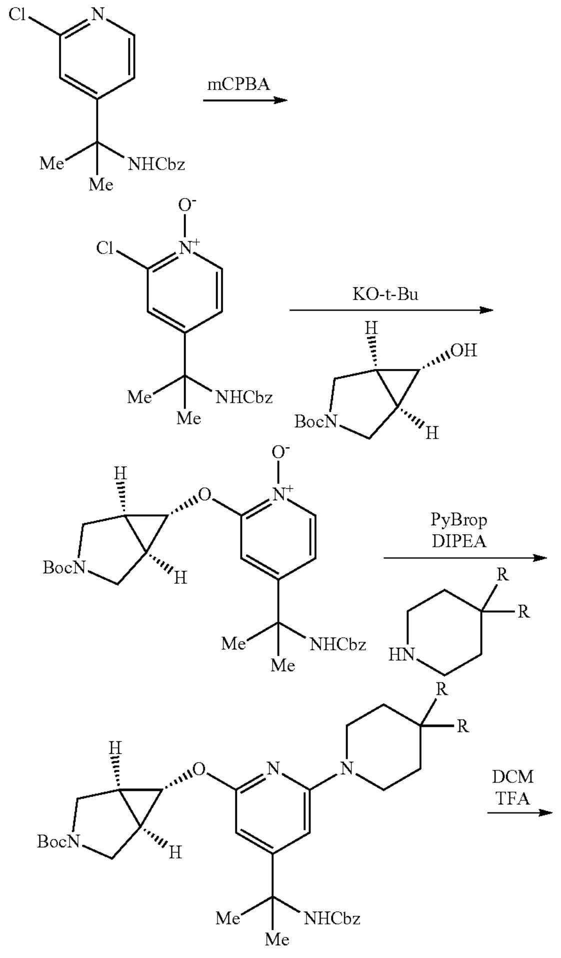

-continued

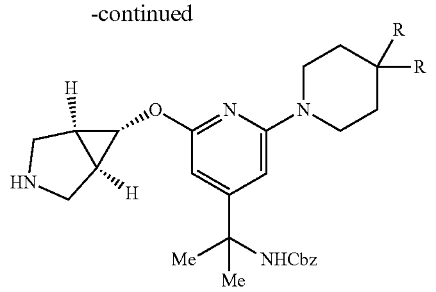

Intermediate H-09 benzyl (2-(2-(((1R,5S,6s)-3-azabicyclo[3.1.0]hexan-6-yl)oxy)-6-(4,4-dimethylpiperidin-1-yl)pyridin-4-yl)propan-2-yl)carbamate

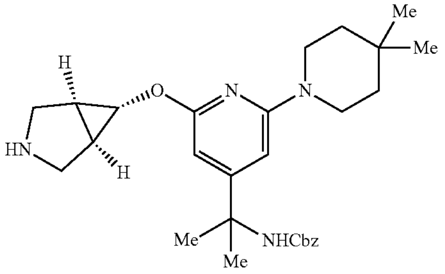 [SMILES: CC1(C)CCN(c2cc(C(C)(C)NC(=O)OCc3ccccc3)cc(O[C@H]3[C@@H]4CNC[C@@H]43)n2)CC1]

Step 1: benzyl (2-(2-chloropyridin-4-yl)propan-2-yl) carbamate 1-oxide

To a solution of benzyl (2-(2-chloropyridin-4-yl)propan-2-yl)carbamate (Int. A-2, 4.4 g, 14 mmol) in DCM (72 mL) was added 3-chloroperoxybenzoic acid (77 wt. % with water, 4.8 g, 22 mmol). The mixture was stirred at rt for 16 h. The reaction was diluted with DCM (75 mL) and washed with sodium sulfite (saturated aqueous, 100 mL), sodium bicarbonate (saturated aqueous, 100 mL), and brine (100 mL). The organic solution was dried over anhydrous magnesium sulfate, filtered, and concentrated under reduced pressure. The residue was subjected to silica gel chromatography (0-20% (3:1 EtOAc:EtOH)/DCM) to afford the title compound.

Step 2: tert-butyl (1R,5S,6s)-6-((4-(2-(((benzyloxy)carbonyl)amino)propan-2-yl)pyridin-2-yl)oxy)-3-azabicyclo[3.1.0]hexane-3-carboxylate N-oxide To a solution of benzyl (2-(2-chloropyridin-4-yl)propan-2-yl)carbamate 1-oxide (2.0 g, 6.3 mmol) and tert-butyl (1R,5S,6s)-6-hydroxy-3-azabicyclo[3.1.0]hexane-3-carboxylate (Int. E, 1.3 g, 6.3 mmol) in THF (63 mL) was added potassium tert-butoxide (1.0 M in THF, 6.9 mL, 6.9 mmol). The mixture was heated to 60° C. for 3 d. The mixture was cooled to room temperature and diluted with water (100 mL) and EtOAc (200 mL). The organic solution was washed with brine (150 mL), dried over anhydrous magnesium sulfate, filtered, and concentrated under reduced pressure. The residue was subjected to silica gel chromatography (0-25% (3:1 EtOAc:EtOH)/DCM) to afford the title compound.

Step 3: tert-butyl (1R,5S,6s)-6-((4-(2-(((benzyloxy)carbonyl)amino)propan-2-yl)-6-(4,4-dimethylpiperidin-1-yl)pyridin-2-yl)oxy)-3-azabicyclo[3.1.0]hexane-3-carboxylate To a mixture of tert-butyl (1R,5S,6s)-6-((4-(2-(((benzyloxy)carbonyl)amino)propan-2-yl)pyridin-2-yl)oxy)-3-azabicyclo[3.1.0]hexane-3-carboxylate N-oxide (0.55 g, 1.1 mmol) and 4,4-dimethylpiperidine-HCl (0.21 g, 1.4 mmol) in DCM (4.6 mL) was added DIPEA (0.99 mL, 5.7 mmol) and bromotripyrrolidinophosphonium hexafluorophosphate (0.69 g, 1.5 mmol). The mixture was stirred at rt for 16 h. The mixture was diluted with EtOAc (40 mL) and washed with sodium bicarbonate (saturated aqueous, 40 mL), water (40 mL), and brine (40 mL). The organic solution was dried over anhydrous magnesium sulfate, filtered, and concentrated under reduced pressure. The residue was subjected to silica gel chromatography (0-15% (3:1 EtOAc:EtOH)/hexanes) to afford the title compound.

Step 4: benzyl (2-(2-(((1R,5S,6s)-3-azabicyclo[3.1.0]hexan-6-yl)oxy)-6-(4,4-dimethylpiperidin-1-yl)pyridin-4-yl)propan-2-yl)carbamate To a solution of tert-butyl (1R,5S,6s)-6-((4-(2-(((benzyloxy)carbonyl)amino)propan-2-yl)-6-(4,4-dimethylpiperidin-1-yl)pyridin-2-yl)oxy)-3-azabicyclo[3.1.0]hexane-3-carboxylate (0.36 g, 0.62 mmol) in DCM (4.7 mL) was added TFA (1.6 mL). The mixture was stirred at rt for 16 h. The mixture was poured into sodium hydroxide (1 N aqueous, 50 mL) and the pH was adjusted to >12 with sodium hydroxide (6 N aqueous). The mixture was extracted with DCM (50 mL×3) and the combined organic extracts were dried over anhydrous magnesium sulfate, filtered, and concentrated under reduced pressure to afford the title compound.

Scheme

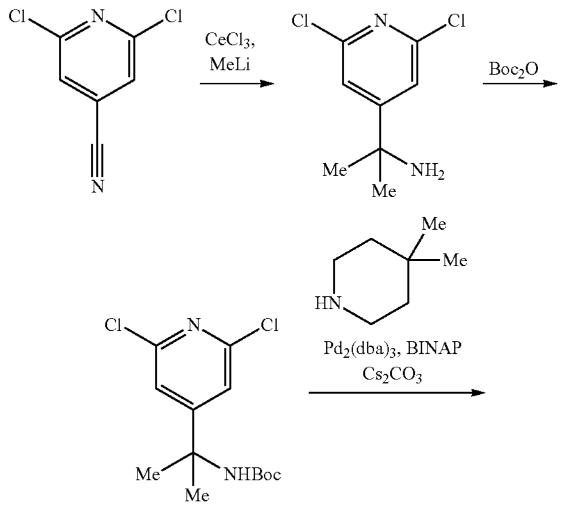

-continued

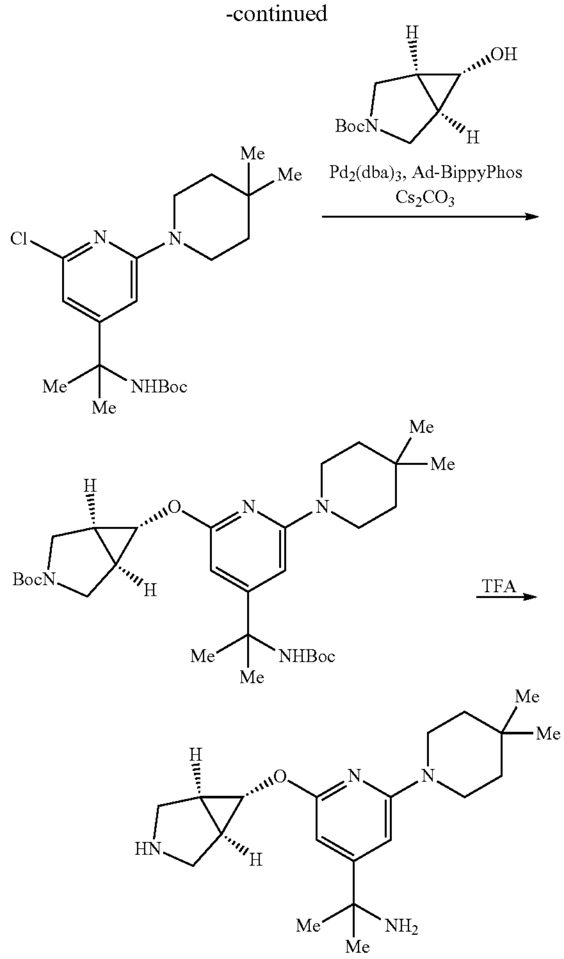

Intermediate H-09-2

2-(2-(((1R,5S,6s)-3-azabicyclo[3.1.0]hexan-6-yl)oxy)-6-(4,4-dimethylpiperidin-1-yl)pyridin-4-yl)propan-2-amine

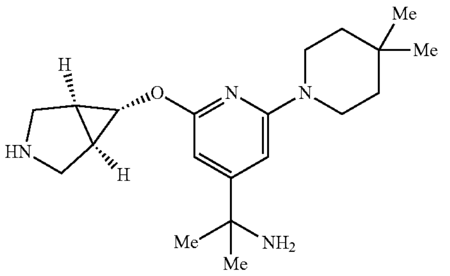 [SMILES: CC1(C)CCN(c2cc(C(C)(C)N)cc(O[C@H]3[C@@H]4CNC[C@@H]43)n2)CC1]

Step 1: 2-(2,6-dichloropyridin-4-yl)propan-2-amine

To a flame dried flask of anhydrous cerium (III) chloride (5.0 g, 0.020 mol) was added THF (0.040 L). The mixture was stirred for 15 min at 25° C. and then cooled to −78° C. To this was added a solution of methyllithium (1.6 M in $Et_2O$, 12 mL, 0.020 mol). After 30 min, a solution of 2,6-dichloroisonicotinonitrile (1.2 g, 6.7 mmol) in THF (5.0 mL) was added. The mixture was warmed to room temperature. The mixture was treated with saturated aqueous ammonium chloride, followed by concentrated $NH_4OH$ until the solution was basic. The resulting emulsion was diluted with water and EtOAc and filtered through a pad of Celite, which was washed with EtOAc. The filtrate layers were separated and the aqueous layer was extracted with EtOAc (3×). The combined organic extracts were dried over anhydrous magnesium sulfate, filtered, and concentrated under reduced pressure to afford the title compound.

Step 2: tert-butyl (2-(2,6-dichloropyridin-4-yl)propan-2-yl)carbamate

To a solution of 2-(2,6-dichloropyridin-4-yl)propan-2-amine (1.4 g, 6.7 mmol) in 1,4-dioxane (0.040 L) was added di-tert-butyl dicarbonate (2.2 g, 0.010 mol). The reaction heated to 100° C. for 1 h. The mixture was cooled to room temperature and concentrated under reduced pressure. The residue was subjected to silica gel chromatography (0-25% EtOAc/heptane) to afford the title compound.

Step 3: tert-butyl (2-(2-chloro-6-(4,4-dimethylpiperidin-1-yl)pyridin-4-yl)propan-2-yl)carbamate A solution of tert-butyl (2-(2,6-dichloropyridin-4-yl)propan-2-yl)carbamate (4.4 g, 14 mmol), 4,4-dimethylpiperidine hydrochloride (1.9 g, 13 mmol), $Pd_2(dba)_3$ (0.30 g, 0.33 mmol), BINAP (0.41 g, 0.65 mmol), cesium carbonate (11 g, 33 mmol) in PhMe (0.10 L) was heated to 100° C. for 16 h. The mixture was cooled to room temperature, diluted with EtOAc (200 mL), and washed with brine (200 mL). The organic extracts were dried over anhydrous magnesium sulfate, filtered, and concentrated under reduced pressure. The residue was subjected to silica gel chromatography (0-10% 3:1 EtOAc:EtOH/hexanes) to afford the title compound.

Step 4: tert-butyl (1R,5S,6s)-6-((4-(2-((tert-butoxycarbonyl)amino)propan-2-yl)-6-(4,4-dimethylpiperidin-1-yl)pyridin-2-yl)oxy)-3-azabicyclo[3.1.0]hexane-3-carboxylate A solution of tert-butyl (1R,5S,6s)-6-hydroxy-3-azabicyclo[3.1.0]hexane-3-carboxylate (Int. E, 0.94 g, 4.7 mmol), tert-butyl (2-(2-chloro-6-(4,4-dimethylpiperidin-1-yl)pyridin-4-yl)propan-2-yl)carbamate (1.5 g, 3.9 mmol), $Pd_2(dba)_3$ (0.072 g, 0.079 mmol), 5-(di((3S,5S,7S)-adamantan-1-yl)phosphaneyl)-1',3',5'-triphenyl-1'H-1,4'-bipyrazole (0.10 g, 0.16 mmol), cesium carbonate (3.8 g, 12 mmol) in 1,4-dioxane (0.020 L) was heated to 85° C. for 14 h. The mixture was cooled to room temperature, diluted with EtOAc (60 mL) and washed with water (60 mL) and brine (60 mL). The organic layer was dried over anhydrous magnesium sulfate, filtered, and concentrated under reduced pressure. The residue was subjected to silica gel chromatography (0-20% EtOAc/hexanes) to afford the title compound.

Step 5: 2-(2-(((1R,5S,6s)-3-azabicyclo[3.1.0]hexan-6-yl)oxy)-6-(4,4-dimethylpiperidin-1-yl)pyridin-4-yl)propan-2-amine To a solution of tert-butyl (1R,5S,6s)-6-((4-(2-((tert-butoxycarbonyl)amino)propan-2-yl)-6-(4,4-dimethylpiperidin-1-yl)pyridin-2-yl)oxy)-3-azabicyclo[3.1.0]hexane-3-carboxylate (1.0 g, 1.9 mmol) in DCM (14 mL) was added TFA (4.7 mL). The mixture was stirred at 25° C. for 16 h and then poured into sodium hydroxide (1N aqueous, pH >12) and extracted with DCM (50 mL×3). The combined organic extracts were dried over anhydrous magnesium sulfate, filtered, and concentrated under reduced pressure to afford the title compound.

Utilizing the procedures described in the synthesis of Intermediate H-09, the below compound was prepared substituting the appropriate reagents for 4,4-dimethylpiperidine-HCl.

| Int. | Structure | Name |
|---|---|---|
| H-10 | 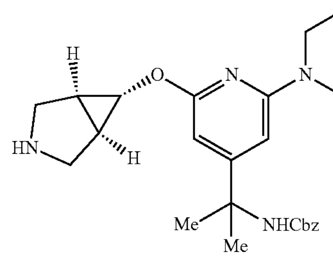 | benzyl (2-(2-(((1R,5S,6s)-3-azabicyclo[3.1.0]hexan-6-yl)oxy)-6-(4-(trifluoromethyl)piperidin-1-yl)pyridin-4-yl)propan-2-yl)carbamate |

Intermediate H-10-2

2-(2-(((1R,5S,6s)-3-azabicyclo[3.1.0]hexan-6-yl)oxy)-6-(4-(trifluoromethyl)piperidin-1-yl)pyridin-4-yl)propan-2-amine

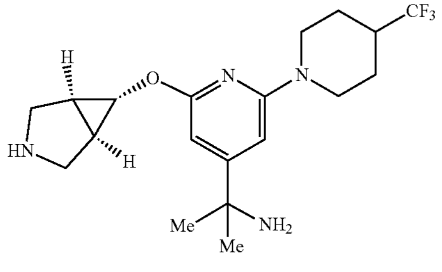 [SMILES: CC(C)(N)c1cc(O[C@H]2[C@@H]3CNC[C@@H]32)nc(N2CCC(C(F)(F)F)CC2)c1]

A solution of tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 45 mg, 0.090 mmol), 4-(trifluoromethyl)piperidine hydrochloride (0.020 g, 0.11 mmol) and chloro(2-dicyclohexylphosphino-2',6'-diisopropoxy-1,1'-biphenyl)[2-(2'-amino-1,1'-biphenyl)]palladium(II) (7.0 mg, 9.0 μmol) in THF (0.30 mL) was degassed. Sodium tert-butoxide (0.13 mL, 0.27 mmol) was added and the reaction was heated to 60° C. for 18 h. The reaction was cooled to room temperature, diluted with EtOAc, filtered over celite and concentrated under reduced pressure. The mixture was dissolved in DCM (0.30 mL) and treated with HCl (4 M in 1,4-dioxane, 0.22 mL, 0.90 mmol). The reaction was stirred at 25° C. for 1 h. The mixture was concentrated under reduced pressure and subjected to reverse phase HPLC (10-50% MeCN/water with 0.1% TFA modifier) to afford the title compound.

Scheme

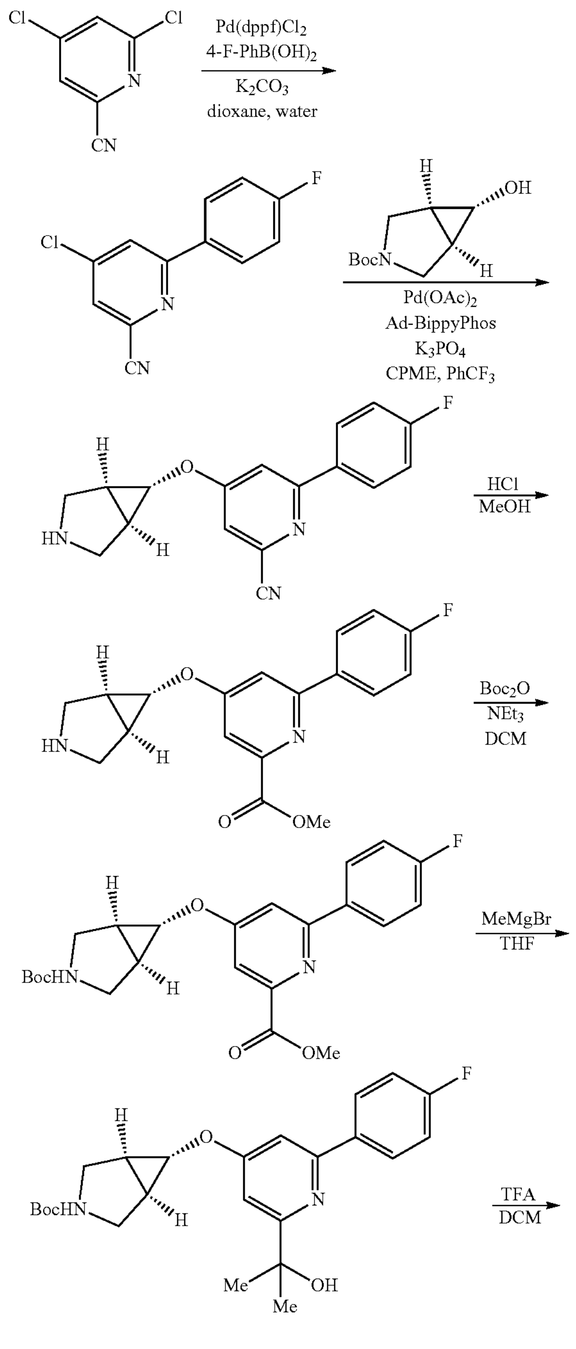

-continued

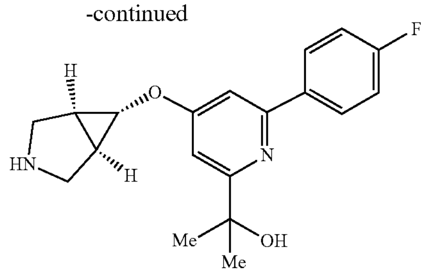

Intermediate H-11

2-(4-(((1R,5S,6s)-3-azabicyclo[3.1.0]hexan-6-yl)oxy)-6-(4-fluorophenyl)pyridin-2-yl)propan-2-ol

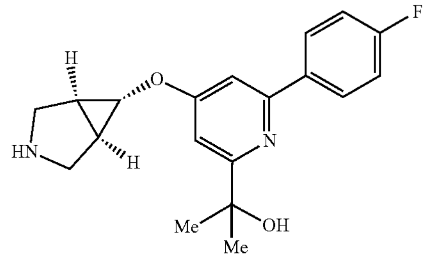 [SMILES: CC(C)(O)c1cc(O[C@H]2[C@@H]3CNC[C@@H]32)cc(-c2ccc(F)cc2)n1]

Step 1: 4-chloro-6-(4-fluorophenyl)picolinonitrile

Under an atmosphere of nitrogen, a mixture of 6-bromo-4-chloropicolinonitrile (2.7 g, 7.5 mmol), (4-fluorophenyl) boronic acid (1.0 g, 7.4 mmol), potassium carbonate (2.1 g, 15 mmol), Pd(dppf)$Cl_2$ (0.55 g, 0.75 mmol), 1,4-dioxane (18 mL), and water (2.0 mL) was stirred at 100° C. for 2 h. The mixture was filtered and concentrated under reduced pressure. The residue was subjected to silica gel chromatography (0-10% EtOAc/petroleum ether) to afford the title compound.

Step 2: tert-butyl (1R,5S,6s)-6-((2-cyano-6-(4-fluorophenyl)pyridin-4-yl)oxy)-3-azabicyclo[3.1.0]hexane-3-carboxylate Under an atmosphere of argon, a mixture of 4-chloro-6-(4-fluorophenyl)picolinonitrile (0.71 g, 3.1 mmol), tert-butyl (1R,5S,6s)-6-hydroxy-3-azabicyclo[3.1.0]hexane-3-carboxylate (Int. E, 0.61 g, 3.1 mmol), potassium phosphate (1.9 g, 9.2 mmol), Ad-BippyPhos (0.20 g, 0.31 mmol), Pd$(OAc)_2$ (34 mg, 0.15 mmol), CPME (0.010 L), and $PhCF_3$ (0.010 mL) was stirred at 90° C. for 16 h. The mixture cooled to rt, filtered through a thin pad of silica gel (eluting with EtOAc), and concentrated under reduced pressure. The residue was subjected to silica gel chromatography (0-17% (EtOAc/petroleum ether) to afford the title compound.

Step 3: methyl 4-(((1R,5S,6s)-3-azabicyclo[3.1.0]hexan-6-yl)oxy)-6-(4-fluorophenyl)picolinate A solution of tert-butyl (1R,5S,6s)-6-((2-cyano-6-(4-fluorophenyl)pyridin-4-yl)oxy)-3-azabicyclo[3.1.0]hexane-3-carboxylate (0.35 g, 0.89 mmol) in methanolic HCl (4.0 M, 7.0 mL) was stirred at 80° C. for 30 min. The mixture was filtered and concentrated under reduced pressure to afford the title compound.

Step 4: tert-butyl (1R,5S,6s)-6-((2-(4-fluorophenyl)-6-(methoxycarbonyl)pyridin-4-yl)oxy)-3-azabicyclo[3.1.0]hexane-3-carboxylate To a solution of methyl 4-(((1R,5S,6s)-3-azabicyclo[3.1.0]hexan-6-yl)oxy)-6-(4-fluorophenyl)picolinate (0.28 g, 0.73 mmol) and triethylamine (0.51 mL, 3.6 mmol) in DCM (4.0 mL) was added di-tert-butyl dicarbonate (0.32 g, 1.5 mmol). The mixture was stirred at rt for 15 min and concentrated under reduced pressure. The residue was subjected to silica gel chromatography (0-18% (EtOAc/petroleum ether) to afford the title compound.

Step 5: tert-butyl (1R,5S,6s)-6-((2-(4-fluorophenyl)-6-(2-hydroxypropan-2-yl)pyridin-4-yl)oxy)-3-azabicyclo[3.1.0]hexane-3-carboxylate To a 0° C. solution of tert-butyl (1R,5S,6s)-6-((2-(4-fluorophenyl)-6-(methoxycarbonyl)pyridin-4-yl)oxy)-3-azabicyclo[3.1.0]hexane-3-carboxylate (0.30 g, 0.70 mmol) in THF (5.0 mL) was added a solution of MeMgBr (3.0 M in Et¬2O, 2.3 mL, 7.0 mmol). The mixture was warmed to room temperature and stirred for 3 h. A solution of ammonium chloride (saturated aqueous, 10 mL) was added and the mixture was extracted with EtOAc (25 mL×3). The combined organic extracts were washed with brine (25 mL), dried over anhydrous sodium sulfate, filtered, and concentrated under reduced pressure. The residue was subjected to silica gel chromatography (0-10% (EtOAc/petroleum ether) to afford the title compound.

Step 6: 2-(4-(((1R,5S,6s)-3-azabicyclo[3.1.0]hexan-6-yl)oxy)-6-(4-fluorophenyl)pyridin-2-yl)propan-2-ol A mixture of tert-butyl (1R,5S,6s)-6-((2-(4-fluorophenyl)-6-(2-hydroxypropan-2-yl)pyridin-4-yl)oxy)-3-azabicyclo[3.1.0]hexane-3-carboxylate (0.22 g, 0.31 mmol), DCM (5.0 mL), and TFA (1.0 mL) was stirred at rt for 1 h. The mixture was concentrated under reduced pressure to afford the title compound.

Scheme

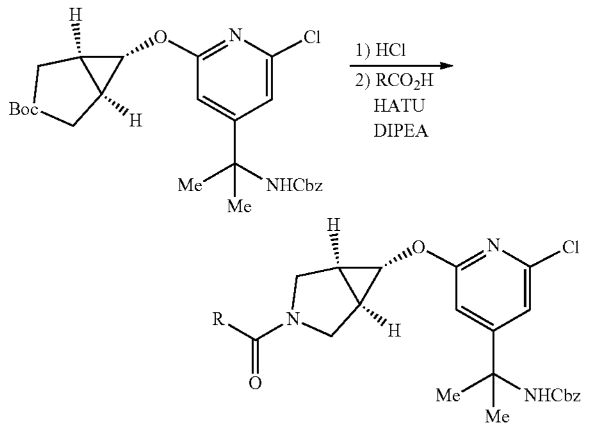

Intermediate I-1 benzyl (2-(2-chloro-6-(((1R,5S,6s)-3-(4-methyl-2-(pyrimidin-2-yl)thiazole-5-carbonyl)-3-azabicyclo[3.1.0]hexan-6-yl)oxy)pyridin-4-yl)propan-2-yl)carbamate

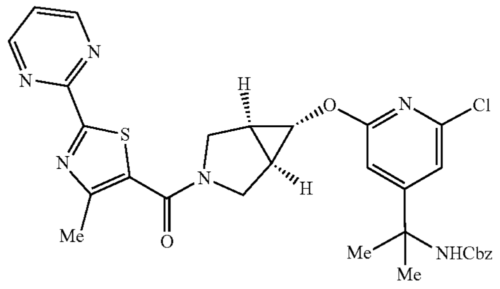 [SMILES: Cc1nc(-c2ncccn2)sc1C(=O)N1C[C@@H]2[C@H](C1)[C@H]2Oc1cc(C(C)(C)NC(=O)OCc2ccccc2)cc(Cl)n1]

Step 1: benzyl (2-(2-(((1R,5S,6s)-3-azabicyclo[3.1.0]hexan-6-yl)oxy)-6-chloropyridin-4-yl)propan-2-yl)carbamate To a solution of tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 2.0 g, 4.0 mmol) in DCM (0.020 L) was added a solution of HCl (4.0 M in 1,4-dioxane, 0.010 L, 0.040 mol). The reaction mixture was stirred at ambient temperature for 1 h. The reaction was concentrated under reduced pressure to afford the title compound as a HCl salt.

Step 2: benzyl (2-(2-chloro-6-(((1R,5S,6s)-3-(4-methyl-2-(pyrimidin-2-yl)thiazole-5-carbonyl)-3-azabicyclo[3.1.0]hexan-6-yl)oxy)pyridin-4-yl)propan-2-yl)carbamate To a stirred solution of benzyl (2-(2-(((1R,5S,6s)-3-azabicyclo[3.1.0]hexan-6-yl)oxy)-6-chloropyridin-4-yl)propan-2-yl)carbamate (1.0 g, 2.5 mmol) and 4-methyl-2-(pyrimidin-2-yl)thiazole-5-carboxylic acid (Int. L-3, 0.61 g, 2.7 mmol) in DMF (12 mL) was added HATU (1.0 g, 2.7 mmol) and DIPEA (1.3 mL, 7.5 mmol). The mixture was stirred at rt for 1 h. The mixture was poured into water (20 mL) and extracted with EtOAc (10 mL×3). The combined organic extracts were washed with sodium bicarbonate (saturated aqueous, 10 mL) and brine (10 mL), dried over anhydrous sodium sulfate, filtered, and concentrated under reduced pressure. The residue was subjected to silica gel chromatography (0-40% (3:1 EtOAc/EtOH)/hexanes) to afford the title compound.

Intermediate I-2 benzyl (2-(2-chloro-6-(((1R,5S,6s)-3-(1-methyl-3-(pyrimidin-2-yl)-1H-pyrazole-5-carbonyl)-3-azabicyclo[3.1.0]hexan-6-yl)oxy)pyridin-4-yl)propan-2-yl)carbamate

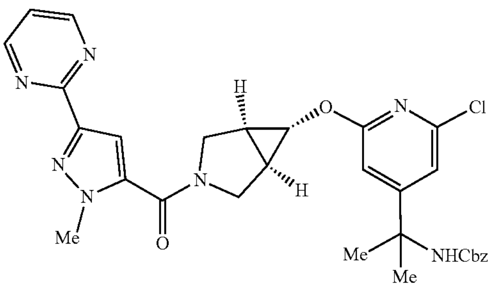 [SMILES: Cn1nc(-c2ncccn2)cc1C(=O)N1C[C@@H]2[C@H](C1)[C@H]2Oc1cc(C(C)(C)NC(=O)OCc2ccccc2)cc(Cl)n1]

Step 1: benzyl (2-(2-(((1R,5S,6s)-3-azabicyclo[3.1.0]hexan-6-yl)oxy)-6-chloropyridin-4-yl)propan-2-yl)carbamate To a solution of tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 2.0 g, 4.0 mmol) in DCM (0.030 L) was added TFA (0.010 L). The mixture was stirred at rt for 16 h. A solution of sodium hydroxide (1N aqueous, 75 mL) was added, and the pH of the aqueous phase was adjusted to >12 with sodium hydroxide (6 N aqueous). The mixture was extracted with DCM (75 mL×3) and the combined organic extracts were dried over anhydrous magnesium sulfate, filtered, and concentrated under reduced pressure to afford the title compound.

Step 2: benzyl (2-(2-chloro-6-(((1R,5S,6s)-3-(1-methyl-3-(pyrimidin-2-yl)-1H-pyrazole-5-carbonyl)-3-azabicyclo[3.1.0]hexan-6-yl)oxy)pyridin-4-yl)propan-2-yl)carbamate To a mixture of benzyl (2-(2-(((1R,5S,6s)-3-azabicyclo[3.1.0]hexan-6-yl)oxy)-6-chloropyridin-4-yl)propan-2-yl)carbamate (0.34 g, 0.85 mmol), 1-methyl-3-(pyrimidin-2-yl)-1H-pyrazole-5-carboxylic acid (Int. M, 0.19 g, 0.93 mmol), DCM (8.0 mL), and DMF (0.42 mL) was added DIPEA (0.44 mL, 2.5 mmol) and HATU (0.39 g, 1.0 mmol). The mixture was stirred for 16 h at rt, diluted with EtOAc (60 mL), and washed with water (60 mL) and brine (60 mL). The organic solution was dried over anhydrous magnesium sulfate, filtered, and concentrated under reduced pressure. The residue was subjected to silica gel chromatography (0-50% (3:1 EtOAc:EtOH)/hexanes) to afford the title compound.

Utilizing the procedures described in the synthesis of Intermediate I-2, the below compounds were prepared substituting the appropriate reagents for 1-methyl-3-(pyrimidin-2-yl)-1H-pyrazole-5-carboxylic acid.

| Int. # | Structure | Name |
|---|---|---|
| I-3 | 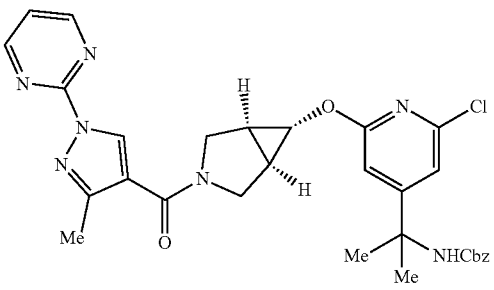 [SMILES: Cc1nn(-c2ncccn2)cc1C(=O)N1C[C@@H]2[C@H](C1)[C@H]2Oc1cc(C(C)(C)NC(=O)OCc2ccccc2)cc(Cl)n1] | benzyl (2-(2-chloro-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate |
| I-4 | 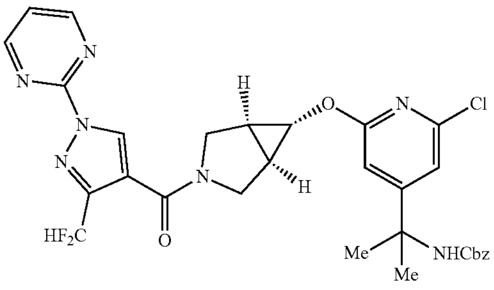 | benzyl (2-(2-chloro-6-(((1R,5S,6s)-3-(3-(difluoromethyl)-1-(pyrimidin-2-yl)-1H-pyrazole-4-carbonyl)-3-azabicyclo[3.1.0]hexan-6-yl)oxy)pyridin-4-yl)propan-2-yl)carbamate |

-continued

| Int. # | Structure | Name |
| --- | --- | --- |
| I-5 | 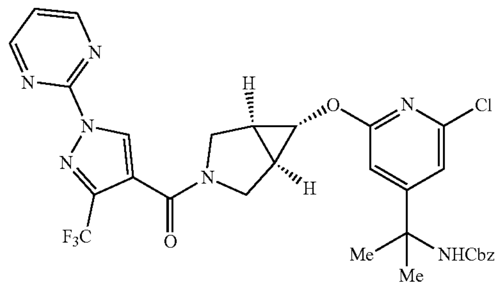 [SMILES: CC(C)(NC(=O)OCc1ccccc1)c1cc(Cl)nc(O[C@H]2[C@@H]3CN(C(=O)c4cn(-c5ncccn5)nc4C(F)(F)F)C[C@@H]32)c1] | benzyl (2-(2-chloro-6-(((1R,5S,6s)-3-(1-(pyrimidin-2-yl)-3-(trifluoromethyl)-1H-pyrazole-4-carbonyl)-3-azabicyclo[3.1.0]hexan-6-yl)oxy)pyridin-4-yl)propan-2-yl)carbamate |

Scheme

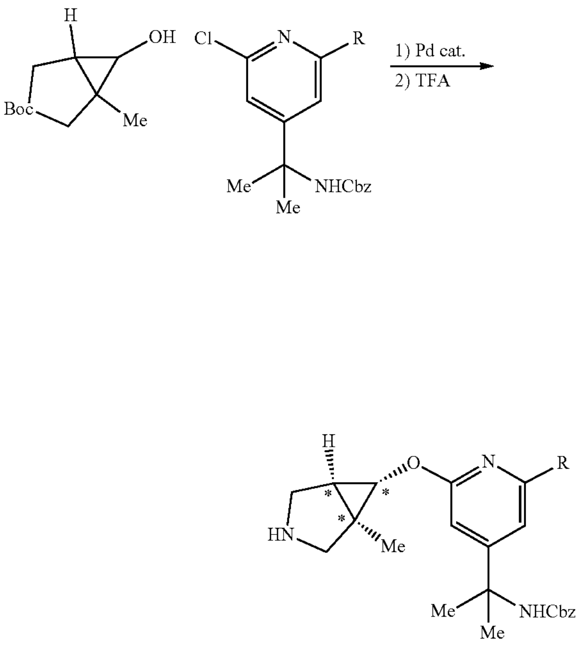

Intermediate J-1-rac benzyl rac-(2-(2-(4-fluorophenyl)-6-(((1R,5S,6s)-1-methyl-3-azabicyclo[3.1.0]hexan-6-yl)oxy)pyridin-4-yl)propan-2-yl)carbamate

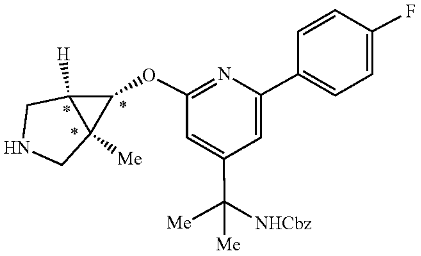 [SMILES: CC(C)(NC(=O)OCc1ccccc1)c1cc(O[C@H]2[C@@H]3CNC[C@@]32C)nc(-c2ccc(F)cc2)c1]

Step 1: tert-butyl rac-(1R,5S,6s)-6-((4-(2-(((benzyloxy)carbonyl)amino)propan-2-yl)-6-(4-fluorophenyl)pyridin-2-yl)oxy)-1-methyl-3-azabicyclo[3.1.0] hexane-3-carboxylate Under an atmosphere of nitrogen, a mixture of tert-butyl 6-hydroxy-1-methyl-3-azabicyclo[3.1.0]hexane-3-carboxylate (Int. F, 1.3 g, 4.3 mmol), benzyl (2-(2-chloro-6-(4-fluorophenyl)pyridin-4-yl)propan-2-yl)carbamate (Int. C-1, 1.7 g, 1.3 mmol), $Pd(OAc)_2$ (48 mg, 0.21 mmol), Ad-BippyPhos (0.28 g, 0.43 mmol), potassium phosphate (2.7 g, 13 mmol), $PhCF_3$ (0.010 L), and CPME (0.010 L) were stirred at 95° C. for 12 h. The mixture was filtered and concentrated under reduced pressure. The residue was subjected to silica gel chromatography (0-15% EtOAc/petroleum ether) to afford the title compound.

Step 2: benzyl rac-(2-(2-(4-fluorophenyl)-6-(((1R, 5S,6s)-1-methyl-3-azabicyclo[3.1.0]hexan-6-yl)oxy) pyridin-4-yl)propan-2-yl)carbamate To a mixture of tert-butyl rac-(1R,5S,6s)-6-((4-(2-(((benzyloxy)carbonyl)amino)propan-2-yl)-6-(4-fluorophenyl) pyridin-2-yl)oxy)-1-methyl-3-azabicyclo[3.1.0]hexane-3-carboxylate (0.15 mg, 0.26 mmol) in DCM (4.0 mL) was added TFA (1.0 mL). The resulting mixture was stirred at rt for 1 h. The mixture was concentrated under reduced pressure to afford the title compound.

Utilizing the procedures described in the synthesis of Intermediate J-1, the below compound was prepared substituting the appropriate reagents for benzyl (2-(2-chloro-6-(4-fluorophenyl)pyridin-4-yl)propan-2-yl)carbamate.

| Int. | Structure | Name | Comments |
|---|---|---|---|
| J-2-rac | 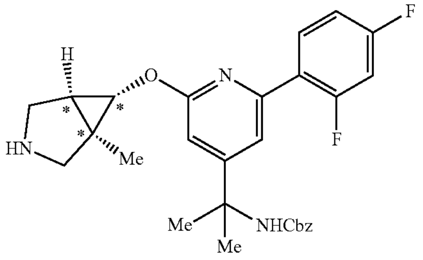 [SMILES: CC(C)(NC(=O)OCc1ccccc1)c1cc(O[C@H]2[C@@H]3CNC[C@@]32C)nc(-c2ccc(F)cc2F)c1] | benzyl rac-(2-(2-(2,4-difluorophenyl)-6-(((1R,5S,6s)-1-methyl-3-azabicyclo[3.1.0]hexan-6-yl)oxy)pyridin-4-yl)propan-2-yl)carbamate | Step 1: Int. C-5 (2.2 mmol), Int. F (2.2 mmol), Ad-BippyPhos (0.22 mmol), $Pd_2(dba)_3$ (0.11 mmol), cesium carbonate (6.5 mmol), PhMe (0.010 L), 90° C., 12 h |
| J-3-rac | 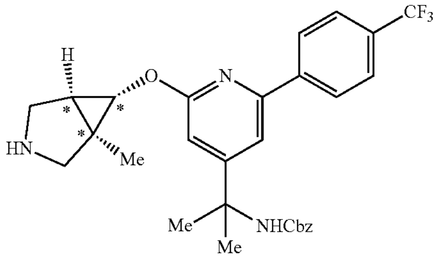 [SMILES: CC(C)(NC(=O)OCc1ccccc1)c1cc(O[C@H]2[C@@H]3CNC[C@@]32C)nc(-c2ccc(C(F)(F)F)cc2)c1] | benzyl rac-(2-(2-(((1R,5S,6s)-1-methyl-3-azabicyclo[3.1.0]hexan-6-yl)oxy)-6-(4-(trifluoromethyl)phenyl)pyridin-4-yl)propan-2-yl)carbamate | Step 1: Int. C-03 (1.6 mmol), Int. F (1.6 mmol), Ad-BippyPhos (0.17 mmol), $Pd_2(dba)_3$ (0.082 mmol), cesium carbonate (5.0 mmol), PhMe (5.0 mL), 90° C., 12 h |

Intermediates J-1-ent-1 and J-1-ent-2 benzyl rel-(2-(2-(4-fluorophenyl)-6-(((1R,5S,6s)-1-methyl-3-azabicyclo[3.1.0]hexan-6-yl)oxy)pyridin-4-yl)propan-2-yl)carbamate (Enantiomers 1 and 2)

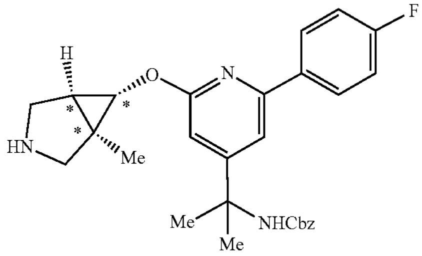 [SMILES: CC(C)(NC(=O)OCc1ccccc1)c1cc(O[C@H]2[C@@H]3CNC[C@@]32C)nc(-c2ccc(F)cc2)c1]

Step 1: tert-butyl rel-(1R,5S,6s)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (Enantiomers 1 and 2)

tert-butyl rac-(1R,5S,6s)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (prepared according to Int. J-1-rac Step 1, 0.65 g, 1.1 mmol) was subjected to chiral SFC (ChiralPak OJ-H, 5-40% EtOH (with 0.05% DEA modifier)/$CO_2$) to afford tert-butyl rel-(1R,5S,6s)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (enantiomer 1, faster eluting) and tert-butyl rel-(1R,5S,6s)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (enantiomer 2, slower eluting).

Step 2-1: benzyl rel-(2-(2-(4-fluorophenyl)-6-(((1R,5S,6s)-1-methyl-3-azabicyclo[3.1.0]hexan-6-yl)oxy)pyridin-4-yl)propan-2-yl)carbamate (Enantiomer 1, Int. J-1-ent-1)

To a mixture of tert-butyl rel-(1R,5S,6s)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (enantiomer 1, 0.31 mg, 0.53 mmol) in DCM (5.0 mL) was added TFA (1.0 mL). The resulting mixture was stirred at rt for 1 h. The mixture was concentrated under reduced pressure to afford the title compound.

Step 2-2: benzyl rel-(2-(2-(4-fluorophenyl)-6-(((1R,5S,6s)-1-methyl-3-azabicyclo[3.1.0]hexan-6-yl)oxy)pyridin-4-yl)propan-2-yl)carbamate (Enantiomer 2, Int. J-1-ent-2)

To a mixture of tert-butyl rel-(1R,5S,6s)-6-((4-(2-(((benzyloxy)carbonyl)amino)propan-2-yl)-6-(4-fluorophenyl)pyridin-2-yl)oxy)-1-methyl-3-azabicyclo[3.1.0]hexane-3-carboxylate (enantiomer 2, 0.30 mg, 0.52 mmol) in DCM (5.0 mL) was added TFA (1.0 mL). The resulting mixture was stirred at rt for 1 h. The mixture was concentrated under reduced pressure to afford the title compound.

Intermediates J-4-ent-1 and J-4-ent-2 benzyl rel-(2-(2-(3,4-difluorophenyl)-6-(((1R,5S,6s)-1-methyl-3-azabicyclo[3.1.0]hexan-6-yl)oxy)pyridin-4-yl)propan-2-yl)carbamate (Enantiomers 1 and 2)

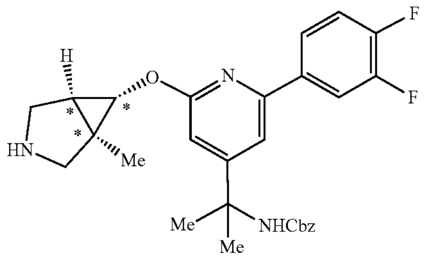 [SMILES: CC(C)(NC(=O)OCc1ccccc1)c1cc(O[C@H]2[C@@H]3CNC[C@@]32C)nc(-c2ccc(F)c(F)c2)c1]

Step 1: tert-butyl rel-(1R,5S,6s)-6-((4-(2-(((benzyloxy)carbonyl)amino)propan-2-yl)-6-(3,4-difluorophenyl)pyridin-2-yl)oxy)-1-methyl-3-azabicyclo[3.1.0]hexane-3-carboxylate (Enantiomers 1 and 2)

Under an atmosphere of nitrogen, a mixture of tert-butyl 6-hydroxy-1-methyl-3-azabicyclo[3.1.0]hexane-3-carboxylate (Int. F, 0.36 g, 1.2 mmol), benzyl (2-(2-chloro-6-(3,4-difluorophenyl)pyridin-4-yl)propan-2-yl)carbamate (Int. C-4, 0.49 g, 1.2 mmol), $Pd(OAc)_2$ (13 mg, 0.059 mmol), Ad-BippyPhos (78 mg, 0.12 mmol), cesium carbonate (1.1 g, 3.5 mmol), and toluene (12 mL) were stirred at 90° C. for 16 h. The mixture was filtered and concentrated under reduced pressure. The residue was subjected to silica gel chromatography (0-15% EtOAc/petroleum ether). The mixture of two stereoisomers was subjected to chiral SFC (ChiralPak AD, 15% MeOH (with 0.1% $NH_4OH$ modifier)/$CO_2$) to afford tert-butyl rel-(1R,5S,6s)-6-((4-(2-(((benzyloxy)carbonyl)amino)propan-2-yl)-6-(3,4-difluorophenyl)pyridin-2-yl)oxy)-1-methyl-3-azabicyclo[3.1.0]hexane-3-carboxylate (enantiomer 1, faster eluting) and tert-butyl rel-(1R,5S,6s)-6-((4-(2-(((benzyloxy)carbonyl)amino)propan-2-yl)-6-(3,4-difluorophenyl)pyridin-2-yl)oxy)-1-methyl-3-azabicyclo[3.1.0]hexane-3-carboxylate (enantiomer 2, slower eluting).

Step 2-1: benzyl rel-(2-(2-(3,4-difluorophenyl)-6-(((1R,5S,6s)-1-methyl-3-azabicyclo[3.1.0]hexan-6-yl)oxy)pyridin-4-yl)propan-2-yl)carbamate (Enantiomer 1, Int. J-4-ent-1)

To a mixture of tert-butyl rel-(1R,5S,6s)-6-((4-(2-(((benzyloxy)carbonyl)amino)propan-2-yl)-6-(3,4-difluorophenyl)pyridin-2-yl)oxy)-1-methyl-3-azabicyclo[3.1.0]hexane-3-carboxylate (enantiomer 1, 0.12 mg, 0.20 mmol) in DCM (4.0 mL) was added TFA (1.0 mL). The resulting mixture was stirred at rt for 1 h. The mixture was concentrated under reduced pressure to afford the title compound.

Step 2-2: benzyl rel-(2-(2-(3,4-difluorophenyl)-6-(((1R,5S,6s)-1-methyl-3-azabicyclo[3.1.0]hexan-6-yl)oxy)pyridin-4-yl)propan-2-yl)carbamate (Enantiomer 2, Int. J-4-ent-2)

To a mixture of tert-butyl rel-(1R,5S,6s)-6-((4-(2-(((benzyloxy)carbonyl)amino)propan-2-yl)-6-(3,4-difluorophenyl)pyridin-2-yl)oxy)-1-methyl-3-azabicyclo[3.1.0]hexane-3-carboxylate (enantiomer 2, 0.12 mg, 0.20 mmol) in DCM (4.0 mL) was added TFA (1.0 mL). The resulting mixture was stirred at rt for 1 h. The mixture was concentrated under reduced pressure to afford the title compound.

Intermediate K-1 benzyl (2-(2-(((1R,5S,6s)-3-(3-bromo-1-methyl-1H-pyrazole-5-carbonyl)-3-azabicyclo[3.1.0]hexan-6-yl)oxy)-6-(4-fluorophenyl)pyridin-4-yl)propan-2-yl)carbamate

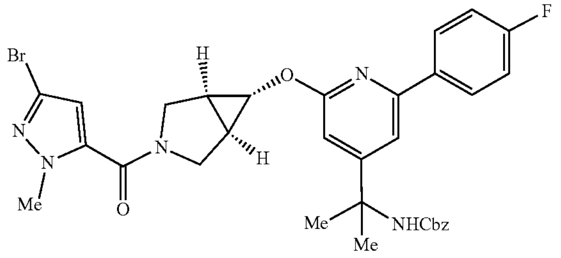 [SMILES: Cn1nc(Br)cc1C(=O)N1C[C@@H]2[C@H](C1)[C@H]2Oc1cc(C(C)(C)NC(=O)OCc2ccccc2)cc(-c2ccc(F)cc2)n1]

To a mixture of 3-bromo-1-methyl-1H-pyrazole-5-carboxylic acid (0.020 g, 0.98 mmol), HATU (0.45 g, 1.2 mmol), and DCM (2.5 mL) was added benzyl (2-(2-(((1R,5S,6s)-3-azabicyclo[3.1.0]hexan-6-yl)oxy)-6-(4-fluorophenyl)pyridin-4-yl)propan-2-yl)carbamate·HCl (Int. H-02, 0.49 g, 0.98 mmol) and triethylamine (0.41 mL, 2.9 mmol). The mixture was stirred for 16 h and subjected to silica gel chromatography (0-50% EtOAc/hexanes) to afford the title compound.

Utilizing the procedure described in the synthesis of Intermediate K-1, the below compound was prepared substituting 2-chloro-4-(difluoromethyl)thiazole-5-carboxylic acid for 3-bromo-1-methyl-1H-pyrazole-5-carboxylic acid.

| Int. # | Structure | Name |
|---|---|---|
| K-2 | 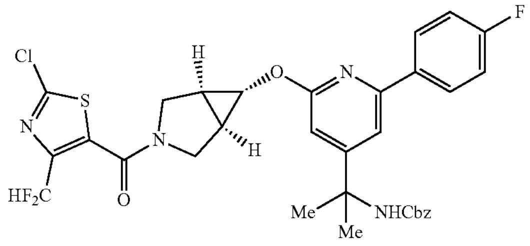 | benzyl (2-(2-(((1R,5S,6s)-3-(2-chloro-4-(difluoromethyl)thiazole-5-carbonyl)-3-azabicyclo[3.1.0]hexan-6-yl)oxy)-6-(4-fluorophenyl)pyridin-4-yl)propan-2-yl)carbamate |

Scheme

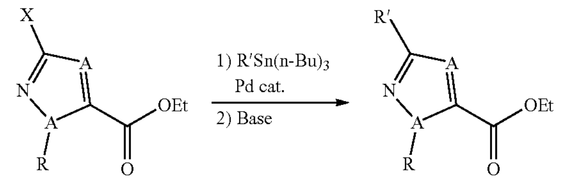

Intermediate L-1

4-Methyl-2-(pyrimidin-2-yl)oxazole-5-carboxylic acid

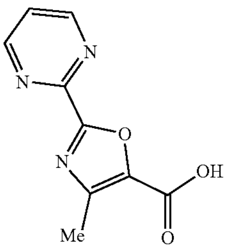 [SMILES: Cc1nc(-c2ncccn2)oc1C(=O)O]

Step 1: ethyl 4-methyl-2-(pyrimidin-2-yl)oxazole-5-carboxylate

Ethyl 2-chloro-4-methyloxazole-5-carboxylate (0.10 g, 0.53 mmol), 2-(tributylstannyl)pyrimidine (0.39 g, 1.1 mmol), $Pd(PPh_3)_4$ (61 mg, 0.050 mmol), and copper(I) iodide (26 mg, 0.14 mmol) were combined in a screw cap vial. 1,4-dioxane (3.0 mL) was added and $N_2$ was bubbled through the mixture for 1 min. The vial was capped then heated to 100° C. overnight. The resulting mixture was cooled to rt, diluted with EtOAc, filtered through a pad of Celite® (eluted with EtOAc), and concentrated. The residue was subjected to silica gel chromatography (0-100% EtOAc/heptane) to afford the title compound.

Step 2: 4-methyl-2-(pyrimidin-2-yl)oxazole-5-carboxylic acid

To a suspension of ethyl 4-methyl-2-(pyrimidin-2-yl) oxazole-5-carboxylate (87 mg, 0.37 mmol) in EtOH (2.0 mL) was added sodium hydroxide (2.0 M aqueous, 0.56 mL, 1.1 mmol). After 2 h, HCl (1 N, 1.2 mL) was added then the mixture was concentrated. The residue was taken up in water and extracted with EtOAc (3×). The combined organic extracts were filtered through a pad of celite (eluted with EtOAc) and concentrated to afford the title compound.

Intermediate L-2

4-methyl-2-(pyrimidin-2-yl)-1H-imidazole-5-carboxylic acid

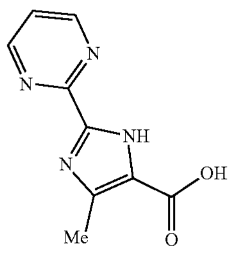 [SMILES: Cc1nc(-c2ncccn2)[nH]c1C(=O)O]

Step 1: ethyl 4-methyl-2-(pyrimidin-2-yl)-1H-imidazole-5-carboxylate

Ethyl 2-bromo-4-methyl-1H-imidazole-5-carboxylate (0.10 g, 0.43 mmol), copper(I) iodide (0.020 g, 0.11 mmol) and $Pd(PPh_3)_4$ (0.050 mg, 0.040 mmol) were combined in a microwave vial. The vial was purged with $N_2$ then sealed. To this was added 1,4-dioxane (2.0 mL) and 2-(tributylstannyl) pyrimidine (0.32 g, 0.89 mmol). The mixture was heated to 80° C. in a conventional heating block. After heating overnight, the reaction was deemed incomplete by LC/MS analysis. The temperature was raised to 100° C. After 48 h the mixture was cooled to room temperature then filtered through a pad of celite (eluted with EtOAc). The filtrate was concentrated, and the residue was subjected to silica gel chromatography (0-100% EtOAc/hexanes) to afford the title compound.

Step 2: 4-methyl-2-(pyrimidin-2-yl)-1H-imidazole-5-carboxylic acid

To a mixture of ethyl 4-methyl-2-(pyrimidin-2-yl)-1H-imidazole-5-carboxylate (29 mg, 0.13 mmol), THF (0.50 mL), and EtOH (0.50 mL) was added sodium hydroxide (1.0 M aqueous, 0.19 mL, 0.19 mmol). After stirring at rt for 48 h, the reaction was deemed incomplete by LC/MS analysis. The temperature was increased to 60° C. for 2 h then 100° C. for 2 h. The mixture was cooled to rt, made acidic with HCl (1 N), and concentrated to dryness to afford the title compound.

Intermediate L-3

4-methyl-2-(pyrimidin-2-yl)thiazole-5-carboxylic acid

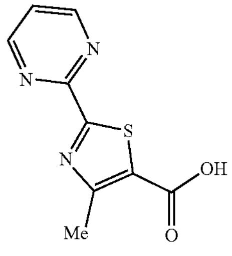 [SMILES: Cc1nc(-c2ncccn2)sc1C(=O)O]

Step 1: ethyl 4-methyl-2-(pyrimidin-2-yl)thiazole-5-carboxylate

A mixture of ethyl 2-bromo-4-methylthiazole-5-carboxylate (1.8 g, 7.2 mmol), 2-(tributylstannyl)pyrimidine (3.5 g, 9.5 mmol), $Pd(Ph_3P)_4$ (0.83 g, 0.72 mmol), and copper(I) iodide (0.34 g, 1.8 mmol) in 1,4-dioxane (36 mL) was placed under an atmosphere of $N_2$ and heated to 100° C. for 16 h. The mixture was cooled to room temperature and concentrated under reduced pressure. The residue was diluted with DCM, filtered through celite and concentrated under reduced pressure. The residue was subjected to silica gel chromatography (0-50% 3:1 EtOAc:EtOH/heptane) to afford the title compound.

Step 2: 4-methyl-2-(pyrimidin-2-yl)thiazole-5-carboxylic acid

To a solution of ethyl 4-methyl-2-(pyrimidin-2-yl)thiazole-5-carboxylate (1.6 g, 6.6 mmol) in THF (25 mL) was added a solution of lithium hydroxide (0.47 g, 20 mmol) in water (0.010 L). The mixture was stirred at 25° C. for 3 h and then diluted with water and EtOAc and filtered. The layers were separated and the aqueous layer was e with EtOAc (2×). The aqueous layer was acidified and the resulting precipitate was filtered and dried under vacuum to afford the title compound.

Scheme

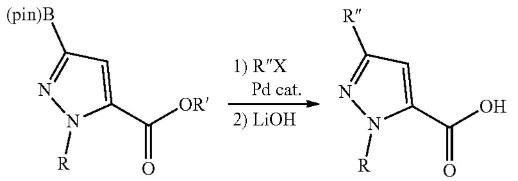

Intermediate M 1-methyl-3-(pyrimidin-2-yl)-1H-pyrazole-5-carboxylic acid

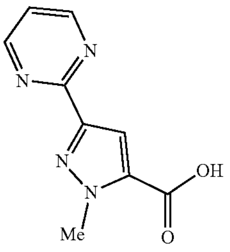 [SMILES: Cn1nc(-c2ncccn2)cc1C(=O)O]

Step 1: methyl 1-methyl-3-(pyrimidin-2-yl)-1H-pyrazole-5-carboxylate

To a mixture of methyl 1-methyl-3-(4,4,5,5-tetramethyl-1,3,2-dioxaborolan-2-yl)-1H-pyrazole-5-carboxylate (2.0 g, 7.5 mmol), 2-chloropyrimidine (1.3 g, 11 mmol), and sodium carbonate (2.4 g, 23 mmol) in DME (0.020 L) and water (2.0 mL) was added $Pd(dtbpf)Cl_2$ (0.25 g, 0.38 mmol). The mixture was heated at 90° C. for 12 h under $N_2$. The mixture was cooled to room temperature, diluted with water, then extracted with EtOAc (3×). The combined organic extracts were washed with brine, dried over anhydrous sodium sulfate, filtered, and concentrated. The residue was subjected to silica gel chromatography (90-95% EtOAc/petroleum ether) to afford the title compound.

Step 2: 1-methyl-3-(pyrimidin-2-yl)-1H-pyrazole-5-carboxylic acid

To a mixture of methyl 1-methyl-3-(pyrimidin-2-yl)-1H-pyrazole-5-carboxylate (1.1 g, 4.8 mmol) in THF (0.010 L) and water (0.010 L) was added lithium hydroxide (0.58 g, 24 mmol). The mixture was stirred at rt for 30 min. The mixture was concentrated under reduced pressure and washed with DCM (2×). The aqueous solution was acidified (pH=4) with HCl (1 N) and concentrated under reduced pressure. MeOH (10 mL) and DCM (10 mL) were added, and the mixture was stirred at rt for 1 h. The mixture was filtered and concentrated under reduced pressure to afford the title compound.

Scheme

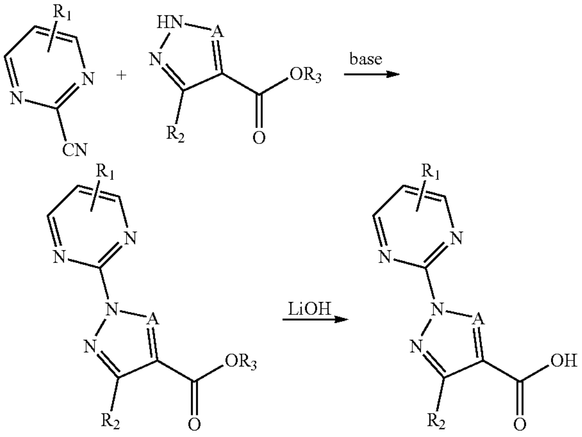

Intermediate N-1

3-ethyl-1-(pyrimidin-2-yl)-1H-pyrazole-4-carboxylic acid

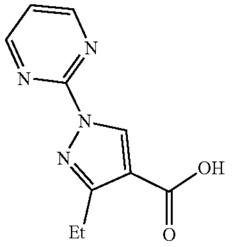 [SMILES: CCc1nn(-c2ncccn2)cc1C(=O)O]

Step 1: ethyl 3-ethyl-1-(pyrimidin-2-yl)-1H-pyrazole-4-carboxylate

2-Chloropyrimidine (0.34 g, 3.0 mmol), ethyl 3-ethyl-1H-pyrazole-4-carboxylate (0.51 g, 3.0 mmol), potassium carbonate (0.83 g, 6.0 mmol), and NMP (6.0 mL) were added to a 20 mL microwave vial. The mixture was heated to 150° C. for 8 h in a microwave reactor. The mixture was diluted with EtOAc (50 mL), washed with water (50 mL) and brine (50 mL), dried over anhydrous magnesium sulfate, filtered, and concentrated under reduced pressure. The residue was subjected to silica gel chromatography (0-20% (3:1 EtOAc:EtOH)/hexanes) to afford the title compound.

Step 2: 3-ethyl-1-(pyrimidin-2-yl)-1H-pyrazole-4-carboxylic acid

To a mixture of ethyl 3-ethyl-1-(pyrimidin-2-yl)-1H-pyrazole-4-carboxylate (0.53 g, 2.2 mmol) in 1,4-dioxane (11 mL) and water (11 mL) was added lithium hydroxide (0.10 g, 4.3 mmol). The mixture was stirred at rt for 16 h. The mixture was poured into a solution of sodium hydroxide (0.1 N aqueous, 25 mL) and washed with DCM (25 mL×2). The aqueous mixture was acidified (pH=1-2) with HCl (1 N). After 10 min, the mixture was filtered, and the filter cake was washed with water (5 mL×3). The filter cake was dried under reduced pressure to afford the title compound.

Utilizing the procedures described in the synthesis of Intermediate N-1, the below compounds were prepared substituting the appropriate reagents for ethyl 3-ethyl-1H-pyrazole-4-carboxylate and 2-chloropyrimidine.

| Int. | Structure | Name | Comments |
|---|---|---|---|
| N-2 | 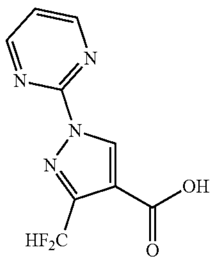 | 3-(difluoromethyl)-1-(pyrimidin-2-yl)-1H-pyrazole-4-carboxylic acid | Step 1: 1 h reaction time |
| N-3 | 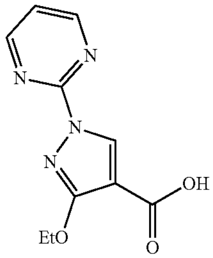 [SMILES: CCOc1nn(-c2ncccn2)cc1C(=O)O] | 3-ethoxy-1-(pyrimidin-2-yl)-1H-pyrazole-4-carboxylic acid | Step 1: ethyl 3-ethoxy-1H-pyrazole-4-carboxylate (0.88 mmol), 2-chloropyrimidine (1.1 mmol), cesium carbonate (1.3 mmol), MeCN (1.8 mL), 130° C., 1 h |
| N-4 | 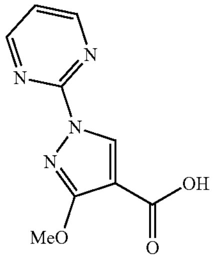 [SMILES: COc1nn(-c2ncccn2)cc1C(=O)O] | 3-methoxy-1-(pyrimidin-2-yl)-1H-pyrazole-4-carboxylic acid | Step 1: ethyl 3-methoxy-1H-pyrazole-4-carboxylate (8.8 mmol), 2-chloropyrimidine (11 mmol), cesium carbonate (13 mmol), MeCN (18 mL), 130° C., 1 h |

Intermediate N-5

3,5-dimethyl-1-(pyrimidin-2-yl)-1H-pyrazole-4-carboxylic acid

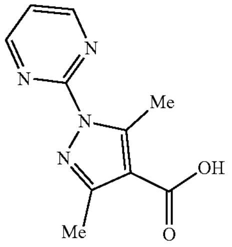 [SMILES: Cc1nn(-c2ncccn2)c(C)c1C(=O)O]

Step 1: ethyl 3,5-dimethyl-1-(pyrimidin-2-yl)-1H-pyrazole-4-carboxylate

2-Chloropyrimidine (0.23 g, 2.0 mmol), ethyl 3,5-dimethyl-1H-pyrazole-4-carboxylate (0.34 g, 2.0 mmol), potassium carbonate (0.55 g, 4.0 mmol), and NMP (4.0 mL) were added to a 2-5 mL microwave vial. The mixture was heated to 150° C. for 2 h in a microwave reactor. The mixture was diluted with EtOAc (40 mL), washed with water (40 mL) and brine (40 mL), dried over anhydrous magnesium sulfate, filtered, and concentrated under reduced pressure. The residue was subjected to silica gel chromatography (0-40% (3:1 EtOAc:EtOH)/hexanes) to afford the title compound.

Step 2: 3,5-dimethyl-1-(pyrimidin-2-yl)-1H-pyrazole-4-carboxylic acid

To a solution of ethyl 3,5-dimethyl-1-(pyrimidin-2-yl)-1H-pyrazole-4-carboxylate (0.11 g, 0.45 mmol) in THF (4.5 mL) was added potassium trimethylsilanolate (87 mg, 0.68 mmol). The mixture was stirred at rt for 16 h and concentrated under reduced pressure. The material was dissolved in a solution of sodium hydroxide (0.1 N aqueous, 20 mL) and washed with DCM (20 mL×2). The aqueous mixture was acidified (pH=1) with HCl (1 N) and extracted with DCM (20 mL×2). The combined organic extracts were dried over anhydrous magnesium sulfate, filtered, and concentrated under reduced pressure to afford the title compound.

Intermediate N-6

3-(difluoromethoxy)-1-(pyrimidin-2-yl)-1H-pyrazole-4-carboxylic acid

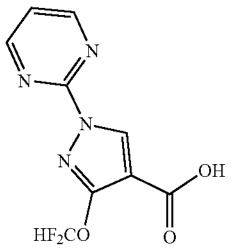

Step 1: ethyl 3-(difluoromethoxy)-1-(pyrimidin-2-yl)-1H-pyrazole-4-carboxylate

A mixture of sodium 2-chloro-2,2-difluoroacetate (1.8 g, 12 mmol), 1-(tert-butyl) 4-ethyl 3-hydroxy-1H-pyrazole-1,4-dicarboxylate (1.0 g, 3.9 mmol), potassium carbonate (0.81 g, 5.9 mmol) and DMF (7.8 mL) was stirred at 80° C. for 14 h. The mixture was cooled to rt, diluted with EtOAc (60 mL), and washed with water (60 mL) and brine (60 mL). The organic solution was dried over anhydrous magnesium sulfate, filtered, and concentrated under reduced pressure. The material was transferred to a 20 mL microwave vial and 2-chloropyrimidine (0.54 g, 4.7 mmol), cesium carbonate (1.9 g, 5.9 mmol), and MeCN (7.8 mL) were added. The mixture was heated to 130° C. for 1 h in a microwave reactor. The mixture was cooled to room temperature, diluted with EtOAc (75 mL), and washed with water (75 mL) and brine (75 mL). The organic solution was dried over anhydrous magnesium sulfate, filtered, and concentrated under reduced pressure. The residue was subjected to silica gel chromatography (0-10% (3:1 EtOAc:EtOH)/hexanes) and resubjected to silica gel chromatography (0-5% EtOAc/DCM) to afford the title compound.

Step 2: 3-(difluoromethoxy)-1-(pyrimidin-2-yl)-1H-pyrazole-4-carboxylic acid

To a solution of ethyl 3-(difluoromethoxy)-1-(pyrimidin-2-yl)-1H-pyrazole-4-carboxylate (0.28 g, 0.97 mmol) in EtOH (2.4 mL) and THF (2.4 mL) was added a solution of sodium hydroxide (1.0 N aqueous, 1.5 mL, 1.5 mmol). The mixture was stirred at rt for 14 h and concentrated under reduced pressure. The mixture was diluted with water (10 mL) and acidified (pH=2) with HCl (1 N). The mixture was filtered, and the filter cake was washed with water (1 mL×3). The filter cake was dried under reduced pressure to afford the title compound.

Intermediate N-7 sodium 3-methyl-1-(4-methylpyrimidin-2-yl)-1H-pyrazole-4-carboxylate

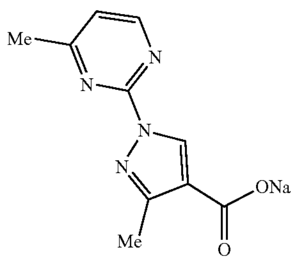

Step 1: Ethyl 3-methyl-1-(4-methylpyrimidin-2-yl)-1H-pyrazole-4-carboxylate

2-Chloro-4-methylpyrimidine (0.26 g, 2.0 mmol), ethyl 3-methyl-1H-pyrazole-4-carboxylate (0.31 g, 2.0 mmol), potassium carbonate (0.55 g, 4.0 mmol), and NMP (4.0 mL) were added to a 2-5 mL microwave vial. The mixture was heated to 150° C. for 1 h in a microwave reactor. The mixture was diluted with EtOAc (50 mL), washed with brine (50 mL), dried over anhydrous magnesium sulfate, filtered, and concentrated under reduced pressure. The residue was subjected to silica gel chromatography (0-25% (3:1 EtOAc:EtOH)/hexanes) to afford the title compound.

Step 2: sodium 3-methyl-1-(4-methylpyrimidin-2-yl)-1H-pyrazole-4-carboxylate

Ethyl 3-methyl-1-(4-methylpyrimidin-2-yl)-1H-pyrazole-4-carboxylate (0.35 g, 1.4 mmol), MeOH (14 mL), and sodium hydroxide (1.0 N aqueous, 1.4 mL, 1.4 mmol) were stirred at 30° C. for 16 h. The mixture was concentrated under reduced pressure and azeotropically dried with toluene (1 mL×3) to afford the title compound.

Scheme

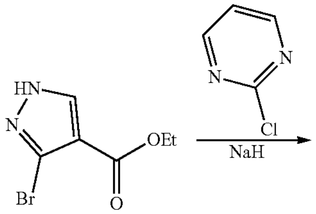

-continued

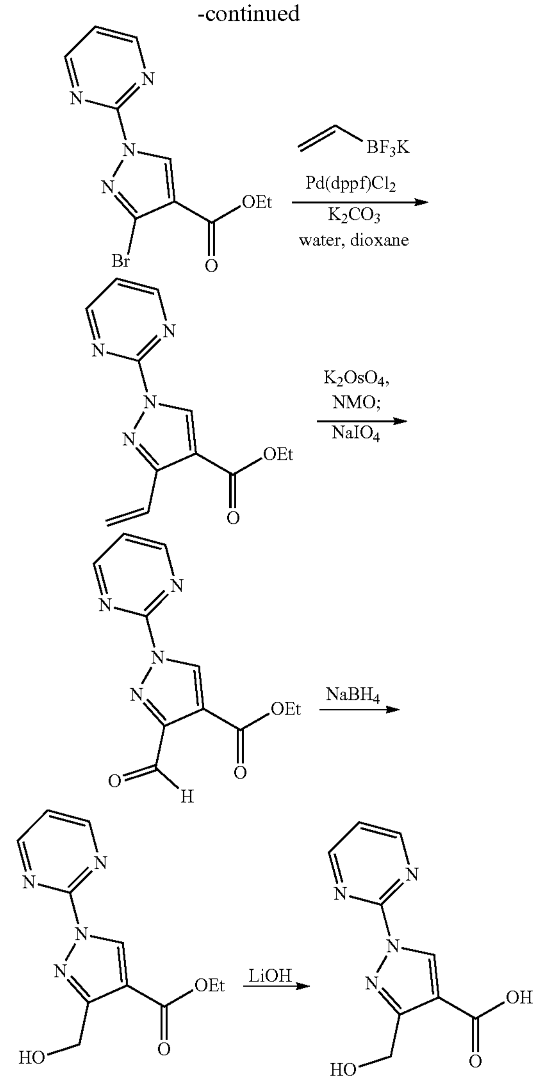

Intermediate N-8

3-(hydroxymethyl)-1-(pyrimidin-2-yl)-1H-pyrazole-4-carboxylic acid

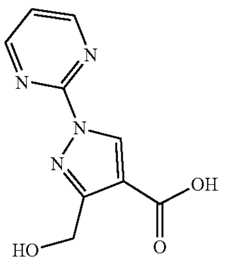 [SMILES: O=C(O)c1cn(-c2ncccn2)nc1CO]

Step 1: ethyl 3-bromo-1-(pyrimidin-2-yl)-1H-pyrazole-4-carboxylate

Under an atmosphere of nitrogen, to a −78° C. suspension of sodium hydride (1.2 g, 29 mmol) in THF (0.040 L) was added ethyl 3-bromo-1H-pyrazole-4-carboxylate (4.0 g, 18 mmol). The mixture was stirred for 30 min and a solution of 2-chloropyrimidine (4.2 g, 37 mmol) in THF (25 mL) was added. The mixture was warmed to 60° C. and stirred for 12 h. The mixture was cooled to rt, a solution of ammonium chloride (saturated aqueous, 30 mL) was added, and the mixture was extracted with EtOAc (50 mL×3). The combined organic extracts were washed with brine (50 mL), dried over anhydrous sodium sulfate, filtered, and concentrated under reduced pressure. The residue was subjected to silica gel chromatography (0-50% EtOAc/petroleum ether) to afford the title compound.

Step 2: ethyl 1-(pyrimidin-2-yl)-3-vinyl-1H-pyrazole-4-carboxylate

Under an atmosphere of nitrogen, a mixture of ethyl 3-bromo-1-(pyrimidin-2-yl)-1H-pyrazole-4-carboxylate (2.0 g, 6.7 mmol), potassium vinyltrifluoroborate (1.1 g, 8.1 mmol), Pd(dppf)$Cl_2$ (0.99 g, 1.3 mmol), potassium carbonate (1.4 g, 0.010 mol), 1,4-dioxane (0.030 L), and water (3.0 mL) was stirred at 100° C. for 12 h. The mixture was cooled to room temperature, water (10 mL) was added, and the mixture was extracted with EtOAc (15 mL×3). The combined organic extracts were washed with brine (15 mL×2), dried over anhydrous sodium sulfate, filtered, and concentrated under reduced pressure. The residue was subjected to silica gel chromatography (0-50% EtOAc/petroleum ether) to afford the title compound.

Step 3: ethyl 3-formyl-1-(pyrimidin-2-yl)-1H-pyrazole-4-carboxylate

To a mixture of ethyl 1-(pyrimidin-2-yl)-3-vinyl-1H-pyrazole-4-carboxylate (0.20 g, 0.82 mmol), 4-methylmorpholine N-oxide (0.19 g, 1.6 mmol), THF (5.0 mL), and water (0.50 mL) was added potassium osmate(VI) dihydrate (0.060 g, 0.16 mmol) and the mixture was stirred for 1 h. Sodium periodate (0.53 g, 2.5 mmol) was added, and the mixture was stirred for 12 h. A solution of sodium sulfite (saturated aqueous, 5 mL) was added and the mixture was extracted with EtOAc (20 mL×3). The combined organic extracts were dried over anhydrous sodium sulfate, filtered, and concentrated under reduced pressure. The residue was subjected to prep-TLC (EtOAc, Rf=0.55) to afford the title compound.

Step 4: ethyl 3-(hydroxymethyl)-1-(pyrimidin-2-yl)-1H-pyrazole-4-carboxylate

To a 0° C. mixture of ethyl 3-formyl-1-(pyrimidin-2-yl)-1H-pyrazole-4-carboxylate (0.050 g, 0.20 mmol) and MeOH (0.010 L) was added sodium borohydride (7.7 mg, 0.20 mmol). The mixture was stirred at 0° C. for 10 min, water (10 mL) was added, and the mixture was extracted with EtOAc (20 mL×3). The combined organic extracts were washed with brine (20 mL), dried over anhydrous sodium sulfate, filtered, and concentrated under reduced pressure to afford the title compound.

Step 5: 3-(hydroxymethyl)-1-(pyrimidin-2-yl)-1H-pyrazole-4-carboxylic acid

To a mixture of ethyl 3-(hydroxymethyl)-1-(pyrimidin-2-yl)-1H-pyrazole-4-carboxylate (0.040 g, 0.16 mmol), THF (1.0 mL), and water (1.0 mL) was added lithium hydroxide (19 mg, 0.81 mmol). The mixture was stirred at rt for 1 h, concentrated under reduced pressure, and washed with DCM (10 mL×2). The aqueous mixture was acidified (pH=4) with HCl (1N) and concentrated under reduced pressure. MeOH (5 mL) and DCM (5 mL) were added, and the mixture was stirred at rt for 1 h. The mixture was filtered and concentrated under reduced pressure to afford the title compound.

Scheme

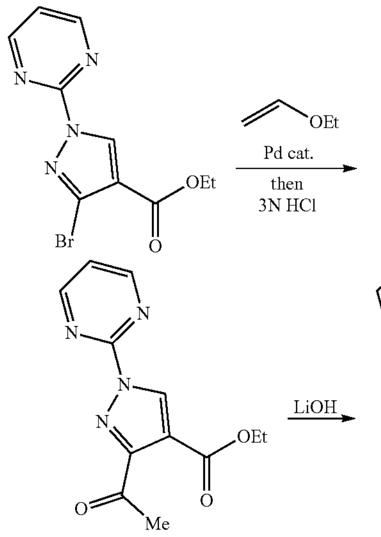

Intermediate N-9

3-acetyl-1-(pyrimidin-2-yl)-1H-pyrazole-4-carboxylic acid

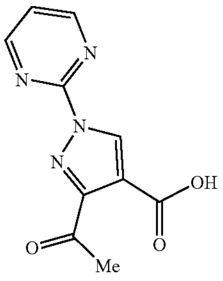 [SMILES: CC(=O)c1nn(-c2ncccn2)cc1C(=O)O]

Step 1: ethyl 3-acetyl-1-(pyrimidin-2-yl)-1H-pyrazole-4-carboxylate

To a solution of ethyl 3-bromo-1-(pyrimidin-2-yl)-1H-pyrazole-4-carboxylate (prepared as in Int. N-7 Step 1, 0.50 g, 1.7 mmol) in 1,4-dioxane (0.010 L) was added tributyl (1-ethoxyvinyl)tin (1.8 mL, 5.4 mmol) and Pd(PPh3)4 (0.19 g, 0.17 mmol). The mixture was heated under an atmosphere of nitrogen at 110° C. for 12 h. HCl (1 M, 5.0 mL) and potassium fluoride (saturated aqueous, 0.020 L) were added, and the mixture was stirred for 2 h. The mixture was cooled to room temperature and extracted with EtOAc (10 mL×3). The combined organic extracts were washed with brine (10 mL), dried over anhydrous sodium sulfate, filtered, and concentrated under reduced pressure. The residue was subjected to silica gel chromatography (0-45% EtOAc/petroleum ether) to afford the title compound.

Step 2: 3-acetyl-1-(pyrimidin-2-yl)-1H-pyrazole-4-carboxylic acid

To a mixture of ethyl 3-acetyl-1-(pyrimidin-2-yl)-1H-pyrazole-4-carboxylate (0.10 g, 0.38 mmol) in THF (2.0 mL) and water (0.50 mL) was added lithium hydroxide (18 mg, 0.77 mmol. The mixture was stirred at rt for 1 h. Water was added (10 mL) and the mixture was acidified (pH=3) with HCl (1 N) and extracted with EtOAc (10 mL×4). The combined organic extracts were dried over anhydrous sodium sulfate, filtered, and concentrated under reduced pressure to afford the title compound.

Intermediate O 5-methyl-2-(pyrimidin-2-yl)-2H-1,2,3-triazole-4-carboxylic acid

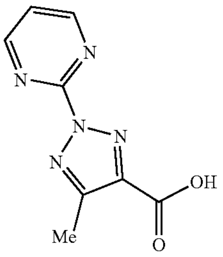 [SMILES: Cc1nn(-c2ncccn2)nc1C(=O)O]

Step 1: ethyl 5-methyl-2-(pyrimidin-2-yl)-2H-1,2,3-triazole-4-carboxylate

A mixture of ethyl 5-methyl-2H-1,2,3-triazole-4-carboxylate (0.10 g, 0.65 mmol), potassium carbonate (0.22 g, 1.6 mmol), 2-chloropyrimidine (74 mg, 0.65 mmol), and DMF (3.0 mL) was stirred at 100° C. for 1 h. The mixture was cooled to room temperature, water (10 mL) was added, and the mixture was extracted with EtOAc (10 mL×3). The combined organic extracts were dried over anhydrous sodium sulfate, filtered, and concentrated under reduced pressure. The residue was subjected to prep-TLC (EtOAc, Rf=0.35) to afford the title compound.

Step 2: 5-methyl-2-(pyrimidin-2-yl)-2H-1,2,3-triazole-4-carboxylic acid

To a mixture of ethyl 5-methyl-2-(pyrimidin-2-yl)-2H-1,2,3-triazole-4-carboxylate (0.20 g, 0.86 mmol) in THF (5.0 mL) and water (5.0 mL) was added lithium hydroxide (62 mg, 2.6 mmol). The mixture was stirred at rt for 2 h, concentrated under reduced pressure, and washed with DCM (10 mL×2). The aqueous mixture was acidified (pH=4) with HCl (1 N aqueous) and concentrated under reduced pressure. The material was stirred in MeOH/DCM (20 mL of a 1:10 mixture) at rt for 1 h. The mixture was filtered and concentrated under reduced pressure to afford the title compound.

Scheme

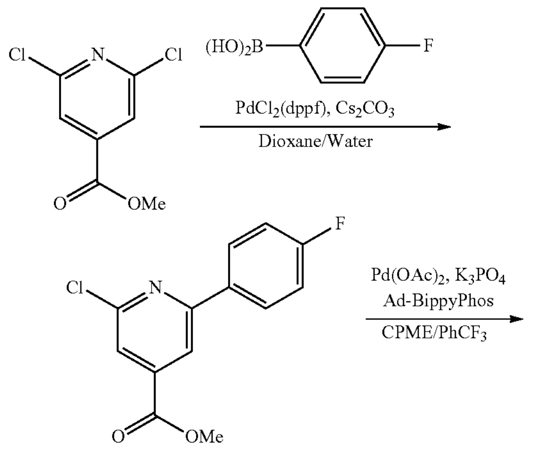

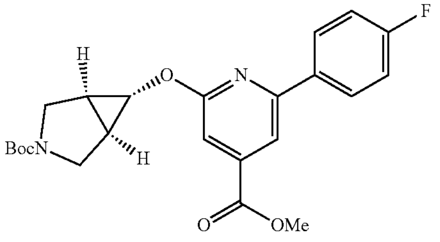

Intermediate P tert-butyl (1R,5S,6s)-6-((6-(4-fluorophenyl)-4-(methoxycarbonyl)pyridin-2-yl)oxy)-3-azabicyclo[3.1.0]hexane-3-carboxylate

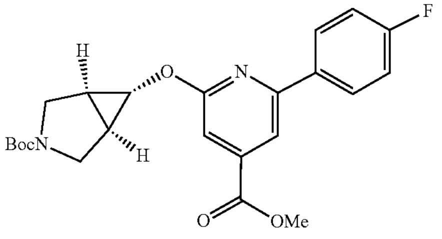 [SMILES: COC(=O)c1cc(O[C@H]2[C@@H]3CN(C(=O)OC(C)(C)C)C[C@@H]32)nc(-c2ccc(F)cc2)c1]

Step 1: methyl 2-chloro-6-(4-fluorophenyl)isonicotinate

To a mixture of methyl 2,6-dichloroisonicotinate (0.010 kg, 49 mmol), (4-fluorophenyl)boronic acid (6.6 g, 47 mmol) and cesium carbonate (24 g, 73 mmol) in 1,4-dioxane (0.50 L) and water (26 mL) was added $PdCl_2(dppf)$ (2.7 g, 3.6 mmol). The mixture was stirred at 25° C. for 12 h. The mixture was filtered and extracted with EtOAc (100 mL×3). The combined organic extracts were washed with brine (50 mL×2), dried over anhydrous sodium sulfate, filtered, and concentrated under reduced pressure. The residue was subjected to silica gel chromatography (0-10% EtOAc/petroleum ether) to afford the title compound.

Step 2: tert-butyl (1R,5S,6s)-6-((6-(4-fluorophenyl)-4-(methoxycarbonyl)pyridin-2-yl)oxy)-3-azabicyclo[3.1.0]hexane-3-carboxylate In glove box, to a solution of methyl 2-chloro-6-(4-fluorophenyl)isonicotinate (1.7 g, 6.4 mmol), tert-butyl (1R,5S,6s)-6-hydroxy-3-azabicyclo[3.1.0]hexane-3-carboxylate (Int. E, 1.3 g, 6.4 mmol), potassium phosphate (4.1 g, 19 mmol), 5-(di((3S,5S,7S)-adamantan-1-yl)phosphaneyl)-1',3',5'-triphenyl-1'H-1,4'-bipyrazole (0.42 g, 0.64 mmol) in CPME (0.020 L) and $CF_3Ph$ (0.020 L) was added $Pd(OAc)_2$ (0.072 g, 0.32 mmol). The mixture was heated to 90° C. for 12 h. The mixture was cooled, filtered through a thin pad of silica gel (eluting with EtOAc) and the filtrated was concentrated under reduced pressure. The residue was subjected to silica gel chromatography (0-50% EtOAc/petroleum ether) to afford the title compound.

Scheme

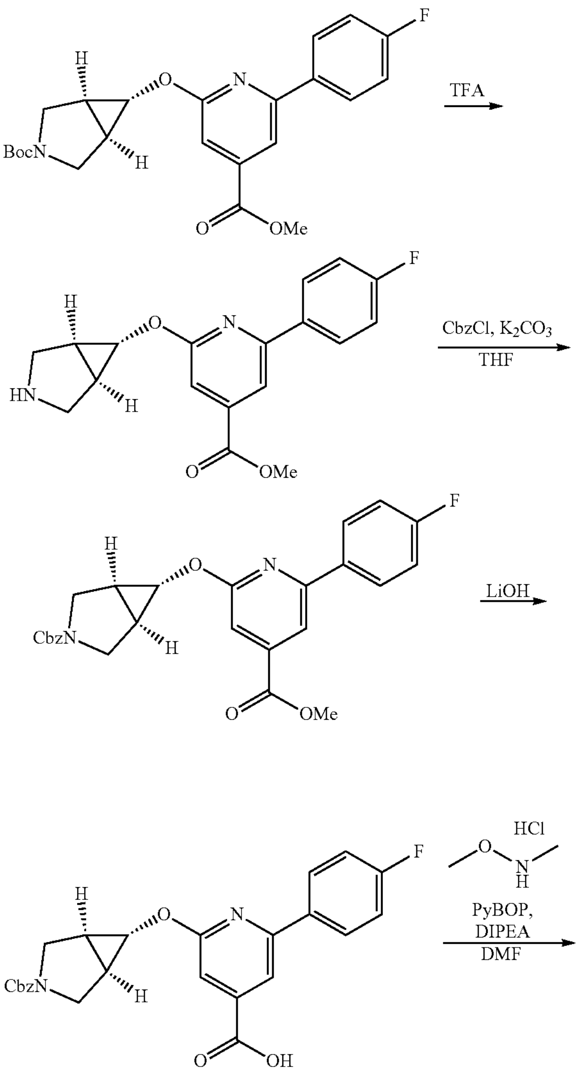

-continued

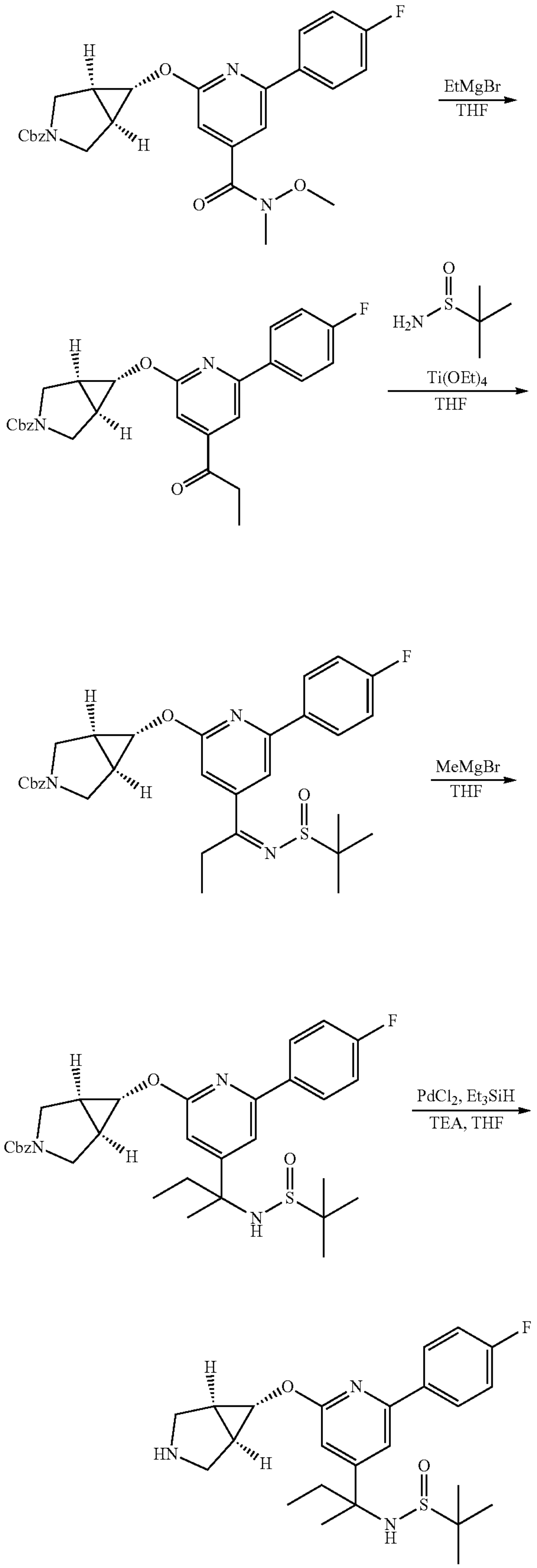

Intermediate Q

N-(2-(2-(((1R,5S,6s)-3-azabicyclo[3.1.0]hexan-6-yl)oxy)-6-(4-fluorophenyl)pyridin-4-yl)butan-2-yl-2-methylpropane-2-sulfinamide

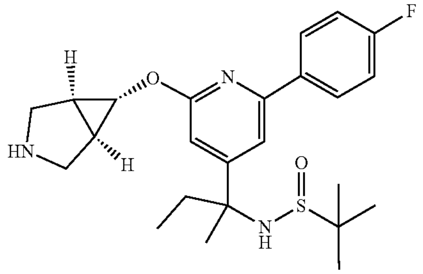 [SMILES: CCC(C)(NS(=O)C(C)(C)C)c1cc(O[C@H]2[C@@H]3CNC[C@@H]32)nc(-c2ccc(F)cc2)c1]

Step 1: methyl 2-(((1R,5S,6s)-3-azabicyclo[3.1.0]hexan-6-yl)oxy)-6-(4-fluorophenyl)isonicotinate To a solution of tert-butyl (1R,5S,6s)-6-((6-(4-fluorophenyl)-4-(methoxycarbonyl)pyridin-2-yl)oxy)-3-azabicyclo[3.1.0]hexane-3-carboxylate (Int. P, 1.2 g, 2.8 mmol) in DCM (9.0 mL) was added TFA (3.0 mL, 39 mmol). The mixture was stirred for 25° C. for 1 h and then concentrated under reduced pressure to afford the title compound.

Step 2: benzyl (1R,5S,6s)-6-((6-(4-fluorophenyl)-4-(methoxycarbonyl)pyridin-2-yl)oxy)-3-azabicyclo[3.1.0]hexane-3-carboxylate To a 0° C. solution of methyl 2-(((1R,5S,6s)-3-azabicyclo[3.1.0]hexan-6-yl)oxy)-6-(4-fluorophenyl)isonicotinate (0.90 g, 2.7 mmol) in THF (0.010 L) was added potassium carbonate (1.9 g, 14 mmol) and benzyl chloroformate (0.58 mL, 4.1 mmol). The mixture was stirred at 25° C. for 2 h and then diluted with water (10 mL) and extracted with EtOAc (20 mL×3). The combined organic extracts were washed with brine (15 mL×2), dried over anhydrous sodium sulfate, filtered, and concentrated under reduced pressure. The residue was subjected to silica gel chromatography (0-20% EtOAc/petroleum ether) to afford the title compound.

Step 3: 2-(((1R,5S,6s)-3-((benzyloxy)carbonyl)-3-azabicyclo[3.1.0]hexan-6-yl)oxy)-6-(4-fluorophenyl)isonicotinic acid To a mixture of benzyl (1R,5S,6s)-6-((6-(4-fluorophenyl)-4-(methoxycarbonyl)pyridin-2-yl)oxy)-3-azabicyclo[3.1.0]hexane-3-carboxylate (0.60 g, 1.3 mmol) in THF (5.0 mL) and water (5.0 mL) was added lithium hydroxide (93 mg, 3.9 mmol). The mixture was stirred at 25° C. for 1 h and then washed with DCM (15 mL×2). The aqueous phase was adjust to pH=4 with 1 M aqueous HCl. The aqueous mixture was extracted with EtOAc (15 mL×2) and the combined organic extracts were dried over anhydrous sodium sulfate, filtered and concentrated under reduced pressure to afford the title compound.

Step 4: benzyl (1R,5S,6s)-6-((6-(4-fluorophenyl)-4-(methoxy(methyl)carbamoyl)pyridin-2-yl)oxy)-3-azabicyclo[3.1.0]hexane-3-carboxylate To a solution of 2-(((1R,5S,6s)-3-((benzyloxy)carbonyl)-3-azabicyclo[3.1.0]hexan-6-yl)oxy)-6-(4-fluorophenyl)

isonicotinic acid (0.55 g, 1.2 mmol) in DMF (5.0 mL) was added DIPEA (0.64 mL, 3.7 mmol), N,O-Dimethylhydroxylamine hydrochloride (0.12 mg, 1.2 mmol) and PyBOP (0.77 mg, 1.5 mmol). The mixture was stirred at 25° C. for 1 h. The mixture was diluted with water (10 mL) and extracted with EtOAc (20 mL×3). The combined organic extracts were washed with brine (10 mL×2), dried over anhydrous sodium sulfate, filtered, and concentrated under reduced pressure. The residue was subjected to silica gel chromatography (0-50% EtOAc/petroleum ether) to afford the title compound.

Step 5: benzyl (1R,5S,6s)-6-((6-(4-fluorophenyl)-4-propionylpyridin-2-yl)oxy)-3-azabicyclo[3.1.0]hexane-3-carboxylate To a 0° C. solution of benzyl (1R,5S,6s)-6-((6-(4-fluorophenyl)-4-(methoxy(methyl)carbamoyl)pyridin-2-yl)oxy)-3-azabicyclo[3.1.0]hexane-3-carboxylate (0.35 g, 0.71 mmol) in THF (5.0 mL) was added ethylmagnesium bromide (3.0 M in 2-MeTHF, 0.71 mL, 2.1 mmol). The mixture was stirred at 0° C. for 1 h after which ammonium chloride (10 mL) was added and the mixture was extracted with EtOAc (20 mL×3). The combined organic extracts were washed was brine (20 mL×2), dried over anhydrous sodium sulfate, filtered, and concentrated under reduced pressure. The residue was subjected to silica gel chromatography (0-33% EtOAc/petroleum ether) to afford the title compound.

Step 6: benzyl (1R,5S,6s)-6-((4-((Z)-1-((tert-butylsulfinyl)imino)propyl)-6-(4-fluorophenyl)pyridin-2-yl)oxy)-3-azabicyclo[3.1.0]hexane-3-carboxylate A solution of benzyl (1R,5S,6s)-6-((6-(4-fluorophenyl)-4-propionylpyridin-2-yl)oxy)-3-azabicyclo[3.1.0]hexane-3-carboxylate (0.030 g, 0.065 mmol) and titanium (IV) ethoxide (45 mg, 0.20 mmol) in THF (1.0 mL) was stirred for 5 min. 2-Methylpropane-2-sulfinamide (12 mg, 0.098 mmol) was added and the mixture was heated at 70° C. for 3 h. The mixture was cooled to room temperature and a solution of saturated aqueous sodium bicarbonate was added until a white precipitate formed. The suspension was filtered through a pad of Celite and washed with EtOAc. The mixture was extracted with EtOAc (10 mL×3). The combined organic extracts were washed with brine (10 mL×2), dried over anhydrous sodium sulfate, filtered, and concentrated under reduced pressure. The mixture was subjected to prep-TLC (50% EtOAc/petroleum ether) to afford the title compound.

Step 7: benzyl (1R,5S,6s)-6-((4-(2-((tert-butylsulfinyl)amino)butan-2-yl)-6-(4-fluorophenyl)pyridin-2-yl)oxy)-3-azabicyclo[3.1.0]hexane-3-carboxylate To a solution of benzyl (1R,5S,6s)-6-((4-((Z)-1-((tert-butylsulfinyl)imino)propyl)-6-(4-fluorophenyl)pyridin-2-yl)oxy)-3-azabicyclo[3.1.0]hexane-3-carboxylate (0.16 g, 0.28 mmol) in THF (5.0 mL) was added a solution of methylmagnesium bromide (3.0 M in diethyl ether, 0.28 mL, 0.85 mmol). The mixture was stirred at 25° C. for 1 h. A solution of saturated aqueous ammonium chloride (6 mL) was added and the mixture was extracted with EtOAc (15 mL×3). The combined organic extracts were washed with brine (10 mL), dried over anhydrous sodium sulfate, filtered, and concentrated. The mixture was subjected to prep-TLC (50% EtOAc/petroleum ether) to afford the title compound.

Step 8: N-(2-(2-(((1R,5S,6s)-3-azabicyclo[3.1.0]hexan-6-yl)oxy)-6-(4-fluorophenyl)pyridin-4-yl)butan-2-yl)-2-methylpropane-2-sulfinamide To a solution of benzyl (1R,5S,6s)-6-((4-(2-((tert-butylsulfinyl)amino)butan-2-yl)-6-(4-fluorophenyl)pyridin-2-yl)oxy)-3-azabicyclo[3.1.0]hexane-3-carboxylate (0.070 g, 0.12 mmol) in THF (2.0 mL) was added triethylamine (0.084 mL, 0.60 mmol), triethylsilane (0.096 mL, 0.60 mmol) and palladium(II) chloride (4.3 mg, 0.024 mmol). The mixture was stirred at 25° C. for 1 h. The mixture was filtered and concentrated under reduced pressure to afford the title compound.

Scheme

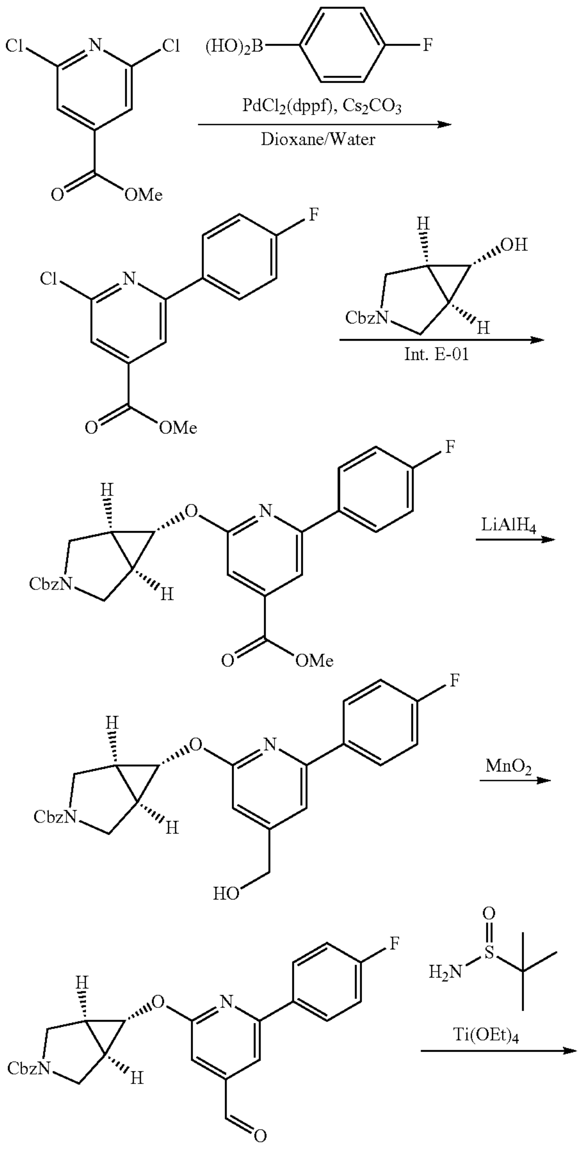

-continued

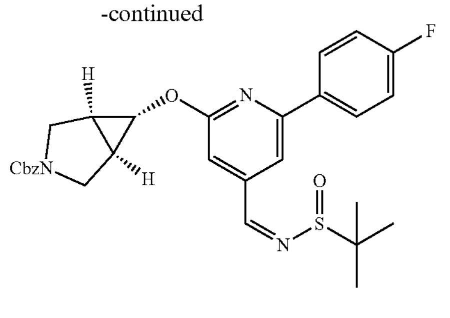

Intermediate R-1

N—((Z)-(2-(((1R,5S,6s)-3-azabicyclo[3.1.0]hexan-6-yl)oxy)-6-(4-fluorophenyl)pyridin-4-yl)methylene)-2-methylpropane-2-sulfinamide

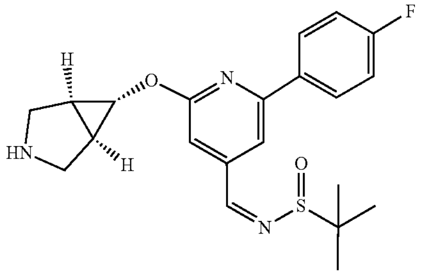 [SMILES: CC(C)(C)S(=O)/N=C\c1cc(O[C@H]2[C@@H]3CNC[C@@H]32)nc(-c2ccc(F)cc2)c1]

Step 1: methyl 2-chloro-6-(4-fluorophenyl)isonicotinate

To a mixture of methyl 2,6-dichloroisonicotinate (0.010 kg, 49 mmol), (4-fluorophenyl)boronic acid (6.6 g, 47 mmol) and cesium carbonate (24 g, 73 mmol) in 1,4-dioxane (0.50 L) and water (26 mL) was added $PdCl_2$(dppf) (2.7 g, 3.6 mmol). The mixture was stirred at 25° C. After 12 h, the mixture was filtered and extracted with EtOAc (100 mL×3). The combined organic extracts were washed with brine (50 mL×2), dried over anhydrous sodium sulfate, filtered, and concentrated under reduced pressure. The residue was subjected to silica gel chromatography (0-10% EtOAc/petroleum ether) to afford the title compound.

Step 2: benzyl (1R,5S,6s)-6-((6-(4-fluorophenyl)-4-(methoxycarbonyl)pyridin-2-yl)oxy)-3-azabicyclo[3.1.0]hexane-3-carboxylate In glove box, to a solution of benzyl (1R,5S,6s)-6-hydroxy-3-azabicyclo[3.1.0]hexane-3-carboxylate (Int. E-01, 1.8 g, 7.5 mmol), methyl 2-chloro-6-(4-fluorophenyl)isonicotinate (2.0 g, 7.5 mmol), potassium phosphate (4.8 g, 23 mmol), 5-(di((3S,5S,7S)-adamantan-1-yl)phosphaneyl)-1',3',5'-triphenyl-1'H-1,4'-bipyrazole (0.50 g, 0.75 mmol) in CPME (0.020 L) and $CF_3Ph$ (0.020 L) was added $Pd(OAc)_2$ (0.085 g, 0.38 mmol). The mixture was stirred at 90° C. After 16 h, the mixture was cooled to room temperature, filtered through a pad of silica gel (eluting with EtOAc), and concentrated under reduced pressure. The residue was subjected to silica gel chromatography (0-25% EtOAc/petroleum ether) to afford the title compound.

Step 3: benzyl (1R,5S,6s)-6-((6-(4-fluorophenyl)-4-(hydroxymethyl)pyridin-2-yl)oxy)-3-azabicyclo[3.1.0]hexane-3-carboxylate To a mixture of benzyl (1R,5S,6s)-6-((6-(4-fluorophenyl)-4-(methoxycarbonyl)pyridin-2-yl)oxy)-3-azabicyclo[3.1.0]hexane-3-carboxylate (1.5 g, 3.2 mmol) in THF (15 mL) was added LiAlH4 (1.0 M in THF, 8.1 mL, 8.1 mmol) at −78° C. The resulting mixture was stirred at −78° C. for 30 min and then treated with water (0.20 mL), 15% sodium hydroxide (0.60 mL) and additional water (0.20 mL). The mixture was warned 0° C. and after 10 min, magnesium sulfate was added. The mixture was filtered and concentrated under reduced pressure to afford the title compound.

Step 4: benzyl (1R,5S,6s)-6-((6-(4-fluorophenyl)-4-formylpyridin-2-yl)oxy)-3-azabicyclo[3.1.0]hexane-3-carboxylate To a solution of benzyl (1R,5S,6s)-6-((6-(4-fluorophenyl)-4-(hydroxymethyl)pyridin-2-yl)oxy)-3-azabicyclo[3.1.0]hexane-3-carboxylate (0.90 g, 2.1 mmol) in DCM (0.020 L) was added manganese(IV) oxide (1.8 g, 21 mmol). The resulting mixture was stirred at 40° C. After 18 h, the reaction mixture was filtered and concentrated under reduced pressure to afford the title compound.

Step 5: benzyl (1R,5S,6s)-6-((4-((Z)-((tert-butylsulfinyl)imino)methyl)-6-(4-fluorophenyl)pyridin-2-yl)oxy)-3-azabicyclo[3.1.0]hexane-3-carboxylate To a mixture of benzyl (1R,5S,6s)-6-((6-(4-fluorophenyl)-4-formylpyridin-2-yl)oxy)-3-azabicyclo[3.1.0]hexane-3-carboxylate (0.85 g, 2.0 mmol) and 2-methylpropane-2-sulfinamide (0.29 g, 2.4 mmol) in THF (0.020 L) was added tetraethoxytitanium (0.89 g, 3.9 mmol). The resulting mixture was stirred at 25° C. for 18 h. The mixture was treated with brine (25 mL), filtered, and extracted with EtOAc (50 mL×3). The combined organic extracts were dried over anhydrous sodium sulfate, filtered, and concentrated under reduced pressure. The residue was subjected to silica gel chromatography (0-30% EtOAc/petroleum ether) to afford the title compound.

Scheme

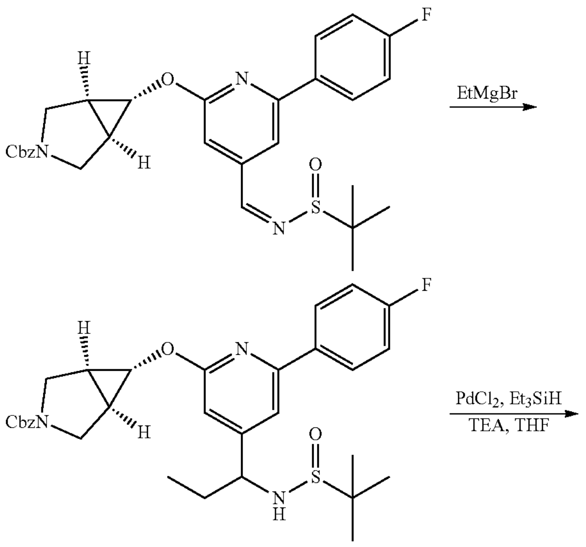

-continued

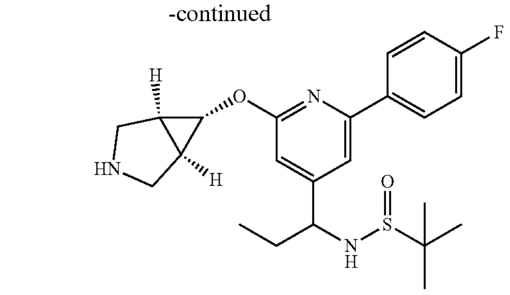

Intermediate R-2

N-(1-(2-(((1R,5S,6s)-3-azabicyclo[3.1.0]hexan-6-yl)oxy)-6-(4-fluorophenyl)pyridin-4-yl)propyl)-2-methylpropane-2-sulfinamide

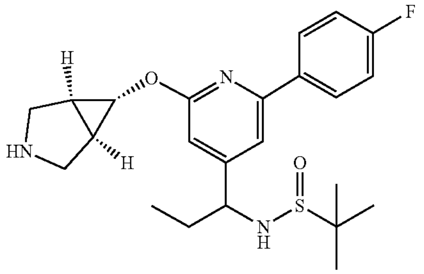 [SMILES: CCC(NS(=O)C(C)(C)C)c1cc(O[C@H]2[C@@H]3CNC[C@@H]32)nc(-c2ccc(F)cc2)c1]

Step 1: benzyl (1R,5S,6s)-6-((4-(1-((tert-butylsulfinyl)amino)propyl)-6-(4-fluorophenyl)pyridin-2-yl)oxy)-3-azabicyclo[3.1.0]hexane-3-carboxylate To a 0° C. solution of benzyl (1R,5S,6s)-6-((4-((Z)-((tert-butylsulfinyl)imino)methyl)-6-(4-fluorophenyl)pyridin-2-yl)oxy)-3-azabicyclo[3.1.0]hexane-3-carboxylate (Int. R-1, 250 mg, 0.47 mmol) in THF (5.0 mL) was added ethylmagnesium bromide (3.0 M in $Et_2O$, 0.23 mL, 0.70 mmol). After stirring for 1 h at 0° C., the mixture was treated with ammonium chloride (15 mL, saturated aqueous) and extracted with EtOAc (25 mL×3). The combined organic extracts were washed with brine (20 mL), dried over anhydrous sodium sulfate, filtered, and concentrated under reduced pressure to afford the title compound.

Step 2: N-(1-(2-(((1R,5S,6s)-3-azabicyclo[3.1.0]hexan-6-yl)oxy)-6-(4-fluorophenyl)pyridin-4-yl)propyl)-2-methylpropane-2-sulfinamide To a solution of benzyl (1R,5S,6s)-6-((4-(1-((tert-butylsulfinyl)amino)propyl)-6-(4-fluorophenyl)pyridin-2-yl)oxy)-3-azabicyclo[3.1.0]hexane-3-carboxylate (0.24 g, 0.42 mmol) in THF (5.0 mL) was added triethylamine (0.30 mL, 2.1 mmol), triethylsilane (0.25 mL, 2.1 mmol) and palladium(II) chloride (15 mg, 0.085 mmol). The mixture was stirred at 25° C. After 1 h, the mixture was filtered and concentrated under reduced pressure to afford the title compound.

Utilizing the procedure described in the synthesis of Intermediate R-2, the below compound was prepared substituting isopropylmagnesium bromide for ethylmagnesium bromide Scheme

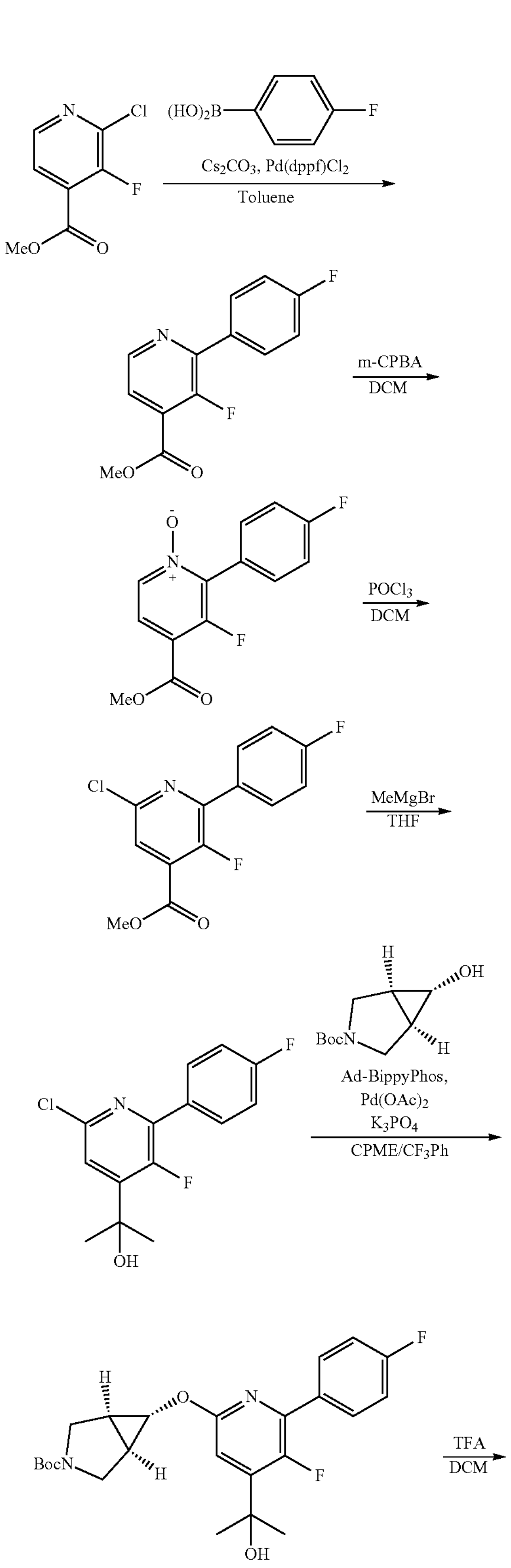

-continued

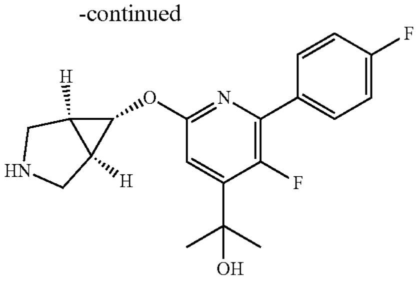

Intermediate S 2-(6-(((1R,5S,6s)-3-azabicyclo[3.1.0]hexan-6-yl)oxy)-3-fluoro-2-(4-fluorophenyl)pyridin-4-yl)propan-2-ol

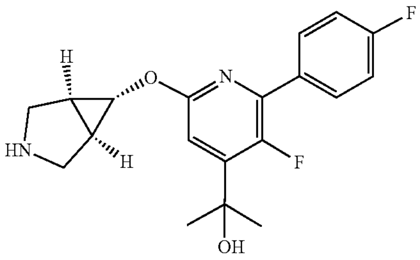 [SMILES: CC(C)(O)c1cc(O[C@H]2[C@@H]3CNC[C@@H]32)nc(-c2ccc(F)cc2)c1F]

Step 1: methyl 3-fluoro-2-(4-fluorophenyl)isonicotinate

To a mixture of methyl 2-chloro-3-fluoroisonicotinate (4.5 g, 24 mmol), (4-fluorophenyl)boronic acid (3.2 g, 23 mmol) and cesium carbonate (12 g, 36 mmol) in PhMe (25 mL) was added Pd(dppf)$Cl_2$ (1.3 g, 1.8 mmol). The mixture was heated to 90° C. for 2 h. The mixture was cooled to room temperature, filtered, and concentrated under reduced pressure. The residue was subjected to silica gel chromatography (0-10% EtOAc/petroleum ether) to afford the title compound.

Step 2: 3-fluoro-2-(4-fluorophenyl)-4-(methoxycarbonyl)pyridine 1-oxide

To a 0° C. solution of methyl 3-fluoro-2-(4-fluorophenyl)isonicotinate (1.0 g, 4.0 mmol) in DCM (0.030 L) was added m-CPBA (1.4 g, 8.0 mmol). The mixture was warmed to 25° C. and stirred for 12 h. The mixture was diluted with sodium sulfite (saturated aqueous, 5 mL) and sodium bicarbonate (saturated aqueous, 15 mL) and extracted with DCM (30 mL×3). The combined organic extracts were washed with brine (20 mL), dried over anhydrous sodium sulfate, filtered, and concentrated under reduced pressure. The residue was subjected to silica gel chromatography (0-50% EtOAc/petroleum ether) to afford the title compound.

Step 3: methyl 6-chloro-3-fluoro-2-(4-fluorophenyl)isonicotinate

To a solution of 3-fluoro-2-(4-fluorophenyl)-4-(methoxycarbonyl)pyridine 1-oxide (0.90 g, 3.4 mmol) in DCE (0.010 L) was added $POCl_3$ (1.6 mL, 17 mmol). The mixture was heated at 75° C. for 12 h. The mixture was cooled to room temperature, treated with water (50 mL), the pH of the aqueous mixture was adjusted to pH 8.0 with sodium bicarbonate (saturated aqueous), and then extracted with DCM (30 mL×3). The combined organic extracts were washed with brine (30 mL), dried over anhydrous sodium sulfate, filtered, and concentrated under reduced pressure. The residue was subjected to silica gel chromatography (0-30% EtOAc/petroleum ether) to afford the title compound.

Step 4: 2-(6-chloro-3-fluoro-2-(4-fluorophenyl)pyridin-4-yl)propan-2-ol

To a 0° C. solution of methyl 6-chloro-3-fluoro-2-(4-fluorophenyl)isonicotinate (0.70 g, 2.5 mmol) in THF (5.0 mL) was added methylmagnesium bromide (3.0M in $Et_2O$, 4.9 mL, 15 mmol). The reaction warmed to 25° C. and stirred for 3 h. The reaction was quenched with ammonium chloride (saturated aqueous, 5 mL) and extracted with EtOAc (10 mL×3). The combined organic extracts were dried over anhydrous sodium sulfate, filtered, and concentrated under reduced pressure. The residue was subjected to silica gel chromatography (0-25% EtOAc/petroleum ether) to afford the title compound.

Step 5: tert-butyl (1R,5S,6s)-6-((5-fluoro-6-(4-fluorophenyl)-4-(2-hydroxypropan-2-yl)pyridin-2-yl)oxy)-3-azabicyclo[3.1.0]hexane-3-carboxylate In an $N_2$ filled glove box, to a mixture of 2-(6-chloro-3-fluoro-2-(4-fluorophenyl)pyridin-4-yl)propan-2-ol (0.30 g, 1.1 mmol), tert-butyl (1R,5S,6s)-6-hydroxy-3-azabicyclo[3.1.0]hexane-3-carboxylate (Int. E, 0.21 g, 1.1 mmol), potassium phosphate (0.67 g, 3.2 mmol), 5-(di((3S,5S,7S)-adamantan-1-yl)phosphaneyl)-1',3',5'-triphenyl-1'H-1,4'-bi-pyrazole (0.070 g, 0.10 mmol), CPME (3.0 mL), and $CF_3Ph$ (3.0 mL) was added Pd$(OAc)_2$ (12 mg, 0.053 mmol). The mixture was heated at 90° C. for 12 h, cooled to room temperature, filtered through a thin pad of silica gel (eluting with EtOAc), and concentrated under reduced pressure. The residue was subjected to silica gel chromatography (0-25% EtOAc/petroleum ether) to afford the title compound.

Step 6: tert-butyl (1R,5S,6s)-6-((5-fluoro-6-(4-fluorophenyl)-4-(2-hydroxypropan-2-yl)pyridin-2-yl)oxy)-3-azabicyclo[3.1.0]hexane-3-carboxylate To a solution of tert-butyl (1R,5S,6s)-6-((5-fluoro-6-(4-fluorophenyl)-4-(2-hydroxypropan-2-yl)pyridin-2-yl)oxy)-3-azabicyclo[3.1.0]hexane-3-carboxylate (0.26 g, 0.60 mmol) in DCM (5.0 mL) was added TFA (2.0 mL, 26 mmol). The mixture was stirred at 25° C. for 1 h and then concentrated under reduced pressure to afford the title compound.

Scheme

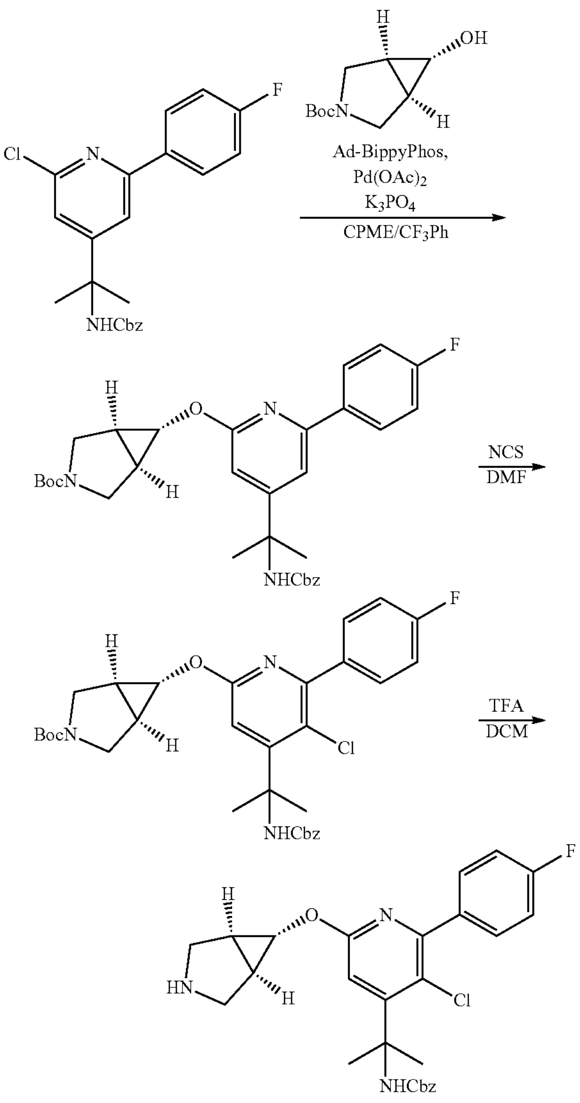

Intermediate T benzyl (2-(6-(((1R,5S,6s)-3-azabicyclo[3.1.0]hexan-6-yl)oxy)-3-chloro-2-(4-fluorophenyl)pyridin-4-yl)propan-2-yl)carbamate

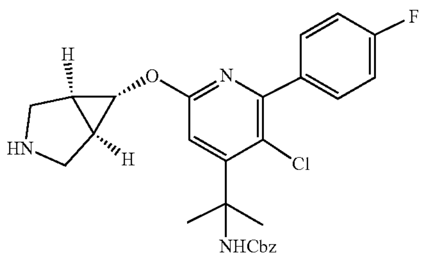 [SMILES: CC(C)(NC(=O)OCc1ccccc1)c1cc(O[C@H]2[C@@H]3CNC[C@@H]32)nc(-c2ccc(F)cc2)c1Cl]

Step 1: tert-butyl (1R,5S,6s)-6-((4-(2-(((benzyloxy)carbonyl)amino)propan-2-yl)-6-(4-fluorophenyl)pyridin-2-yl)oxy)-3-azabicyclo[3.1.0]hexane-3-carboxylate In an $N_2$ filled glove box, to a solution of benzyl (2-(2-chloro-6-(4-fluorophenyl)pyridin-4-yl)propan-2-yl)carbamate (Int. C-1, 0.50 g, 1.3 mmol), tert-butyl (1R,5S,6s)-6-hydroxy-3-azabicyclo[3.1.0]hexane-3-carboxylate (Int. E, 0.25 g, 1.3 mmol), potassium phosphate (0.80 g, 3.8 mmol) and Ad-BippyPhos (83 mg, 0.13 mmol) in CPME (0.010 L) and $CF_3Ph$ (0.010 L) was added $Pd(OAc)_2$ (14 mg, 0.063 mmol). The mixture was stirred at 90° C. for 16 h, cooled to room temperature, filtered through a thin pad of silica gel (eluting with EtOAc), and concentrated under reduced pressure. The mixture was subjected to silica gel chromatography (0-25% EtOAc/petroleum ether) to afford the title compound.

Step 2: tert-butyl (1R,5S,6s)-6-((4-(2-(((benzyloxy)carbonyl)amino)propan-2-yl)-5-chloro-6-(4-fluorophenyl)pyridin-2-yl)oxy)-3-azabicyclo[3.1.0]hexane-3-carboxylate To a solution of tert-butyl (1R,5S,6s)-6-((4-(2-(((benzyloxy)carbonyl)amino)propan-2-yl)-6-(4-fluorophenyl)pyridin-2-yl)oxy)-3-azabicyclo[3.1.0]hexane-3-carboxylate (0.15 g, 0.27 mmol) in DMF (4.0 mL) was added N-chlorosuccinimide (43 mg, 0.32 mmol). The mixture was heated at 65° C. for 6 h, cooled to ambient temperature, and then subjected to reverse phase HPLC (75-100% MeCN/water with (0.05% $NH_3H_2O$+10 mM $(NH_4)HCO_3$ modifier) to afford the title compound.

Step 3: benzyl (2-(6-(((1R,5S,6s)-3-azabicyclo[3.1.0]hexan-6-yl)oxy)-3-chloro-2-(4-fluorophenyl)pyridin-4-yl)propan-2-yl)carbamate To a mixture of tert-butyl (1R,5S,6s)-6-((4-(2-(((benzyloxy)carbonyl)amino)propan-2-yl)-5-chloro-6-(4-fluorophenyl)pyridin-2-yl)oxy)-3-azabicyclo[3.1.0]hexane-3-carboxylate (0.080 g, 0.13 mmol) in DCM (5.0 mL) was added TFA (1.0 mL, 13 mmol). The mixture was stirred at 25° C. for 2 h and then concentrated under reduced pressure to afford the title compound.

Scheme

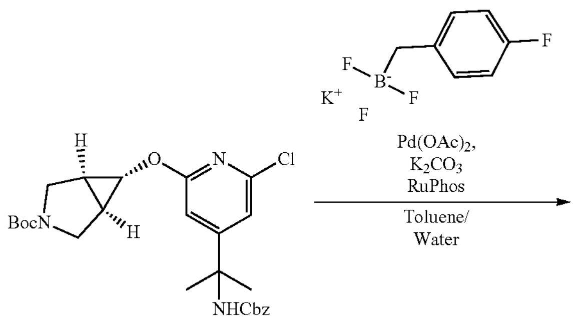

-continued

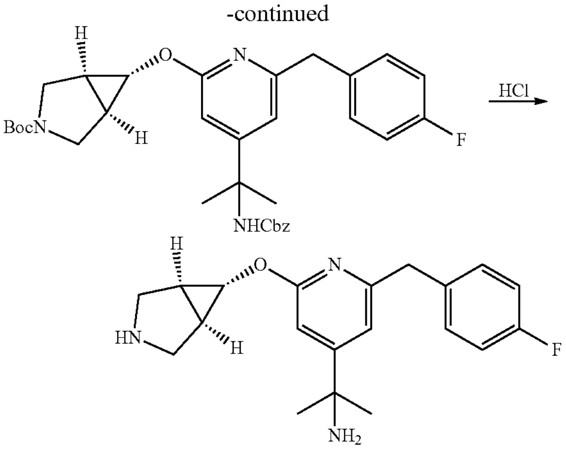

Intermediate U 2-(2-(((1R,5S,6s)-3-azabicyclo[3.1.0]hexan-6-yl)oxy)-6-(4-fluorobenzyl)pyridin-4-yl)propan-2-amine

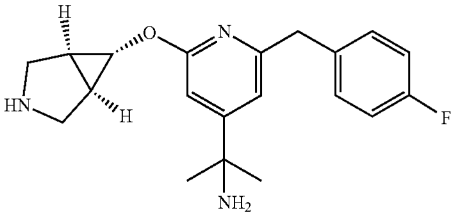 [SMILES: CC(C)(N)c1cc(Cc2ccc(F)cc2)nc(O[C@H]2[C@@H]3CNC[C@@H]32)c1]

Step 1: tert-butyl (1R,5S,6s)-6-((4-(2-(((benzyloxy)carbonyl)amino)propan-2-yl)-6-(4-fluorobenzyl)pyridin-2-yl)oxy)-3-azabicyclo[3.1.0]hexane-3-carboxylate A mixture of tert-butyl (1R,5S,6s)-6-((4-(2-(((benzyloxy)carbonyl)amino)propan-2-yl)-6-chloropyridin-2-yl)oxy)-3-azabicyclo[3.1.0]hexane-3-carboxylate (Int. G, 0.050 g, 0.10 mmol), potassium trifluoro[(4-fluorophenyl)methyl]boranuide (22 mg, 0.10 mmol), $Pd(OAc)_2$ (4.5 mg, 0.020 mmol), RuPhos (19 mg, 0.040 mmol) and potassium carbonate (41 mg, 0.30 mmol), toluene (0.36 mL), and water (36 μL) was heated to 80° C. for 66 h. The mixture was cooled to room temperature, diluted with EtOAc, filtered through a pad of celite, and concentrated under reduced pressure. The mixture was subjected to silica gel chromatography (0-60% (3:1 EtOAc:EtOH)/hexanes) to afford the title compound.

Step 2: 2-(2-(((1R,5S,6s)-3-azabicyclo[3.1.0]hexan-6-yl)oxy)-6-(4-fluorobenzyl)pyridin-4-yl)propan-2-amine To a solution of tert-butyl (1R,5S,6s)-6-((4-(2-(((benzyloxy)carbonyl)amino)propan-2-yl)-6-(4-fluorobenzyl)pyridin-2-yl)oxy)-3-azabicyclo[3.1.0]hexane-3-carboxylate (67 mg, 0.12 mmol) in DCM (0.58 mL) was added HCl (4.0 M in 1,4-dioxane, 0.12 mmol). The mixture was stirred at 25° C. for 16 h and then concentrated under reduced pressure. HCl (37%, aqueous) was added and the mixture was heated at 80° C. for 10 min. The mixture was cooled to ambient temperature and concentrated under reduced pressure to afford the title compound.

Scheme

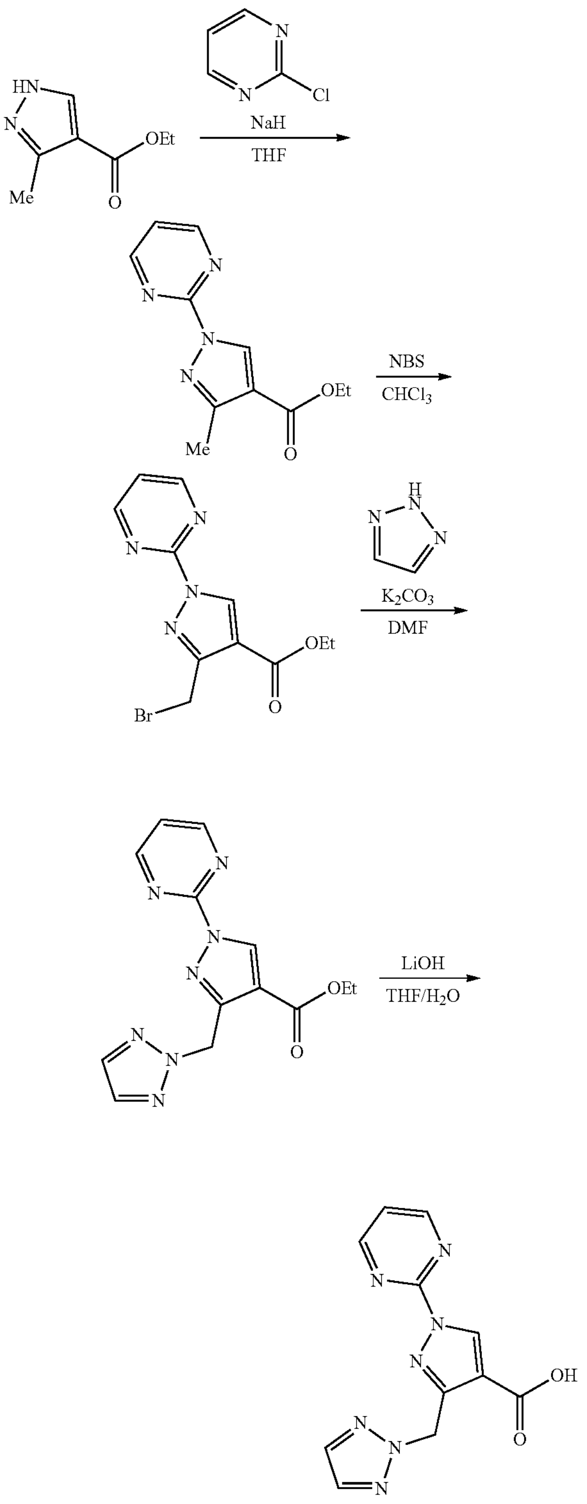

Intermediate V 3-((2H-1,2,3-triazol-2-yl)methyl)-1-(pyrimidin-2-yl)-1H-pyrazole-4-carboxylic acid

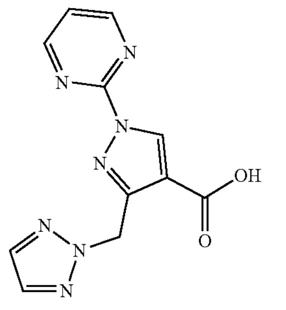 [SMILES: O=C(O)c1cn(-c2ncccn2)nc1Cn1nccn1]

Step 1: ethyl 3-methyl-1-(pyrimidin-2-yl)-1H-pyrazole-4-carboxylate

To a −78° C. mixture of sodium hydride (0.33 g, 8.3 mmol) and THF (0.020 L) was added ethyl 3-methyl-1H-pyrazole-4-carboxylate (0.80 g, 5.2 mmol) under $N_2$. The mixture was stirred at −78° C. for 30 min, 2-chloropyrimidine (0.65 mg, 5.7 mmol) was added, and then the mixture was warmed to 20° C. and stirred for an additional 12 h. The mixture was treated with saturated aqueous ammonium chloride (20 mL) and extracted with EtOAc (20 mL×3). The combined organic extracts were washed with brine (30 mL), dried over sodium sulfate, filtered, and concentrated under reduced pressure. The mixture was subjected to silica gel chromatography (0-60% EtOAc/petroleum ether) to afford the title compound.

Step 2: ethyl 3-(bromomethyl)-1-(pyrimidin-2-yl)-1H-pyrazole-4-carboxylate

To a solution of ethyl 3-methyl-1-(pyrimidin-2-yl)-1H-pyrazole-4-carboxylate (0.50 g, 2.2 mmol) and N-bromo-succinimide (0.58 g, 3.2 mmol) in chloroform (15 mL) was added benzoyl peroxide (52 mg, 0.22 mmol). The mixture was heated at 70° C. for 12 h, cooled to room temperature, and then poured into ice water (20 mL). The resulting mixture was extracted with DCM (30 mL×3) and the combined organic extracts were washed with brine (30 mL), dried over anhydrous sodium sulfate, filtered, and concentrated under reduced pressure. The mixture was subjected to silica gel chromatography (0-70% EtOAc/petroleum either) to afford the title compound.

Step 3: ethyl 3-((2H-1,2,3-triazol-2-yl)methyl)-1-(pyrimidin-2-yl)-1H-pyrazole-4-carboxylate To a mixture of ethyl 5-(bromomethyl)-2-(pyrimidin-2-yl)-2H-pyrrole-4-carboxylate (0.12 g, 0.39 mmol) in DMF (0.010 L) was added potassium carbonate (0.10 g, 0.77 mmol) and 1H-1,2,3-triazole (53 mg, 0.77 mmol). The resulting mixture was stirred at 20° C. for 12 h, then treated with water (10 mL), and extracted with EtOAc (10 mL×3). The combined organic extracts were washed with brine (10 mL), dried over anhydrous sodium sulfate, filtered, and concentrated under reduced pressure. The residue was subjected to prep-TLC (EtOAc) to afford the title compound.

Step 4: 3-((2H-1,2,3-triazol-2-yl)methyl)-1-(pyrimidin-2-yl)-1H-pyrazole-4-carboxylic acid To a mixture of ethyl 3-((2H-1,2,3-triazol-2-yl)methyl)-1-(pyrimidin-2-yl)-1H-pyrazole-4-carboxylate (35 mg, 0.12 mmol) in water (5.0 mL) and THF (5.0 mL) was added lithium hydroxide (14 mg, 0.59 mmol). The mixture was stirred at 25° C. for 1 h. The mixture was concentrated under reduced pressure and pH of the aqueous layer was adjusted to pH 6.0 with HCl (1 M, aqueous). The resulting precipitate was filtered, washed with water, and dried under vacuum to afford the title compound.

Scheme

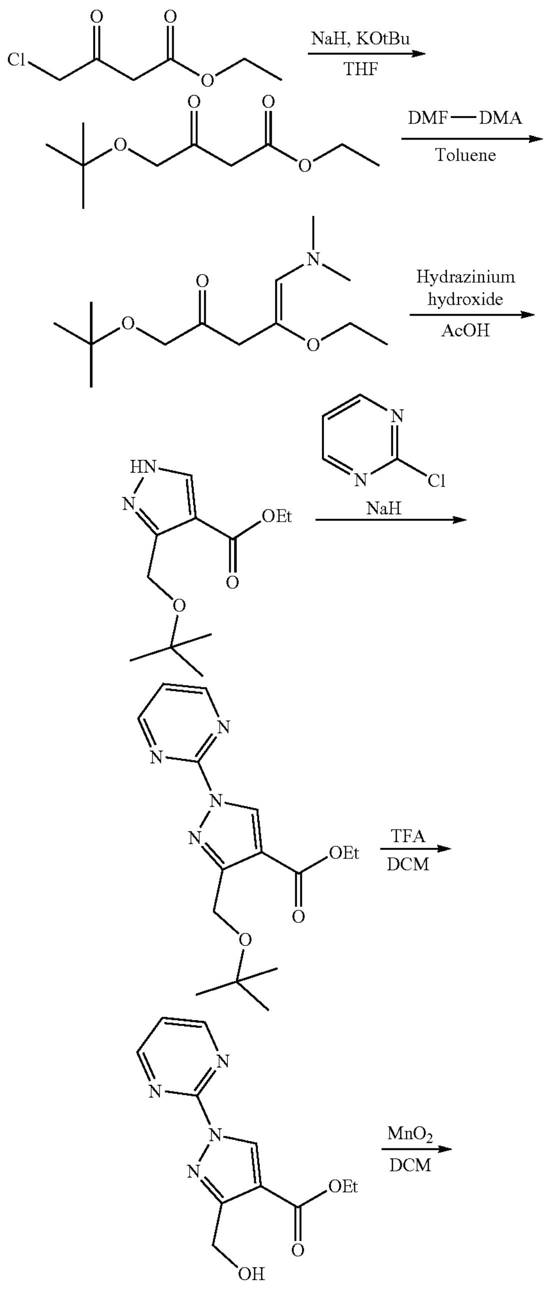

-continued

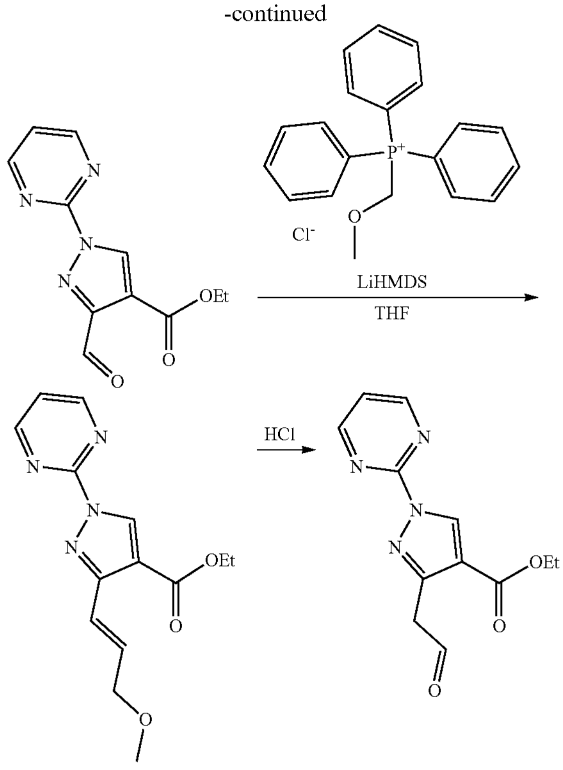

Intermediate W-01 ethyl 3-(2-oxoethyl)-1-(pyrimidin-2-yl)-1H-pyrazole-4-carboxylate

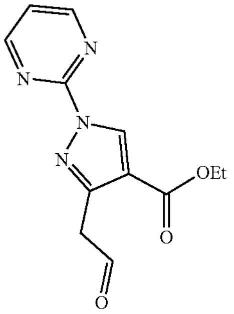 [SMILES: CCOC(=O)c1cn(-c2ncccn2)nc1CC=O]

Step 1: ethyl 4-(tert-butoxy)-3-oxobutanoate

A solution of ethyl 4-chloro-3-oxobutanoate (0.020 kg, 12 mmol) in THF (0.040 L) was added dropwise to a stirred suspension of sodium hydride (60% in oil, 7.3 g, 180 mmol) and potassium tert-butoxide (14 g, 120 mmol) in THF (0.16 L) over 30 min. The mixture was stirred at 25° C. for 12 h, poured into HCl (5% aqueous, 120 mL) at 5° C., and extracted with EtOAc (120 mL×3). The combined organic extracts were washed with sodium bicarbonate (100 mL×2) and brine (100 mL), dried over anhydrous sodium sulfate, filtered, and concentrated under reduced pressure. The mixture was subjected to silica gel chromatography (0-10% EtOAc/petroleum ether) to afford the title compound.

Step 2: ethyl (Z)-4-(tert-butoxy)-2-((dimethylamino)methylene)-3-oxobutanoate

To a solution of ethyl 4-(tert-butoxy)-3-oxobutanoate (15 g, 74 mmol) in PhMe (0.20 L) was added DMF-DMA (15 mL, 110 mmol). The mixture was stirred at 65° C. for 16 h, cooled to room temperature, and concentrated under reduced pressure to afford the title compound.

Step 3: ethyl 3-(tert-butoxymethyl)-1H-pyrazole-4-carboxylate

To a mixture of ethyl (Z)-4-(tert-butoxy)-2-((dimethylamino)methylene)-3-oxobutanoate (18 g, 56 mmol) in acetic acid (0.030 L) was added hydrazinium hydroxide (5.6 g, 110 mmol). The mixture was stirred at 25° C. for 12 h, diluted with EtOAc (200 mL) and was washed with sodium bicarbonate (saturated aqueous, 400 mL) and brine (300 mL). The organic layer was dried over anhydrous sodium sulfate, filtered, and concentrated under reduced pressure. The mixture was subjected to silica gel chromatography (50% EtOAc) to afford the title compound.

Step 4: ethyl 3-(tert-butoxymethyl)-1-(pyrimidin-2-yl)-1H-pyrazole-4-carboxylate To a suspension of sodium hydride (3.5 g, 88 mmol) in THF (0.050 L) was added ethyl 3-(tert-butoxymethyl)-1H-pyrazole-4-carboxylate (0.010 kg, 44 mmol) in THF (0.050 L) at □78° C. After stirring for 30 min, 2-chloropyrimidine (0.010 kg, 88 mmol) in THF (25 mL) was added and the mixture was then heated at 60° C. for 12 h. The mixture was cooled to ambient temperature, treated with ammonium chloride (saturated aqueous, 100 mL), and extracted with EtOAc (100 mL×3). The combined organic extracts were washed with brine (100 mL), dried over anhydrous sodium sulfate, filtered, and concentrated under reduced pressure. The mixture was subjected to silica gel chromatography (0-50% EtOAc/petroleum ether) to afford the title compound.

Step 5: ethyl 3-(hydroxymethyl)-1-(pyrimidin-2-yl)-1H-pyrazole-4-carboxylate

To a solution of ethyl 3-(tert-butoxymethyl)-1-(pyrimidin-2-yl)-1H-pyrazole-4-carboxylate (0.010 kg, 33 mmol) in DCM (0.050 L) was added TFA (0.020 L). The mixture was stirred at 25° C. for 12 h. The mixture was diluted with water (50 mL), the pH of solution was adjusted to pH 10 with sodium hydroxide (1 M, aqueous), and then extracted with EtOAc (50 mL×3). The combined organic extracts were washed with brine, dried over anhydrous sodium sulfate, filtered, and concentrated under reduced pressure to afford the title compound.

Step 6: ethyl 3-formyl-1-(pyrimidin-2-yl)-1H-pyrazole-4-carboxylate

To a mixture of ethyl 3-(hydroxymethyl)-1-(pyrimidin-2-yl)-1H-pyrazole-4-carboxylate (5.0 g, 0.020 mol) in DCM (0.050 L) was added manganese (IV) oxide (18 g, 0.20 mol). The mixture was heated at 40° C. for 12 h, cooled to ambient temperature, and then filtered through a thin pad of silica gel (eluting with DCM). The filtrate was concentrated under reduced pressure. The mixture was subjected to silica gel chromatography (0-100% EtOAc/petroleum ether) to afford the title compound.

Step 7: ethyl 3-(2-methoxyvinyl)-1-(pyrimidin-2-yl)-1H-pyrazole-4-carboxylate

A solution of (methoxymethyl)triphenylphosphonium chloride (4.2 g, 12 mmol) in THF (0.040 L) was cooled to −78° C. Lithium bis(trimethylsilyl)amide (1 M solution in THF, 2.2 mL, 12 mmol) was added, the mixture was warmed to 0° C. and then stirred for 30 min. The mixture was cooled to −78° C. and a solution of ethyl 3-formyl-1-(pyrimidin-2-yl)-1H-pyrazole-4-carboxylate (2.0 g, 8.1 mmol) in THF (0.020 L) was added dropwise. The mixture was stirred for 2 h, treated with ammonium chloride (saturated aqueous, 50 mL), warmed to ambient temperature, and extracted with EtOAc (50 mL). The organic layer was dried over anhydrous sodium sulfate, filtered, and concentrated under reduced pressure. The mixture was subjected to silica gel chromatography (0-100% EtOAc/petroleum ether) followed by reverse phase HPLC (18-38% MeCN/water with 0.1% TFA modifier) to afford the title compound.

Step 8: ethyl 3-(2-oxoethyl)-1-(pyrimidin-2-yl)-1H-pyrazole-4-carboxylate

To a mixture of ethyl 3-(2-methoxyvinyl)-1-(pyrimidin-2-yl)-1H-pyrazole-4-carboxylate (0.40 g, 1.5 mmol) in THF (0.010 L) was added HCl (6 M aqueous, 0.97 mL, 5.8 mmol). The mixture was stirred at 25° C. for 12 h, diluted with water (10 mL), treated with sodium bicarbonate (saturated aqueous) until pH 7, and then extracted with EtOAc (10 mL). The combined organic extracts were washed with brine, dried over anhydrous sodium sulfate, filtered, and concentrated under reduced pressure to provide the title compound.

Scheme

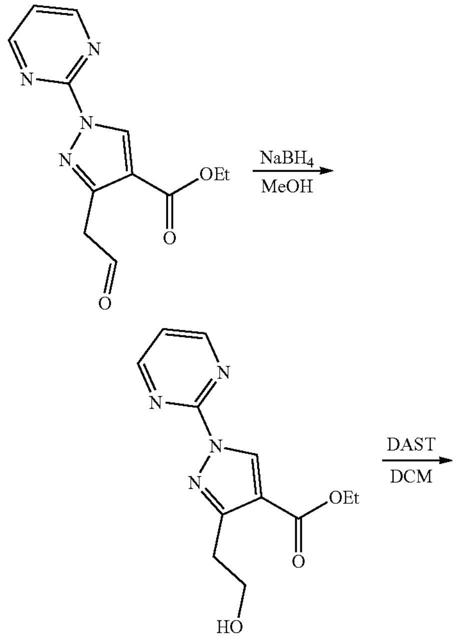

-continued

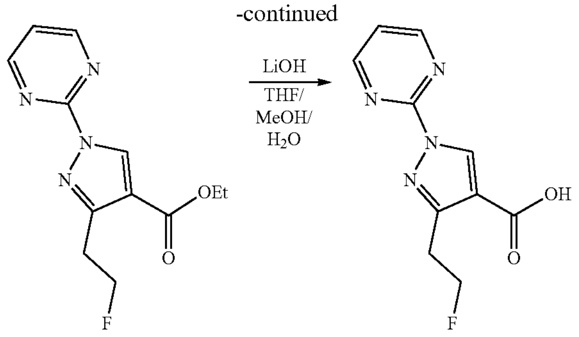

Intermediate W-02

3-(2-fluoroethyl)-1-(pyrimidin-2-yl)-1H-pyrazole-4-carboxylic acid

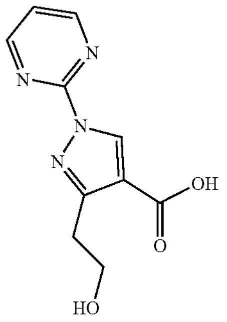 [SMILES: O=C(O)c1cn(-c2ncccn2)nc1CCO]

Step 1: ethyl 3-(2-hydroxyethyl)-1-(pyrimidin-2-yl)-1H-pyrazole-4-carboxylate

To a solution of ethyl 3-(2-oxoethyl)-1-(pyrimidin-2-yl)-1H-pyrazole-4-carboxylate (Int. W-01, 0.10 g, 0.31 mmol) in MeOH (5.0 mL) was added NaBH4 (5.8 mg, 0.15 mmol) at 0° C. The mixture was stirred at 25° C. for 1 h, treated with water (10 mL), and then extracted with EtOAc (30 mL×3). The combined organic extracts were washed with brine (20 mL×3), dried over anhydrous sodium sulfate, filtered, and concentrated under reduced pressure to afford the title compound.

Step 2: ethyl 3-(2-fluoroethyl)-1-(pyrimidin-2-yl)-1H-pyrazole-4-carboxylate

To a solution of ethyl 3-(2-hydroxyethyl)-1-(pyrimidin-2-yl)-1H-pyrazole-4-carboxylate (0.25 g, 0.76 mmol) in DCM (5.0 mL) was added diethylaminosulfur trifluoride (0.25 g, 1.5 mmol) at 0° C. The mixture was warmed to 25° C. and stirred for 12 h. The mixture was poured into water (10 mL) and extracted with EtOAc (30 mL×3). The combined organic extracts were washed with brine (20 mL×3), dried over anhydrous sodium sulfate, filtered, and concentrated under reduced pressure. The mixture was subjected to prep-TLC (EtOAc) to afford the title compound.

Step 3: 3-(2-fluoroethyl)-1-(pyrimidin-2-yl)-1H-pyrazole-4-carboxylic acid

To a mixture of ethyl 3-(2-fluoroethyl)-1-(pyrimidin-2-yl)-1H-pyrazole-4-carboxylate (0.10 g, 0.38 mmol) in THF (2.0 mL), MeOH (0.50 mL), and water (2.0 mL) was added lithium hydroxide (45 mg, 1.9 mmol). The mixture was stirred at 25° C. for 30 min and then extracted with DCM (5 mL×2). The aqueous layer was adjusted to pH=4.0 with HCl (1 M, aqueous) and then concentrated under reduced pressure. The residue was diluted with 1/1 MeOH/DCM (10 mL) and stirred at 25° C. for 1 h. The mixture was filtered and concentrated under reduced pressure to afford the title compound.

Scheme

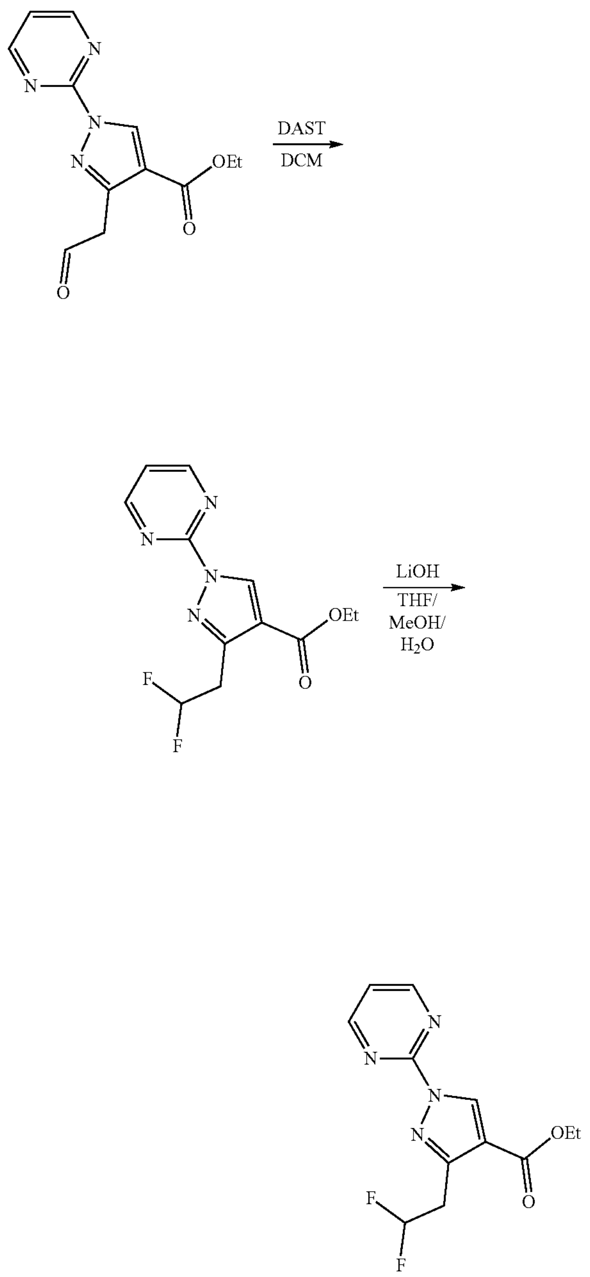

Intermediate W-03

3-(2,2-difluoroethyl)-1-(pyrimidin-2-yl)-1H-pyrazole-4-carboxylic acid

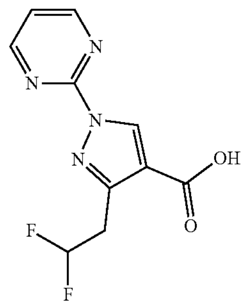 [SMILES: O=C(O)c1cn(-c2ncccn2)nc1CC(F)F]

Step 1: ethyl 3-(2,2-difluoroethyl)-1-(pyrimidin-2-yl)-1H-pyrazole-4-carboxylate To a solution of ethyl 3-(2-oxoethyl)-1-(pyrimidin-2-yl)-1H-pyrazole-4-carboxylate (Int. W-01, 0.25 g, 0.77 mmol) in DCM (5.0 mL) was added diethylaminosulfur trifluoride (0.25 mg, 1.5 mmol) at 0° C. The mixture was stirred at 25° C. for 12 h, treated with water (10 mL), and extracted with EtOAc (30 mL×3). The combined organic extracts were washed with brine (20 mL×3), dried over anhydrous sodium sulfate, filtered, and concentrated under reduced pressure. The mixture was subjected to prep-TLC (EtOAc) to afford the title compound.

Step 2: 3-(2,2-difluoroethyl)-1-(pyrimidin-2-yl)-1H-pyrazole-4-carboxylic acid

To a mixture of ethyl 3-(2,2-difluoroethyl)-1-(pyrimidin-2-yl)-1H-pyrazole-4-carboxylate (0.060 g, 0.21 mmol) in THF (1.0 mL), MeOH (0.50 mL), and Water (1.0 mL) was added lithium hydroxide (26 mg, 1.1 mmol). The mixture was stirred at 25° C. for 30 min, partially concentrated, and extracted with DCM (5 mL×2). The pH of the aqueous phase was adjusted to pH 4 with HCl (1 M, aqueous) and then concentrated under reduced pressure. The residue was taken up in 1:1 DCM:MeOH (10 mL), stirred at 25° C. for 1 h, filtered, and concentrated under reduced pressure to afford the title compound.

EXAMPLES

Scheme

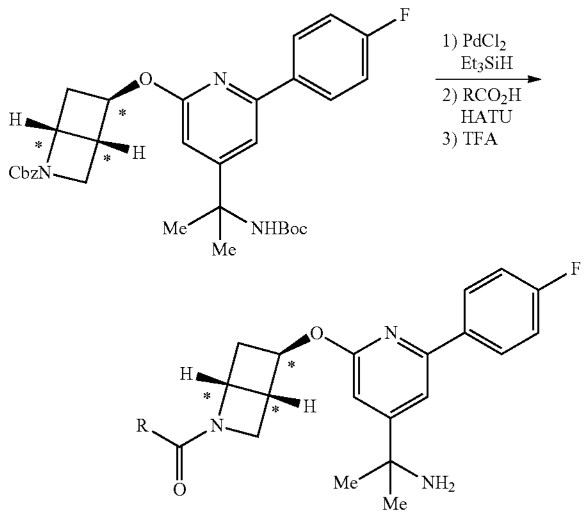

Example 1A rel-((1R,4R,5R)-5-((4-(2-aminopropan-2-yl)-6-(4-fluorophenyl)pyridin-2-yl)oxy)-2-azabicyclo [2.2.0] hexan-2-yl)(4-methyl-2-(pyrimidin-2-yl)thiazol-5-yl) methanone (Enantiomer 1)

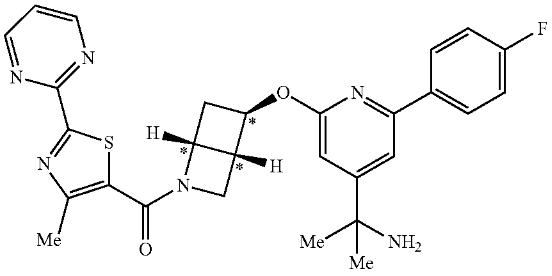 [SMILES: Cc1nc(-c2ncccn2)sc1C(=O)N1C[C@@H]2[C@H]1C[C@H]2Oc1cc(C(C)(C)N)cc(-c2ccc(F)cc2)n1]

To a mixture of benzyl rel-(1R,4R,5R)-5-((4-(2-((tert-butoxycarbonyl)amino)propan-2-yl)-6-(4-fluorophenyl) pyridin-2-yl)oxy)-2-azabicyclo[2.2.0]hexane-2-carboxylate (enantiomer 1, Int. D-ent-1, 84 mg, 0.15 mmol) and palladium(II) chloride (2.7 mg, 0.015 mmol) in DCM (1.5 mL) was added triethylamine (0.11 mL, 0.75 mmol) and triethylsilane (0.24 mL, 1.5 mmol). The mixture was stirred at rt for 1 h, filtered through a pad of celite, which was washed with DCM (5 mL×3), and the filtrate was concentrated under reduced pressure. 4-Methyl-2-(pyrimidin-2-yl)thiazole-5-carboxylic acid (Int. L-3, 37 mg, 0.17 mmol), DCM (1.4 mL), DMF (0.075 mL), DIPEA (0.079 mL, 0.45 mmol), and HATU (63 mg, 0.17 mmol) were added, and the mixture was stirred at rt for 16 h. Brine (25 mL) was added and the mixture was extracted with DCM (25 mL×3). The combined organic extracts were dried with anhydrous magnesium sulfate, filtered, and concentrated under reduced pressure. DCM (1.3 mL) and TFA (0.38 mL) were added, and the mixture was stirred at rt for 16 h. A solution of sodium hydroxide (1 N aqueous, 25 mL) was added, and the mixture was extracted with DCM (25 mL×3). The combined organic extracts were dried with anhydrous magnesium sulfate, filtered, and concentrated under reduced pressure. The mixture was subjected to reverse phase HPLC (10-100% MeCN/water with 0.1% TFA modifier). The appropriate fractions were passaged through a SCX-2 column, which was washed with MeOH (2 mL×3) and eluted with a methanolic solution of ammonia (2N, 2 mL×3) to afford the title compound. MS m/z $(M+H)^+$: calculated 531.2, observed 531.4. $^1H$ NMR (500 MHz, DMSO-$d^6$) rotameric mixture: δ 8.99-8.95 (m, 2H), 8.16-8.07 (m, 2H), 7.74-7.68 (m, J=9.6 Hz, 1H), 7.65-7.60 (m, 1H), 7.36-7.27 (m, 2H), 6.92-6.90 (m, 1H), 5.58-5.52 (m, 1H), 5.07-5.02 and 4.87-4.82 (m, 1H) 4.79-4.73 and 4.50-4.43 (m, 1H), 4.66-4.61 and 4.33-4.27 (m, 1H), 3.15-3.10 (m, 1H), 3.05-2.95 (m, 1H), 2.76-2.62 (m, 4H), 2.10 (br s, 2H), 1.38 (s, 6H) ppm.

Utilizing the procedure described in EXAMPLE 1A, the below compound was prepared substituting Int. D-ent-2 for Int. D-ent-1.

| Ex # | Structure | Name | Calc'd $[M + H]^+$ | Observed $[M + H]^+$ |
|---|---|---|---|---|
| 1B | 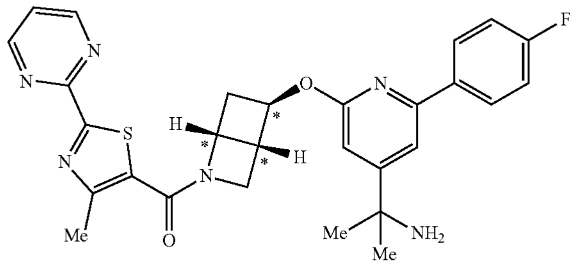 [SMILES: Cc1nc(-c2ncccn2)sc1C(=O)N1C[C@@H]2[C@H]1C[C@H]2Oc1cc(C(C)(C)N)cc(-c2ccc(F)cc2)n1] | rel-((1R,4R,5R)-5-((4-(2-aminopropan-2-yl)-6-(4-fluorophenyl)pyridin-2-yl)oxy)-2-azabicyclo[2.2.0]hexan-2-yl)(4-methyl-2-(pyrimidin-2-yl)thiazol-5-yl)methanone (enantiomer 2) | 531.2 | 531.4 |

Example 2 rel-((1R,4R,5R)-5-((4-(2-aminopropan-2-yl)-6-(4-fluorophenyl)pyridin-2-yl)oxy)-2-azabicyclo[2.2.0]hexan-2-yl)(2-(pyrimidin-2-yl)thiazol-5-yl)methanone (Enantiomer 2)

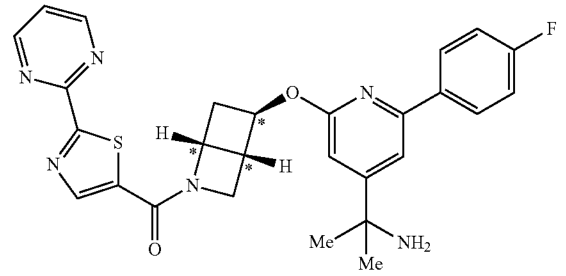 [SMILES: CC(C)(N)c1cc(O[C@@H]2C[C@@H]3[C@H]2CN3C(=O)c2cnc(-c3ncccn3)s2)nc(-c2ccc(F)cc2)c1]

Step 1: tert-butyl rel-(2-(2-(((1R,4R,5R)-2-azabicyclo[2.2.0]hexan-5-yl)oxy)-6-(4-fluorophenyl)pyridin-4-yl)propan-2-yl)carbamate (Enantiomer 2)

To a mixture of benzyl rel-(1R,4R,5R)-5-((4-(2-((tert-butoxycarbonyl)amino)propan-2-yl)-6-(4-fluorophenyl) pyridin-2-yl)oxy)-2-azabicyclo[2.2.0]hexane-2-carboxylate (Int. D-ent-2, 0.32 g, 0.56 mmol) and palladium(II) chloride (9.9 mg, 0.056 mmol) in DCM (5.6 mL) was added triethylamine (0.39 mL, 2.8 mmol) and triethylsilane (0.45 mL, 2.8 mmol). The mixture was stirred at rt for 2 h and then filtered through a pad of celite (eluted with DCM, 5 mL×3). A solution of sodium hydroxide (1 N aqueous, 30 mL) was added, and the mixture was extracted with DCM (25 mL×3). The combined organic extracts were dried with anhydrous magnesium sulfate, filtered, and concentrated under reduced pressure to afford the title compound.

Step 2: rel-((1R,4R,5R)-5-((4-(2-aminopropan-2-yl)-6-(4-fluorophenyl)pyridin-2-yl)oxy)-2-azabicyclo[2.2.0]hexan-2-yl)(2-(pyrimidin-2-yl)thiazol-5-yl) methanone (enantiomer 2)

A solution of HATU (13 mg, 0.035 mmol) and DIPEA (0.012 mL, 0.070 mmol) in DCM (0.35 mL) was added to 2-(pyrimidin-2-yl)thiazole-5-carboxylic acid (7.3 mg, 0.035 mmol). tert-Butyl rel-(2-(2-(((1R,4R,5R)-2-azabicyclo[2.2.0]hexan-5-yl)oxy)-6-(4-fluorophenyl)pyridin-4-yl)propan-2-yl)carbamate (enantiomer 2, 15 mg, 0.035 mmol) was added and the mixture was stirred at rt for 16 h. TFA (0.030 mL) was added and the mixture was stirred at rt for 1 h. The mixture was concentrated under reduced pressure and the residue was subjected to reverse phase HPLC (MeCN/water with 0.1% TFA modifier), providing the title compound as a TFA salt. MS m/z $(M+H)^+$: calculated 517.2, observed 517.4. $^1H$ NMR (500 MHz, DMSO-$d^6$) rotameric mixture: δ 9.01-8.97 (m, 2H), 8.56 (s, 3H), 8.51 and 8.31 (s, 1H), 8.17-8.12 (m, 2H), 7.73-7.70 (m, 1H), 7.67-7.63 (m, 1H), 7.41-7.35 (m, 2H), 6.93-6.90 (m, 1H), 5.65-5.58 (m, 1H), 5.32-5.27 and 5.51-4.95 (m, 1H), 4.92-4.85 and 4.54-4.47 and 4.39-4.33 (m, 2H), 3.23-3.18 (m, 1H), 3.13-3.01 (m, 1H), 2.86-2.78 and 2.69-2.62 (m, 1H), 1.66 (s, 6H) ppm.

Utilizing the procedures described in EXAMPLE 2, the below compounds were prepared substituting the appropriate reagents for 2-(pyrimidin-2-yl)thiazole-5-carboxylic acid.

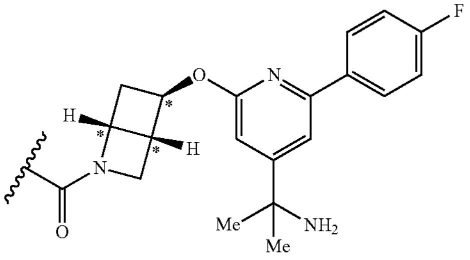 [SMILES: *C(=O)N1C[C@@H]2[C@H]1C[C@H]2Oc1cc(C(C)(C)N)cc(-c2ccc(F)cc2)n1]

| Ex. # | Structure | Name | Calc'd $[M + H]^+$ | Observed $[M + H]^+$ |
|---|---|---|---|---|
| 3 | 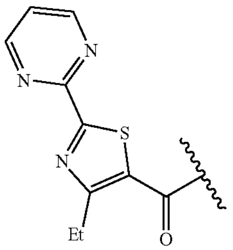 [SMILES: *C(=O)c1sc(-c2ncccn2)nc1CC] | rel-((1R,4R,5R)-5-((4-(2-aminopropan-2-yl)-6-(4-fluorophenyl)pyridin-2-yl)oxy)-2-azabicyclo[2.2.0]hexan-2-yl)(4-ethyl-2-(pyrimidin-2-yl)thiazol-5-yl)methanone (enantiomer 2) | 545.2 | 545.4 |
| 4 | 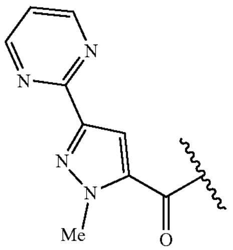 [SMILES: *C(=O)c1cc(-c2ncccn2)nn1C] | rel-((1R,4R,5R)-5-((4-(2-aminopropan-2-yl)-6-(4-fluorophenyl)pyridin-2-yl)oxy)-2-azabicyclo[2.2.0]hexan-2-yl)(1-methyl-3-(pyrimidin-2-yl)-1H-pyrazol-5-yl)methanone (enantiomer 2) | 514.2 | 514.4 |

-continued

| Ex. # | Structure | Name | Calc'd [M + H]+ | Observed [M + H]+ |
|---|---|---|---|---|
| 5 | 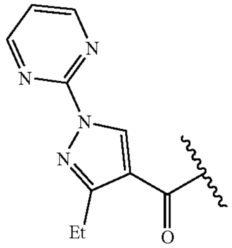 [SMILES: *C(=O)c1cn(-c2ncccn2)nc1CC] | rel-((1R,4R,5R)-5-((4-(2-aminopropan-2-yl)-6-(4-fluorophenyl)pyridin-2-yl)oxy)-2-azabicyclo[2.2.0]hexan-2-yl)(3-ethyl-1-(pyrimidin-2-yl)-1H-pyrazol-4-yl)methanone (enantiomer 2) | 528.2 | 528.4 |
| 6 | 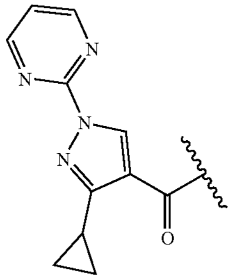 [SMILES: *C(=O)c1cn(-c2ncccn2)nc1C1CC1] | rel-((1R,4R,5R)-5-((4-(2-aminopropan-2-yl)-6-(4-fluorophenyl)pyridin-2-yl)oxy)-2-azabicyclo[2.2.0]hexan-2-yl)(3-cyclopropyl-1-(pyrimidin-2-yl)-1H-pyrazol-4-yl)methanone (enantiomer 2) | 540.2 | 540.5 |

Scheme

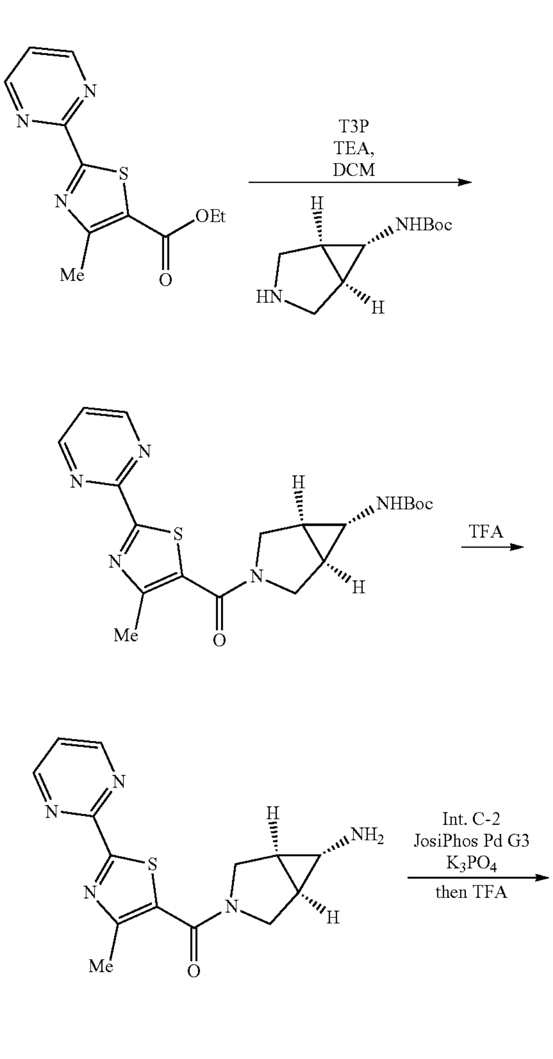

-continued

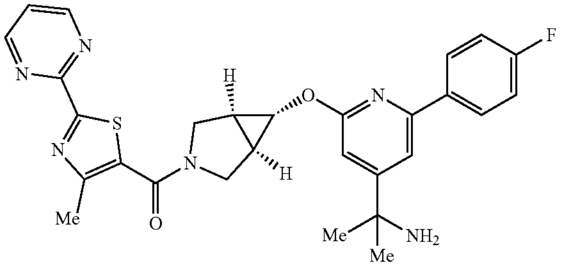

Example 7

((1R,5S,6s)-6-((4-(2-aminopropan-2-yl)-6-(4-fluorophenyl)pyridin-2-yl)amino)-3-azabicyclo[3.1.0]hexan-3-yl)(4-methyl-2-(pyrimidin-2-yl)thiazol-5-yl)methanone

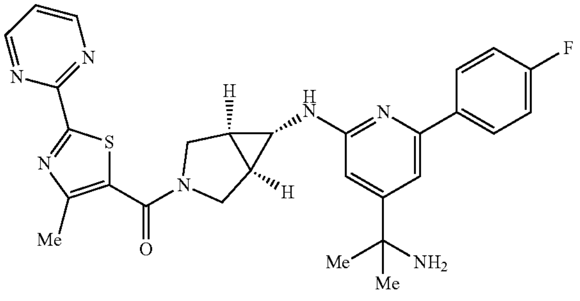 [SMILES: Cc1nc(-c2ncccn2)sc1C(=O)N1C[C@@H]2[C@H](C1)[C@H]2Nc1cc(C(C)(C)N)cc(-c2ccc(F)cc2)n1]

Step 1: tert-butyl ((1R,5S,6s)-3-(4-methyl-2-(pyrimidin-2-yl)thiazole-5-carbonyl)-3-azabicyclo[3.1.0]hexan-6-yl)carbamate To a of solution of 4-methyl-2-(pyrimidin-2-yl)thiazole-5-carboxylic acid (Int. L-3, 0.93 g, 4.2 mmol), tert-butyl ((1R,5S,6s)-3-azabicyclo[3.1.0]hexan-6-yl)carbamate (1.0 g, 5.1 mmol), and triethylamine (2.9 mL, 21 mmol) in DCM (25 mL) was added T3P (50 wt. % in EtOAc, 6.0 mL, 0.010 mol). The mixture was stirred at rt for 4 h. Water (75 mL) was added and the mixture was extracted with DCM (25 mL×2). The combined organic extracts were dried with anhydrous sodium sulfate, filtered, and concentrated under reduced pressure. The residue was subjected to silica gel chromatography (0-75% (3:1 EtOAc:EtOH)/hexanes) to afford the title compound.

Step 2: ((1R,5S,6s)-6-amino-3-azabicyclo[3.1.0]hexan-3-yl)(4-methyl-2-(pyrimidin-2-yl)thiazol-5-yl)methanone To a solution of tert-butyl ((1R,5S,6s)-3-(4-methyl-2-(pyrimidin-2-yl)thiazole-5-carbonyl)-3-azabicyclo[3.1.0]hexan-6-yl)carbamate (1.2 g, 3.0 mmol) in DCM (0.010 L) was added TFA (2.3 mL, 0.030 mol). The mixture was stirred at rt for 2 h and concentrated under reduced pressure. The material was passaged through a SCX-2 column which was washed with MeOH (30 mL×3), eluted with a methanolic solution of ammonia (2 N, 30 mL×3), and concentrated under reduced pressure to afford the title compound.

Step 3: ((1R,5S,6s)-6-((4-(2-aminopropan-2-yl)-6-(4-fluorophenyl)pyridin-2-yl)amino)-3-azabicyclo[3.1.0]hexan-3-yl)(4-methyl-2-(pyrimidin-2-yl)thiazol-5-yl)methanone Under an atmosphere of argon, a mixture of tert-butyl (2-(2-chloro-6-(4-fluorophenyl)pyridin-4-yl)propan-2-yl) carbamate (Int. C-2, 15 mg, 0.040 mmol), ((1R,5S,6s)-6-amino-3-azabicyclo[3.1.0]hexan-3-yl)(4-methyl-2-(pyrimidin-2-yl)thiazol-5-yl)methanone (0.010 g, 0.033 mmol), {(R)-1-[(Sp)-2-(dicyclohexylphosphino)ferrocenyl]ethyldi-tert-butylphosphine}[2-(2'-amino-1,1'-biphenyl)]palladium (II) methanesulfonate (3.1 mg, 3.3 μmol), potassium phosphate (21 mg, 0.10 mmol), and 1,4-dioxane (0.33 mL) was stirred at 100° C. for 22 h. The mixture was cooled to room temperature and concentrated under reduced pressure. DCM (0.25 mL) and TFA (0.13 mL, 1.7 mmol) were added, and the mixture was stirred at rt for 1 h. The mixture was concentrated under reduced pressure. The residue was subjected to reverse phase HPLC (10-100% MeCN/water with 0.05% $NH_4OH$ modifier) to afford the title compound. MS m/z $(M+H)^+$: calculated 530.2, observed 530.3. $^1H$ NMR (500 MHz, $CDCl_3$) δ 8.87 (d, J=4.9 Hz, 2H), 7.96-7.89 (m, 2H), 7.35 (t, J=4.9 Hz, 1H), 7.20 (s, 1H), 7.15-7.09 (m, 2H), 6.69 (s, 1H), 5.00 (s, 1H), 4.33-4.17 (m, 1H), 3.92-3.70 (m, 3H), 2.64 (s, 3H), 2.48 (s, 1H), 1.51 (s, 6H) ppm.

Scheme

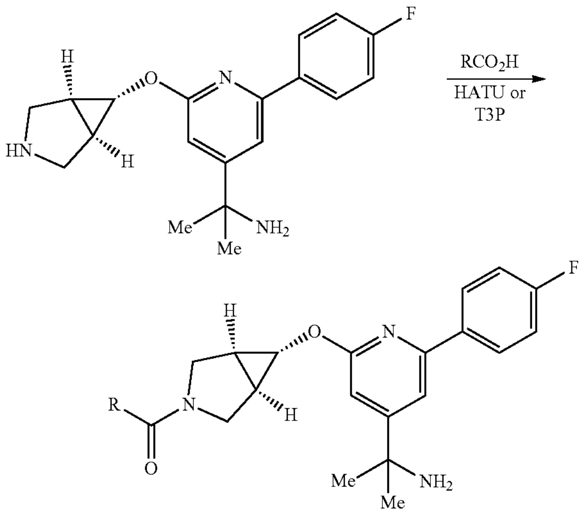

Example 8

((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(pyrimidin-2-yl)thiazol-5-yl)methanone

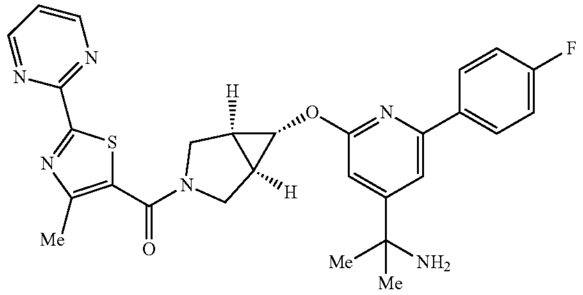 [SMILES: Cc1nc(-c2ncccn2)sc1C(=O)N1C[C@@H]2[C@H](C1)[C@H]2Oc1cc(C(C)(C)N)cc(-c2ccc(F)cc2)n1]

Step 1: benzyl (2-(2-(4-fluorophenyl)-6-(((1R,5S,6s)-3-(4-methyl-2-(pyrimidin-2-yl)thiazole-5-carbonyl)-3-azabicyclo[3.1.0]hexan-6-yl)oxy)pyridin-4-yl)propan-2-yl)carbamate To a mixture of 4-methyl-2-(pyrimidin-2-yl)thiazole-5-carboxylic acid (Int. L-3, 0.96 g, 4.3 mmol), benzyl (2-(2-(((1R,5S,6s)-3-azabicyclo[3.1.0]hexan-6-yl)oxy)-6-(4-fluorophenyl)pyridin-4-yl)propan-2-yl)carbamate hydrochloride (Int. H-1, 2.3 g, 4.6 mmol), DCM (0.040 mL), DMF (1.0 mL), and DIPEA (3.0 mL, 17 mmol) was added HATU (2.0 g, 5.2 mmol). The mixture was stirred at rt for 2 h, poured into a solution of sodium carbonate (saturated aqueous, 75 mL), and extracted with DCM (75 mL×2). The combined organic extracts were dried with anhydrous magnesium sulfate, filtered, and concentrated under reduced pressure. The residue was subjected to silica gel chromatography (0-50% (3:1 EtOAc:EtOH)/hexanes) to afford the title compound.

Step 2: ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(pyrimidin-2-yl)thiazol-5-yl)methanone A mixture of benzyl (2-(2-(4-fluorophenyl)-6-(((1R,5S,6s)-3-(4-methyl-2-(pyrimidin-2-yl)thiazole-5-carbonyl)-3-azabicyclo[3.1.0]hexan-6-yl)oxy)pyridin-4-yl)propan-2-yl) carbamate (2.4 g, 3.6 mmol) and HCl (37% aqueous, 7.0 mL) was stirred at 80° C. for 10 min. The mixture was cooled to ambient temperature, filtered, and subjected to reverse phase HPLC (0-70% MeCN/water with 0.1% TFA modifier). The material was concentrated under reduced pressure, poured into sodium hydroxide (1 N aqueous, 100 mL), and extracted with DCM (100 mL×3). The combined organic extracts were dried with anhydrous magnesium sulfate, filtered, and concentrated under reduced pressure to afford the title compound. MS m/z $(M+H)^+$: calculated 531.2, observed 531.1. $^1H$ NMR (500 MHz, $CDCl_3$) δ 8.89 (d, J=4.9 Hz, 2H), 8.07-8.00 (m, 2H), 7.52 (d, J=1.1 Hz, 1H), 7.37 (t, J=4.9 Hz, 1H), 7.20 (t, J=8.7 Hz, 2H), 6.78 (d, J=1.1 Hz, 1H), 4.34-4.18 (m, 1H), 4.10-4.07 (m, 1H), 4.01-3.87 (s, 1H), 3.80-3.72 (m, 2H), 2.65 (s, 3H), 2.18-1.86 (m, 2H), 1.50 (s, 6H) ppm.

Example 9

((1R,5S,6s)-6-((4-(2-aminopropan-2-yl)-6-(4-fluorophenyl)pyridin-2-yl)oxy)-3-azabicyclo[3.1.0]hexan-3-yl)(2-(pyrimidin-2-yl)thiazol-5-yl)methanone

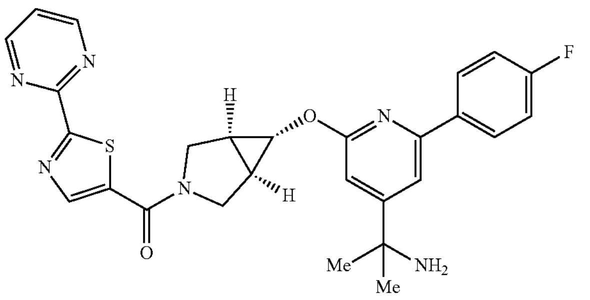 [SMILES: CC(C)(N)c1cc(O[C@H]2[C@@H]3CN(C(=O)c4cnc(-c5ncccn5)s4)C[C@@H]32)nc(-c2ccc(F)cc2)c1]

A mixture of 2-(2-(((1R,5S,6s)-3-azabicyclo[3.1.0]hexan-6-yl)oxy)-6-(4-fluorophenyl)pyridin-4-yl)propan-2-amine·HCl (Int. H-1, 31 mg, 0.070 mmol), 2-(pyrimidin-2-yl)thiazole-5-carboxylic acid (17 mg, 0.084 mmol), DMF (0.70 mL), DIPEA (37 μL, 0.21 mmol), and HATU (29 mg, 0.077 mmol) was stirred at rt for 16 h. The mixture was subjected to reverse phase HPLC (10-100% MeCN/water with 0.1% TFA modifier) to afford the title compound. MS m/z $(M+H)^+$: calculated 517.2, observed 517.2. $^1H$ NMR (500 MHz, DMSO-$d^6$) δ 9.00 (d, J=4.9 Hz, 2H), 8.58 (s, 3H), 8.49 (s, 1H), 8.23-8.16 (m, 2H), 7.76 (d, J=1.2 Hz, 1H), 7.65 (t, J=4.9 Hz, 1H), 7.39-7.33 (m, 2H), 6.91 (d, J=1.2 Hz, 1H), 4.17-4.04 (m, 4H), 3.74 (dd, J=12.2, 5.1 Hz, 1H), 2.21-2.15 (m, 1H), 2.10-2.04 (m, 1H), 1.66 (s, 6H) ppm.

Utilizing the procedures described in EXAMPLE 9, the below compounds were prepared substituting the appropriate reagents for 2-(pyrimidin-2-yl)thiazole-5-carboxylic acid.

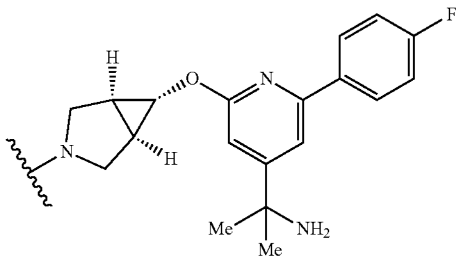 [SMILES: *N1C[C@@H]2[C@H](C1)[C@H]2Oc1cc(C(C)(C)N)cc(-c2ccc(F)cc2)n1]

| Ex # | Structure | Name | Calc'd $[M + H]^+$ | Observed $[M + H]^+$ |
|---|---|---|---|---|
| 10 | 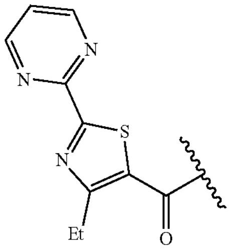 [SMILES: *C(=O)c1sc(-c2ncccn2)nc1CC] | ((1R,5S,6s)-6-((4-(2-aminopropan-2-yl)-6-(4-fluorophenyl)pyridin-2-yl)oxy)-3-azabicyclo[3.1.0]hexan-3-yl)(4-ethyl-2-(pyrimidin-2-yl)thiazol-5-yl)methanone | 545.2 | 545.3 |

-continued

| Ex # | Structure | Name | Calc'd [M + H]+ | Observed [M + H]+ |
|---|---|---|---|---|
| 11 | 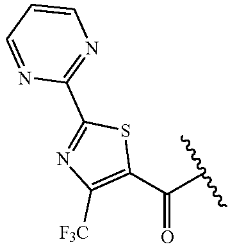 [SMILES: *C(=O)c1sc(-c2ncccn2)nc1C(F)(F)F] | ((1R,5S,6s)-6-((4-(2-aminopropan-2-yl)-6-(4-fluorophenyl)pyridin-2-yl)oxy)-3-azabicyclo[3.1.0]hexan-3-yl)(2-(pyrimidin-2-yl)-4-(trifluoromethyl)thiazol-5-yl)methanone | 584.2 | 584.1 |
| 12 | 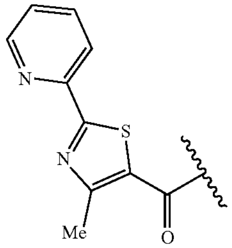 [SMILES: *C(=O)c1sc(-c2ccccn2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(pyridin-2-yl)thiazol-5-yl)methanone | 530.2 | 530.4 |

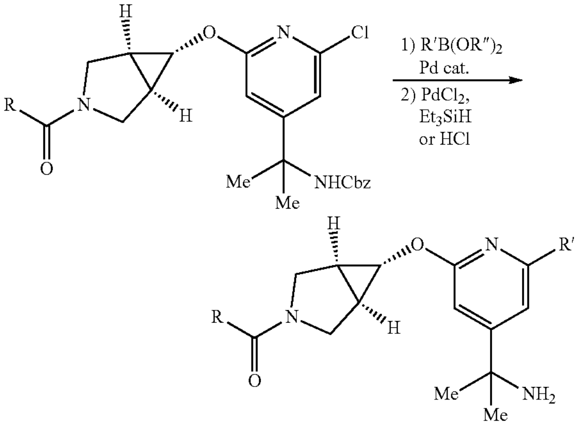

Example 13

((1R,5S,6s)-6-((4-(2-aminopropan-2-yl)-6-(3,4,5-trifluorophenyl)pyridin-2-yl)oxy)-3-azabicyclo[3.1.0]hexan-3-yl)(4-methyl-2-(pyrimidin-2-yl)thiazol-5-yl)methanone

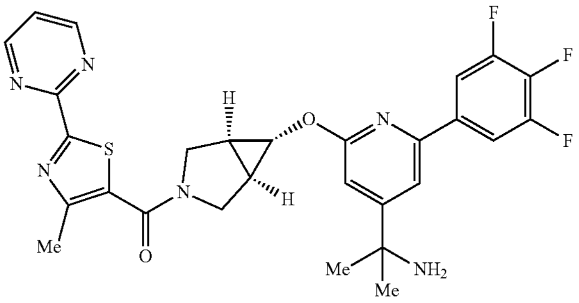 [SMILES: Cc1nc(-c2ncccn2)sc1C(=O)N1C[C@@H]2[C@H](C1)[C@H]2Oc1cc(C(C)(C)N)cc(-c2cc(F)c(F)c(F)c2)n1]

Under an atmosphere of nitrogen, a mixture of benzyl (2-(2-chloro-6-(((1R,5S,6s)-3-(4-methyl-2-(pyrimidin-2-yl)thiazole-5-carbonyl)-3-azabicyclo[3.1.0]hexan-6-yl)oxy)pyridin-4-yl)propan-2-yl)carbamate (Int. I-1, 75 mg, 0.12 mmol), 3,4,5-trifluorophenylboronic acid pinacol ester (38 mg, 0.15 mmol), XPhos Pd G2 (9.8 mg, 0.012 mmol), potassium phosphate (1.0 M aqueous, 0.37 mL, 0.37 mmol), and 1,4-dioxane (1.2 mL) were combined and heated at 100° C. for 16 h. The mixture was cooled to rt, filtered, and concentrated under reduced pressure. HCl (37%, 0.20 mL) was added, the mixture was heated at 80° C. for 10 min and then concentrated. The residue was subjected to reverse phase HPLC (10-100% MeCN/water with 0.1% TFA modifier) and the appropriate fractions poured into sodium bicarbonate (saturated aqueous) and extracted with DCM. The combined organic extracts were washed with brine, dried with anhydrous sodium sulfate, filtered, and concentrated under reduced pressure to afford the title compound. MS m/z $(M+H)^+$: calculated 567.2; found 567.4. $^1H$ NMR (500 MHz, $CDCl_3$) δ 8.90-8.82 (m, 2H), 7.68-7.59 (m, 2H), 7.47 (s, 1H), 7.35 (t, J=4.8 Hz, 1H), 6.85 (s, 1H), 4.24 (s, 1H), 4.02 (s, 1H), 3.90 (s, 1H), 3.79 (dd, J=11.4, 4.3 Hz, 2H), 2.65 (s, 3H), 2.15-2.05 (m, 2H), 1.71-1.61 (m, 2H), 1.50 (s, 6H) ppm.

Utilizing the procedures described in EXAMPLE 13, the below compounds were prepared substituting the appropriate reagents for 3,4,5-trifluorophenylboronic acid pinacol ester.

Optionally, following HPLC purification, free bases may be prepared as in EXAMPLE 13, or mixtures may be concentrated under reduced pressure to generate salt forms such as trifluoroacetate (TFA) salts.

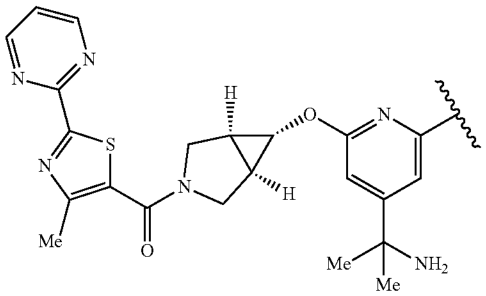 [SMILES: *c1cc(C(C)(C)N)cc(O[C@H]2[C@@H]3CN(C(=O)c4sc(-c5ncccn5)nc4C)C[C@@H]32)n1]

| Ex # | Structure | Name | Calc'd [M + H]$^+$ | Observed [M + H]$^+$ | Optional Form |
|---|---|---|---|---|---|
| 14 | 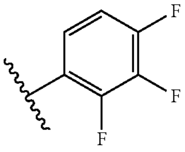 [SMILES: *c1ccc(F)c(F)c1F] | ((1R,5S,6s)-6-((4-(2-aminopropan-2-yl)-6-(2,3,4-trifluorophenyl)pyridin-2-yl)oxy)-3-azabicyclo[3.1.0]hexan-3-yl)(4-methyl-2-(pyrimidin-2-yl)thiazol-5-yl)methanone | 567.2 | 567.3 | TFA salt |
| 15 | 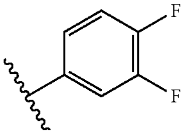 [SMILES: *c1ccc(F)c(F)c1] | ((1R,5S,6s)-6-((4-(2-aminopropan-2-yl)-6-(3,4-difluorophenyl)pyridin-2-yl)oxy)-3-azabicyclo[3.1.0]hexan-3-yl)(4-methyl-2-(pyrimidin-2-yl)thiazol-5-yl)methanone | 549.2 | 549.3 | TFA salt |
| 16 | 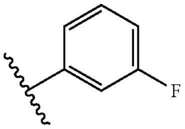 [SMILES: *c1cccc(F)c1] | ((1R,5S,6s)-6-((4-(2-aminopropan-2-yl)-6-(3-fluorophenyl)pyridin-2-yl)oxy)-3-azabicyclo[3.1.0]hexan-3-yl)(4-methyl-2-(pyrimidin-2-yl)thiazol-5-yl)methanone | 531.2 | 531.3 | TFA salt |
| 17 | 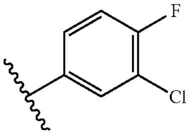 [SMILES: *c1ccc(F)c(Cl)c1] | ((1R,5S,6s)-6-((4-(2-aminopropan-2-yl)-6-(3-chloro-4-fluorophenyl)pyridin-2-yl)oxy)-3-azabicyclo[3.1.0]hexan-3-yl)(4-methyl-2-(pyrimidin-2-yl)thiazol-5-yl)methanone | 565.2 | 565.3 | TFA salt |
| 18 | 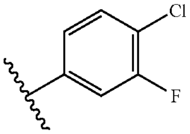 [SMILES: *c1ccc(Cl)c(F)c1] | ((1R,5S,6s)-6-((4-(2-aminopropan-2-yl)-6-(4-chloro-3-fluorophenyl)pyridin-2-yl)oxy)-3-azabicyclo[3.1.0]hexan-3-yl)(4-methyl-2-(pyrimidin-2-yl)thiazol-5-yl)methanone | 565.2 | 565.3 | Free base |
| 19 | 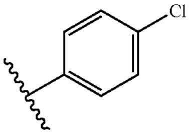 [SMILES: *c1ccc(Cl)cc1] | ((1R,5S,6s)-6-((4-(2-aminopropan-2-yl)-6-(4-chlorophenyl)pyridin-2-yl)oxy)-3-azabicyclo[3.1.0]hexan-3-yl)(4-methyl-2-(pyrimidin-2-yl)thiazol-5-yl)methanone | 547.2 | 547.3 | TFA salt |
| 20 | 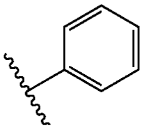 [SMILES: *c1ccccc1] | ((1R,5S,6s)-6-((4-(2-aminopropan-2-yl)-6-phenylpyridin-2-yl)oxy)-3-azabicyclo[3.1.0]hexan-3-yl)(4-methyl-2-(pyrimidin-2-yl)thiazol-5-yl)methanone | 513.2 | 513.3 | TFA salt |

-continued

| Ex # | Structure | Name | Calc'd [M + H]+ | Observed [M + H]+ | Optional Form |
|---|---|---|---|---|---|
| 21 | 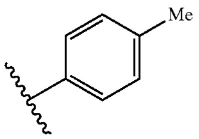 [SMILES: *c1ccc(C)cc1] | ((1R,5S,6s)-6-((4-(2-aminopropan-2-yl)-6-(p-tolyl)pyridin-2-yl)oxy)-3-azabicyclo[3.1.0]hexan-3-yl)(4-methyl-2-(pyrimidin-2-yl)thiazol-5-yl)methanone | 527.2 | 527.3 | TFA salt |
| 22 | 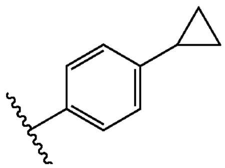 [SMILES: *c1ccc(C2CC2)cc1] | ((1R,5S,6s)-6-((4-(2-aminopropan-2-yl)-6-(4-cyclopropylphenyl)pyridin-2-yl)oxy)-3-azabicyclo[3.1.0]hexan-3-yl)(4-methyl-2-(pyrimidin-2-yl)thiazol-5-yl)methanone | 553.3 | 553.4 | TFA salt |
| 23 | 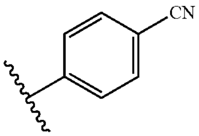 [SMILES: *c1ccc(C#N)cc1] | 4-(4-(2-aminopropan-2-yl)-6-(((1R,5S,6s)-3-(4-methyl-2-(pyrimidin-2-yl)thiazole-5-carbonyl)-3-azabicyclo[3.1.0]hexan-6-yl)oxy)pyridin-2-yl)benzonitrile | 538.2 | 538.3 | TFA salt |
| 24 | 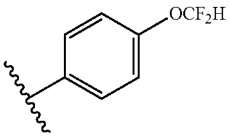 | ((1R,5S,6s)-6-((4-(2-aminopropan-2-yl)-6-(4-(difluoromethoxy)phenyl) pyridin-2-yl)oxy)-3-azabicyclo[3.1.0]hexan-3-yl)(4-methyl-2-(pyrimidin-2-yl)thiazol-5-yl)methanone | 579.2 | 579.3 | TFA salt |
| 25 | 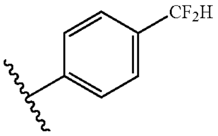 [SMILES: *c1ccc(C(F)F)cc1] | ((1R,5S,6s)-6-((4-(2-aminopropan-2-yl)-6-(4-(difluoromethyl)phenyl)pyridin-2-yl)oxy)-3-azabicyclo[3.1.0]hexan-3-yl)(4-methyl-2-(pyrimidin-2-yl)thiazol-5-yl)methanone | 563.2 | 563.3 | TFA salt |
| 26 | 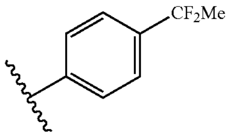 | ((1R,5S,6s)-6-((4-(2-aminopropan-2-yl)-6-(4-(1,1-difluoroethyl)phenyl)pyridin-2-yl)oxy)-3-azabicyclo[3.1.0]hexan-3-yl)(4-methyl-2-(pyrimidin-2-yl)thiazol-5-yl)methanone | 577.2 | 577.3 | TFA salt |
| 27 | 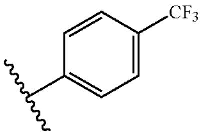 [SMILES: *c1ccc(C(F)(F)F)cc1] | ((1R,5S,6s)-6-((4-(2-aminopropan-2-yl)-6-(4-(trifluoromethyl)phenyl)pyridin-2-yl)oxy)-3-azabicyclo[3.1.0]hexan-3-yl)(4-methyl-2-(pyrimidin-2-yl)thiazol-5-yl)methanone | 581.2 | 581.4 | Free base |
| 28 | 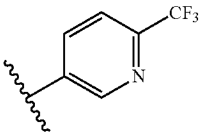 [SMILES: *c1ccc(C(F)(F)F)nc1] | ((1R,5S,6s)-6-((4-(2-aminopropan-2-yl)-6'-(trifluoromethyl)-[2,3'-bipyridin]-6-yl)oxy)-3-azabicyclo[3.1.0]hexan-3-yl)(4-methyl-2-(pyrimidin-2-yl)thiazol-5-yl)methanone | 582.2 | 582.3 | TFA salt |
| 29 | 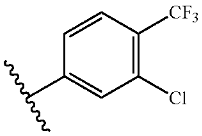 [SMILES: *c1ccc(C(F)(F)F)c(Cl)c1] | ((1R,5S,6s)-6-((4-(2-aminopropan-2-yl)-6-(3-chloro-4-(trifluoromethyl)phenyl)pyridin-2-yl)oxy)-3-azabicyclo[3.1.0]hexan-3-yl)(4-methyl-2-(pyrimidin-2-yl)thiazol-5-yl)methanone | 615.1 | 615.3 | TFA salt |

-continued

| Ex # | Structure | Name | Calc'd $[M + H]^+$ | Observed $[M + H]^+$ | Optional Form |
|---|---|---|---|---|---|
| 30 | 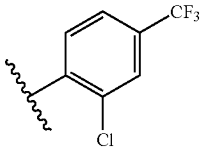 [SMILES: *c1ccc(C(F)(F)F)cc1Cl] | ((1R,5S,6s)-6-((4-(2-aminopropan-2-yl)-6-(2-chloro-4-(trifluoromethyl)phenyl)pyridin-2-yl)oxy)-3-azabicyclo[3.1.0]hexan-3-yl)(4-methyl-2-(pyrimidin-2-yl)thiazol-5-yl)methanone | 615.1 | 615.3 | TFA salt |
| 31 | 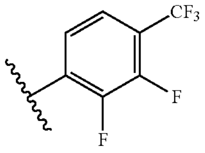 [SMILES: *c1ccc(C(F)(F)F)c(F)c1F] | ((1R,5S,6s)-6-((4-(2-aminopropan-2-yl)-6-(2,3-difluoro-4-(trifluoromethyl)phenyl)pyridin-2-yl)oxy)-3-azabicyclo[3.1.0]hexan-3-yl)(4-methyl-2-(pyrimidin-2-yl)thiazol-5-yl)methanone | 617.2 | 617.3 | TFA salt |
| 32 | 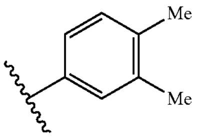 [SMILES: *c1ccc(C)c(C)c1] | ((1R,5S,6s)-6-((4-(2-aminopropan-2-yl)-6-(3,4-dimethylphenyl)pyridin-2-yl)oxy)-3-azabicyclo[3.1.0]hexan-3-yl)(4-methyl-2-(pyrimidin-2-yl)thiazol-5-yl)methanone | 541.2 | 541.4 | TFA salt |
| 33 | 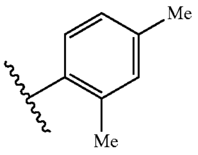 [SMILES: *c1ccc(C)cc1C] | ((1R,5S,6s)-6-((4-(2-aminopropan-2-yl)-6-(2,4-dimethylphenyl)pyridin-2-yl)oxy)-3-azabicyclo[3.1.0]hexan-3-yl)(4-methyl-2-(pyrimidin-2-yl)thiazol-5-yl)methanone | 541.2 | 541.4 | TFA salt |
| 34 | 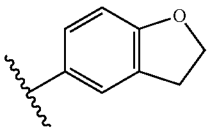 [SMILES: *c1ccc2c(c1)CCO2] | ((1R,5S,6s)-6-((4-(2-aminopropan-2-yl)-6-(2,3-dihydrobenzofuran-5-yl)pyridin-2-yl)oxy)-3-azabicyclo[3.1.0]hexan-3-yl)(4-methyl-2-(pyrimidin-2-yl)thiazol-5-yl)methanone | 555.2 | 555.0 | TFA salt |
| 35 | 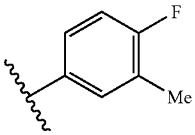 [SMILES: *c1ccc(F)c(C)c1] | ((1R,5S,6s)-6-((4-(2-aminopropan-2-yl)-6-(4-fluoro-3-methylphenyl)pyridin-2-yl)oxy)-3-azabicyclo[3.1.0]hexan-3-yl)(4-methyl-2-(pyrimidin-2-yl)thiazol-5-yl)methanone | 545.3 | 545.3 | TFA salt |
| 36 | 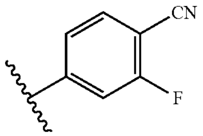 [SMILES: *c1ccc(C#N)c(F)c1] | 4-(4-(2-aminopropan-2-yl)-6-(((1R,5S,6s)-3-(4-methyl-2-(pyrimidin-2-yl)thiazole-5-carbonyl)-3-azabicyclo[3.1.0]hexan-6-yl)oxy)pyridin-2-yl)-2-fluorobenzonitrile | 556.2 | 556.3 | TFA salt |
| 37 | 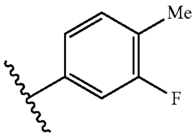 [SMILES: *c1ccc(C)c(F)c1] | ((1R,5S,6s)-6-((4-(2-aminopropan-2-yl)-6-(3-fluoro-4-methylphenyl)pyridin-2-yl)oxy)-3-azabicyclo[3.1.0]hexan-3-yl)(4-methyl-2-(pyrimidin-2-yl)thiazol-5-yl)methanone | 545.2 | 545.3 | TFA salt |
| 38 | 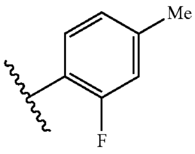 [SMILES: *c1ccc(C)cc1F] | ((1R,5S,6s)-6-((4-(2-aminopropan-2-yl)-6-(2-fluoro-4-methylphenyl)pyridin-2-yl)oxy)-3-azabicyclo[3.1.0]hexan-3- | 545.2 | 545.3 | TFA salt |

-continued

| Ex # | Structure | Name | Calc'd [M + H]+ | Observed [M + H]+ | Optional Form |
|---|---|---|---|---|---|
| | | yl)(4-methyl-2-(pyrimidin-2-yl)thiazol-5-yl)methanone | | | |
| 39 | 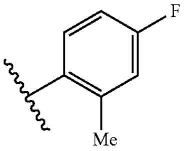 [SMILES: *c1ccc(F)cc1C] | ((1R,5S,6s)-6-((4-(2-aminopropan-2-yl)-6-(4-fluoro-2-methylphenyl)pyridin-2-yl)oxy)-3-azabicyclo[3.1.0]hexan-3-yl)(4-methyl-2-(pyrimidin-2-yl)thiazol-5-yl)methanone | 545.2 | 545.3 | TFA salt |
| 40 | 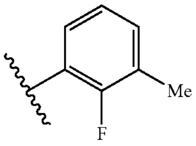 [SMILES: *c1cccc(C)c1F] | ((1R,5S,6s)-6-((4-(2-aminopropan-2-yl)-6-(2-fluoro-3-methylphenyl)pyridin-2-yl)oxy)-3-azabicyclo[3.1.0]hexan-3-yl)(4-methyl-2-(pyrimidin-2-yl)thiazol-5-yl)methanone | 545.2 | 545.4 | TFA salt |
| 41 | 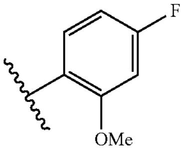 [SMILES: *c1ccc(F)cc1OC] | ((1R,5S,6s)-6-((4-(2-aminopropan-2-yl)-6-(4-fluoro-2-methoxyphenyl)pyridin-2-yl)oxy)-3-azabicyclo[3.1.0]hexan-3-yl)(4-methyl-2-(pyrimidin-2-yl)thiazol-5-yl)methanone | 561.2 | 561.4 | TFA salt |
| 42 | 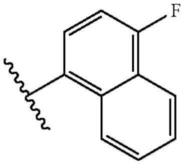 [SMILES: *c1ccc(F)c2ccccc12] | ((1R,5S,6s)-6-((4-(2-aminopropan-2-yl)-6-(4-fluoronaphthalen-1-yl)pyridin-2-yl)oxy)-3-azabicyclo[3.1.0]hexan-3-yl)(4-methyl-2-(pyrimidin-2-yl)thiazol-5-yl)methanone | 581.2 | 581.4 | TFA salt |
| 43 | 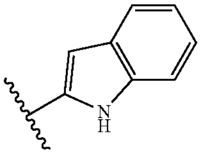 [SMILES: *c1cc2ccccc2[nH]1] | ((1R,5S,6s)-6-((4-(2-aminopropan-2-yl)-6-(1H-indol-2-yl)pyridin-2-yl)oxy)-3-azabicyclo[3.1.0]hexan-3-yl)(4-methyl-2-(pyrimidin-2-yl)thiazol-5-yl)methanone | 552.2 | 552.2 | TFA salt |
| 44 | 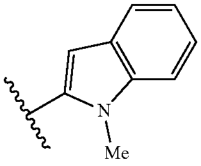 [SMILES: *c1cc2ccccc2n1C] | ((1R,5S,6s)-6-((4-(2-aminopropan-2-yl)-6-(1-methyl-1H-indol-2-yl)pyridin-2-yl)oxy)-3-azabicyclo[3.1.0]hexan-3-yl)(4-methyl-2-(pyrimidin-2-yl)thiazol-5-yl)methanone | 566.2 | 566.2 | TFA salt |
| 45 | 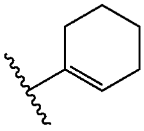 [SMILES: *C1=CCCCC1] | ((1R,5S,6s)-6-((4-(2-aminopropan-2-yl)-6-(cyclohex-1-en-1-yl)pyridin-2-yl)oxy)-3-azabicyclo[3.1.0]hexan-3-yl)(4-methyl-2-(pyrimidin-2-yl)thiazol-5-yl)methanone | 517.2 | 517.4 | TFA salt |
| 46 | 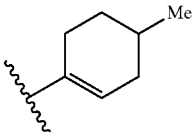 [SMILES: *C1=CCC(C)CC1] | rac-((1R,5S,6s)-6-((4-(2-aminopropan-2-yl)-6-(4-methylcyclohex-1-en-1-yl)pyridin-2-yl)oxy)-3-azabicyclo[3.1.0]hexan-3-yl)(4-methyl-2-(pyrimidin-2-yl)thiazol-5-yl)methanone | 531.2 | 531.4 | TFA salt |

-continued

| Ex # | Structure | Name | Calc'd $[M + H]^+$ | Observed $[M + H]^+$ | Optional Form |
|---|---|---|---|---|---|
| 47 | 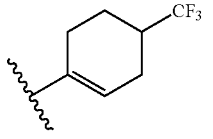 [SMILES: *C1=CCC(C(F)(F)F)CC1] | rac-((1R,5S,6s)-6-((4-(2-aminopropan-2-yl)-6-(4-(trifluoromethyl)cyclohex-1-en-1-yl)pyridin-2-yl)oxy)-3-azabicyclo[3.1.0]hexan-3-yl)(4-methyl-2-(pyrimidin-2-yl)thiazol-5-yl)methanone | 585.2 | 585.4 | TFA salt |
| 48 | 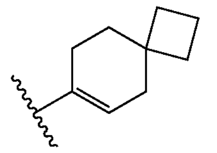 [SMILES: *C1=CCC2(CCC2)CC1] | ((1R,5S,6s)-6-((4-(2-aminopropan-2-yl)-6-(spiro[3.5]non-6-en-7-yl)pyridin-2-yl)oxy)-3-azabicyclo[3.1.0]hexan-3-yl)(4-methyl-2-(pyrimidin-2-yl)thiazol-5-yl)methanone | 557.3 | 557.3 | TFA salt |

Scheme

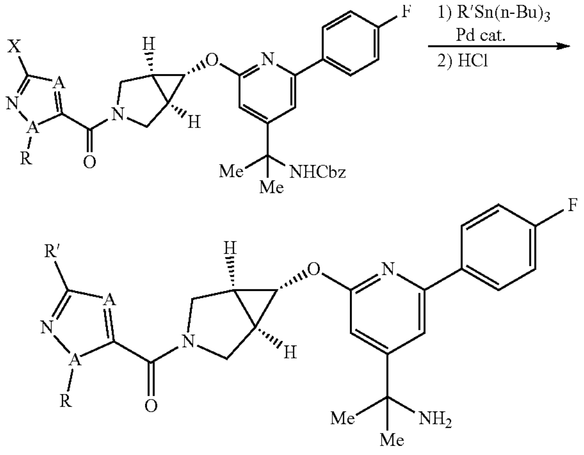

Example 49

((1R,5S,6s)-6-((4-(2-aminopropan-2-yl)-6-(4-fluorophenyl)pyridin-2-yl)oxy)-3-azabicyclo[3.1.0]hexan-3-yl)(4-(difluoromethyl)-2-(pyrimidin-2-yl)thiazol-5-yl)methanone

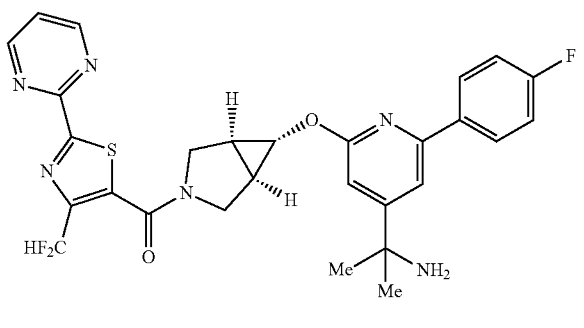

Under an atmosphere of nitrogen, benzyl (2-(2-(((1R,5S,6s)-3-(2-chloro-4-(difluoromethyl)thiazole-5-carbonyl)-3-azabicyclo[3.1.0]hexan-6-yl)oxy)-6-(4-fluorophenyl)pyridin-4-yl)propan-2-yl)carbamate (Int. K-2, 15 mg, 0.020 mmol), 2-(tributylstannyl)pyrimidine (16 mg, 0.040 mmol), Pd(PPh3)4 (2.5 mg, 2.0 μmol), and 1,4-dioxane (0.50 mL) were combined and heated at 100° C. for 16 h. The mixture was cooled to rt, filtered, and concentrated under reduced pressure. HCl (37% aqueous, 0.20 mL) was added, the mixture was stirred at 80° C. for 10 min, and then concentrated under reduced pressure. The residue was subjected to reverse phase HPLC (MeCN/water with 0.1% TFA modifier) to afford the title compound as a TFA salt. MS m/z $(M+H)^+$: calculated 567.2; found 567.3. $^1H$ NMR (500 MHz, DMSO-$d^6$) δ 9.01 (d, J=4.9 Hz, 2H), 8.57 (br s, 3H), 8.23-8.16 (m, 2H), 7.73 (d, J=1.1 Hz, 1H), 7.70 (t, J=4.9 Hz, 1H), 7.36-7.30 (m, 2H), 7.26 (t, J=54 Hz, 1H), 6.85 (d, J=1.1 Hz, 1H), 4.15-4.13 (m, 1H), 4.05 (d, J=12.2 Hz, 1H), 3.77-3.50 (m, 3H), 2.19-2.11 (m, 1H), 2.03-1.93 (m, 1H), 1.64 (s, 6H) ppm.

Example 50

((1R,5S,6s)-6-((4-(2-aminopropan-2-yl)-6-(4-fluorophenyl)pyridin-2-yl)oxy)-3-azabicyclo[3.1.0]hexan-3-yl)(3-(6-fluoropyridin-2-yl)-1-methyl-1H-pyrazol-5-yl)methanone

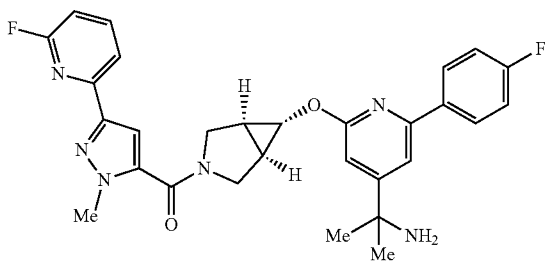 [SMILES: Cn1nc(-c2cccc(F)n2)cc1C(=O)N1C[C@@H]2[C@H](C1)[C@H]2Oc1cc(C(C)(C)N)cc(-c2ccc(F)cc2)n1]

A mixture of benzyl (2-(2-((3-(3-bromo-1-methyl-1H-pyrazole-5-carbonyl)-3-azabicyclo[3.1.0]hexan-6-yl)oxy)-6-(4-fluorophenyl)pyridin-4-yl)propan-2-yl)carbamate (Int. K-1, 22 mg, 0.034 mmol), Pd(PPh3)4 (5.9 mg, 0.050 mmol), 2-fluoro-6-(tributylstannyl)pyridine (33 mg, 0.085 mmol), and 1,4-dioxane (0.50 mL) were combined then heated at 80° C. for 48 h. The mixture was cooled to room temperature and concentrated under reduced pressure. The mixture was subjected to reverse phase HPLC (MeCN/water with 0.1%

TFA modifier) and the appropriate fractions were concentrated under reduced pressure to afford the title compound as a TFA salt. MS m/z $(M+H)^+$: calculated 531.2, observed 531.1. $^1H$ NMR (500 MHz, DMSO-$d^6$) δ 8.09 (dd, J=8.3, 5.7 Hz, 2H), 7.98 (q, J=8.1 Hz, 1H), 7.80 (dd, J=7.5, 2.1 Hz, 1H), 7.65 (s, 1H), 7.25 (t, J=8.7 Hz, 2H), 7.09 (s, 1H), 7.05 (dd, J=8.1, 2.2 Hz, 1H), 6.79 (s, 1H), 4.02-3.95 (m, 2H), 3.91 (s, 3H), 3.91-3.81 (m, 2H), 3.60 (dd, J=12.3, 4.6 Hz, 1H), 2.02-1.93 (m, 2H), 1.56 (s, 6H) ppm.

Utilizing the procedure described in EXAMPLE 50, the below compound was prepared substituting the appropriate reagents for 2-fluoro-6-(tributylstannyl)pyridine.

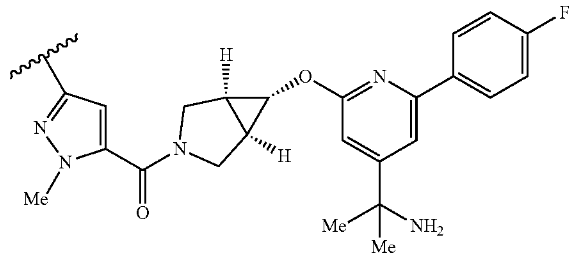 [SMILES: *c1cc(C(=O)N2C[C@@H]3[C@H](C2)[C@H]3Oc2cc(C(C)(C)N)cc(-c3ccc(F)cc3)n2)n(C)n1]

To mixture of 1-methyl-3-(pyrimidin-2-yl)-1H-pyrazole-5-carboxylic acid (Int. M, 13 mg, 0.062 mmol), HATU (57 mg, 0.15 mmol), and DMF (1.0 mL) was added 2-(2-(((1R,5S,6s)-3-azabicyclo[3.1.0]hexan-6-yl)oxy)-6-(4-fluorophenyl)pyridin-4-yl)propan-2-amine hydrochloride (Int. H-01, 0.050 g, 0.13 mmol) and triethylamine (0.052 mL, 0.38 mmol). The mixture was stirred at rt for 30 min and then subjected to reverse phase HPLC (5-95% MeCN/water with 0.1% TFA modifier). The appropriate fractions were lyophilized to afford the title compound as a TFA salt. MS m/z $(M+H)^+$: calculated 514.2, observed 514.1. $^1H$ NMR (500 MHz, $CD_3OD$) δ 8.86 (d, J=4.0 Hz, 2H), 8.17-8.12 (m, 2H), 7.60 (d, J=1.2 Hz, 1H), 7.44 (t, J=4.1 Hz, 1H), 7.36 (s, 1H), 7.26-7.18 (m, 2H), 6.81 (d, J=1.2 Hz, 1H), 4.25 (d, J=12.4 Hz, 1H), 4.10 (s, 3H), 4.09-4.04 (m, 2H), 4.00 (dd, J=10.7, 4.4 Hz, 1H), 3.77 (dd, J=12.4, 4.6 Hz, 1H), 2.16-2.10 (m, 1H), 2.10-2.04 (m, 1H), 1.75 (s, 6H) ppm.

| Ex # | Structure | Name | Calc'd $[M + H]^+$ | Observed $[M + H]^+$ |
|---|---|---|---|---|
| 51 | 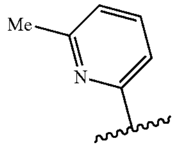 [SMILES: *c1cccc(C)n1] | ((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(6-methylpyridin-2-yl)-1H-pyrazol-5-yl)methanone | 527.3 | 527.2 |

Example 52

((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(pyrimidin-2-yl)-1H-pyrazol-5-yl)methanone

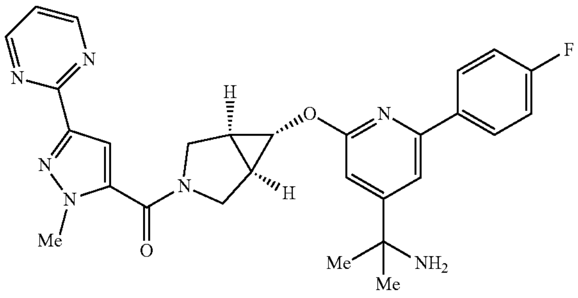 [SMILES: Cn1nc(-c2ncccn2)cc1C(=O)N1C[C@@H]2[C@H](C1)[C@H]2Oc1cc(C(C)(C)N)cc(-c2ccc(F)cc2)n1]

Example 53

((1R,5S,6s)-6-((4-(2-aminopropan-2-yl)-6-(4-fluorophenyl)pyridin-2-yl)oxy)-3-azabicyclo[3.1.0]hexan-3-yl)(4-chloro-1-methyl-3-(pyrimidin-2-yl)-1H-pyrazol-5-yl)methanone

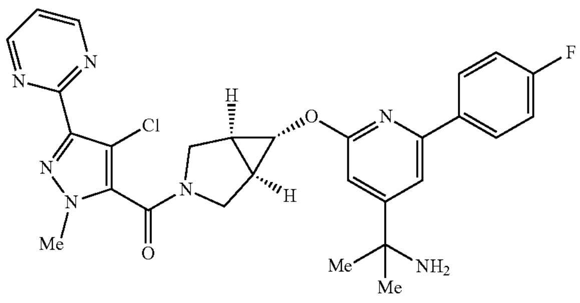 [SMILES: Cn1nc(-c2ncccn2)c(Cl)c1C(=O)N1C[C@@H]2[C@H](C1)[C@H]2Oc1cc(C(C)(C)N)cc(-c2ccc(F)cc2)n1]

Example 54

((1R,5S,6s)-6-((4-(2-aminopropan-2-yl)-6-(4-fluorophenyl)pyridin-2-yl)oxy)-3-azabicyclo[3.1.0]hexan-3-yl)(4-fluoro-1-methyl-3-(pyrimidin-2-yl)-1H-pyrazol-5-yl)methanone

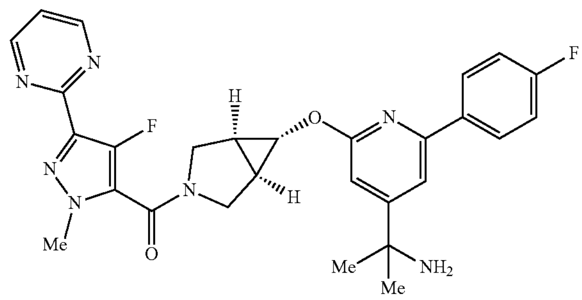 [SMILES: Cn1nc(-c2ncccn2)c(F)c1C(=O)N1C[C@@H]2[C@H](C1)[C@H]2Oc1cc(C(C)(C)N)cc(-c2ccc(F)cc2)n1]

To a solution of ethyl 1-methyl-3-(pyrimidin-2-yl)-1H-pyrazole-5-carboxylate (0.10 g, 0.43 mmol) in MeCN (4.3 mL) was added 1-chloromethyl-4-fluoro-1,4-diazoniabicyclo[2.2.2]octane bis(tetrafluoroborate) (0.34 g, 0.95 mmol). The mixture was heated at 80° C. for 16 h and then cooled to rt, diluted with water (20 mL), and extracted with DCM (20 mL×3). The combined organic extracts were dried with anhydrous magnesium sulfate, filtered, and concentrated under reduced pressure. The residue was subjected to silica gel chromatography (0-6% (3:1 EtOAc:EtOH) in DCM) to afford a mixture of ethyl 4-fluoro-1-methyl-3-(pyrimidin-2-yl)-1H-pyrazole-5-carboxylate and ethyl 4-chloro-1-methyl-3-(pyrimidin-2-yl)-1H-pyrazole-5-carboxylate. The mixture was dissolved in 1,4-dioxane (1.0 mL) and water (1.0 mL) and lithium hydroxide (9.6 mg, 0.40 mmol) was added. The mixture was stirred at rt for 16 h, diluted with a solution of sodium hydroxide (1 N aqueous, 20 mL), and washed with DCM (20 mL×2). The aqueous solution was acidified to pH=1-2 with HCl (1 N aqueous) and extracted with DCM (30 mL×3). The combined organic extracts were dried with anhydrous magnesium sulfate, filtered, and concentrated under reduced pressure to afford a mixture of 4-fluoro-1-methyl-3-(pyrimidin-2-yl)-1H-pyrazole-5-carboxylic acid and 4-chloro-1-methyl-3-(pyrimidin-2-yl)-1H-pyrazole-5-carboxylic acid. To the mixture was added 2-(2-(((1R,5S,6s)-3-azabicyclo[3.1.0]hexan-6-yl)oxy)-6-(4-fluorophenyl)pyridin-4-yl)propan-2-amine hydrochloride (Int. H-01, 22 mg, 0.050 mmol), DMF (0.45 mL), DIPEA (0.039 mL, 0.23 mmol) and HATU (17 mg, 0.045 mmol). The mixture was stirred at rt for 3 h and subjected to reverse phase HPLC (10-100% MeCN/water with 0.1% TFA modifier). Fractions containing ((1R,5S,6s)-6-((4-(2-aminopropan-2-yl)-6-(4-fluorophenyl)pyridin-2-yl)oxy)-3-azabicyclo[3.1.0]hexan-3-yl)(4-chloro-1-methyl-3-(pyrimidin-2-yl)-1H-pyrazol-5-yl)methanone were passaged through a SCX-2 column, which was washed with MeOH (2 mL×3) and eluted with a methanolic solution of ammonia (2 N, 2 mL×3) to afford EXAMPLE 53: MS m/z $(M+H)^+$: calculated 548.2, observed 548.3. Fractions containing ((1R,5S,6s)-6-((4-(2-aminopropan-2-yl)-6-(4-fluorophenyl)pyridin-2-yl)oxy)-3-azabicyclo[3.1.0]hexan-3-yl)(4-fluoro-1-methyl-3-(pyrimidin-2-yl)-1H-pyrazol-5-yl)methanone were passaged through a SCX-2 column, which was washed with MeOH (2 mL×3) and eluted with a methanolic solution of ammonia (2N, 2 mL×3) to afford EXAMPLE 54. MS m/z $(M+H)^+$: calculated 532.2, observed 532.4. $^1$H NMR (500 MHz, DMSO-$d^6$) δ 8.93 (d, J=4.9 Hz, 2H), 8.26-822 (m, 2H), 7.78 (d, J=1.0 Hz, 1H), 7.53 (t, J=4.9 Hz, 1H), 7.43-7.38 (m, 2H), 6.89 (d, J=1.0 Hz, 1H), 4.06-4.02 (m, 2H), 3.96-3.91 (m, 4H), 3.86-3.81 (m, 1H), 3.71-3.66 (m, 1H), 2.19-2.14 (m, 1H), 1.98-1.94 (m, 1H), 1.43 (s, 6H) ppm.

Example 55

((1R,5S,6s)-6-((4-(2-aminopropan-2-yl)-6-(3,4-difluorophenyl)pyridin-2-yl)oxy)-3-azabicyclo[3.1.0]hexan-3-yl)(1-methyl-3-(pyrimidin-2-yl)-1H-pyrazol-5-yl)methanone

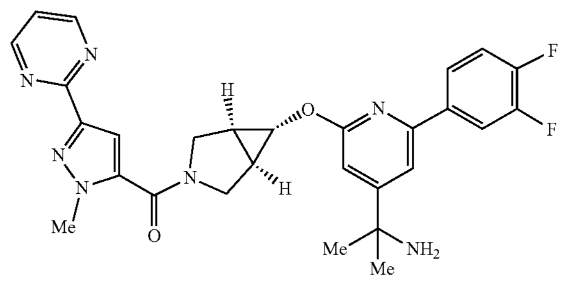 [SMILES: Cn1nc(-c2ncccn2)cc1C(=O)N1C[C@@H]2[C@H](C1)[C@H]2Oc1cc(C(C)(C)N)cc(-c2ccc(F)c(F)c2)n1]

Under an atmosphere of nitrogen, a mixture of benzyl (2-(2-chloro-6-(((1R,5S,6s)-3-(1-methyl-3-(pyrimidin-2-yl)-1H-pyrazole-5-carbonyl)-3-azabicyclo[3.1.0]hexan-6-yl)oxy)pyridin-4-yl)propan-2-yl)carbamate (Int. I-2, 0.060 g, 0.10 mmol), (3,4-difluorophenyl)boronic acid (19 mg, 0.12 mmol), chloro(2-dicyclohexylphosphino-2',4',6'-triisopropyl-1,1'-biphenyl)[2-(2'-amino-1,1'-biphenyl)]palladium (II) (4.0 mg, 5.1 μmol), potassium phosphate (32 mg, 0.15 mmol), and 1,4-dioxane (1.0 mL) were combined and then stirred at 100° C. for 16 h. The mixture was cooled to room temperature and filtered through celite, which was further eluted with EtOAc (1 mL×3). The filtrate was concentrated under reduced pressure and the residue was treated with HCl (37%, 1.0 mL). The mixture was stirred at 80° C. for 10 min, cooled to rt, poured into a solution of sodium hydroxide (1 N aqueous, 30 mL), and extracted with DCM (15 mL×3). The combined organic extracts were dried with anhydrous magnesium sulfate, filtered, and concentrated under reduced pressure. The residue was subjected to reverse phase HPLC (10-100% MeCN/water with 0.1% TFA modifier). The resulting material was passaged through a SCX-2 column, which was washed with MeOH (2 mL×3) and eluted with a methanolic solution of ammonia (2 N, 2 mL×3) to afford the title compound. MS m/z $(M+H)^+$: calculated 532.2, observed 532.4. $^1$H NMR (500 MHz, DMSO-$d^6$) δ 8.86 (d, J=4.9 Hz, 2H), 8.16 (ddd, J=12.3, 8.0, 2.1 Hz, 1H), 8.03-7.99 (m, 1H), 7.80 (d, J=1.1 Hz, 1H), 7.54 (dt, J=10.4, 8.6 Hz, 1H), 7.45 (t, J=4.9 Hz, 1H), 7.28 (s, 1H), 6.94 (d, J=1.1 Hz, 1H), 4.11-4.06 (m, 1H), 4.04-4.02 (m, 1H), 4.02 (s, 3H), 4.00-3.96 (m, 1H), 3.93-3.88 (m, 1H), 3.71-3.65 (m, 1H), 2.12 (br s, 2H), 2.07-2.03 (m, 2H), 1.38 (s, 6H) ppm.

Utilizing the procedure described in EXAMPLE 55, the below compounds were prepared substituting the appropriate reagents for (3,4-difluorophenyl)boronic acid.

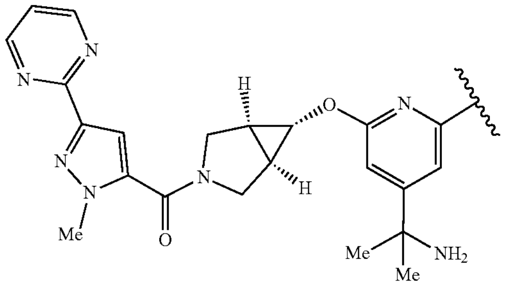 [SMILES: *c1cc(C(C)(C)N)cc(O[C@H]2[C@@H]3CN(C(=O)c4cc(-c5ncccn5)nn4C)C[C@@H]32)n1]

| Ex # | Structure | Name | Calc'd [M + H]$^+$ | Observed [M + H]$^+$ | Comments |
|---|---|---|---|---|---|
| 56 | 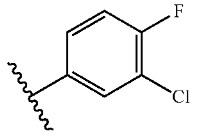 [SMILES: *c1ccc(F)c(Cl)c1] | ((1R,5S,6s)-6-((4-(2-aminopropan-2-yl)-6-(3-chloro-4-fluorophenyl)pyridin-2-yl)oxy)-3-azabicyclo[3.1.0]hexan-3-yl)(1-methyl-3-(pyrimidin-2-yl)-1H-pyrazol-5-yl)methanone | 548.2 | 548.3 | Pd catalyst = 5 mol % $Pd(PPh_3)_4$ |
| 57 | 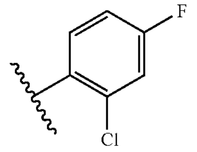 [SMILES: *c1ccc(F)cc1Cl] | ((1R,5S,6s)-6-((4-(2-aminopropan-2-yl)-6-(2-chloro-4-fluorophenyl)pyridin-2-yl)oxy)-3-azabicyclo[3.1.0]hexan-3-yl)(1-methyl-3-(pyrimidin-2-yl)-1H-pyrazol-5-yl)methanone | 548.2 | 548.3 | Pd catalyst = 5 mol % $Pd(PPh_3)_4$ |
| 58 | 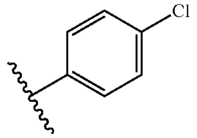 [SMILES: *c1ccc(Cl)cc1] | ((1R,5S,6s)-6-((4-(2-aminopropan-2-yl)-6-(4-chlorophenyl)pyridin-2-yl)oxy)-3-azabicyclo[3.1.0]hexan-3-yl)(1-methyl-3-(pyrimidin-2-yl)-1H-pyrazol-5-yl)methanone | 530.2 | 530.3 | Pd catalyst = 5 mol % $Pd(PPh_3)_4$ |
| 59 | 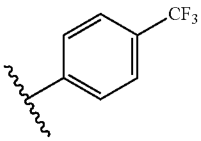 [SMILES: *c1ccc(C(F)(F)F)cc1] | ((1R,5S,6s)-6-((4-(2-aminopropan-2-yl)-6-(4-(trifluoromethyl)phenyl) pyridin-2-yl)oxy)-3-azabicyclo[3.1.0]hexan-3-yl)(1-methyl-3-(pyrimidin-2-yl)-1H-pyrazol-5-yl)methanone | 564.2 | 564.3 | |

Example 60

((1R,5S,6s)-6-((4-(2-aminopropan-2-yl)-6-(4-fluoro-1H-indol-1-yl)pyridin-2-yl)oxy)-3-azabicyclo[3.1.0]hexan-3-yl)(1-methyl-3-(pyrimidin-2-yl)-1H-pyrazol-5-yl)methanone

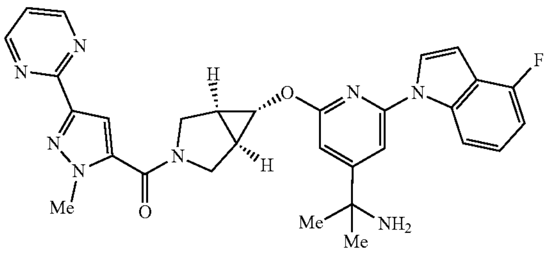 [SMILES: Cn1nc(-c2ncccn2)cc1C(=O)N1C[C@@H]2[C@H](C1)[C@H]2Oc1cc(C(C)(C)N)cc(-n2ccc3c(F)cccc32)n1]

Under an atmosphere of nitrogen, a mixture of benzyl (2-(2-chloro-6-(((1R,5S,6s)-3-(1-methyl-3-(pyrimidin-2-yl)-1H-pyrazole-5-carbonyl)-3-azabicyclo[3.1.0]hexan-6-yl)oxy)pyridin-4-yl)propan-2-yl)carbamate (Int. I-2, 71 mg, 0.12 mmol), 4-fluoro-1H-indole (24 mg, 0.18 mmol), 5-(di-tert-butylphosphino)-1',3',5'-triphenyl-1'H-[1,4']bipyrazole (6.1 mg, 0.012 mmol), Pd2(dba)3 (5.5 mg, 6.0 ρmol), potassium phosphate (76 mg, 0.36 mmol), and 1,4-dioxane (1.2 mL) was stirred at 100° C. for 16 h. The mixture was cooled to room temperature and filtered through celite, which was further eluted with EtOAc (1 mL×3). The filtrate was concentrated under reduced pressure, the residue was treated with HCl (37%, 1.0 mL), and the mixture was then stirred at 80° C. for 10 min. The mixture was cooled to rt, poured into a solution of sodium hydroxide (1 N aqueous, 30 mL), and extracted with DCM (15 mL×3). The combined organic extracts were dried with anhydrous magnesium sulfate, filtered, and concentrated under reduced pressure. The mixture was subjected to reverse phase HPLC (10-100% MeCN/water with 0.1% TFA modifier) and lyophilized to afford the title compound as a TFA salt. MS m/z $(M+H)^+$: calculated 553.2, observed 553.6. $^1$H NMR (500 MHz, DMSO-$d^6$) δ 8.88 (d, J=4.8 Hz, 2H), 8.61 (br s, 3H), 8.36 (d, J=8.3 Hz, 1H), 8.10 (d, J=3.6 Hz, 1H), 7.50 (d, J=0.8 Hz, 1H), 7.46 (t, J=4.9 Hz, 1H), 7.27 (s, 1H), 7.02 (td, J=8.2, 5.9 Hz, 1H), 6.88 (d, J=3.5 Hz, 1H), 6.85 (d, J=0.8 Hz, 1H), 6.75 (dd, J=10.2, 7.7 Hz, 1H), 4.21 (d, J=12.7 Hz, 1H), 4.13-4.11 (m, 1H), 4.07-4.03 (m, 1H), 4.01 (s, 3H), 3.95 (d, J=11.0 Hz, 1H), 3.67-3.62 (m, 1H), 2.14-2.12 (m, 2H), 1.67 (s, 6H) ppm.

Example 61

((1R,5S,6s)-6-((4-(2-aminopropan-2-yl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone

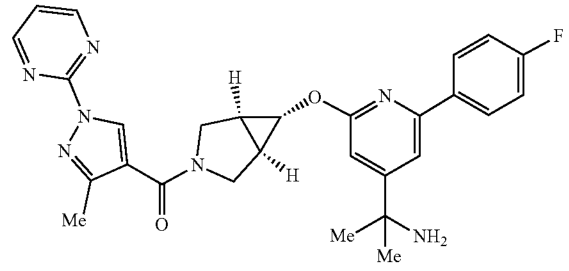 [SMILES: Cc1nn(-c2ncccn2)cc1C(=O)N1C[C@@H]2[C@H](C1)[C@H]2Oc1cc(C(C)(C)N)cc(-c2ccc(F)cc2)n1]

To a mixture of 3-methyl-1-(pyrimidin-2-yl)-1H-pyrazole-4-carboxylic acid (0.32 g, 1.6 mmol) and 2-(2-(((1R,5S,6s)-3-azabicyclo[3.1.0]hexan-6-yl)oxy)-6-(4-fluorophenyl)pyridin-4-yl)propan-2-amine·HCl (Int. H-01, 0.76 g, 1.7 mmol) in DMF (16 mL) was added DIPEA (1.4 mL, 7.9 mmol) and HATU (0.60 g, 1.6 mmol). The mixture was stirred at rt for 3 h and then subjected to reverse phase HPLC (10-100% MeCN/water with 0.1% TFA modifier). The appropriate fractions were passaged through a SCX-2 column, which was washed with MeOH (2 mL×3) and eluted with a methanolic solution of ammonia (2 N, 2 mL×3), to afford the title compound. MS m/z $(M+H)^+$: calculated 514.2, observed 514.4. $^1H$ NMR (500 MHz, $CDCl_3$) δ 8.78 (d, J=4.8 Hz, 2H), 8.74 (s, 1H), 8.05-8.00 (m, 2H), 7.51 (d, J=1.2 Hz, 1H), 7.25 (t, J=4.8 Hz, 1H), 7.15 (t, J=8.7 Hz, 2H), 6.80 (d, J=1.2 Hz, 1H), 4.30-4.00 (m, 1H), 4.07-3.98 (m, 2H), 3.93-3.86 (m, 1H), 3.82-3.73 (m, 1H), 2.58 (s, 3H), 2.09-2.00 (m, 2H), 1.53 (br s, 2H), 1.50 (s, 6H) ppm.

Example 62

((1R,5S,6s)-6-((4-(2-aminopropan-2-yl)-6-(4-fluorophenyl)pyridin-2-yl)oxy)-3-azabicyclo[3.1.0]hexan-3-yl)(3-methoxy-1-(pyrimidin-2-yl)-1H-pyrazol-4-yl)methanone

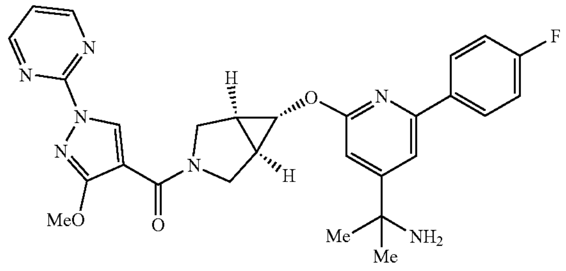 [SMILES: COc1nn(-c2ncccn2)cc1C(=O)N1C[C@@H]2[C@H](C1)[C@H]2Oc1cc(C(C)(C)N)cc(-c2ccc(F)cc2)n1]

To a mixture of 3-methoxy-1-(pyrimidin-2-yl)-1H-pyrazole-4-carboxylic acid (Int. N-4, 25 mg, 0.11 mmol) and 2-(2-(((1R,5S,6s)-3-azabicyclo[3.1.0]hexan-6-yl)oxy)-6-(4-fluorophenyl)pyridin-4-yl)propan-2-amine·HCl (Int. H-01, 0.050 g, 0.11 mmol) in DMF (1.1 mL) was added DIPEA (0.10 mL, 0.57 mmol) and HATU (43 mg, 0.11 mmol). The mixture was stirred at rt for 16 h, subjected to reverse phase HPLC (10-100% MeCN/water with 0.1% TFA modifier), and the appropriate fractions were lyophilized to afford the title compound as a TFA salt. MS m/z $(M+H)^+$: calculated 530.2, observed 530.5. $^1H$ NMR (500 MHz, DMSO-$d^6$) δ8.86 (d, J=4.8 Hz, 2H), 8.77 (s, 1H), 8.55 (br s, 3H), 8.19-8.14 (m, 2H), 7.75 (s, 1H), 7.47 (t, J=4.8 Hz, 1H), 7.35-7.30 (m, 2H), 6.89 (s, 1H), 4.08-4.02 (m, 1H), 3.99-3.95 (m, 4H), 3.89-3.82 (m, 2H), 3.60-3.55 (m, 1H), 2.05-2.00 (i, 2H), 1.65 (s, 6H) ppm.

Utilizing the procedures described in EXAMPLE 62, the below compounds were prepared substituting the appropriate reagents for 3-methoxy-1-(pyrimidin-2-yl)-1H-pyrazole-4-carboxylic acid. Following HPLC purification (10-100% MeCN/water with 0.1% TFA or HCl modifier), exemplified compounds were either concentrated to afford TFA or HCl salts or extracted under basic conditions to afford free bases.

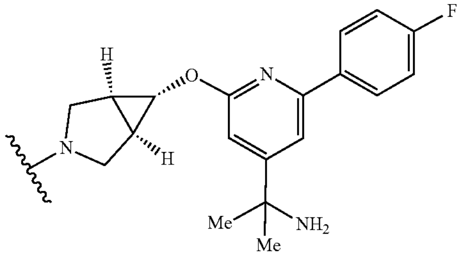 [SMILES: *N1C[C@@H]2[C@H](C1)[C@H]2Oc1cc(C(C)(C)N)cc(-c2ccc(F)cc2)n1]

| Ex # | Structure | Name | Calc'd $[M + H]^+$ | Observed $[M + H]^+$ | Optional Form |
|---|---|---|---|---|---|
| 63 | 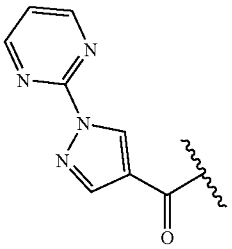 [SMILES: *C(=O)c1cnn(-c2ncccn2)c1] | ((1R,5S,6s)-6-((4-(2-aminopropan-2-yl)-6-(4-fluorophenyl)pyridin-2-yl)oxy)-3-azabicyclo[3.1.0]hexan-3-yl)(1-(pyrimidin-2-yl)-1H-pyrazol-4-yl)methanone | 500.2 | 500.3 | TFA salt |
| 64 | 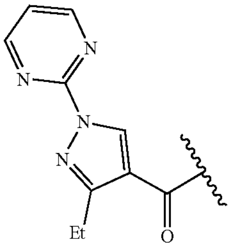 [SMILES: *C(=O)c1cn(-c2ncccn2)nc1CC] | ((1R,5S,6s)-6-((4-(2-aminopropan-2-yl)-6-(4-fluorophenyl)pyridin-2-yl)oxy)-3-azabicyclo[3.1.0]hexan-3-yl)(3-ethyl-1-(pyrimidin-2-yl)-1H-pyrazol-4-yl)methanone | 528.2 | 528.4 | Free base |
| 65 | 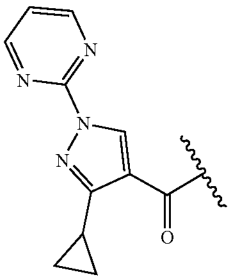 [SMILES: *C(=O)c1cn(-c2ncccn2)nc1C1CC1] | ((1R,5S,6s)-6-((4-(2-aminopropan-2-yl)-6-(4-fluorophenyl)pyridin-2-yl)oxy)-3-azabicyclo[3.1.0]hexan-3-yl)(3-cyclopropyl-1-(pyrimidin-2-yl)-1H-pyrazol-4-yl)methanone | 540.2 | 540.4 | Free base |
| 66 | 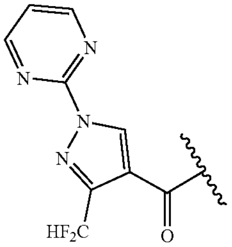 | ((1R,5S,6s)-6-((4-(2-aminopropan-2-yl)-6-(4-fluorophenyl)pyridin-2-yl)oxy)-3-azabicyclo[3.1.0]hexan-3-yl)(3-(difluoromethyl)-1-(pyrimidin-2-yl)-1H-pyrazol-4-yl)methanone | 550.2 | 550.4 | Free base |
| 67 | 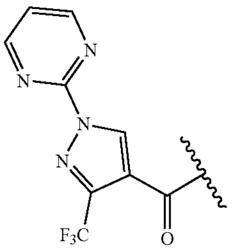 [SMILES: *C(=O)c1cn(-c2ncccn2)nc1C(F)(F)F] | ((1R,5S,6s)-6-((4-(2-aminopropan-2-yl)-6-(4-fluorophenyl)pyridin-2-yl)oxy)-3-azabicyclo[3.1.0]hexan-3-yl)(1-(pyrimidin-2-yl)-3-(trifluoromethyl)-1H-pyrazol-4-yl)methanone | 568.2 | 568.3 | TFA salt |
| 68 | 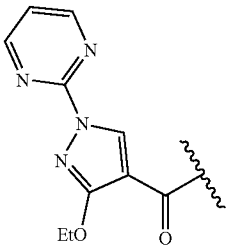 [SMILES: *C(=O)c1cn(-c2ncccn2)nc1OCC] | ((1R,5S,6s)-6-((4-(2-aminopropan-2-yl)-6-(4-fluorophenyl)pyridin-2-yl)oxy)-3-azabicyclo[3.1.0]hexan-3-yl)(3-ethoxy-1-(pyrimidin-2-yl)-1H-pyrazol-4-yl)methanone | 544.2 | 544.4 | Free base |

-continued

| Ex # | Structure | Name | Calc'd [M + H]+ | Observed [M + H]+ | Optional Form |
|---|---|---|---|---|---|
| 69 | 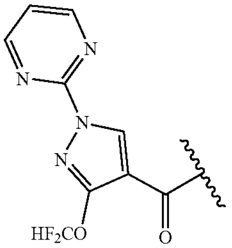 | ((1R,5S,6s)-6-((4-(2-aminopropan-2-yl)-6-(4-fluorophenyl)pyridin-2-yl)oxy)-3-azabicyclo[3.1.0]hexan-3-yl)(3-(difluoromethoxy)-1-(pyrimidin-2-yl)-1H-pyrazol-4-yl)methanone | 566.2 | 566.4 | TFA salt |
| 70 | 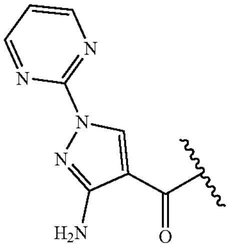 | (3-amino-1-(pyrimidin-2-yl)-1H-pyrazol-4-yl)((1R,5S,6s)-6-((4-(2-aminopropan-2-yl)-6-(4-fluorophenyl)pyridin-2-yl)oxy)-3-azabicyclo[3.1.0]hexan-3-yl)methanone | 515.2 | 515.3 | TFA salt |
| 71 | 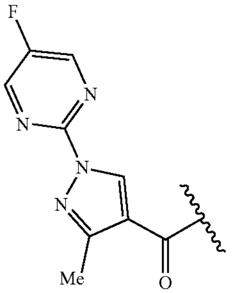 [SMILES: *C(=O)c1cn(-c2ncc(F)cn2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(1-(5-fluoropyrimidin-2-yl)-3-methyl-1H-pyrazol-4-yl)methanone | 532.2 | 532.3 | Free base |
| 72 | 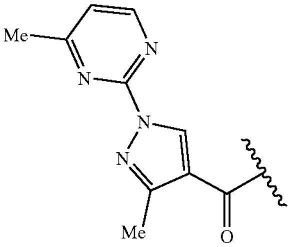 [SMILES: *C(=O)c1cn(-c2nccc(C)n2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(3-methyl-1-(4-methylpyrimidin-2-yl)-1H-pyrazol-4-yl)methanone | 528.2 | 528.2 | TFA salt |
| 73 | 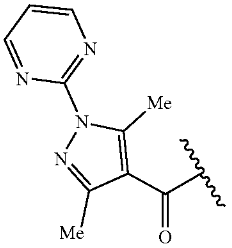 [SMILES: *C(=O)c1c(C)nn(-c2ncccn2)c1C] | ((1R,5S,6s)-6-((4-(2-aminopropan-2-yl)-6-(4-fluorophenyl)pyridin-2-yl)oxy)-3-azabicyclo[3.1.0]hexan-3-yl)(3,5-dimethyl-1-(pyrimidin-2-yl)-1H-pyrazol-4-yl)methanone | 528.2 | 528.3 | TFA salt |
| 74 | 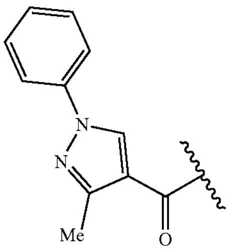 [SMILES: *C(=O)c1cn(-c2ccccc2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(3-methyl-1-phenyl-1H-pyrazol-4-yl)methanone | 512.2 | 512.3 | TFA salt |

-continued

| Ex # | Structure | Name | Calc'd $[M + H]^+$ | Observed $[M + H]^+$ | Optional Form |
|---|---|---|---|---|---|
| 75 | 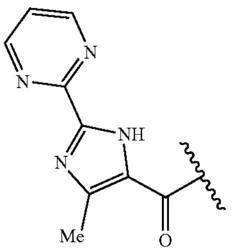 [SMILES: *C(=O)c1[nH]c(-c2ncccn2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(pyrimidin-2-yl)-1H-imidazol-5-yl)methanone | 514.2 | 514.2 | TFA salt |
| 76 | 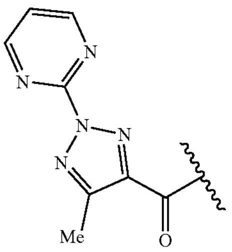 [SMILES: *C(=O)c1nn(-c2ncccn2)nc1C] | ((1R,5S,6s)-6-((4-(2-aminopropan-2-yl)-6-(4-fluorophenyl)pyridin-2-yl)oxy)-3-azabicyclo[3.1.0]hexan-3-yl)(5-methyl-2-(pyrimidin-2-yl)-2H-1,2,3-triazol-4-yl)methanone | 515.2 | 515.3 | Free base |
| 77 | 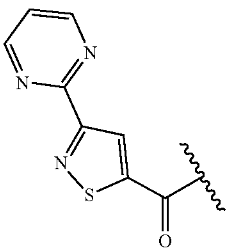 [SMILES: *C(=O)c1cc(-c2ncccn2)ns1] | ((1R,5S,6s)-6-((4-(2-aminopropan-2-yl)-6-(4-fluorophenyl)pyridin-2-yl)oxy)-3-azabicyclo[3.1.0]hexan-3-yl)(3-(pyrimidin-2-yl)isothiazol-5-yl)methanone | 517.2 | 517.1 | HCl salt |

Example 78

((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(pyrimidin-2-yl)oxazol-5-yl)methanone

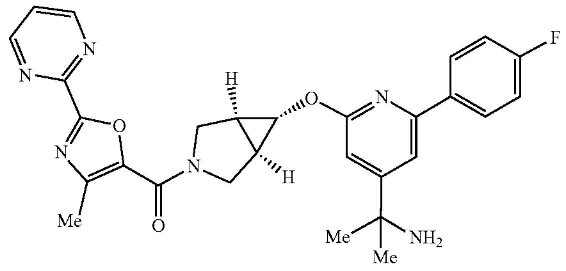 [SMILES: Cc1nc(-c2ncccn2)oc1C(=O)N1C[C@@H]2[C@H](C1)[C@H]2Oc1cc(C(C)(C)N)cc(-c2ccc(F)cc2)n1]

To a mixture of 4-methyl-2-(pyrimidin-2-yl)oxazole-5-carboxylic acid (Int. L-1, 57 mg, 0.27 mmol), HATU (130 mg, 0.33 mmol), and DMF (2.5 mL) was added benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 57 mg, 0.28 mmol) and DIPEA (0.15 mL, 0.86 mmol). The mixture was stirred at rt for 5 h, concentrated under reduced pressure, and subjected to silica gel chromatography (0-100% (3:1 EtOAc:EtOH)/heptane). The residue was combined with Pd/carbon (10 wt %, 0.030 g, 0.028 mmol), EtOAc (2.5 mL), and MeOH (2.5 mL). The mixture was degassed and sparged thrice with nitrogen and then 1,4-cyclohexadiene (0.30 mL, 3.2 mL) was added. The mixture was heated to 100° C. for 5 min in a sealed vessel. The mixture was cooled to ambient temperature, filtered through a pad of celite, which was washed with MeOH, and the filtrate was concentrated under reduced pressure. The residue was subjected to reverse phase HPLC (5-50% MeCN/water with 0.1% TFA modifier) and the appropriate fractions were concentrated, dissolved in MeOH, and passaged through a Dowex 1×2 ion exchange column. The column was eluted with MeOH and the material was concentrated to afford the title compound. MS m/z $(M+H)^+$: calculated 515.2, observed 515.1. $^1H$ NMR (500 MHz, DMSO-$d^6$) δ 9.02 (d, J=4.9 Hz, 2H), 8.20-8.14 (m, 2H), 7.75 (d, J=1.1 Hz, 1H), 7.69 (t, J=4.9 Hz, 1H), 7.26-7.18 (m, 2H), 6.92 (d, J=1.1 Hz, 1H), 4.36 (d, J=11.1 Hz, 1H), 4.08 (dd, J=10.9, 4.8 Hz, 1H), 4.02 (d, J=12.4 Hz, 1H), 4.00-3.97 (m, 1H), 3.73 (dd, J=12.0, 4.6 Hz, 1H), 2.48 (s, 3H), 2.23-2.15 (m, 1H), 2.06-2.00 (m, 3H), 1.38 (s, 6H) ppm.

Scheme

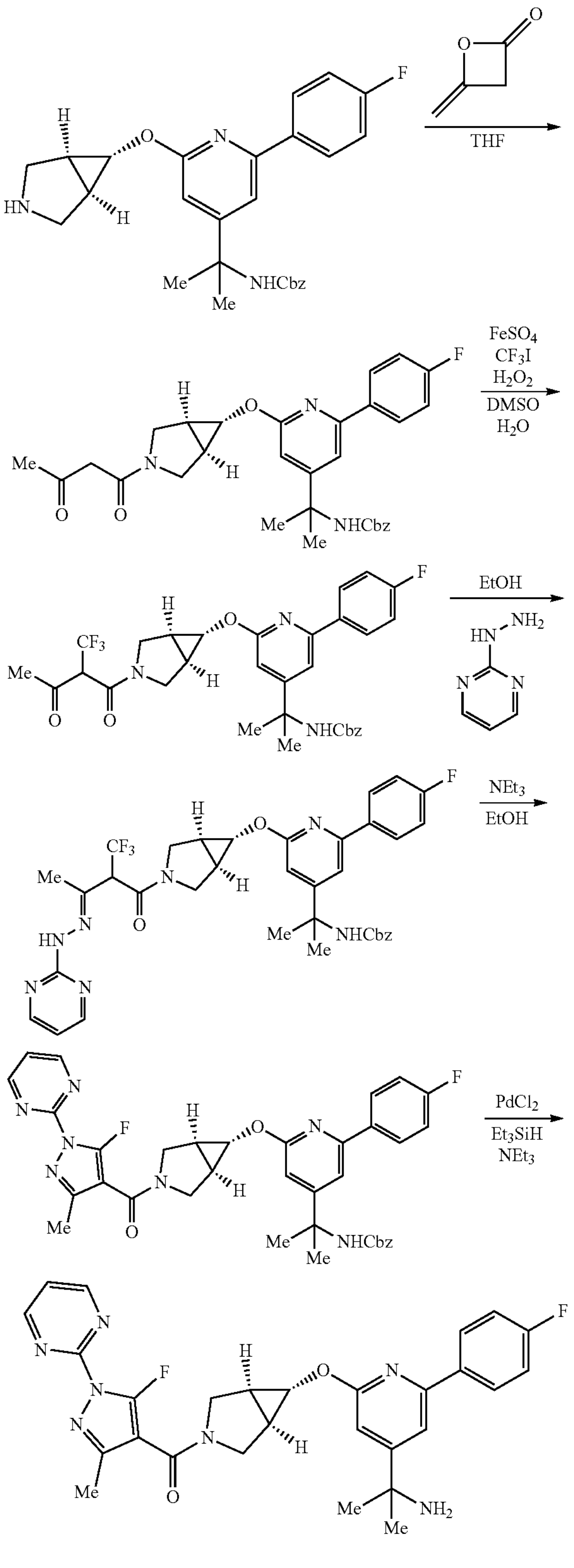

Example 79

((1R,5S,6s)-6-((4-(2-aminopropan-2-yl)-6-(4-fluorophenyl)pyridin-2-yl)oxy)-3-azabicyclo[3.1.0]hexan-3-yl)(5-fluoro-3-methyl-1-(pyrimidin-2-yl)-1H-pyrazol-4-yl)methanone

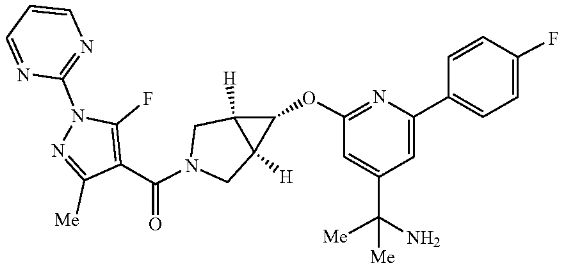 [SMILES: Cc1nn(-c2ncccn2)c(F)c1C(=O)N1C[C@@H]2[C@H](C1)[C@H]2Oc1cc(C(C)(C)N)cc(-c2ccc(F)cc2)n1]

Step 1: benzyl (2-(2-(4-fluorophenyl)-6-(((1R,5S,6s)-3-(3-oxobutanoyl)-3-azabicyclo[3.1.0]hexan-6-yl)oxy)pyridin-4-yl)propan-2-yl)carbamate To a solution of benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 0.40 g, 0.87 mmol) in THF (5.0 mL) was added 4-methyleneoxetan-2-one (73 mg, 0.87 mmol) in THF (2.0 mL) under an atmosphere of nitrogen at 0° C. The mixture was stirred at 0° C. for 2 h, warmed to rt, and stirred for an additional 12 h. The mixture was concentrated under reduced pressure and subjected to prep-TLC (50% EtOAc/petroleum ether) to afford the title compound.

Step 2: benzyl (2-(2-(4-fluorophenyl)-6-(((1R,5S,6s)-3-(3-oxo-2-(trifluoromethyl)butanoyl)-3-azabicyclo[3.1.0]hexan-6-yl)oxy)pyridin-4-yl)propan-2-yl)carbamate A hydrogen peroxide solution (30 wt % in water, 1.0 mL) was added dropwise to a mixture of benzyl (2-(2-(4-fluorophenyl)-6-(((1R,5S,6s)-3-(3-oxobutanoyl)-3-azabicyclo[3.1.0]hexan-6-yl)oxy)pyridin-4-yl)propan-2-yl)carbamate (0.43 g, 0.79 mmol), $CF_3I$ (3.0 M in DMSO, 1.0 mL) and $FeSO_4$ (1.0 M aqueous, 1.0 mL) in DMSO (6.0 mL) under an atmosphere of nitrogen at rt. The mixture was stirred for 1 h and additional $CF_3I$ (3.0 M in DMSO, 1.0 mL), $FeSO_4$ (1.0 M aqueous, 1.0 mL), and $H_2O_2$ (30 wt % in water, 1.0 mL) were added. After 1 h, additional aliquots of $CF_3I$ (3.0 M in DMSO, 1.0 mL), $FeSO_4$ (1.0 M aqueous, 1.0 mL), and $H_2O_2$ (30 wt % in water, 1.0 mL) were added. The mixture was stirred for 12 h, water (10 mL) was added, and the mixture was extracted with EtOAc (10 mL×3). The combined organic extracts were washed with brine (10 mL), dried with anhydrous sodium sulfate, filtered, and concentrated under reduced pressure. The residue was subjected to prep-TLC (EtOAc) to afford the title compound.

Step 3: benzyl (2-(2-(4-fluorophenyl)-6-(((1R,5S,6s)-3-((E)-3-(2-(pyrimidin-2-yl)hydrazono)-2-(trifluoromethyl)butanoyl)-3-azabicyclo[3.1.0]hexan-6-yl)oxy)pyridin-4-yl)propan-2-yl)carbamate A solution of benzyl (2-(2-(4-fluorophenyl)-6-(((1R,5S,6s)-3-(3-oxo-2-(trifluoromethyl)butanoyl)-3-azabicyclo[3.1.0]hexan-6-yl)oxy)pyridin-4-yl)propan-2-yl)carbamate (0.23 mg, 0.38 mmol) and 2-hydrazineylpyrimidine (62 mg, 0.56 mmol) in EtOH (5.0 mL) was stirred under an atmosphere of nitrogen at 80° C. for 2 h. The mixture was cooled to rt, concentrated under reduced pressure, and subjected to prep-TLC (EtOAc) to afford the title compound.

Step 4: benzyl (2-(2-(((1R,5S,6s)-3-(5-fluoro-3-methyl-1-(pyrimidin-2-yl)-1H-pyrazole-4-carbonyl)-3-azabicyclo[3.1.0]hexan-6-yl)oxy)-6-(4-fluorophenyl)pyridin-4-yl)propan-2-yl)carbamate A solution of benzyl (2-(2-(4-fluorophenyl)-6-(((1R,5S,6s)-3-((E)-3-(2-(pyrimidin-2-yl)hydrazono)-2-(trifluoromethyl)butanoyl)-3-azabicyclo[3.1.0]hexan-6-yl)oxy)pyridin-4-yl)propan-2-yl)carbamate (0.080 g, 0.11 mmol) and triethylamine (0.10 mL, 0.66 mmol) in EtOH (3.0 mL) was stirred under an atmosphere of nitrogen at 80° C. for 2 h. The mixture was cooled to rt, concentrated under reduced pressure, and subjected to prep-TLC (EtOAc) to afford the title compound.

Step 5: ((1R,5S,6s)-6-((4-(2-aminopropan-2-yl)-6-(4-fluorophenyl)pyridin-2-yl)oxy)-3-azabicyclo[3.1.0]hexan-3-yl)(5-fluoro-3-methyl-1-(pyrimidin-2-yl)-1H-pyrazol-4-yl)methanone To a solution of benzyl (2-(2-(((1R,5S,6s)-3-(5-fluoro-3-methyl-1-(pyrimidin-2-yl)-1H-pyrazole-4-carbonyl)-3-azabicyclo[3.1.0]hexan-6-yl)oxy)-6-(4-fluorophenyl)pyridin-4-yl)propan-2-yl)carbamate (35 mg, 0.053 mmol), triethylsilane (31 mg, 0.26 mmol) and triethylamine (21 mg, 0.21 mmol) in DMF (2.0 mL) was added palladium(II) chloride (3.7 mg, 0.021 mmol) under an atmosphere of nitrogen. The mixture was stirred at rt for 30 min. The mixture was filtered and the filtrate was concentrated under reduced pressure. The residue was subjected to reverse phase HPLC (20-50% MeCN/water with 0.1% TFA modifier) to afford the title compound. MS m/z $(M+H)^+$: calculated 532.2, observed 532.2. $^1H$ NMR (400 MHz, $CD_3OD$) δ 8.90 (d, J=4.8 Hz, 2H), 8.15 (dd, J=8.8, 5.6 Hz, 2H), 7.64 (d, J=1.0 Hz, 1H), 7.52 (t, J=4.8 Hz, 1H), 7.23 (t, J=8.8 Hz, 2H), 6.83 (d, J=1.0 Hz, 1H), 4.19 (d, J=12.2 Hz, 1H), 4.04-3.99 (m, 2H), 3.86 (dd, J=10.6, 4.4 Hz, 1H), 3.69 (dd, J=12.2, 4.6 Hz, 1H), 2.39 (s, 3H), 2.19-2.11 (m, 1H), 1.97 (d, J=4.0 Hz, 1H), 1.51 (s, 6H) ppm.

Example 80

((1R,5S,6s)-6-((4-(2-aminopropan-2-yl)-6-(3,4-difluorophenyl)pyridin-2-yl)oxy)-3-azabicyclo[3.1.0]hexan-3-yl)(3-methyl-1-(pyrimidin-2-yl)-1H-pyrazol-4-yl)methanone

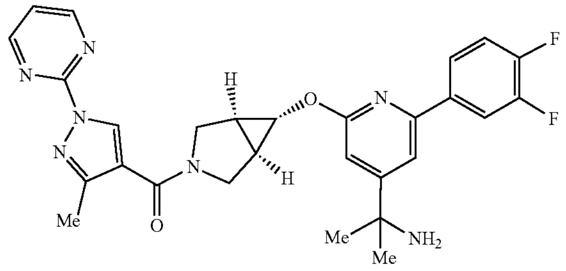 [SMILES: Cc1nn(-c2ncccn2)cc1C(=O)N1C[C@@H]2[C@H](C1)[C@H]2Oc1cc(C(C)(C)N)cc(-c2ccc(F)c(F)c2)n1]

Under an atmosphere of nitrogen, a mixture of benzyl (2-(2-chloro-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate (Int. I-3, 0.080 g, 0.14 mmol), (3,4-difluorophenyl)boronic acid (26 mg, 0.16 mmol), chloro(2-dicyclohexylphosphino-2',4',6'-triisopropyl-1,1'-biphenyl)[2-(2'-amino-1,1'-biphenyl)]palladium (II) (5.4 mg, 6.8 μmol), potassium phosphate (43 mg, 0.20 mmol), and 1,4-dioxane (1.4 mL) was stirred at 100° C. for 16 h. The mixture was cooled to rt, filtered through celite, which was further eluted with EtOAc (1 mL×3), and the filtrate was concentrated under reduced pressure. HCl (37% aqueous, 1.4 mL) was added, and the mixture was stirred at 80° C. for 10 min. The mixture was cooled to rt, poured into sodium hydroxide (1 N aqueous, 30 mL), and extracted with DCM (15 mL×3). The combined organic extracts were dried with anhydrous magnesium sulfate, filtered, and concentrated under reduced pressure. The mixture was subjected to reverse phase HPLC (10-100% MeCN/water with 0.1% TFA modifier). The appropriate fractions were passaged through a SCX-2 column, which was washed with MeOH (2 mL×3) and eluted with a methanolic solution of ammonia (2 N, 2 mL×3) to afford the title compound. MS m/z $(M+H)^+$: calculated 532.2, observed 532.3. $^1H$ NMR (500 MHz, DMSO-$d^6$) δ 8.90-8.86 (m, 3H), 8.14 (ddd, J=12.3, 8.0, 2.1 Hz, 1H), 8.02-7.97 (m, 1H), 7.80 (d, J=1.0 Hz, 1H), 7.55-7.46 (m, 2H), 6.94 (d, J=1.0 Hz, 1H), 4.09-4.02 (m, 1H), 4.01-4.87 (m, 3H), 3.67-3.60 (m, 1H), 2.38 (s, 3H), 2.15-1.98 (m, 4H), 1.38 (s, 6H) ppm.

Utilizing the procedures described in EXAMPLE 80, the below compounds were prepared substituting the appropriate reagents for Intermediate I-3 and (3,4-difluorophenyl) boronic acid.

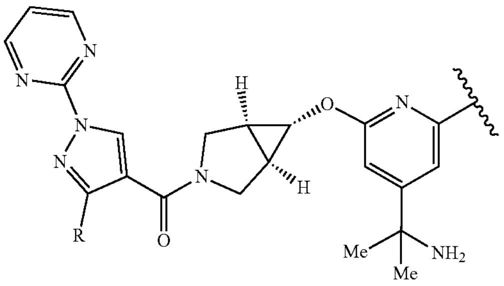

| Ex # | R | Structure | Name | Calc'd [M + H]+ | Observed [M + H]+ | Comments |
|---|---|---|---|---|---|---|
| 81 | Me | 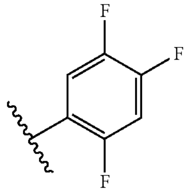 [SMILES: *c1cc(F)c(F)cc1F] | ((1R,5S,6s)-6-((4-(2-aminopropan-2-yl)-6-(2,4,5-trifluorophenyl)pyridin-2-yl)oxy)-3-azabicyclo[3.1.0]hexan-3-yl)(3-methyl-1-(pyrimidin-2-yl)-1H-pyrazol-4-yl)methanone | 550.2 | 550.3 | — |
| 82 | Me | 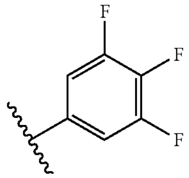 [SMILES: *c1cc(F)c(F)c(F)c1] | ((1R,5S,6s)-6-((4-(2-aminopropan-2-yl)-6-(3,4,5-trifluorophenyl)pyridin-2-yl)oxy)-3-azabicyclo[3.1.0]hexan-3-yl)(3-methyl-1-(pyrimidin-2-yl)-1H-pyrazol-4-yl)methanone | 550.2 | 550.2 | — |
| 83 | Me | 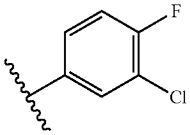 [SMILES: *c1ccc(F)c(Cl)c1] | ((1R,5S,6s)-6-((4-(2-aminopropan-2-yl)-6-(3-chloro-4-fluorophenyl)pyridin-2-yl)oxy)-3-azabicyclo[3.1.0]hexan-3-yl)(3-methyl-1-(pyrimidin-2-yl)-1H-pyrazol-4-yl)methanone | 548.2 | 548.3 | Pd catalyst = 5 mol % $Pd(PPh_3)_4$ |
| 84 | Me | 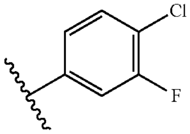 [SMILES: *c1ccc(Cl)c(F)c1] | ((1R,5S,6s)-6-((4-(2-aminopropan-2-yl)-6-(4-chloro-3-fluorophenyl)pyridin-2-yl)oxy)-3-azabicyclo[3.1.0]hexan-3-yl)(3-methyl-1-(pyrimidin-2-yl)-1H-pyrazol-4-yl)methanone | 548.2 | 548.3 | Pd catalyst = 5 mol % $Pd(PPh_3)_4$ |
| 85 | Me | 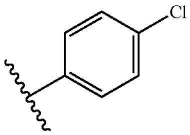 [SMILES: *c1ccc(Cl)cc1] | ((1R,5S,6s)-6-((4-(2-aminopropan-2-yl)-6-(4-chlorophenyl)pyridin-2-yl)oxy)-3-azabicyclo[3.1.0]hexan-3-yl)(3-methyl-1-(pyrimidin-2-yl)-1H-pyrazol-4-yl)methanone | 530.2 | 530.3 | Pd catalyst = 5 mol % $Pd(PPh_3)_4$ |
| 86 | Me | 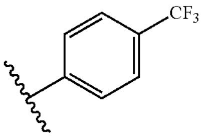 [SMILES: *c1ccc(C(F)(F)F)cc1] | ((1R,5S,6s)-6-((4-(2-aminopropan-2-yl)-6-(4-(trifluoromethyl)phenyl)pyridin-2-yl)oxy)-3-azabicyclo[3.1.0]hexan-3-yl)(3-methyl-1-(pyrimidin-2-yl)-1H-pyrazol-4-yl)methanone | 564.2 | 564.3 | — |

-continued

| Ex # | R | Structure | Name | Calc'd [M + H]+ | Observed [M + H]+ | Comments |
|---|---|---|---|---|---|---|
| 87 | Me | 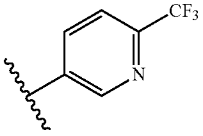 [SMILES: *c1ccc(C(F)(F)F)nc1] | ((1R,5S,6s)-6-((4-(2-aminopropan-2-yl)-6'-(trifluoromethyl)-[2,3'-bipyridin]-6-yl)oxy)-3-azabicyclo[3.1.0]hexan-3-yl)(3-methyl-1-(pyrimidin-2-yl)-1H-pyrazol-4-yl)methanone | 565.2 | 565.3 | — |
| 88 | Me | 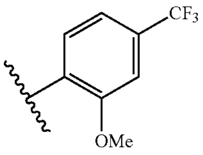 [SMILES: *c1ccc(C(F)(F)F)cc1OC] | ((1R,5S,6s)-6-((4-(2-aminopropan-2-yl)-6-(2-methoxy-4-(trifluoromethyl)phenyl) pyridin-2-yl)oxy)-3-azabicyclo[3.1.0]hexan-3-yl)(3-methyl-1-(pyrimidin-2-yl)-1H-pyrazol-4-yl)methanone | 594.2 | 594.3 | — |
| 89 | Me | 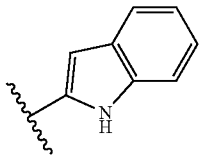 [SMILES: *c1cc2ccccc2[nH]1] | ((1R,5S,6s)-6-((4-(2-aminopropan-2-yl)-6-(1H-indol-2-yl)pyridin-2-yl)oxy)-3-azabicyclo[3.1.0]hexan-3-yl)(3-methyl-1-(pyrimidin-2-yl)-1H-pyrazol-4-yl)methanone | 535.3 | 535.5 | — |
| 90 | Me | 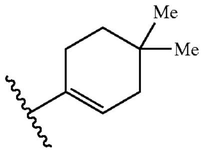 [SMILES: *C1=CCC(C)(C)CC1] | ((1R,5S,6s)-6-((4-(2-aminopropan-2-yl)-6-(4,4-dimethylcyclohex-1-en-1-yl)pyridin-2-yl)oxy)-3-azabicyclo[3.1.0]hexan-3-yl)(3-methyl-1-(pyrimidin-2-yl)-1H-pyrazol-4-yl)methanone | 528.3 | 528.4 | — |
| 91 | $CF_2H$ | 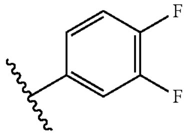 [SMILES: *c1ccc(F)c(F)c1] | ((1R,5S,6s)-6-((4-(2-aminopropan-2-yl)-6-(3,4-difluorophenyl)pyridin-2-yl)oxy)-3-azabicyclo[3.1.0]hexan-3-yl)(3-(difluoromethyl)-1-(pyrimidin-2-yl)-1H-pyrazol-4-yl)methanone | 568.2 | 568.4 | — |
| 92 | $CF_3$ | 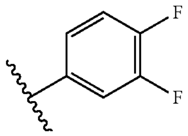 [SMILES: *c1ccc(F)c(F)c1] | ((1R,5S,6s)-6-((4-(2-aminopropan-2-yl)-6-(3,4-difluorophenyl)pyridin-2-yl)oxy)-3-azabicyclo[3.1.0]hexan-3-yl)(1-(pyrimidin-2-yl)-3-(trifluoromethyl)-1H-pyrazol-4-yl)methanone | 586.2 | 586.3 | — |
| 93 | $CF_3$ | 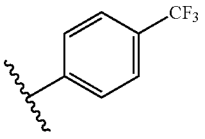 [SMILES: *c1ccc(C(F)(F)F)cc1] | ((1R,5S,6s)-6-((4-(2-aminopropan-2-yl)-6-(4-(trifluoromethyl)phenyl) pyridin-2-yl)oxy)-3-azabicyclo[3.1.0]hexan-3-yl)(1-(pyrimidin-2-yl)-3-(trifluoromethyl)-1H-pyrazol-4-yl)methanone | 618.2 | 618.3 | — |

Example 94

((1R,5S,6s)-6-((4-(2-aminopropan-2-yl)-6-(4-chloro-1H-indazol-1-yl)pyridin-2-yl)oxy)-3-azabicyclo[3.1.0]hexan-3-yl)(3-methyl-1-(pyrimidin-2-yl)-1H-pyrazol-4-yl)methanone

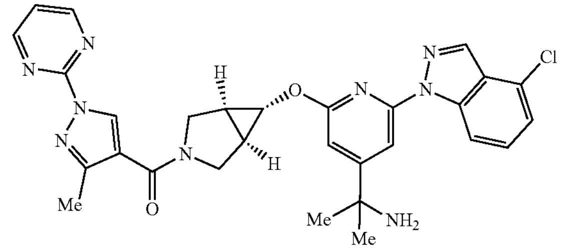 [SMILES: Cc1nn(-c2ncccn2)cc1C(=O)N1C[C@@H]2[C@H](C1)[C@H]2Oc1cc(C(C)(C)N)cc(-n2ncc3c(Cl)cccc32)n1]

Under an atmosphere of nitrogen, a mixture of benzyl (2-(2-chloro-6-1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate (Int. I-3, 0.030 g, 0.051 mmol), 4-chloro-1H-indazole (12 mg, 0.077 mmol), [(4,5-bis(diphenylphosphino)-9,9-dimethylxanthene)-2-(2'-amino-1,1'-biphenyl)]palladium(II) methanesulfonate (4.8 mg, 6.0 ρmol), Zn(OAc)2 (5.6 mg, 0.031 mmol), potassium carbonate (14 mg, 0.10 mmol), and 1,4-dioxane (0.51 mL) was stirred at 100° C. for 16 h. The mixture was cooled to rt, filtered through celite, which was further eluted with EtOAc (1 mL×3), and the filtrate was concentrated under reduced pressure. HCl (37% aqueous, 0.68 mL) was added and the mixture was stirred at 80° C. for 10 min, cooled to room temperature, poured into a solution of sodium hydroxide (1 N aqueous, 30 mL), and extracted with DCM (15 mL×3). The combined organic extracts were dried with anhydrous magnesium sulfate, filtered, and concentrated under reduced pressure. The mixture was subjected to reverse phase HPLC (10-100% MeCN/water with 0.1% TFA modifier) and the appropriate fractions were lyophilized to afford the title compound as a TFA salt. MS m/z $(M+H)^+$: calculated 570.2, observed 570.4. $^1H$ NMR (500 MHz, DMSO-d$^6$) δ 8.89 (d, J=4.8 Hz, 2H), 8.85 (s, 1H), 8.69 (d, J=8.4 Hz, 1H), 8.51 (s, 1H), 7.80 (s, 1H), 7.53 (t, J=4.8 Hz, 1H), 7.24 (t, J=7.9 Hz, 1H), 7.15 (d, J=7.4 Hz, 1H), 6.93 (s, 1H), 4.29-4.21 (m, 1H), 4.09-4.06 (s, 1H), 4.06-3.98 (m, 1H), 3.98-3.90 (m, 1H), 3.62-3.52 (s, 1H), 2.40 (s, 3H), 2.16-2.06 (m, 2H), 1.47 (s, 6H) ppm.

Example 95

((1R,5S,6s)-6-((4-(2-aminopropan-2-yl)-6-(3,4-difluorophenyl)pyridin-2-yl)oxy)-3-azabicyclo[3.1.0]hexan-3-yl)(3-(hydroxymethyl)-1-(pyrimidin-2-yl)-1H-pyrazol-4-yl)methanone

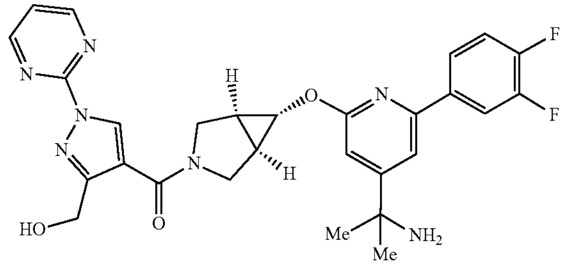 [SMILES: CC(C)(N)c1cc(O[C@H]2[C@@H]3CN(C(=O)c4cn(-c5ncccn5)nc4CO)C[C@@H]32)nc(-c2ccc(F)c(F)c2)c1]

Step 1: benzyl (2-(2-(3,4-difluorophenyl)-6-(((1R,5S,6s)-3-(3-(hydroxymethyl)-1-(pyrimidin-2-yl)-1H-pyrazole-4-carbonyl)-3-azabicyclo[3.1.0]hexan-6-yl)oxy)pyridin-4-yl)propan-2-yl)carbamate A mixture of 3-(hydroxymethyl)-1-(pyrimidin-2-yl)-1H-pyrazole-4-carboxylic acid (Int. N-8, 25 mg, 0.11 mmol), benzyl (2-(2-(((1R,5S,6s)-3-azabicyclo[3.1.0]hexan-6-yl)oxy)-6-(3,4-difluorophenyl)pyridin-4-yl)propan-2-yl)carbamate (Int. H-03, 54 mg, 0.11 mmol), PyBOP (0.12 g, 0.23 mmol), and DIPEA (0.059 mL, 0.34 mmol) in DMF (5.0 mL) was stirred at rt for 1 h. Water (5 mL) was added and the mixture was extracted with EtOAc (10 mL×3). The combined organic extracts were washed with brine (10 mL×3), dried with anhydrous sodium sulfate, filtered, and concentrated under reduced pressure. The residue was subjected to prep-TLC (9% MeOH/DCM) to afford the title compound.

Step 2: ((1R,5S,6s)-6-((4-(2-aminopropan-2-yl)-6-(3,4-difluorophenyl)pyridin-2-yl)oxy)-3-azabicyclo[3.1.0]hexan-3-yl)(3-(hydroxymethyl)-1-(pyrimidin-2-yl)-1H-pyrazol-4-yl)methanone A mixture of benzyl (2-(2-(3,4-difluorophenyl)-6-(((1R,5S,6s)-3-(3-(hydroxymethyl)-1-(pyrimidin-2-yl)-1H-pyrazole-4-carbonyl)-3-azabicyclo[3.1.0]hexan-6-yl)oxy)pyridin-4-yl)propan-2-yl)carbamate (0.040 mg, 0.059 mmol) and HCl (37% aqueous, 1.0 mL) was stirred at 80° C. for 5 min. The mixture was filtered, concentrated under reduced pressure, and subjected to reverse phase HPLC (20-40% MeCN/water with 0.05% HCl modifier). The appropriate fractions were concentrated under reduced pressure to afford the title compound as a HCl salt. MS m/z $(M+H)^+$: calculated 548.2, observed 548.3. $^1H$ NMR (500 MHz, $CD_3OD$) δ 9.02 (s, 1H), 8.86 (d, J=5.0 Hz, 2H), 8.11-7.91 (m, 2H), 7.62 (s, 1H), 7.48 (t, J=5.0 Hz, 1H), 7.42-7.31 (m, 1H), 6.84 (s, 1H), 4.80 (d, J=3.5 Hz, 2H), 4.26-4.20 (m, 1H), 4.12-4.03 (m, 3H), 3.76-3.73 (m, 1H), 2.16-2.06 (m, 2H), 1.76 (s, 6H) ppm.

Scheme

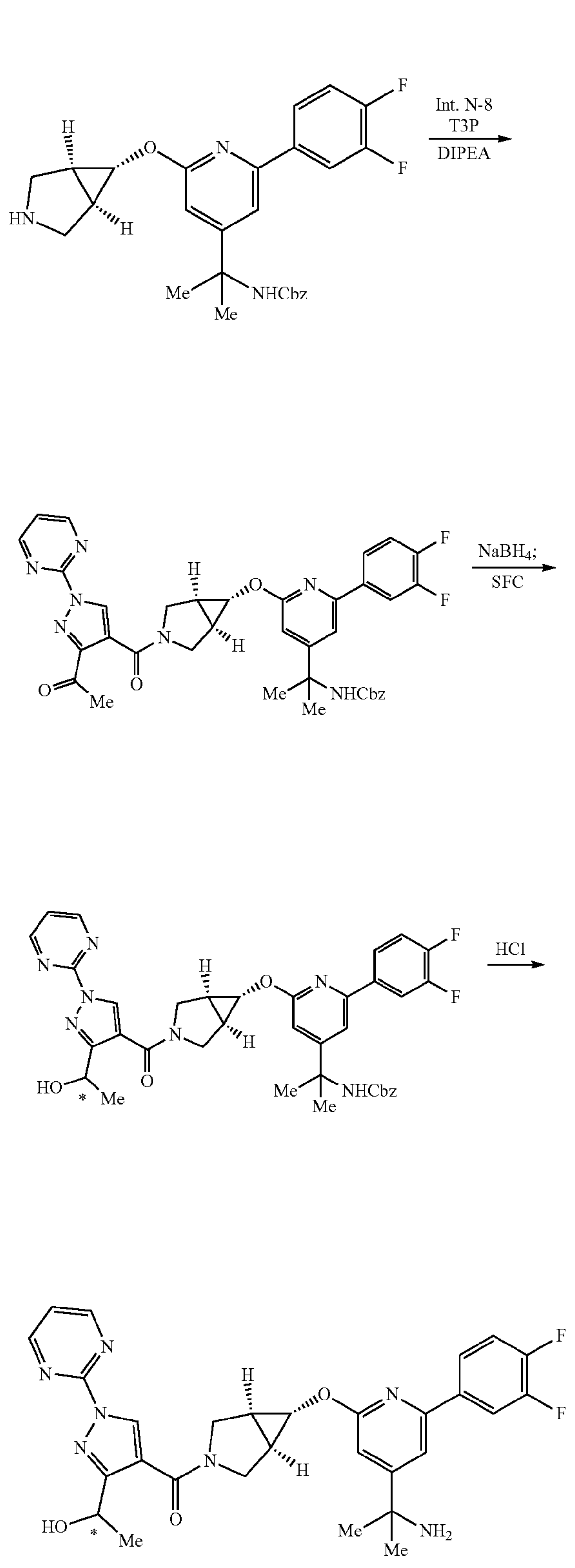

Example 96A ent-((1R,5S,6s)-6-((4-(2-aminopropan-2-yl)-6-(3,4-difluorophenyl)pyridin-2-yl)oxy)-3-azabicyclo[3.1.0]hexan-3-yl)(hydroxyethyl)-1-(pyrimidin-2-yl)-1H-pyrazol-4-yl)methanone (enantiomer 1)

and

Example 96B ent-((1R,5S,6s)-6-((4-(2-aminopropan-2-yl)-6-(3,4-difluorophenyl)pyridin-2-yl)oxy)-3-azabicyclo[3.1.0]hexan-3-yl)(hydroxyethyl)-1-(pyrimidin-2-yl)-1H-pyrazol-4-yl)methanone (enantiomer 2)

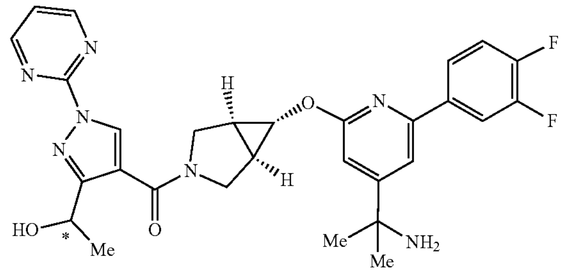 [SMILES: CC(O)c1nn(-c2ncccn2)cc1C(=O)N1C[C@@H]2[C@H](C1)[C@H]2Oc1cc(C(C)(C)N)cc(-c2ccc(F)c(F)c2)n1]

Step 1: benzyl (2-(2-(((1R,5S,6s)-3-(3-acetyl-1-(pyrimidin-2-yl)-1H-pyrazole-4-carbonyl)-3-azabicyclo[3.1.0]hexan-6-yl)oxy)-6-(3,4-difluorophenyl)pyridin-4-yl)propan-2-yl)carbamate To a solution of benzyl (2-(2-(((1R,5S,6s)-3-azabicyclo[3.1.0]hexan-6-yl)oxy)-6-(3,4-difluorophenyl)pyridin-4-yl)propan-2-yl)carbamate (Int. H-03, 0.11 g, 0.24 mmol) and 3-acetyl-1-(pyrimidin-2-yl)-1H-pyrazole-4-carboxylic acid (Int. N-9, 0.050 g, 0.22 mmol) in DMF (2.0 mL) were added T3P (50 wt % in EtOAc, 0.27 g, 0.43 mmol) and DIPEA (0.20 mL, 0.65 mmol). The mixture was stirred at rt for 1 h Water (20 mL) was added, and the mixture was extracted with EtOAc (10 mL×3). The combined organic extracts were washed with brine (15 mL), dried with anhydrous sodium sulfate, filtered, and concentrated under reduced pressure. The residue was subjected to prep-TLC (65% EtOAc/petroleum ether) to afford the title compound.

Step 2: benzyl ent-(2-(2-(3,4-difluorophenyl)-6-(((1R,5S,6R)-3-(3-(−1-hydroxyethyl)-1-(pyrimidin-2-yl)-1H-pyrazole-4-carbonyl)-3-azabicyclo[3.1.0]hexan-6-yl)oxy)pyridin-4-yl)propan-2-yl)carbamate (Enantiomers 1 and 2)

To a mixture of benzyl (2-(2-(((1R,5S,6s)-3-(3-acetyl-1-(pyrimidin-2-yl)-1H-pyrazole-4-carbonyl)-3-azabicyclo[3.1.0]hexan-6-yl)oxy)-6-(3,4-difluorophenyl)pyridin-4-yl)propan-2-yl)carbamate (0.12 g, 0.17 mmol) in MeOH (5.0 mL) was added sodium borohydride (13 mg, 0.35 mmol). The mixture was stirred at rt for 30 min, a solution of ammonium chloride (saturated aqueous, 3 mL) was added, and the mixture was extracted with EtOAc (10 mL×3). The combined organic extracts were dried with anhydrous sodium sulfate, filtered, and concentrated under reduced pressure. The residue was subjected to prep-TLC (10%

MeOH/DCM) to afford the title compound as a racemic mixture. The mixture of two stereoisomers was subjected to chiral SFC (Phenomenex-Cellulose-2, 50% EtOH (with 0.1% $NH_4OH$ modifier)/CO2) to afford the title compounds, enantiomer 1 (faster eluting) and enantiomer 2 (slower eluting).

Step 3-1: ent-((1R,5S,6s)-6-((4-(2-aminopropan-2-yl)-6-(3,4-difluorophenyl)pyridin-2-yl)oxy)-3-azabicyclo[3.1.0]hexan-3-yl)(3-(1-hydroxyethyl)-1-(pyrimidin-2-yl)-1H-pyrazol-4-yl)methanone (Enantiomer 1)

A mixture of benzyl ent-(2-(2-(3,4-difluorophenyl)-6-(((1R,5S,6R)-3-(3-(1-hydroxyethyl)-1-(pyrimidin-2-yl)-1H-pyrazole-4-carbonyl)-3-azabicyclo[3.1.0]hexan-6-yl)oxy)pyridin-4-yl)propan-2-yl)carbamate (enantiomer 1, 0.030 g, 0.043 mmol) in HCl (37% aqueous, 1.0 mL) was stirred at 80° C. for 10 min. The mixture was cooled to rt, concentrated under reduced pressure. The mixture was subjected to reverse phase HPLC (18-38% MeCN/water with 0.04% HCl modifier) and the appropriate fractions concentrated to afford the title compound as a HCl salt. MS m/z $(M+H)^+$: calculated 562.2, observed 562.2. $^1$H NMR (400 MHz, $CD_3OD$) δ 8.99 (s, 1H), 8.88-8.85 (m, 2H), 8.11-7.93 (m, 2H), 7.66 (s, 1H), 7.48 (s, 1H), 7.42-7.33 (m, 1H), 6.86 (s, 1H), 5.12-5.10 (m, 1H), 4.32-4.21 (m, 1H), 4.12-4.01 (m, 3H), 3.77-3.74 (m, 1H), 2.15-2.05 (m, 2H), 1.76 (s, 6H), 1.63-1.60 (m, 3H) ppm.

Step 3-2: ent-((1R,5S,6s)-6-((4-(2-aminopropan-2-yl)-6-(3,4-difluorophenyl)pyridin-2-yl)oxy)-3-azabicyclo[3.1.0]hexan-3-yl)(3-(1-hydroxyethyl)-1-(pyrimidin-2-yl)-1H-pyrazol-4-yl)methanone (Enantiomer 2)

A mixture of benzyl ent-(2-(2-(3,4-difluorophenyl)-6-(((1R,5S,6R)-3-(3-(1-hydroxyethyl)-1-(pyrimidin-2-yl)-1H-pyrazole-4-carbonyl)-3-azabicyclo[3.1.0]hexan-6-yl)oxy)pyridin-4-yl)propan-2-yl)carbamate (enantiomer 2, 0.030 g, 0.043 mmol) in HCl (37% aqueous, 1.0 mL) was stirred at 80° C. for 10 min. The mixture was cooled to room temperature and concentrated under reduced pressure. The mixture was subjected to reverse phase HPLC (18-38% MeCN/water with 0.04% HCl modifier) the appropriate fractions were concentrated to afford the title compound as a HCl salt. MS m/z $(M+H)^+$: calculated 562.2, observed 562.2. $^1$H NMR (400 MHz, $CD_3OD$) δ 9.01-8.97 (m, 1H), 8.87 (d, J=4.8 Hz, 2H), 8.10-7.94 (m, 2H), 7.66 (s, 1H), 7.49 (t, J=4.8 Hz, 1H), 7.43-7.32 (m, 1H), 6.86 (d, J=1.2 Hz, 1H), 5.13-5.09 (m, 1H), 4.34-4.19 (m, 1H), 4.11-3.98 (m, 3H), 3.81-3.71 (m, 1H), 2.16-2.06 (m, 2H), 1.76 (s, 6H), 1.60 (t, J=7.6 Hz, 3H) ppm.

Example 97

((1R,5S,6s)-6-((4-(2-aminopropan-2-yl)-6-(2,4-difluorophenyl)pyridin-2-yl)oxy)-3-azabicyclo[3.1.0]hexan-3-yl)(4-methyl-2-(pyrimidin-2-yl)thiazol-5-yl)methanone

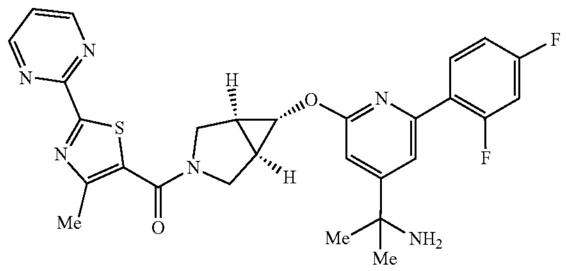 [SMILES: Cc1nc(-c2ncccn2)sc1C(=O)N1C[C@@H]2[C@H](C1)[C@H]2Oc1cc(C(C)(C)N)cc(-c2ccc(F)cc2F)n1]

To a stirred solution of benzyl (2-(2-(((1R,5S,6s)-3-azabicyclo[3.1.0]hexan-6-yl)oxy)-6-(2,4-difluorophenyl)pyridin-4-yl)propan-2-yl)carbamate (Int. H-07, 15 mg, 0.029 mmol) and 4-methyl-2-(pyrimidin-2-yl)thiazole-5-carboxylic acid (Int. L-3, 6.5 mg, 0.029 mmol) in DCM (0.50 mL) was added HATU (11 mg, 0.029 mmol) and then DIPEA (15 μL, 0.087 mmol). The mixture was stirred at rt for 1 h and then concentrated under reduced pressure. HCl (37% aqueous, 0.20 mL) was added, and the mixture was heated at 80° C. for 10 min, cooled to rt, and concentrated. The residue was dissolved in DMSO (1 mL) and subjected to mass directed reverse phase HPLC (MeCN/water with 0.1% TFA modifier) to afford the title compound as a TFA salt. MS m/z $(M+H)^+$: calculated 549.2; found 549.2. $^1$H NMR (500 MHz, DMSO-$d^6$) δ 8.95 (d, J=4.9 Hz, 2H), 8.59 (br s, 3H), 8.06-7.99 (m, 1H), 7.62 (t, J=4.9 Hz, 1H), 7.56 (s, 1H), 7.42-7.35 (m, 1H), 7.22 (td, J=8.5, 2.2 Hz, 1H), 6.94 (s, 1H), 4.04 (s, 1H), 3.79-3.30 (m, 4H), 2.46 (s, 3H), 2.15-2.07 (m, 1H), 2.02-1.92 (m, 1H), 1.62 (s, 6H) ppm.

Utilizing the procedures described in EXAMPLE 97, the below compounds were prepared substituting the appropriate reagents for benzyl (2-(2-(((1R,5S,6s)-3-azabicyclo[3.1.0]hexan-6-yl)oxy)-6-(2,4-difluorophenyl)pyridin-4-yl)propan-2-yl)carbamate and 4-methyl-2-(pyrimidin-2-yl)thiazole-5-carboxylic acid. Following HPLC purification, examples were concentrated directly to afford TFA or HCl salts or extracted under basic conditions to afford free bases. Names are provided for each compound.

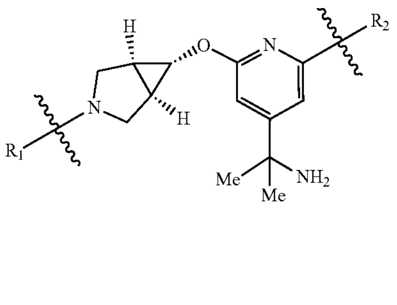

| Ex # | $R_1$ | $R_2$ | Calc'd $[M + H]^+$ | Observed $[M + H]^+$ | Comments |
|---|---|---|---|---|---|
| 98 | 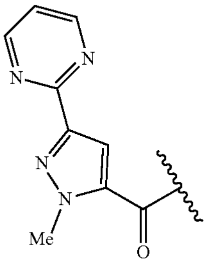 [SMILES: *C(=O)c1cc(-c2ncccn2)nn1C] | 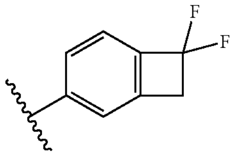 [SMILES: *c1ccc2c(c1)CC2(F)F] | 558.2 | 558.3 | Free base |
| | ((1R,5S,6s)-6-((4-(2-aminopropan-2-yl)-6-(7,7-difluorobicyclo[4.2.0]octa-1(6),2,4-trien-3-yl)pyridin-2-yl)oxy)-3-azabicyclo[3.1.0]hexan-3-yl)(1-methyl-3-(pyrimidin-2-yl)-1H-pyrazol-5-yl)methanone | | | | |
| 99 | 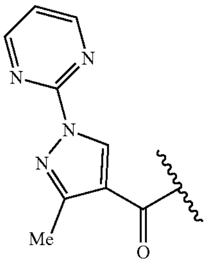 [SMILES: *C(=O)c1cn(-c2ncccn2)nc1C] | 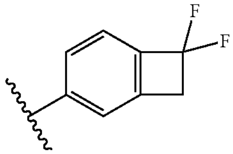 [SMILES: *c1ccc2c(c1)CC2(F)F] | 558.2 | 558.3 | Free base |
| | ((1R,5S,6s)-6-((4-(2-aminopropan-2-yl)-6-(7,7-difluorobicyclo[4.2.0]octa-1(6),2,4-trien-3-yl)pyridin-2-yl)oxy)-3-azabicyclo[3.1.0]hexan-3-yl)(3-methyl-1-(pyrimidin-2-yl)-1H-pyrazol-4-yl)methanone | | | | |
| 100 | 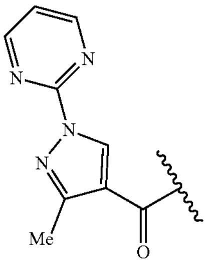 [SMILES: *C(=O)c1cn(-c2ncccn2)nc1C] | 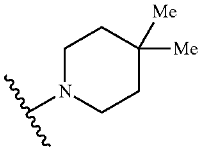 [SMILES: *N1CCC(C)(C)CC1] | 531.3 | 531.5 | Free base |
| | ((1R,5S,6s)-6-((4-(2-aminopropan-2-yl)-6-(4,4-dimethylpiperidin-1-yl)pyridin-2-yl)oxy)-3-azabicyclo[3.1.0]hexan-3-yl)(3-methyl-1-(pyrimidin-2-yl)-1H-pyrazol-4-yl)methanone | | | | |
| 101 | 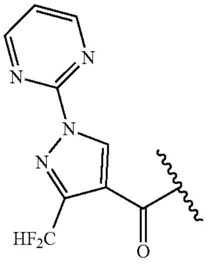 | 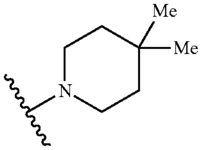 [SMILES: *N1CCC(C)(C)CC1] | 567.3 | 567.5 | Free base |
| | ((1R,5S,6s)-6-((4-(2-aminopropan-2-yl)-6-(4,4-dimethylpiperidin-1-yl)pyridin-2-yl)oxy)-3-azabicyclo[3.1.0]hexan-3-yl)(3-(difluoromethyl)-1-(pyrimidin-2-yl)-1H-pyrazol-4-yl)methanone | | | | |

-continued

| Ex # | $R_1$ | $R_2$ | Calc'd $[M + H]^+$ | Observed $[M + H]^+$ | Comments |
|---|---|---|---|---|---|
| 102 | 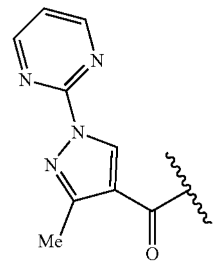 [SMILES: *C(=O)c1cn(-c2ncccn2)nc1C] | 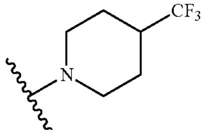 [SMILES: *N1CCC(C(F)(F)F)CC1] | 571.3 | 571.3 | Free base |

((1R,5S,6s)-6-((4-(2-aminopropan-2-yl)-6-(4-(trifluoromethyl)piperidin-1-yl)pyridin-2-yl)oxy)-3-azabicyclo[3.1.0]hexan-3-yl)(3-methyl-1-(pyrimidin-2-yl)-1H-pyrazol-4-yl)methanone

Example 103A rel-((1R,5S,6s)-6-((4-(2-aminopropan-2-yl)-6-(4-fluorophenyl)pyridin-2-yl)oxy)-1-methyl-3-azabicyclo[3.1.0]hexan-3-yl)(4-methyl-2-(pyrimidin-2-yl)thiazol-5-yl)methanone (Enantiomer 1)

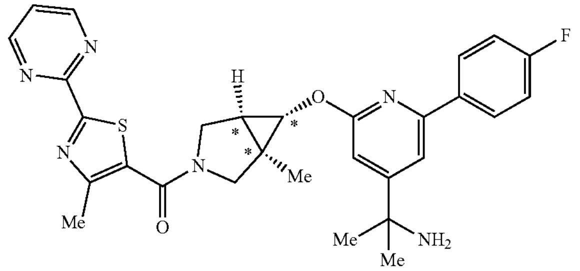 [SMILES: Cc1nc(-c2ncccn2)sc1C(=O)N1C[C@H]2[C@H](Oc3cc(C(C)(C)N)cc(-c4ccc(F)cc4)n3)[C@@]2(C)C1]

Step 1: benzyl rel-(2-(2-(4-fluorophenyl)-6-(((1R,5S,6s)-1-methyl-3-(4-methyl-2-(pyrimidin-2-yl)thiazole-5-carbonyl)-3-azabicyclo[3.1.0]hexan-6-yl)oxy)pyridin-4-yl)propan-2-yl)carbamate (Enantiomer 1)

To a of solution of 4-methyl-2-(pyrimidin-2-yl)thiazole-5-carboxylic acid (Int. L-3, 19 mg, 0.084 mmol) and T3P (50 wt. % in EtOAc, 0.080 g, 0.13 mmol) in DMF (3.0 mL) were added DIPEA (0.10 mL, 0.25 mmol) and benzyl rel-(2-(2-(4-fluorophenyl)-6-(((1R,5S,6s)-1-methyl-3-azabicyclo[3.1.0]hexan-6-yl)oxy)pyridin-4-yl)propan-2-yl)carbamate (Int. J-1-ent-1, 0.040 g, 0.084 mmol). The mixture was stirred at rt for 1 h, water (5 mL) was added, and the mixture was extracted with EtOAc (10 mL×3). The combined organic extracts were dried with anhydrous sodium sulfate, filtered, and concentrated under reduced pressure. The residue was subjected to prep-TLC (EtOAc) to afford the title compound.

Step 2: rel-((1R,5S,6s)-6-((4-(2-aminopropan-2-yl)-6-(4-fluorophenyl)pyridin-2-yl)oxy)-1-methyl-3-azabicyclo[3.1.0]hexan-3-yl)(4-methyl-2-(pyrimidin-2-yl)thiazol-5-yl)methanone (Enantiomer 1)

A mixture of benzyl rel-(2-(2-(4-fluorophenyl)-6-(((1R,5S,6s)-1-methyl-3-(4-methyl-2-(pyrimidin-2-yl)thiazole-5-carbonyl)-3-azabicyclo[3.1.0]hexan-6-yl)oxy)pyridin-4-yl)propan-2-yl)carbamate (enantiomer 1, 36 mg, 0.053 mmol) and HCl (37%, 1.5 mL) was stirred at 80° C. for 10 min. The mixture was cooled to rt, concentrated under reduced pressure, and subjected to reverse phase HPLC (24-44% MeCN/water with 0.1% TFA modifier). The appropriate fractions were lyophilized to afford the title compound as a TFA salt. MS m/z $(M+H)^+$: calculated 545.2, observed 545.1. $^1H$ NMR ($CD_3OD$, 500 MHz) δ 8.94 (d, J=4.5 Hz, 2H), 8.14 (s, 2H), 7.66-7.53 (m, 2H), 7.24 (t, J=8.5 Hz, 2H), 6.86 (s, 1H), 4.24 (s, 1H), 4.11 (s, 1H), 3.88 (s, 1H), 3.96-3.55 (m, 2H), 2.56 (s, 3H), 1.85-1.79 (m, 0.5H), 1.77 (s, 6H), 1.65-1.54 (m, 0.5H), 1.44-1.17 (m, 3H) ppm.

Utilizing the procedures described in EXAMPLE 103A, the below compounds were prepared substituting the appropriate reagents for 4-methyl-2-(pyrimidin-2-yl)thiazole-5-carboxylic acid and Int. J-1-ent-1. Cbz removal was accomplished as described in EXAMPLE 103A Step 2 (HCl) or EXAMPLE 107A Step 2-1 ($PdCl_2/Et_3SiH$). Examples were subjected to reverse phase HPLC (MeCN/water with either 0.1% TFA or 0.05% HCl modifiers) and lyophilized to afford TFA or HCl salt.

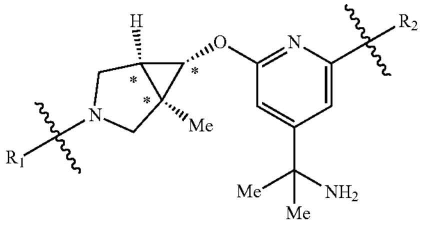

names are noted for each compound.

| Ex # | $R_1$ | $R_2$ | Calc'd $[M + H]^+$ | Observed $[M + H]^+$ | Comments |
|---|---|---|---|---|---|
| 103B | 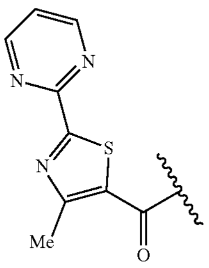 [SMILES: *C(=O)c1sc(-c2ncccn2)nc1C] | 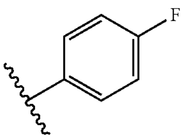 [SMILES: *c1ccc(F)cc1] | 545.2 | 545.1 | Step 1: Int. J-1-ent-2<br>Step 2: HCl<br>Form: HCl salt |
| | rel-((1R,5S,6s)-6-((4-(2-aminopropan-2-yl)-6-(4-fluorophenyl)pyridin-2-yl)oxy)-1-methyl-3-azabicyclo[3.1.0]hexan-3-yl)(4-methyl-2-(pyrimidin-2-yl)thiazol-5-yl)methanone (enantiomer 2) | | | | |
| 104A | 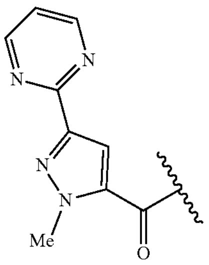 [SMILES: *C(=O)c1cc(-c2ncccn2)nn1C] | 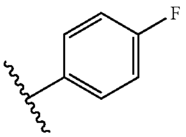 [SMILES: *c1ccc(F)cc1] | 528.2 | 528.2 | Step 1: Int. J-1-ent-1<br>Step 2: $PdCl_2/Et_3SiH$<br>Form: TFA salt |
| | rel-((1R,5S,6s)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 1) | | | | |
| 104B | 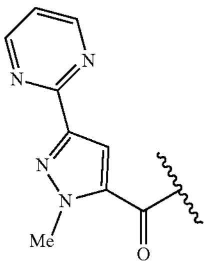 [SMILES: *C(=O)c1cc(-c2ncccn2)nn1C] | 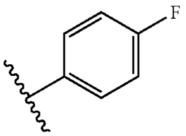 [SMILES: *c1ccc(F)cc1] | 528.2 | 528.2 | Step 1: Int. J-1-ent-2<br>Step 2: $PdCl_2/Et_3SiH$<br>Form: TFA salt |
| | rel-((1R,5S,6s)-6-((4-(2-aminopropan-2-yl)-6-(4-fluorophenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 2) | | | | |
| 105A | 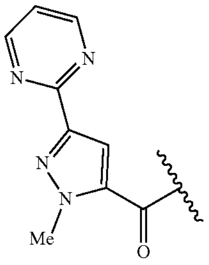 [SMILES: *C(=O)c1cc(-c2ncccn2)nn1C] | 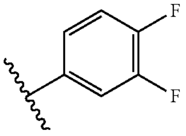 [SMILES: *c1ccc(F)c(F)c1] | 546.2 | 546.2 | Step 1: Int. J-4-ent-1<br>Step 2: $PdCl_2/Et_3SiH$<br>Form: TFA salt |
| | rel-((1R,5S,6s)-6-((4-(2-aminopropan-2-yl)-6-(3,4-difluorophenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 1) | | | | |

-continued

| Ex # | $R_1$ | $R_2$ | Calc'd $[M + H]^+$ | Observed $[M + H]^+$ | Comments |
|---|---|---|---|---|---|
| 105B | 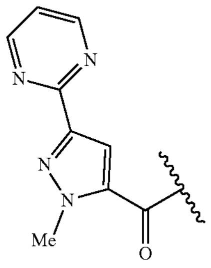 [SMILES: *C(=O)c1cc(-c2ncccn2)nn1C] | 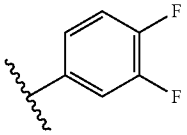 [SMILES: *c1ccc(F)c(F)c1] | 546.2 | 546.2 | Step 1: Int. J-4-ent-2<br>Step 2: $PdCl_2/Et_3SiH$<br>Form: TFA salt |
| | rel-((1R,5S,6s)-6-((4-(2-aminopropan-2-yl)-6-(3,4-difluorophenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 2) | | | | |
| 106A | 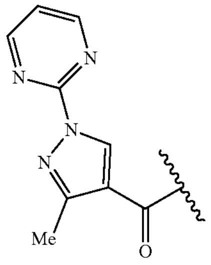 [SMILES: *C(=O)c1cn(-c2ncccn2)nc1C] | 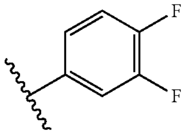 [SMILES: *c1ccc(F)c(F)c1] | 546.2 | 546.2 | Step 1: Int. J-4-ent-1<br>Step 2: $PdCl_2/Et_3SiH$<br>Form: TFA salt |
| | rel-((1R,5S,6s)-6-((4-(2-aminopropan-2-yl)-6-(3,4-difluorophenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (enantiomer 1) | | | | |
| 106B | 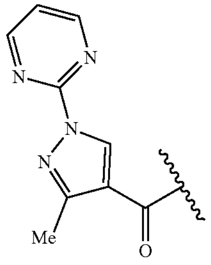 [SMILES: *C(=O)c1cn(-c2ncccn2)nc1C] | 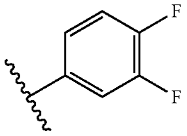 [SMILES: *c1ccc(F)c(F)c1] | 546.2 | 546.2 | Step 1: Int. J-4-ent-2<br>Step 2: $PdCl_2/Et_3SiH$<br>Form: TFA salt |
| | rel-((1R,5S,6s)-6-((4-(2-aminopropan-2-yl)-6-(3,4-difluorophenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (enantiomer 2) | | | | |

Example 107A and Example 107B

Example 107A: rel-((1R,5S,6s)-6-((4-(2-aminopropan-2-yl)-6-(4-fluorophenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (Enantiomer 1)

and

Example 107B: rel-((1R,5S,6s)-6-((4-(2-aminopropan-2-yl)-6-(4-fluorophenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (Enantiomer 2)

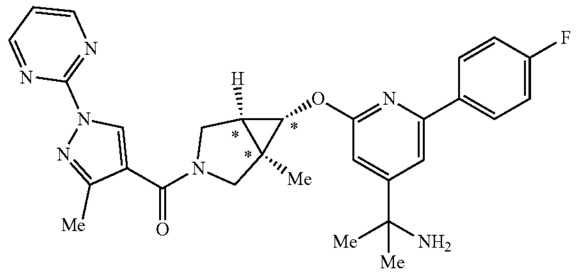 [SMILES: Cc1nn(-c2ncccn2)cc1C(=O)N1C[C@H]2[C@H](Oc3cc(C(C)(C)N)cc(-c4ccc(F)cc4)n3)[C@@]2(C)C1]

Step 1: benzyl rel-(2-(2-(4-fluorophenyl)-6-(((1R,5S,6s)-1-methyl-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate (Enantiomers 1 and 2)

To a of solution of 3-methyl-1-(pyrimidin-2-yl)-1H-pyrazole-4-carboxylic acid (39 mg, 0.19 mmol) in DMF (5.0 mL) were added DIPEA (0.10 mL, 0.57 mmol) and HATU (86 mg, 0.23 mmol). The mixture was stirred at rt for 15 min. Benzyl rac-(2-(2-(4-fluorophenyl)-6-(((1R,5S,6s)-1-methyl-3-azabicyclo[3.1.0]hexan-6-yl)oxy)pyridin-4-yl)propan-2-yl)carbamate (Int. J-1-rac, 0.090 g, 0.19 mmol) was added and the mixture was stirred at rt for 1 h. Water (5 mL) was added, and the mixture was extracted with EtOAc (10 mL×3). The combined organic extracts were dried with anhydrous sodium sulfate, filtered, and concentrated under reduced pressure. The residue was subjected to prep-TLC (EtOAc, Rf=0.35). The mixture of two stereoisomers was subjected to chiral SFC (ChiralPak AD-3, 5-40% IPA (with 0.05% DEA modifier)/CO2) to afford benzyl rel-(2-(2-(4-fluorophenyl)-6-(((1R,5S,6s)-1-methyl-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate (enantiomer 1, faster eluting) and benzyl rel-(2-(2-(4-fluorophenyl)-6-(((1R,5S,6s)-1-methyl-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate (enantiomer 2, slower eluting).

Step 2-1: rel-((1R,5S,6s)-6-((4-(2-aminopropan-2-yl)-6-(4-fluorophenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (Enantiomer 1)

To a solution of benzyl rel-(2-(2-(4-fluorophenyl)-6-(((1R,5S,6s)-1-methyl-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate (enantiomer 1, 46 mg, 0.070 mmol) in THF (5.0 mL) were added triethylamine (0.10 mL, 0.28 mmol), triethylsilane (0.040 g, 0.35 mmol), and $PdCl_2$ (3.7 mg, 0.021 mmol). The mixture was stirred at rt for 30 min, filtered, and concentrated under reduced pressure. The mixture was subjected to reverse phase HPLC (21-41% MeCN/water with 0.1% TFA modifier) and lyophilized to afford EXAMPLE 107A as a TFA salt. MS m/z $(M+H)^+$: calculated 528.2, observed 528.2. $^1H$ NMR (500 MHz, $CD_3OD$) δ 8.96-8.90 (m, 1H), 8.87-8.83 (m, 2H), 8.18-8.06 (m, 2H), 7.60 (s, 1H), 7.49-7.40 (m, 1H), 7.23-7.14 (m, 2H), 6.86 (s, 1H), 4.26-4.23 (m, 1H), 4.16-3.31 (m, 4H), 2.50-2.44 (m, 3H), 1.77 (s, 6H), 1.77-1.70 (m, 1H), 1.38-1.27 (m, 3H) ppm.

Step 2-2: rel-((1R,5S,6s)-6-((4-(2-aminopropan-2-yl)-6-(4-fluorophenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (Enantiomer 2)

To a solution of benzyl rel-(2-(2-(4-fluorophenyl)-6-(((1R,5S,6s)-1-methyl-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate (enantiomer 2, 53 mg, 0.080 mmol) in THF (3.0 mL) were added triethylamine (0.10 mL, 0.28 mmol), triethylsilane (47 mg, 0.40 mmol), and $PdCl_2$ (4.3 mg, 0.024 mmol). The mixture was stirred at rt for 30 min, filtered, and concentrated under reduced pressure. The mixture was subjected to reverse phase HPLC (20-40% MeCN/water with 0.1% TFA modifier) and lyophilized to afford EXAMPLE 107B as a TFA salt. MS m/z $(M+H)^+$: calculated 528.2, observed 528.2. $^1H$ NMR (500 MHz, $CD_3OD$) δ 8.96-8.90 (m, 1H), 8.87-8.83 (m, 2H), 8.18-8.06 (m, 2H), 7.60 (s, 1H), 7.49-7.40 (m, 1H), 7.23-7.14 (m, 2H), 6.86 (s, 1H), 4.26-4.23 (m, 1H), 4.16-3.31 (m, 4H), 2.50-2.44 (m, 3H), 1.77 (s, 6H), 1.77-1.70 (m, 1H), 1.38-1.27 (m, 3H) ppm.

Utilizing the procedures described in EXAMPLE 107A and EXAMPLE 107B, the below compounds were prepared substituting the appropriate reagents for 3-methyl-1-(pyrimidin-2-yl)-1H-pyrazole-4-carboxylic acid and Int. J-1-rac. For Step 1, the procedures described in EXAMPLE 107A Step 1 (HATU) or EXAMPLE 103A Step 1 (T3P) were utilized for amide bond formation and separation of enantiomers was accomplished using SFC conditions listed in the table comments. The procedures described in EXAMPLE 103A Step 2 (HCl) or EXAMPLE 107A Step 2-1 ($PdCl_2/Et_3SiH$) were utilized for N-Cbz protective group removal. Examples were subjected to reverse phase HPLC (MeCN/water with either 0.1% TFA or 0.05% HCl modifiers) and lyophilized to afford TFA or HCl salts.

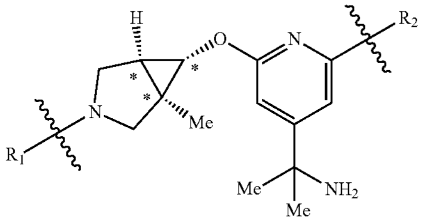

#=Calc'd $[M+H]^+$; ##=Observed $[M+H]^+$. names are noted for each compound.

| Ex # | $R_1$ | $R_2$ | # | ## | Comments |
| --- | --- | --- | --- | --- | --- |
| 108A | 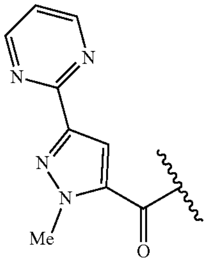 [SMILES: *C(=O)c1cc(-c2ncccn2)nn1C] | 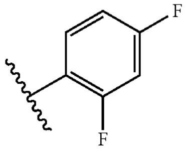 [SMILES: *c1ccc(F)cc1F] | 546.2 | 546.2 | Step 1: T3P<br>SFC: ChiralPak OJ-3, 40% MeOH(with 0.05% DEA modifier)/$CO_2$, faster eluting.<br>Step 2: HCl; Form: HCl salt |
| | rel-((1R,5S,6s)-6-((4-(2-aminopropan-2-yl)-6-(2,4-difluorophenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 1) | | | | |
| 108B | 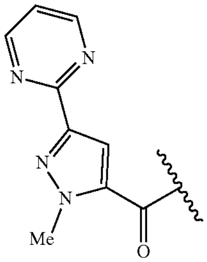 [SMILES: *C(=O)c1cc(-c2ncccn2)nn1C] | 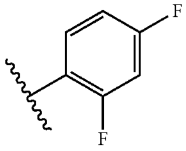 [SMILES: *c1ccc(F)cc1F] | 546.2 | 546.2 | Step 1: T3P<br>SFC: ChiralPak OJ-3, 40% MeOH(with 0.05% DEA modifier)/$CO_2$, slower eluting.<br>Step 2: HCl; Form: HCl salt |
| | rel-((1R,5S,6s)-6-((4-(2-aminopropan-2-yl)-6-(2,4-difluorophenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 2) | | | | |
| 109A | 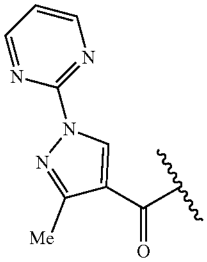 [SMILES: *C(=O)c1cn(-c2ncccn2)nc1C] | 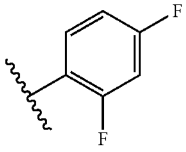 [SMILES: *c1ccc(F)cc1F] | 546.2 | 546.2 | Step 1: T3P<br>SFC: ChiralPak AS-3, 5-40% EtOH(with 0.05% DEA modifier)/$CO_2$, faster eluting.<br>Step 2: HCl; Form: HCl salt |
| | rel-((1R,5S,6s)-6-((4-(2-aminopropan-2-yl)-6-(2,4-difluorophenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (enantiomer 1) | | | | |
| 109B | 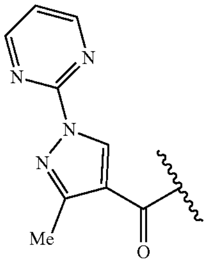 [SMILES: *C(=O)c1cn(-c2ncccn2)nc1C] | 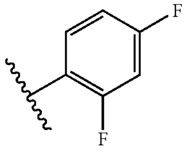 [SMILES: *c1ccc(F)cc1F] | 546.2 | 546.2 | Step 1: T3P<br>SFC: ChiralPak AS-3, 5-40% EtOH (with 0.05% DEA modifier)/$CO_2$, slower eluting.<br>Step 2: HCl; Form: HCl salt |
| | rel-((1R,5S,6s)-6-((4-(2-aminopropan-2-yl)-6-(2,4-difluorophenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (enantiomer 2) | | | | |

-continued

| Ex # | R1 | R2 | # | ## | Comments |
|---|---|---|---|---|---|
| 110A | 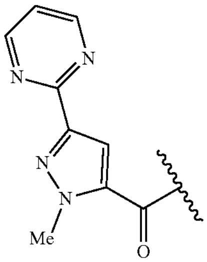 [SMILES: *C(=O)c1cc(-c2ncccn2)nn1C] | 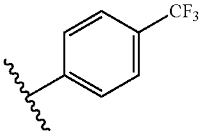 [SMILES: *c1ccc(C(F)(F)F)cc1] | 578.2 | 578.2 | Step 1: T3P SFC: ChiralPak IB-N, 60% hexane(with 0.1% DEA modifier)/ EtOH (with 0.1% DEA modifier), faster eluting. Step 2: $PdCl_2/Et_3SiH$; Form: TFA salt |
| | rel-((1R,5S,6s)-6-((4-(2-aminopropan-2-yl)-6-(4-(trifluoromethyl)phenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 1) | | | | |
| 110B | 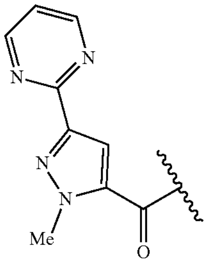 [SMILES: *C(=O)c1cc(-c2ncccn2)nn1C] | 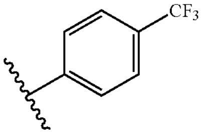 [SMILES: *c1ccc(C(F)(F)F)cc1] | 578.2 | 578.2 | Step 1: T3P SFC: ChiralPak IB-N, 60% hexane(with 0.1% DEA modifier)/ EtOH (with 0.1% DEA modifier), slower eluting. Step 2: $PdCl_2/Et_3SiH$; Form: TFA salt |
| | rel-((1R,5S,6s)-6-((4-(2-aminopropan-2-yl)-6-(4-(trifluoromethyl)phenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 2) | | | | |
| 111A | 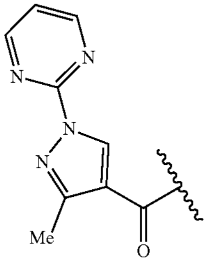 [SMILES: *C(=O)c1cn(-c2ncccn2)nc1C] | 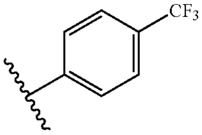 [SMILES: *c1ccc(C(F)(F)F)cc1] | 578.2 | 578.2 | Step 1: HATU SFC: ChiralPak AS-H, 5-40% EtOH (with 0.05% DEA modifier)/$CO_2$, faster eluting. Step 2: $PdCl_2/Et_3SiH$; Form: TFA salt |
| | rel-((1R,5S,6s)-6-((4-(2-aminopropan-2-yl)-6-(4-(trifluoromethyl)phenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (enantiomer 1) | | | | |
| 111B | 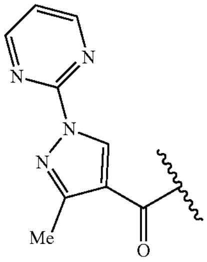 [SMILES: *C(=O)c1cn(-c2ncccn2)nc1C] | 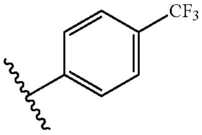 [SMILES: *c1ccc(C(F)(F)F)cc1] | 578.2 | 578.2 | Step 1: HATU SFC: ChiralPak AS-H, 5-40% EtOH (with 0.05% DEA modifier)/$CO_2$, slower eluting. Step 2: $PdCl_2/Et_3SiH$; Form: TFA salt |
| | rel-((1R,5S,6s)-6-((4-(2-aminopropan-2-yl)-6-(4-(trifluoromethyl)phenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (enantiomer 2) | | | | |

Example 112 ent-((1R,5S,6s)-6-((6-(4-fluorophenyl)-4-(2-methylpyrrolidin-2-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 1)

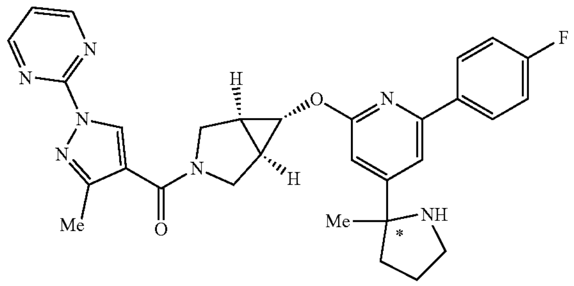 [SMILES: Cc1nn(-c2ncccn2)cc1C(=O)N1C[C@@H]2[C@H](C1)[C@H]2Oc1cc(C2(C)CCCN2)cc(-c2ccc(F)cc2)n1]

Step 1: benzyl ent-2-(2-(4-fluorophenyl)-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)-2-methylpyrrolidine-1-carboxylate (Enantiomer 1)

To a solution of 3-methyl-1-(pyrimidin-2-yl)-1H-pyrazole-4-carboxylic acid (21 mg, 0.10 mmol) in DMF (2.0 mL) was added DIPEA (0.10 mL, 0.10 mmol), benzyl ent-2-(2-(((1R,5S,6s)-3-azabicyclo[3.1.0]hexan-6-yl)oxy)-6-(4-fluorophenyl)pyridin-4-yl)-2-methylpyrrolidine-1-carboxylate·TFA (Int. H-04-ent-1, 0.050 g, 0.10 mmol), and T3P (50 wt % in EtOAc) (65 mg, 0.10 mmol). After 1 h, the mixture was diluted with water and extracted with EtOAc (3×). The combined organic extracts were washed with brine, dried with anhydrous sodium sulfate, filtered, and concentrated. The residue was purified by prep-TLC (EtOAc) to afford the title compound.

Step 2: ent-((1R,5S,6s)-6-((6-(4-fluorophenyl)-4-(2-methylpyrrolidin-2-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 1)

A mixture of benzyl 2-(2-(4-fluorophenyl)-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)-2-methylpyrrolidine-1-carboxylate (35 mg, 0.050 mmol) and HCl (37% aqueous, 1.0 mL) was heated at 80° C. for 5 min. The mixture was cooled to rt, concentrated, and subjected to reverse phase HPLC (16-36% MeCN/water containing 0.05% HCl). The appropriate fractions were concentrated to afford the title compound as an HCl salt. MS m/z $(M+H)^+$: calculated 540.2, observed 540.2. $^1H$ NMR (500 MHz, $CD_3OD$) δ 8.96 (s, 1H), 8.85 (d, J=5.0 Hz, 2H), 8.15 (dd, J=9.0, 5.5 Hz, 2H), 7.57 (d, J=2.5 Hz, 1H), 7.46 (t, J=5.0 Hz, 1H), 7.21 (t, J=9.0 Hz, 2H), 6.81 (d, J=3.0 Hz, 1H), 4.24-4.18 (m, 1H), 4.07-4.00 (m, 3H), 3.74-3.68 (m, 1H), 3.63-3.57 (m, 1H), 3.51-3.49 (m, 1H), 2.55-2.49 (m, 1H), 2.48 (s, 3H), 2.44-2.30 (m, 2H), 2.22-2.17 (m, 1H), 2.10-2.06 (m, 2H), 1.70 (s, 3H) ppm.

Example 113A ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(4-methyl-2-(pyrimidin-2-yl)thiazol-5-yl)methanone (Enantiomer 1)

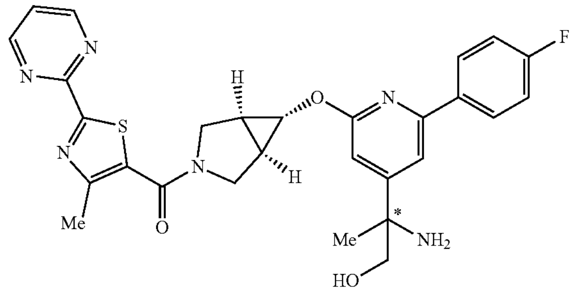 [SMILES: Cc1nc(-c2ncccn2)sc1C(=O)N1C[C@@H]2[C@H](C1)[C@H]2Oc1cc(C(C)(N)CO)cc(-c2ccc(F)cc2)n1]

Step 1: benzyl ent-(1-((tert-butyldiphenylsilyl)oxy)-2-(2-(4-fluorophenyl)-6-(((1R,5S,6s)-3-(4-methyl-2-(pyrimidin-2-yl)thiazole-5-carbonyl)-3-azabicyclo[3.1.0]hexan-6-yl)oxy)pyridin-4-yl)propan-2-yl)carbamate (Enantiomer 1)

A mixture of 4-methyl-2-(pyrimidin-2-yl)thiazole-5-carboxylic acid (Int. L-3, 25 mg, 0.11 mmol), benzyl ent-(2-(2-(((1R,5S,6s)-3-azabicyclo[3.1.0]hexan-6-yl)oxy)-6-(4-fluorophenyl)pyridin-4-yl)-1-((tert-butyldiphenylsilyl)oxy)propan-2-yl)carbamate (Int. H-06-ent-1, 0.060 g, 0.084 mmol), DMF (2.0 mL), DIPEA (0.015 mL, 0.084 mmol), and T3P (50 wt. % in EtOAc, 27 mg, 0.084 mmol) was stirred at rt for 1 h. Water (10 mL) was added and the mixture was extracted with EtOAc (20 mL×3). The combined organic extracts were washed with brine (20 mL×3), dried with anhydrous sodium sulfate, filtered, and concentrated under reduced pressure. The mixture was subjected to prep-TLC (67% EtOAc/petroleum ether, Rf=0.30) to afford the title compound.

Step 2: ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(4-methyl-2-(pyrimidin-2-yl)thiazol-5-yl)methanone (enantiomer 1)

A mixture of benzyl ent-(1-((tert-butyldiphenylsilyl)oxy)-2-(2-(4-fluorophenyl)-6-(((1R,5S,6s)-3-(4-methyl-2-(pyrimidin-2-yl)thiazole-5-carbonyl)-3-azabicyclo[3.1.0]hexan-6-yl)oxy)pyridin-4-yl)propan-2-yl)carbamate (enantiomer 1, 35 mg, 0.038 mmol) and HCl (37% aqueous, 1.0 mL) was stirred at 80° C. for 10 min. The mixture was cooled to rt, concentrated under reduced pressure, subjected to reverse phase HPLC (18-38% MeCN/water containing 0.1% TFA) and lyophilized to afford the title compound as a TFA salt. MS m/z $(M+H)^+$: calculated 547.2, observed 547.1. $^1H$ NMR (400 MHz, $CD_3OD$) δ 8.94 (d, J=4.8 Hz, 2H), 8.19-8.11 (m, 2H), 7.61-7.53 (m, 2H), 7.24 (t, J=8.8 Hz, 2H), 6.80 (s, 1H), 4.23 (d, J=9.6 Hz, 1H), 4.10 (s, 1H), 3.92-3.76 (m, 5H), 2.56 (s, 3H), 2.19-1.96 (m, 2H), 1.70 (s, 3H) ppm.

Utilizing the procedures described in EXAMPLE 113A, the below compound was prepared substituting the appropriate reagent for Int. H-06-ent-1.

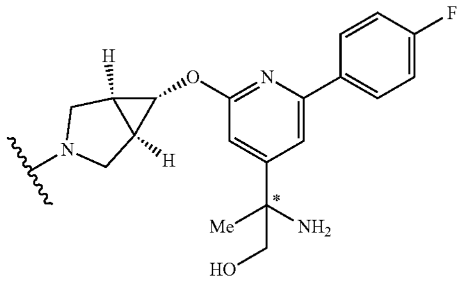 [SMILES: *N1C[C@@H]2[C@H](C1)[C@H]2Oc1cc(C(C)(N)CO)cc(-c2ccc(F)cc2)n1]

-continued

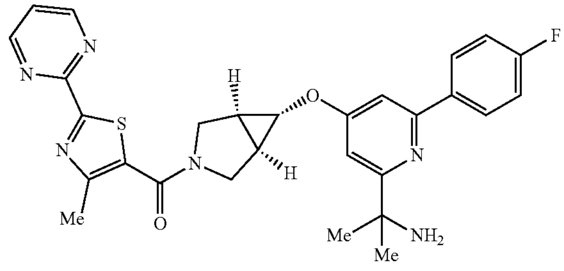

| Ex # | Structure | Name | Calc'd [M + H]+ | Observed [M + H]+ | Comments |
|---|---|---|---|---|---|
| 113B | 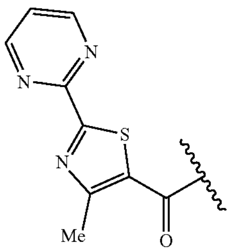 [SMILES: *C(=O)c1sc(-c2ncccn2)nc1C] | ent-((1R,5S,6s)-6-((4-(2-amino-1-hydroxypropan-2-yl)-6-(4-fluorophenyl)pyridin-2-yl)oxy)-3-azabicyclo[3.1.0]hexan-3-yl)(4-methyl-2-(pyrimidin-2-yl)thiazol-5-yl)methanone (enantiomer 2) | 547.2 | 547.2 | Step 1: Int. H-06-ent-2 |

Scheme

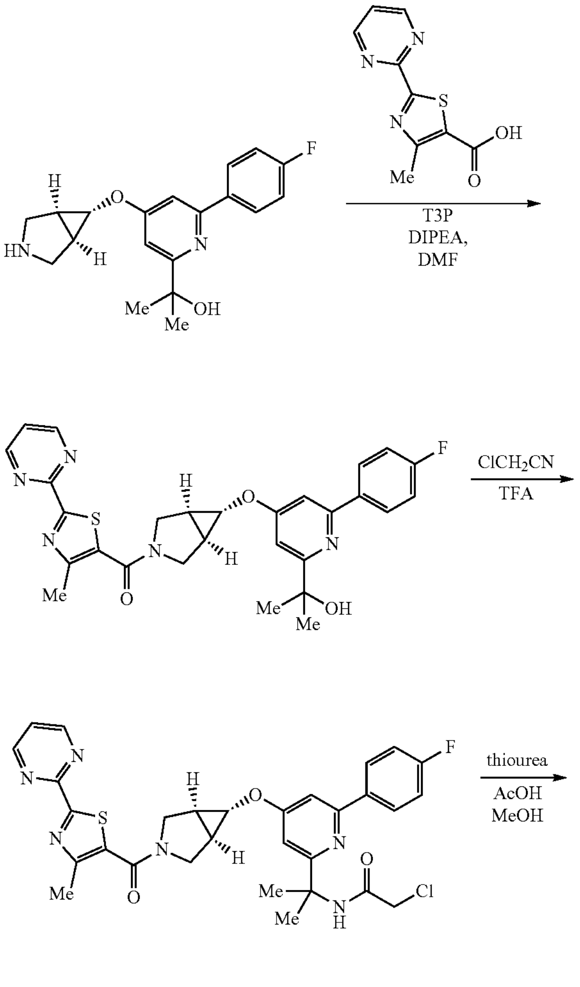

Example 114

((1R,5S,6s)-6-((2-(2-aminopropan-2-yl)-6-(4-fluorophenyl)pyridin-4-yl)oxy)-3-azabicyclo[3.1.0]hexan-3-yl)(4-methyl-2-(pyrimidin-2-yl)thiazol-5-yl)methanone

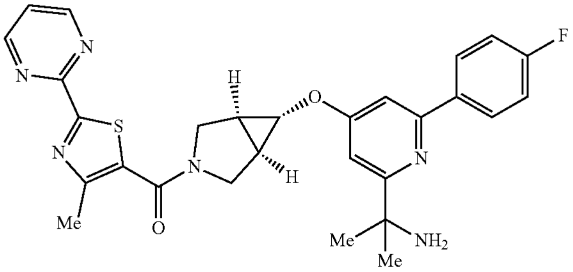

Step 1: ((1R,5S,6s)-6-((2-(4-fluorophenyl)-6-(2-hydroxypropan-2-yl)pyridin-4-yl)oxy)-3-azabicyclo[3.1.0]hexan-3-yl)(4-methyl-2-(pyrimidin-2-yl)thiazol-5-yl)methanone To a solution of 2-(4-(((1R,5S,6s)-3-azabicyclo[3.1.0]hexan-6-yl)oxy)-6-(4-fluorophenyl)pyridin-2-yl)propan-2-ol (Int. H-11, 0.12 g, 0.29 mmol) in DMF (5.0 mL) were added DIPEA (0.10 mL, 0.29 mmol), 4-methyl-2-(pyrimidin-2-yl)thiazole-5-carboxylic acid (Int. L-3, 65 mg, 0.29 mmol), and T3P (50 wt. % in EtOAc, 0.19 g, 0.29 mmol). The mixture was stirred at rt for 1 h, water (5 mL) was added, and the mixture was extracted with EtOAc (10 mL×3). The combined organic extracts were dried with anhydrous sodium sulfate, filtered, and concentrated under reduced pressure. The residue was subjected to prep-TLC (EtOAc, Rf=0.30) to afford the title compound.

Step 2: 2-chloro-N-(2-(6-(4-fluorophenyl)-4-(((1R,5S,6s)-3-(4-methyl-2-(pyrimidin-2-yl)thiazole-5-carbonyl)-3-azabicyclo[3.1.0]hexan-6-yl)oxy)pyridin-2-yl)propan-2-yl)acetamide A mixture of ((1R,5S,6s)-6-((2-(4-fluorophenyl)-6-(2-hydroxypropan-2-yl)pyridin-4-yl)oxy)-3-azabicyclo[3.1.0]hexan-3-yl)(4-methyl-2-(pyrimidin-2-yl)thiazol-5-yl)methanone (0.060 g, 0.11 mmol), TFA (3.0 mL), and 2-chloroacetonitrile (3.0 mL, 0.11 mmol) was heated at 100° C. for 12 h. The mixture was cooled to room temperature, concentrated under reduced pressure, and sodium bicarbonate (saturated aqueous, 5 mL) was added. The mixture was extracted with EtOAc (10 mL×3) and the combined organic extracts were dried with anhydrous sodium sulfate, filtered, and concentrated under reduced pressure. The residue was subjected to silica gel chromatography (0-30% EtOAc/petroleum ether) to afford the title compound.

Step 3: ((1R,5S,6s)-6-((2-(2-aminopropan-2-yl)-6-(4-fluorophenyl)pyridin-4-yl)oxy)-3-azabicyclo[3.1.0]hexan-3-yl)(4-methyl-2-(pyrimidin-2-yl)thiazol-5-yl)methanone A mixture of 2-chloro-N-(2-(6-(4-fluorophenyl)-4-(((1R,5S,6s)-3-(4-methyl-2-(pyrimidin-2-yl)thiazole-5-carbonyl)-3-azabicyclo[3.1.0]hexan-6-yl)oxy)pyridin-2-yl)propan-2-yl)acetamide (75 mg, 0.086 mmol), MeOH (2.0 mL), acetic acid (0.40 mL), and thiourea (6.6 mg, 0.086 mmol) was heated at 80° C. for 4 h. The mixture was cooled to rt, concentrated under reduced pressure, and subjected to reverse phase HPLC (30-50% MeCN/water containing 0.1% TFA). The mixture was further subjected to reverse phase HPLC (27-57% MeCN/water (10 mM $NH_4HCO_3$)) and the appropriate fractions concentrated under reduced pressure to afford the title compound. MS m/z $(M+H)^+$: calculated 531.2, observed 531.2. $^1$H NMR (500 MHz, $CD_3OD$) δ 8.91 (d, J=4.9 Hz, 2H), 8.14 (dd, J=8.8, 5.4 Hz, 2H), 7.54 (t, J=5.0 Hz, 1H), 7.37 (d, J=1.7 Hz, 1H), 7.19 (t, J=8.8 Hz, 2H), 7.10 (d, J=1.7 Hz, 1H), 4.22 (s, 1H), 3.97-3.73 (m, 4H), 2.58 (s, 3H), 2.19-2.09 (m, 2H), 1.60 (s, 6H) ppm.

Example 115

((1R,5S,6s)-6-((6-(2-aminopropan-2-yl)-4-(4-fluorophenyl)pyridin-2-yl)oxy)-3-azabicyclo[3.1.0]hexan-3-yl)(4-methyl-2-(pyrimidin-2-yl)thiazol-5-yl)methanone

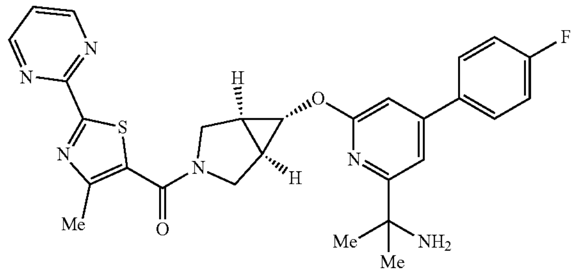 [SMILES: Cc1nc(-c2ncccn2)sc1C(=O)N1C[C@@H]2[C@H](C1)[C@H]2Oc1cc(-c2ccc(F)cc2)cc(C(C)(C)N)n1]

Step 1: benzyl (2-(4-(4-fluorophenyl)-6-(((1R,5S,6s)-3-(4-methyl-2-(pyrimidin-2-yl)thiazole-5-carbonyl)-3-azabicyclo[3.1.0]hexan-6-yl)oxy)pyridin-2-yl)propan-2-yl)carbamate To a solution of 4-methyl-2-(pyrimidin-2-yl)thiazole-5-carboxylic acid (Int. L-3, 14 mg, 0.065 mmol) in DMF (2.0 mL) was added DIPEA (0.10 mL, 0.065 mmol) and HATU (0.030 g, 0.078 mmol). The mixture was stirred at rt for 15 min, then benzyl (2-(6-(((1R,5S,6s)-3-azabicyclo[3.1.0]hexan-6-yl)oxy)-4-(4-fluorophenyl)pyridin-2-yl)propan-2-yl)carbamate (Int. H-05, 0.030 g, 0.065 mmol) was added. The mixture was stirred at rt for 1 h, water (5 mL) was added, and the mixture was extracted with EtOAc (10 mL×3). The combined organic extracts were dried with anhydrous sodium sulfate, filtered, and concentrated under reduced pressure to afford the title compound.

Step 2: ((1R,5S,6s)-6-((6-(2-aminopropan-2-yl)-4-(4-fluorophenyl)pyridin-2-yl)oxy)-3-azabicyclo[3.1.0]hexan-3-yl)(4-methyl-2-(pyrimidin-2-yl)thiazol-5-yl)methanone A solution of benzyl (2-(4-(4-fluorophenyl)-6-(((1R,5S,6s)-3-(4-methyl-2-(pyrimidin-2-yl)thiazole-5-carbonyl)-3-azabicyclo[3.1.0]hexan-6-yl)oxy)pyridin-2-yl)propan-2-yl)carbamate (33 mg, 0.050 mmol) in HCl (37% aqueous, 2.0 mL) was heated at 80° C. for 10 min. The mixture was cooled to rt, concentrated under reduced pressure, and the residue was subjected to reverse phase HPLC (26-46% MeCN/water containing 0.1% TFA) to afford the title compound as a TFA salt. MS m/z $(M+H)^+$: calculated 531.2, observed 531.3. $^1$H NMR (500 MHz, $CD_3OD$) δ 8.97-8.81 (m, 2H), 7.80-7.75 (m, 2H), 7.55 (t, J=4.9 Hz, 1H), 7.45 (d, J=1.2 Hz, 1H), 7.29-7.21 (m, 2H), 7.04 (d, J=1.2 Hz, 1H), 4.28-4.14 (m, 2H), 3.98-3.72 (m, 3H), 2.60-2.55 (m, 3H), 2.21-2.03 (m, 2H), 1.79 (s, 6H) ppm.

Example 116A ent-((1R,5S,6s)-6-((4-(2-aminobutan-2-yl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone (Enantiomer 1)

and

Example 116B ent-((1R,5S,6s)-6-((4-(2-aminobutan-2-yl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone (Enantiomer 2)

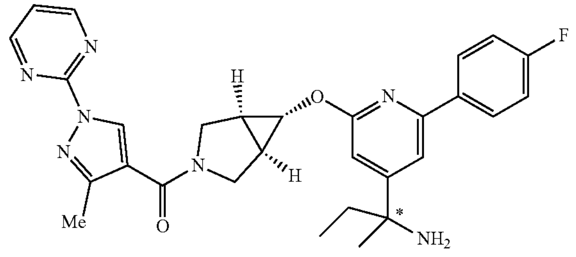 [SMILES: CCC(C)(N)c1cc(O[C@H]2[C@@H]3CN(C(=O)c4cn(-c5ncccn5)nc4C)C[C@@H]32)nc(-c2ccc(F)cc2)c1]

Step 1: N-(2-(2-(4-fluorophenyl)-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)butan-2-yl)-2-methylpropane-2-sulfinamide To a solution of 3-methyl-1-(pyrimidin-2-yl)-1H-pyrazole-4-carboxylic acid (0.010 g, 0.049 mmol) in DMF (1.0 mL) was added DIPEA (0.026 mL, 0.15 mmol) and HATU (28 mg, 0.073 mmol). The mixture was stirred at 25° C. for 5 min, followed by the addition of N-(2-(2-(((1R,5S,6s)-3-azabicyclo[3.1.0]hexan-6-yl)oxy)-6-(4-fluorophenyl)pyridin-4-yl)butan-2-yl)-2-methylpropane-2-sulfinamide (Int. Q, 22 mg, 0.049 mmol). The mixture was stirred at 25° C. for 1 h, poured into water (5 mL), and extracted with EtOAc (10 mL×3). The combined organic extracts were washed with brine (10 mL×2), dried over anhydrous sodium sulfate, filtered and concentrated under reduced pressure. The mixture was subjected to prep-TLC (1% DCM/MeOH) to afford the title compound.

Step 2: ent-((1R,5S,6s)-6-((4-(2-aminobutan-2-yl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone (Enantiomers 1 and 2)

A solution of N-(2-(2-(4-fluorophenyl)-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)butan-2-yl)-2-methylpropane-2-sulfinamide (0.080 g, 0.13 mmol) in methanolic HCl (4.0 M in MeOH, 2.0 mL) stirred at 25° C. for 30 min. The mixture was subjected to reverse phase HPLC (20-40% MeCN/water with 0.1% TFA modifier) and resulting mixture was subjected to chiral SFC (ChiralPak ID, 40% EtOH (with 0.1% DEA modifier)/hexane (with 0.1% DEA modifier)) to afford the title compounds. EXAMPLE 116A (faster eluting enantiomer): MS m/z $(M+H)^+$: calculated 528.3, observed 528.2. $^1H$ NMR (400 MHz, $CD_3OD$) δ 8.95 (s, 1H), 8.84 (d, J=4.8 Hz, 2H), 8.14 (dd, J=5.6, 8.8 Hz, 2H), 7.54 (s, 1H), 7.45 (t, J=5.2 Hz, 1H), 7.21 (t, J=8.4 Hz, 2H), 6.77 (s, 1H), 4.2 (d, J=12.4 Hz, 1H), 4.0 (s, 3H), 3.7 (d, J=12.4 Hz, 1H), 2.5 (s, 3H), 2.1 (q, J=6.8, 12.4 Hz, 2H), 1.7 (s, 3H), 0.88 (t, J=7.6 Hz, 1H). EXAMPLE 116B (slower eluting enantiomer): MS m/z $(M+H)^+$: calculated 528.3, observed 528.2. $^1H$ NMR (400 MHz, $CD_3OD$) δ 8.95 (s, 1H), 8.84 (d, J=4.8 Hz, 2H), 8.13 (dd, J=5.6, 8.8 Hz, 2H), 7.54 (s, 1H), 7.45 (t, J=5.2 Hz, 1H), 7.21 (t, J=8.4 Hz, 2H), 6.78 (s, 1H), 4.2 (d, J=12.4 Hz, 1H), 4.0 (s, 3H), 3.7 (d, J=12.4 Hz, 1H), 2.5 (s, 3H), 2.1 (q, J=6.8, 12.4 Hz, 2H), 1.7 (s, 3H), 0.88 (t, J=7.6 Hz, 1H).

Utilizing the procedures described in EXAMPLE 116, the below compounds were prepared substituting the appropriate reagents for Intermediate Q.

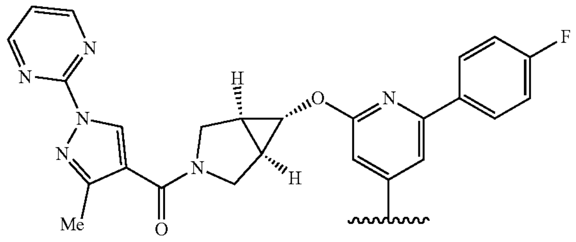 [SMILES: *c1cc(O[C@H]2[C@@H]3CN(C(=O)c4cn(-c5ncccn5)nc4C)C[C@@H]32)nc(-c2ccc(F)cc2)c1]

| Ex # | Structure | Name | Calc'd $[M + H]^+$ | Observed $[M + H]^+$ | Comments |
|---|---|---|---|---|---|
| 117A | 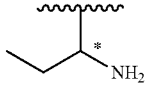 | ent-((1R,5S,6s)-6-((4-(1-aminopropyl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone | 514.2 | 514.2 | Enantiomer 1-faster eluting enantiomer |
| 117B | 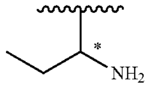 | ent-((1R,5S,6s)-6-((4-(1-aminopropyl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone | 514.2 | 514.2 | Enantiomer 2-slower eluting enantiomer |
| 118A | 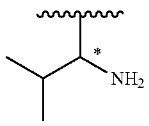 [SMILES: *C(N)C(C)C] | ent-((1R,5S,6s)-6-((4-(1-amino-2-methylpropyl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone | 528.3 | 528.2 | Enantiomer 1-faster eluting enantiomer |
| 118B | 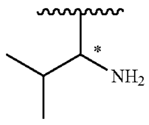 [SMILES: *C(N)C(C)C] | ent-((1R,5S,6s)-6-((4-(1-amino-2-methylpropyl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone | 528.3 | 528.2 | Enantiomer 2-slower eluting enantiomer |

Scheme

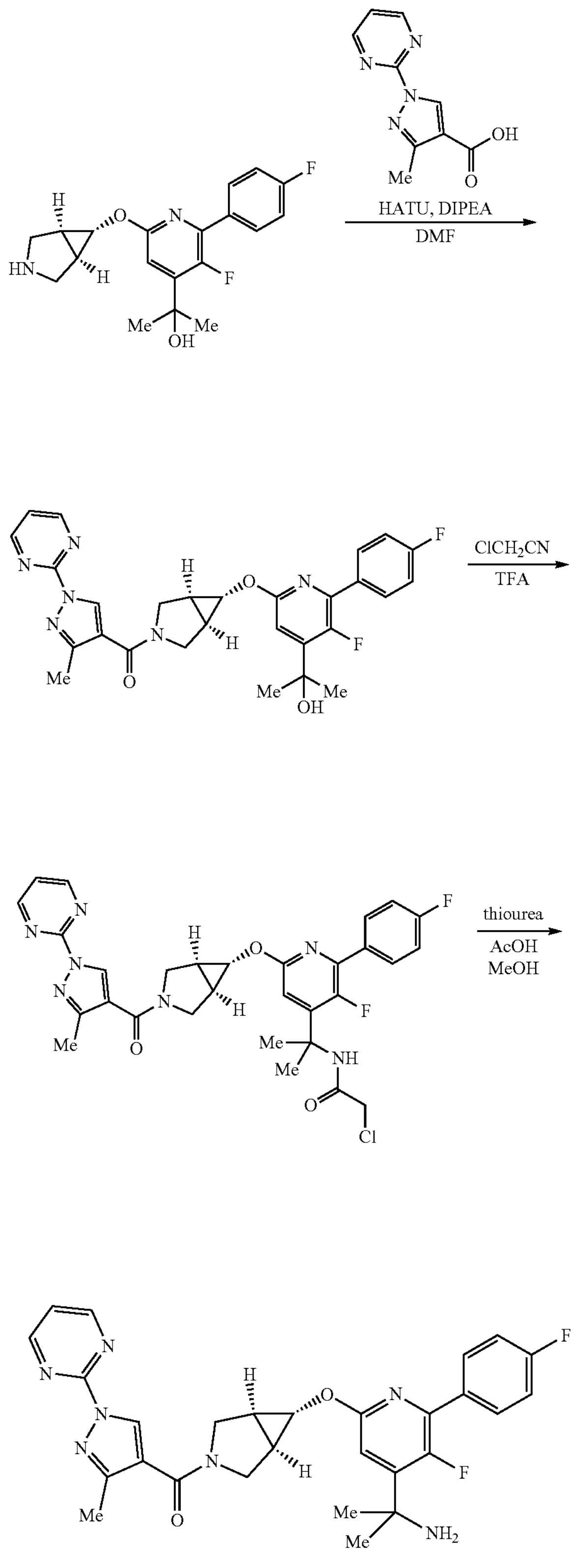

Example 119

((1R,5S,6s)-6-((4-(2-aminopropan-2-yl)-5-fluoro-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone

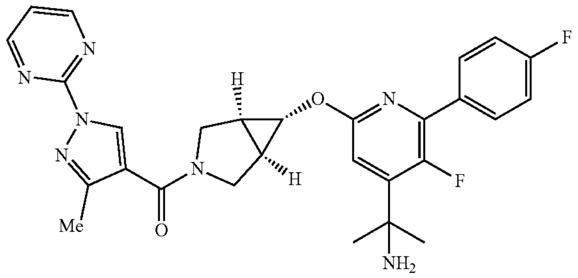 [SMILES: Cc1nn(-c2ncccn2)cc1C(=O)N1C[C@@H]2[C@H](C1)[C@H]2Oc1cc(C(C)(C)N)c(F)c(-c2ccc(F)cc2)n1]

Step 1: ((1R,5S,6s)-6-((5-fluoro-6-(4-fluorophenyl)-4-(2-hydroxypropan-2-yl)pyridin-2-yl)oxy)-3-azabicyclo[3.1.0]hexan-3-yl)(3-methyl-1-(pyrimidin-2-yl)-1H-pyrazol-4-yl)methanone To a solution of 3-methyl-1-(pyrimidin-2-yl)-1H-pyrazole-4-carboxylic acid (0.12 g, 0.60 mmol) in DMF (5.0 mL) were added DIPEA (0.30 mL, 1.7 mmol) and HATU (0.33 mg, 0.90 mmol). The mixture was stirred at ambient temperature for 15 min, then 2-(6-(((1R,5S,6s)-3-azabicyclo[3.1.0]hexan-6-yl)oxy)-3-fluoro-2-(4-fluorophenyl)pyridin-4-yl)propan-2-ol (Int. S, 0.20 g, 0.60 mmol) was added. The mixture was stirred at ambient temperature for 1 h, poured into water (5 mL), and extracted with EtOAc (15 mL×3). The combined organic extracts were washed with brine (15 mL×2), dried over anhydrous sodium sulfate, filtered and concentrated under reduced pressure. The mixture was subjected to prep-TLC (50% EtOAc/petroleum ether) to afford the title compound.

Step 2: 2-chloro-N-(2-(3-fluoro-2-(4-fluorophenyl)-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)acetamide To a solution of ((1R,5S,6s)-6-((5-fluoro-6-(4-fluorophenyl)-4-(2-hydroxypropan-2-yl)pyridin-2-yl)oxy)-3-azabicyclo[3.1.0]hexan-3-yl)(3-methyl-1-(pyrimidin-2-yl)-1H-pyrazol-4-yl)methanone (0.090 g, 0.20 mmol) in TFA (2.0 mL) was added 2-chloroacetonitrile (2.0 mL, 32 mmol). The mixture was heated to 100° C. for 12 h, cooled to room temperature, and concentrated under reduced pressure. The residue was diluted with sodium bicarbonate (saturated aqueous, 5 mL) and extracted with EtOAc (10 mL×3). The combined organic extracts were dried over anhydrous sodium sulfate, filtered and concentrated under reduced pressure. The residue was subjected to prep-TLC (EtOAc) to afford the title compound.

Step 3: ((1R,5S,6s)-6-((4-(2-aminopropan-2-yl)-5-fluoro-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone To a solution of 2-chloro-N-(2-(3-fluoro-2-(4-fluorophenyl)-6-(((1R,5S,6s)-3-(3-methyl-1-(pyrimidin-2-yl)-1H- pyrazole-4-carbonyl)-3-azabicyclo[3.1.0]hexan-6-yl)oxy)pyridin-4-yl)propan-2-yl)acetamide (0.060 g, 0.10 mmol) in MeOH (6.0 mL) and acetic acid (1.2 mL) was added thiourea (9.0 mg, 0.10 mmol). The mixture was heated to 80° C. for 12 h, cooled to room temperature, and concentrated under reduced pressure. The mixture was subjected to reverse phase HPLC (20-40% MeCN/water with 0.1% TFA modifier) to afford the title compound. MS m/z $(M+H)^+$: calculated 532.2, observed 532.2. $^1H$ NMR (400 MHz, $CD_3OD$) δ 8.92 (s, 1H), 8.85 (d, J=3.2 Hz, 2H), 8.03 (d, J=6.0 Hz, 2H), 7.45 (s, 1H), 7.26-7.19 (m, 2H), 6.78 (d, J=4.4 Hz, 1H), 4.59 (s, 1H), 4.19 (d, J=10.4 Hz, 1H), 3.97 (d, J=10.4 Hz, 2H), 3.71 (d, J=14.8 Hz, 1H), 2.46 (s, 3H), 2.08 (s, 2H), 1.81 (s, 6H) ppm.

Scheme

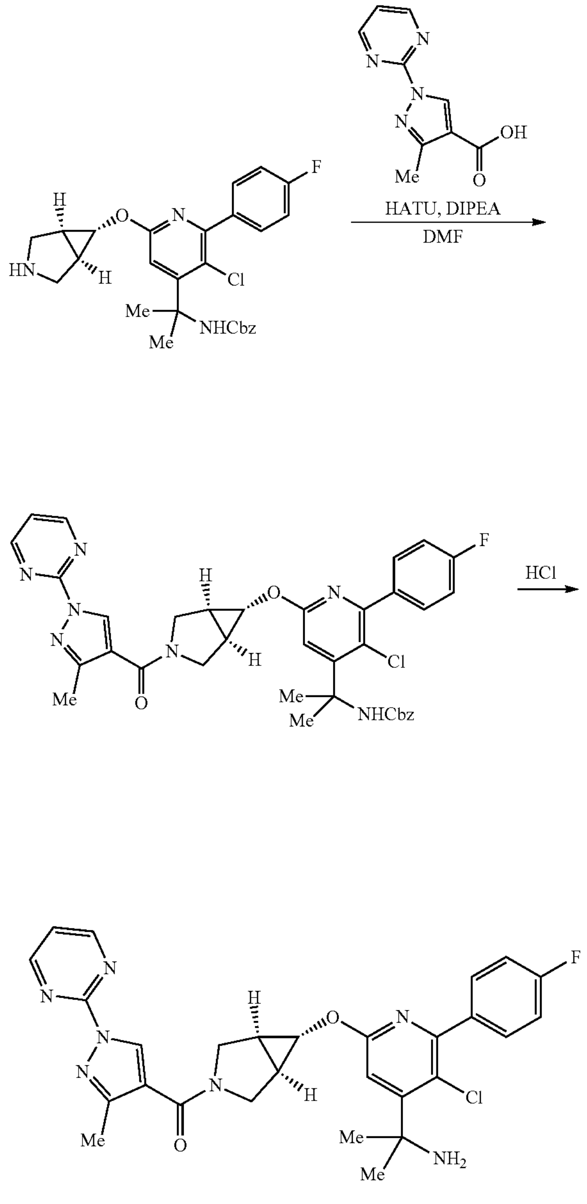

Example 120

((1R,5S,6s)-6-((4-(2-aminopropan-2-yl)-5-chloro-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone

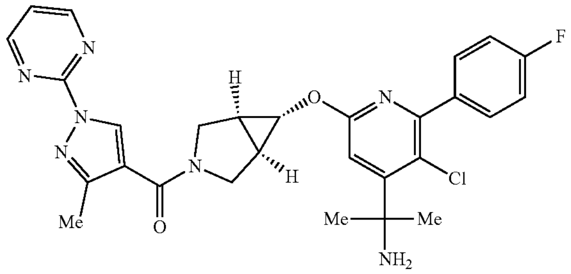 [SMILES: Cc1nn(-c2ncccn2)cc1C(=O)N1C[C@@H]2[C@H](C1)[C@H]2Oc1cc(C(C)(C)N)c(Cl)c(-c2ccc(F)cc2)n1]

Step 1: benzyl (2-(3-chloro-2-(4-fluorophenyl)-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate To a solution of 3-methyl-1-(pyrimidin-2-yl)-1H-pyrazole-4-carboxylic acid (25 mg, 0.12 mmol) in DMF (2.0 mL) was added DIPEA (0.10 mL, 0.37 mmol) and HATU (0.070 g, 0.18 mmol). The mixture was stirred at ambient temperature for 15 min, then benzyl (2-(6-(((1R,5S,6s)-3-azabicyclo[3.1.0]hexan-6-yl)oxy)-3-chloro-2-(4-fluorophenyl)pyridin-4-yl)propan-2-yl)carbamate (Int. T, 61 mg, 0.12 mmol) was added. The mixture was stirred at ambient temperature for 1 h, diluted with water (10 mL), and extracted with EtOAc (15 mL×3). The combined organic extracts were washed with brine (15 mL), dried over anhydrous sodium sulfate, filtered, and concentrated under reduced pressure. The mixture was subjected to prep-TLC (66% EtOAc/petroleum ether) to afford the title compound.

Step 2: ((1R,5S,6s)-6-((4-(2-aminopropan-2-yl)-5-chloro-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone A mixture of benzyl (2-(3-chloro-2-(4-fluorophenyl)-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate (0.070 g, 0.13 mmol) in HCl (12 M aqueous, 2.0 mL) was stirred at 80° C. for 10 min. The mixture was cooled to ambient temperature and subjected to reverse phase HPLC (20-40% MeCN/water (with 0.04% HCl modifier) to afford the title compound. MS m/z $(M+H)^+$: calculated 548.1, observed 548.2. $^1H$ NMR (400 MHz, $CD_3OD$) δ 8.87 (s, 1H), 8.84 (d, J=4.8 Hz, 2H), 7.72-7.64 (m, 2H), 7.45 (t, J=4.8 Hz, 1H), 7.19 (t, J=8.8 Hz, 2H), 6.88 (s, 1H), 4.11-4.09 (m, 1H), 4.00-3.85 (m, 3H), 3.69-3.67 (M, 1H), 2.41 (s, 3H), 2.08 (s, 2H), 1.92 (s, 6H).

Utilizing the procedures described in EXAMPLE 120, the below compound was prepared substituting the appropriate reagents for Intermediate M.

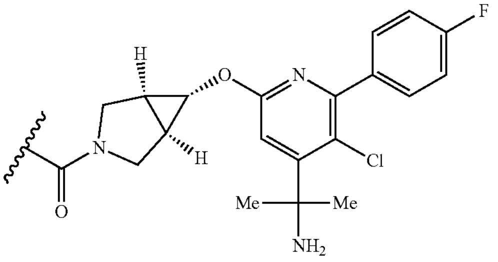 [SMILES: *C(=O)N1C[C@@H]2[C@H](C1)[C@H]2Oc1cc(C(C)(C)N)c(Cl)c(-c2ccc(F)cc2)n1]

| Ex # | Structure | Name | Calc'd $[M + H]^+$ | Observed $[M + H]^+$ |
|---|---|---|---|---|
| 121 | 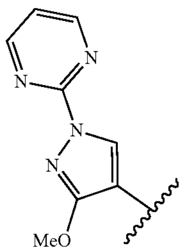 [SMILES: *c1cn(-c2ncccn2)nc1OC] | ((1R,5S,6s)-6-((4-(2-aminopropan-2-yl)-5-chloro-6-(4-fluorophenyl)pyridin-2-yl)oxy)-3-azabicyclo[3.1.0]hexan-3-yl)(3-methoxy-1-(pyrimidin-2-yl)-1H-pyrazol-4-yl)methanone | 564.2 | 564.2 |

Example 122

((1R,5S,6s)-6-((4-(2-aminopropan-2-yl)-6-(4,4-dimethylpiperidin-1-yl)pyridin-2-yl)oxy)-3-azabicyclo[3.1.0]hexan-3-yl)(3-methoxy-1-(pyrimidin-2-yl)-1H-pyrazol-4-yl)methanone

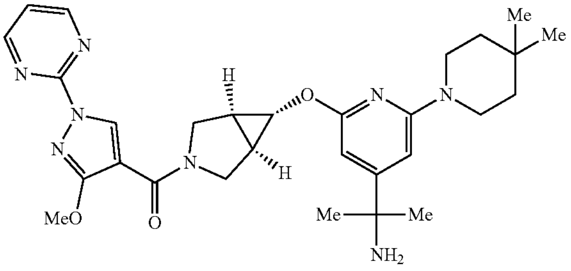 [SMILES: COc1nn(-c2ncccn2)cc1C(=O)N1C[C@@H]2[C@H](C1)[C@H]2Oc1cc(C(C)(C)N)cc(N2CCC(C)(C)CC2)n1]

To a solution of 3-methoxy-1-(pyrimidin-2-yl)-1H-pyrazole-4-carboxylic acid (Int. N-04, 0.30 g, 1.4 mmol) in DMSO (0.010 L) was added 4-methylmorpholine (0.20 mL, 1.5 mmol) and HATU (0.55 g, 1.5 mmol). The mixture was stirred at rt for 10 min, then 2-(2-(((1R,5S,6s)-3-azabicyclo[3.1.0]hexan-6-yl)oxy)-6-(4,4-dimethylpiperidin-1-yl)pyridin-4-yl)propan-2-amine (Int. H-09-2, 0.50 g, 1.5 mmol) was added. The mixture was stirred at rt for 30 min and then subjected to reverse phase HPLC (20-40% MeCN/water with 0.04% HCl modifier), followed by reverse phase HPLC (30-60% MeCN/water with 10 mM-$NH_4HCO_3$ modifier), to afford the title compound. MS m/z $(M+H)^+$: calculated 547.3, observed 547.3. $^1H$ NMR (400 MHz, $CD_3OD$) δ 8.88-8.78 (m, 3H), 7.41 (t, J=4.8 Hz, 1H), 6.34 (d, J=1.2 Hz, 1H), 6.04 (d, J=1.2 Hz, 1H), 4.18 (d, J=12.4 Hz, 1H), 4.10 (s, 3H), 3.95-3.83 (m, 2H), 3.73 (s, 1H), 3.64-3.58 (m, 1H), 3.55 (dd, J=7.2, 4.4 Hz, 4H), 2.03□1.86 (m, 2H), 1.64 (s, 6H), 1.34 (dd, J=6.8, 4.4 Hz, 4H), 0.91 (s, 6H) ppm.

Utilizing the procedures described in EXAMPLE 122, the below compounds were prepared substituting the appropriate reagents for 3-methoxy-1-(pyrimidin-2-yl)-1H-pyrazole-4-carboxylic acid and 2-(2-(((1R,5S,6s)-3-azabicyclo[3.1.0]hexan-6-yl)oxy)-6-(4,4-dimethylpiperidin-1-yl)pyridin-4-yl)propan-2-amine (Int. H-09-2). Modifications to the procedure are listed under comments.

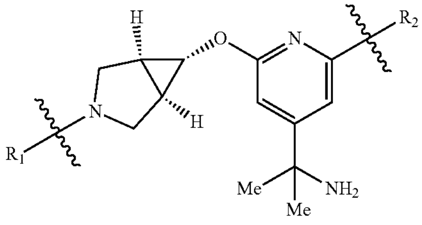

| Ex # | $R_1$ | $R_2$ | Calc'd $[M + H]^+$ | Observed $[M + H]^+$ | Comments |
|---|---|---|---|---|---|
| 123 | 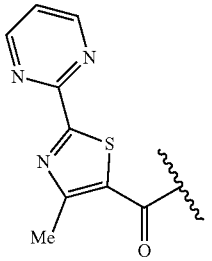 [SMILES: *C(=O)c1sc(-c2ncccn2)nc1C] | 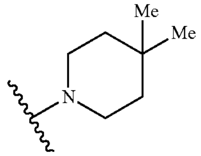 [SMILES: *N1CCC(C)(C)CC1] | 547.3 | 548.4 | Reverse phase HPLC (10-100% MeCN/water with 0.1% TFA modifier) followed by passage through an SPE ion exchange column |
| | ((1R,5S,6s)-6-((4-(2-aminopropan-2-yl)-6-(4,4-dimethylpiperidin-1-yl)pyridin-2-yl)oxy)-3-azabicyclo[3.1.0]hexan-3-yl)(4-methyl-2-(pyrimidin-2-yl)thiazol-5-yl)methanone | | | | |
| 124 | 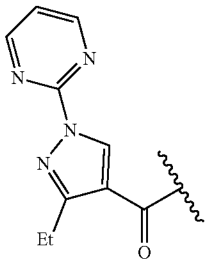 | 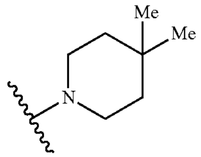 [SMILES: *N1CCC(C)(C)CC1] | 544.3 | 545.4 | silica gel (0-10% (3:1 ethanol:ethyl acetate) in hexanes) |
| | ((1R,5S,6s)-6-((4-(2-aminopropan-2-yl)-6-(4,4-dimethylpiperidin-1-yl)pyridin-2-yl)oxy)-3-azabicyclo[3.1.0]hexan-3-yl)(3-ethyl-1-(pyrimidin-2-yl)-1H-pyrazol-4-yl)methanone | | | | |
| 125 | 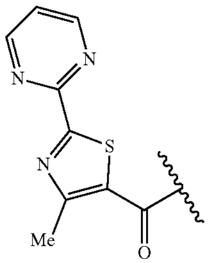 [SMILES: *C(=O)c1sc(-c2ncccn2)nc1C] | 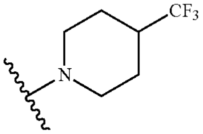 [SMILES: *N1CCC(C(F)(F)F)CC1] | 587.2 | 588.4 | Base: DIPEA Solvent: DMF Reverse phase HPLC (20-40% MeCN/water with 0.1% TFA modifier) |
| | ((1R,5S,6s)-6-((4-(2-aminopropan-2-yl)-6-(4-(trifluoromethyl)piperidin-1-yl)pyridin-2-yl)oxy)-3-azabicyclo[3.1.0]hexan-3-yl)(4-methyl-2-(pyrimidin-2-yl)thiazol-5-yl)methanone | | | | |

Example 126

((1R,5S,6s)-6-((4-(2-aminopropan-2-yl)-6-(4-fluorobenzyl)pyridin-2-yl)oxy)-3-azabicyclo[3.1.0]hexan-3-yl)(4-methyl-2-(pyrimidin-2-yl)thiazol-5-yl)methanone

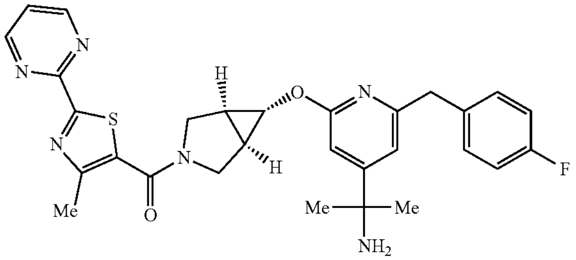 [SMILES: Cc1nc(-c2ncccn2)sc1C(=O)N1C[C@@H]2[C@H](C1)[C@H]2Oc1cc(C(C)(C)N)cc(Cc2ccc(F)cc2)n1]

A solution of 4-methyl-2-(pyrimidin-2-yl)thiazole-5-carboxylic acid (Int. L-3. 1.7 mg, 0.0080 mmol) and HATU (2.9 mg, 0.0080 mmol) in DMF (0.50 mL) were stirred at rt for 15 min. A solution of 2-(2-(((1R,5S,6s)-3-azabicyclo[3.1.0]hexan-6-yl)oxy)-6-(4-fluorobenzyl)pyridin-4-yl)propan-2-amine (Int. U, 5.1 mg, 0.015 mmol) in DMF (0.50 mL) was added followed by DIPEA (0.090 mL, 0.045 mmol). The mixture was stirred at 25° C. for 30 min and then subjected to reverse phase HPLC (MeCN/water, 0.05% TFA modifier) to afford the title compound. MS m/z $(M+H)^+$: calculated 544.2, observed 545.3. $^1H$ NMR (500 MHz, DMSO-$d^6$) δ 8.95 (d, J=4.9 Hz, 2H), 8.48 (br s, 2H), 7.61 (t, J=4.9 Hz, 1H), 7.35-7.29 (m, 2H), 7.16 (d, J=1.3 Hz, 1H), 7.05-6.98 (m, 2H), 6.74 (d, J=1.3 Hz, 1H), 3.99 (s, 2H), 3.47-3.42 (m, 6H), 2.48 (s, 3H), 1.99-1.83 (m, 2H), 1.56 (s, 6H) ppm.

Example 127A ent-((1R,5S,6s)-6-((4-(2-aminopropan-2-yl)-6-(2,4,4-trimethylpiperidin-1-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 1)

and

Example 127B ent-((1R,5S,6s)-6-((4-(2-aminopropan-2-yl)-6-(2,4,4-trimethylpiperidin-1-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 2)

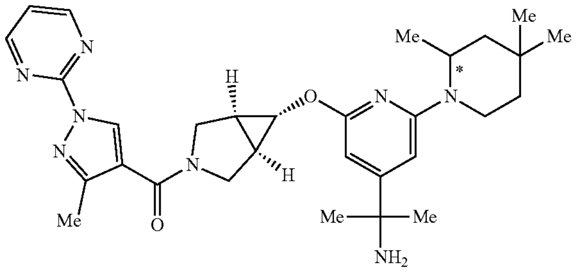 [SMILES: Cc1nn(-c2ncccn2)cc1C(=O)N1C[C@@H]2[C@H](C1)[C@H]2Oc1cc(C(C)(C)N)cc(N2CCC(C)(C)CC2C)n1]

Step 1: ent-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2,4,4-trimethylpiperidin-1-yl)pyridin-4-yl)propan-2-yl)carbamate (Enantiomer 1 and Enantiomer 2)

To a mixture of benzyl (2-(2-chloro-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl) carbamate (Int. I-3, 0.30 g, 0.51 mmol), 2,4,4-trimethylpiperidine (97 mg, 0.77 mmol), cesium carbonate (0.50 g, 1.5 mmol) in 1,4-dioxane (6.0 mL) was added Pd-PEPPSI-IPent$^{Cl}$ (0.050 g, 0.051 mmol). The mixture was heated at 110° C. for 18 h, cooled to room temperature, filtered, and then concentrated under reduced pressure. The residue was subjected to silica gel chromatography (0-100% EtOAc/petroleum ether). The mixture of two stereoisomers was subjected to chiral SFC (Chiralpak IC 50, 20% EtOH (with 0.05% DEA modifier)/hexane (0.1% DEA)) to afford the title compounds, enantiomer 1 (faster eluting) and enantiomer 2 (slower eluting).

Step 2-1: ent-((1R,5S,6s)-6-((4-(2-aminopropan-2-yl)-6-(2,4,4-trimethylpiperidin-1-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 1)

A solution of ent-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2,4,4-trimethylpiperidin-1-yl)pyridin-4-yl)propan-2-yl)carbamate (enantiomer 1, 0.060 g, 0.088 mmol) in HCl (12 M aqueous, 0.50 mL) was heated at 80° C. for 10 min, cooled to room temperature, and concentrated under reduced pressure. The residue was subjected to reverse phase HPLC (15-35% MeCN/water, 0.1% TFA modifier) to afford the title compound. MS m/z $(M+H)^+$: calculated 545.3, observed 545.3. $^1H$ NMR (400 MHz, $CD_3OD$) δ 8.91 (s, 1H), 8.84 (d, J=4.8 Hz, 2H), 7.45 (t, J=4.8 Hz, 1H), 6.69 (s, 1H), 6.41 (s, 1H), 4.33 (s, 1H), 4.22 (d, J=12.0 Hz, 1H), 4.05-3.88 (m, 3H), 3.81 (s, 1H), 3.67 (d, J=9.6 Hz, 1H), 3.27 (s, 1H), 2.46 (s, 3H), 2.11-1.98 (m, 2H), 1.68 (s, 6H), 1.65-1.48 (m, 4H), 1.14 (d, J=6.8 Hz, 3H), 1.02 (s, 3H), 0.91 (s, 3H) ppm.

Step 2-2: ent-((1R,5S,6s)-6-((4-(2-aminopropan-2-yl)-6-(2,4,4-trimethylpiperidin-1-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 2)

A solution of ent-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2,4,4-trimethylpiperidin-1-yl)pyridin-4-yl)propan-2-yl)carbamate (enantiomer 2, 65 mg, 0.096 mmol) in HCl (12 M aqueous, 0.50 mL) was heated at 80° C. for 10 min. The mixture was cooled to room temperature, concentrated under reduced pressure, and subjected to reverse phase HPLC (15-35% MeCN/water, 0.1% TFA modifier) to afford the title compound. MS m/z $(M+H)^+$: calculated 545.3, observed 545.3. $^1H$ NMR (400 MHz, $CD_3OD$) δ 8.91 (s, 1H), 8.84 (d, J=4.9 Hz, 2H), 7.45 (t, J=4.8 Hz, 1H), 6.73 (s, 1H), 6.44 (s, 1H), 4.37-4.14 (m, 2H), 4.07-3.89 (m, 3H), 3.83 (s, 1H), 3.67 (d, J=10.4 Hz, 1H), 3.30-3.22 (m, 1H), 2.46 (s, 3H), 2.05 (d, J=12.3 Hz, 2H), 1.68 (s, 6H), 1.67-1.46 (m, 4H), 1.14 (d, J=6.6 Hz, 3H), 1.02 (s, 3H), 0.91 (s, 3H) ppm.

Example 128A ent-((1R,5S,6s)-6-((4-(2-aminopropan-2-yl)-6-((1-cyclopentylethyl)amino)pyridin-2-yl)oxy)-3-azabicyclo[3.1.0]hexan-3-yl)(3-methyl-1-(pyrimidin-2-yl)-1H-pyrazol-4-yl)methanone (Enantiomer 1)

and

Example 128B ent-((1R,5S,6s)-6-((4-(2-aminopropan-2-yl)-6-((1-cyclopentylethyl)amino)pyridin-2-yl)oxy)-3-azabicyclo[3.1.0]hexan-3-yl)(3-methyl-1-(pyrimidin-2-yl)-1H-pyrazol-4-yl)methanone (Enantiomer 2)

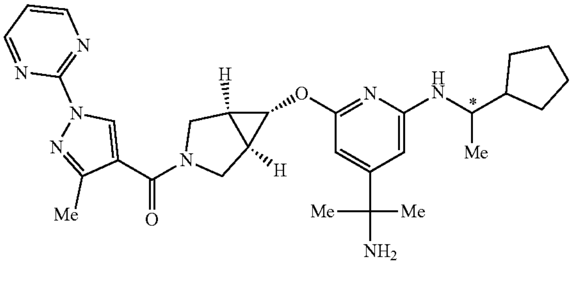 [SMILES: Cc1nn(-c2ncccn2)cc1C(=O)N1C[C@@H]2[C@H](C1)[C@H]2Oc1cc(C(C)(C)N)cc(NC(C)C2CCCC2)n1]

Step 1: benzyl (2-(2-((1-cyclopentylethyl)amino)-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate To a solution of benzyl (2-(2-chloro-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl) carbamate (Int. I-3, 0.10 g, 0.17 mmol), 1-cyclopentylethan-1-amine (77 mg, 0.34 mmol), cesium carbonate (0.17 mg, 0.51 mmol) in 1,4-dioxane (4.0 mL) was added Pd-PEPPSI-IPent$^{Cl}$ (17 mg, 0.017 mmol). The mixture was heated at 110° C. for 18 h under a nitrogen atmosphere. The mixture was cooled to rt, filtered, and concentrated under reduced pressure. The residue was subjected to prep-TLC (EtOAc) to afford the title compound.

Step 2: ent-((1R,5S,6s)-6-((4-(2-aminopropan-2-yl)-6-((1-cyclopentylethyl)amino)pyridin-2-yl)oxy)-3-azabicyclo[3.1.0]hexan-3-yl)(3-methyl-1-(pyrimidin-2-yl)-1H-pyrazol-4-yl)methanone (Enantiomer 1) and ((1R,5S,6s)-6-((4-(2-aminopropan-2-yl)-6-((1-cyclopentylethyl)amino)pyridin-2-yl)oxy)-3-azabicyclo[3.1.0]hexan-3-yl)(3-methyl-1-(pyrimidin-2-yl)-1H-pyrazol-4-yl)methanone (Enantiomer 2)

A solution of benzyl (2-(2-((1-cyclopentylethyl)amino)-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl)carbamate (0.090 g, 0.14 mmol) in HCl (12 M aqueous, 1.0 mL) was stirred at 80° C. for 10 min. The mixture was cooled to rt and subjected to reverse phase HPLC (18-38% MeCN/water with 0.1% TFA modifier). The racemic mixture was subjected to chiral SFC (DAICEL CHIRALCEL IG, 50% IPA (with $NH_3H_2O$ EtOH modifier)/CO2) to afford the title compounds. EXAMPLE 128A (faster eluting enantiomer): MS m/z $(M+H)^+$: calculated 531.3, observed 531.3. $^1H$ NMR (400 MHz, $CD_3OD$) δ 8.92 (s, 1H), 8.84 (d, J=4.8 Hz, 2H), 7.44 (t, J=4.8 Hz, 1H), 6.07 (d, J=6.0 Hz, 1H), 5.94 (d, J=4.4 Hz, 1H), 4.23 (t, J=13.2 Hz, 1H), 4.03-3.92 (m, 2H), 3.82 (d, J=6.8 Hz, 1H), 3.68-3.61 (m, 1H), 2.46 (s, 3H), 2.12□1.73 (m, 4H), 1.62 (s, 7H), 1.56-1.22 (m, 7H), 1.10-1.05 (m, 3H) ppm. EXAMPLE 128B (slower eluting enantiomer): MS m/z $(M+H)^+$: calculated 531.3, observed 531.3. $^1H$ NMR (400 MHz, $CD_3OD$) δ 8.92 (s, 1H), 8.84 (d, J=4.8 Hz, 2H), 7.44 (t, J=4.8 Hz, 1H), 6.06 (d, J=4.4 Hz, 1H), 5.92 (s, 1H), 4.23 (t, J=13.6 Hz, 1H), 4.04-3.90 (m, 2H), 3.82 (d, J=6.8 Hz, 1H), 3.68-3.60 (m, 1H), 2.46 (s, 3H), 2.11-1.71 (m, 4H), 1.62 (s, 7H), 1.52-1.22 (m, 6H), 1.54-1.20 (m, 1H), 1.09-1.08 (m, 3H) ppm.

Example 129A ent-((1R,5S,6s)-6-((4-(2-aminopropan-2-yl)-6-(2-methyl-4-(trifluoromethyl)piperidin-1-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 1)

and

Example 129B ent-((1R,5S,6s)-6-((4-(2-aminopropan-2-yl)-6-(2-methyl-4-(trifluoromethyl)piperidin-1-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 2)

and

Example 129C ent-((1R,5S,6s)-6-((4-(2-aminopropan-2-yl)-6-(2-methyl-4-(trifluoromethyl)piperidin-1-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 3)

and

Example 129D ent-((1R,5S,6s)-6-((4-(2-aminopropan-2-yl)-6-(2-methyl-4-(trifluoromethyl)piperidin-1-yl)pyridin-2-yl)oxy)-3-azabicyclo[3.1.0]hexan-3-yl)(3-methyl-1-(pyrimidin-2-yl)-1H-pyrazol-4-yl)methanone (Enantiomer 4)

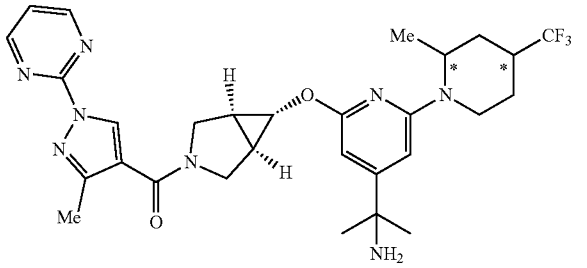 [SMILES: Cc1nn(-c2ncccn2)cc1C(=O)N1C[C@@H]2[C@H](C1)[C@H]2Oc1cc(C(C)(C)N)cc(N2CCC(C(F)(F)F)CC2C)n1]

Step 1: dia-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2-methyl-4-(trifluoromethyl)piperidin-1-yl)pyridin-4-yl)propan-2-yl) carbamate (Diastereomers 1 and 2)

To a mixture of benzyl (2-(2-chloro-6-(((1R,5S,6s)-3-(3-methyl-1-(pyrimidin-2-yl)-1H-pyrazole-4-carbonyl)-3-azabicyclo[3.1.0]hexan-6-yl)oxy)pyridin-4-yl)propan-2-yl) carbamate (Int. I-3, 0.30 g, 0.51 mmol), 2-methyl-4-(trifluoromethyl)piperidine (0.13 g, 0.77 mmol) and cesium carbonate (0.50 g, 1.5 mmol) in 1,4-dioxane (6.0 mL) was added Pd-PEPPSI-IPent$^{Cl}$ (0.050 g, 0.051 mmol). The mixture was heated at 110° C. for 18 h under a nitrogen atmosphere, cooled to rt, and then subjected to reverse phase HPLC (50-83% MeCN/water with 0.01% TFA modifier) to afford the title compounds, diastereomer 1 and diastereomer 2.

Step 2-1: ent-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2-methyl-4-(trifluoromethyl)piperidin-1-yl)pyridin-4-yl)propan-2-yl) carbamate (Enantiomer 1A and Enantiomer 2A)

A racemic mixture of dia-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2-methyl-4-(trifluoromethyl)piperidin-1-yl)pyridin-4-yl)propan-2-yl) carbamate (diastereomer 1, 0.14 g, 0.20 mmol) was subjected to chiral SFC (Chiralpak IC-3 100, 50% EtOH (with 0.05% DEA modifier)/CO2) to afford the title compounds, enantiomer 1A and enantiomer 2A.

Step 2-2: ent-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2-methyl-4-(trifluoromethyl)piperidin-1-yl)pyridin-4-yl)propan-2-yl) carbamate (Enantiomer 3A and Enantiomer 4A)

A racemic mixture of dia-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2-methyl-4-(trifluoromethyl)piperidin-1-yl)pyridin-4-yl)propan-2-yl) carbamate (diastereomer 2, 0.20 g, 0.28 mmol) was subjected to chiral SFC (Cellulose-2, 40% EtOH (with 0.05% DEA modifier)/CO2) to afford the title compounds, enantiomer 3A and enantiomer 4A.

Step 3-1: ent-((1R,5S,6s)-6-((4-(2-aminopropan-2-yl)-6-(2-methyl-4-(trifluoromethyl)piperidin-1-yl) pyridin-2-yl)oxy)-3-azabicyclo[3.1.0]hexan-3-yl)(3-methyl-1-(pyrimidin-2-yl)-1H-pyrazol-4-yl) methanone (Enantiomer 1)

A solution of ent-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2-methyl-4-(trifluoromethyl)piperidin-1-yl)pyridin-4-yl)propan-2-yl)carbamate (enantiomer 1A, 0.060 g, 0.083 mmol) in HCl (12 M aqueous, 0.50 mL) was stirred at 80° C. for 10 min. The mixture was cooled to rt and subjected to reverse phase HPLC (22-42% MeCN/water with 0.01% TFA modifier) to afford the title compound. MS m/z $(M+H)^+$: calculated 585.3, observed 585.3. $^1H$ NMR (400 MHz, $CD_3OD$) δ 8.90 (s, 1H), 8.83 (d, J=4.8 Hz, 2H), 7.44 (t, J=4.8 Hz, 1H), 6.33 (d, J=5.6 Hz, 1H), 6.12 (s, 1H), 4.19 (d, J=12.8 Hz, 1H), 4.15-4.03 (m, 2H), 4.01-3.90 (m, 2H), 3.78 (d, J=12.4 Hz, 1H), 3.72-3.63 (m, 1H), 3.31-3.25 (m, 1H), 2.46 (s, 3H), 2.37-2.26 (m, 1H), 2.11-1.94 (m, 4H), 1.76-1.68 (m, 1H), 1.66 (s, 6H), 1.64-1.57 (m, 1H), 1.23 (d, J=6.4 Hz, 3H) ppm.

Step 3-2: ent-((1R,5S,6s)-6-((4-(2-aminopropan-2-yl)-6-(2-methyl-4-(trifluoromethyl)piperidin-1-yl) pyridin-2-yl)oxy)-3-azabicyclo[3.1.0]hexan-3-yl)(3-methyl-1-(pyrimidin-2-yl)-1H-pyrazol-4-yl) methanone (Enantiomer 2)

A solution of ent-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2-methyl-4-(trifluoromethyl)piperidin-1-yl)pyridin-4-yl)propan-2-yl)carbamate (enantiomer 2A, 65 mg, 0.090 mmol) in HCl (12 M aqueous, 1.0 mL) was stirred at 80° C. for 10 min. The mixture was cooled to rt and subjected to reverse phase HPLC (22-42% MeCN/water with 0.01% TFA modifier) to afford the title compound. MS m/z $(M+H)^+$: calculated 585.3, observed 585.3. $^1H$ NMR (400 MHz, $CD_3OD$) δ 8.90 (s, 1H), 8.83 (d, J=4.8 Hz, 2H), 7.44 (t, J=4.8 Hz, 1H), 6.30 (d, J=4.6 Hz, 1H), 6.10 (s, 1H), 4.19 (d, J=13.2 Hz, 1H), 4.16-4.04 (m, 2H), 4.01-3.88 (m, 2H), 3.78 (d, J=13.2 Hz, 1H), 3.72-3.60 (m, 1H), 3.30-3.20 (m, 1H), 2.46 (s, 3H), 2.37-2.24 (m, 1H), 2.10-1.91 (m, 4H), 1.79-1.67 (m, 1H), 1.66 (s, 6H), 1.64-1.56 (m, 1H), 1.23 (d, J=6.4 Hz, 3H) ppm.

Step 3-3: ent-((1R,5S,6s)-6-((4-(2-aminopropan-2-yl)-6-(2-methyl-4-(trifluoromethyl)piperidin-1-yl) pyridin-2-yl)oxy)-3-azabicyclo[3.1.0]hexan-3-yl)(3-methyl-1-(pyrimidin-2-yl)-1H-pyrazol-4-yl) methanone (Enantiomer 3)

A solution of ent-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2-methyl-4-(trifluoromethyl)piperidin-1-yl)pyridin-4-yl)propan-2-yl)carbamate (enantiomer 3A, 0.060 g, 0.083 mmol) in HCl (12 M aqueous, 0.50 mL) was stirred at 80° C. for 10 min. The mixture was cooled to rt and subjected to reverse phase HPLC (26-46% MeCN/water with 0.01% TFA modifier) to afford the title compound. MS m/z $(M+H)^+$: calculated 585.3, observed 585.3. $^1H$ NMR (400 MHz, $CD_3OD$) δ 8.91 (s, 1H), 8.83 (d, J=4.8 Hz, 2H), 7.44 (t, J=4.8 Hz, 1H), 6.35 (s, 1H), 6.08 (d, J=1.0 Hz, 1H), 4.97-4.90 (m, 1H), 4.31-4.12 (m, 2H), 4.03-3.89 (m, 2H), 3.75 (d, J=6.8 Hz, 1H), 3.67 (d, J=11.8 Hz, 1H), 3.04 (t, J=13.2 Hz, 1H), 2.62 (dd, J=4.0, 8.1, 12.1 Hz, 1H), 2.46 (s, 3H), 2.08-1.88 (m, 3H), 1.84-1.69 (m, 2H), 1.66 (s, 6H), 1.54-1.42 (m, 1H), 1.16 (d, J=6.8 Hz, 3H) ppm.

Step 3-4: ent-((1R,5S,6s)-6-((4-(2-aminopropan-2-yl)-6-(2-methyl-4-(trifluoromethyl)piperidin-1-yl) pyridin-2-yl)oxy)-3-azabicyclo[3.1.0]hexan-3-yl)(3-methyl-1-(pyrimidin-2-yl)-1H-pyrazol-4-yl) methanone (Enantiomer 4)

A solution of ent-benzyl (2-(2-(((1R,5S,6s)-3-(3-methyl-1-(pyrimidin-2-yl)-1H-pyrazole-4-carbonyl)-3-azabicyclo[3.1.0]hexan-6-yl)oxy)-6-(2-methyl-4-(trifluoromethyl)piperidin-1-yl)pyridin-4-yl)propan-2-yl)carbamate (enantiomer 4A, 55 mg, 0.077 mmol) in HCl (12 M aqueous, 0.50 mL) was stirred at 80° C. for 10 min. The mixture was cooled to rt and subjected to reverse phase HPLC (22-42% MeCN/water with 0.01% TFA modifier) to afford the title compound. MS m/z $(M+H)^+$: calculated 585.3, observed 585.3. $^1H$ NMR (400 MHz, $CD_3OD$) δ 8.91 (s, 1H), 8.83 (d, J=4.8 Hz, 2H), 7.44 (t, J=4.8 Hz, 1H), 6.35 (s, 1H), 6.08 (s, 1H), 4.91 (d, J=5.6 Hz, 1H), 4.29-4.13 (m, 2H), 4.03-3.90 (m, 2H), 3.75 (d, J=6.7 Hz, 1H), 3.67 (d, J=11.6 Hz, 1H), 3.04 (t, J=12.6 Hz, 1H), 2.62 (dd, J=3.8, 8.1, 12.0 Hz, 1H), 2.46 (s, 3H), 2.05-1.88 (m, 3H), 1.84-1.68 (m, 2H), 1.66 (s, 6H), 1.54-1.41 (m, 1H), 1.16 (d, J=6.8 Hz, 3H) ppm.

Example 130

(3-((2H-1,2,3-triazol-2-yl)methyl)-1-(pyrimidin-2-yl)-1H-pyrazol-4-yl)((1R,5S,6s)-6-((4-(2-aminopropan-2-yl)-6-(4-fluorophenyl)pyridin-2-yl)oxy)-3-azabicyclo[3.1.0]hexan-3-yl)methanone

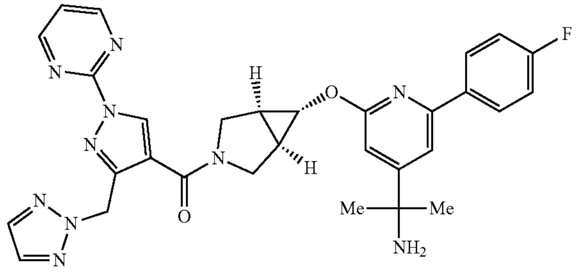 [SMILES: CC(C)(N)c1cc(O[C@H]2[C@@H]3CN(C(=O)c4cn(-c5ncccn5)nc4Cn4nccn4)C[C@@H]32)nc(-c2ccc(F)cc2)c1]

Step 1: benzyl (2-(2-(((1R,5S,6s)-3-(3-((2H-1,2,3-triazol-2-yl)methyl)-1-(pyrimidin-2-yl)-1H-pyrazole-4-carbonyl)-3-azabicyclo[3.1.0]hexan-6-yl)oxy)-6-(4-fluorophenyl)pyridin-4-yl)propan-2-yl)carbamate To a solution of benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 37 mg, 0.081 mmol) in DMF (5.0 mL) was added DIPEA (0.10 mL, 0.24 mmol), 3-((2H-1,2,3-triazol-2-yl)methyl)-1-(pyrimidin-2-yl)-1H-pyrazole-4-carboxylic acid (Int. V, 22 mg, 0.081 mmol) and T3P (50% in EtOAc, 77 mg, 0.12 mmol). The mixture was stirred at 20° C. for 1 h, diluted water (10 mL), and extracted with EtOAc (10 mL×3). The combined organic extracts were dried over anhydrous sodium sulfate, washed with brine (10 mL), filtered, and concentrated under reduced pressure. The mixture was subjected to prep-TLC (EtOAc) to afford the title compound.

Step 2: (3-((2H-1,2,3-triazol-2-yl)methyl)-1-(pyrimidin-2-yl)-1H-pyrazol-4-yl)((1R,5S,6s)-6-((4-(2-aminopropan-2-yl)-6-(4-fluorophenyl)pyridin-2-yl)oxy)-3-azabicyclo[3.1.0]hexan-3-yl)methanone A solution of benzyl (2-(2-(((1R,5S,6s)-3-(3-((2H-1,2,3-triazol-2-yl)methyl)-1-(pyrimidin-2-yl)-1H-pyrazole-4-carbonyl)-3-azabicyclo[3.1.0]hexan-6-yl)oxy)-6-(4-fluorophenyl)pyridin-4-yl)propan-2-yl)carbamate (22 mg, 0.031 mmol) in HCl (12 M aqueous, 2.0 mL) was stirred at 80° C. for 10 min. The mixture was cooled to rt, diluted with MeOH (2 mL), filtered, and concentrated under reduced pressure. The mixture was subjected to reverse phase HPLC (16-36% MeCN/water with 0.05% HCl modifier) to afford the title compound. MS m/z $(M+H)^+$: calculated 581.1, observed 581.2. $^1H$ NMR (400 MHz, $CD_3OD$) δ 9.05 (s, 1H), 8.90 (d, J=4.8 Hz, 2H), 8.21-8.07 (m, 2H), 7.66 (s, 1H), 7.57-7.47 (m, 3H), 7.15 (t, J=8.8 Hz, 2H), 6.87 (s, 1H), 6.06-5.95 (m, 1H), 5.88-5.76 (m, 1H), 4.19 (d, J=12.4 Hz, 1H), 4.08-3.88 (m, 3H), 3.70-3.56 (m, 1H), 2.16-2.00 (m, 2H), 1.79 (s, 6H) ppm.

Example 131

((1R,5S,6s)-6-((4-(2-aminopropan-2-yl)-6-(4-fluorophenyl)pyridin-2-yl)oxy)-3-azabicyclo[3.1.0]hexan-3-yl)(3-(2-fluoroethyl)-1-(pyrimidin-2-yl)-1H-pyrazol-4-yl)methanone

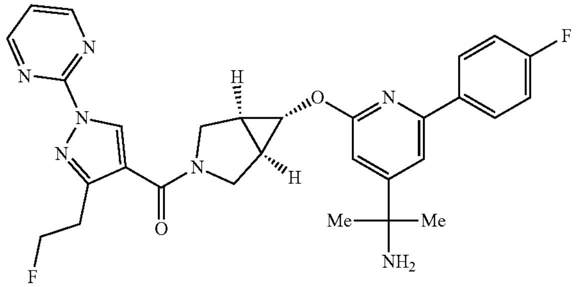 [SMILES: CC(C)(N)c1cc(O[C@H]2[C@@H]3CN(C(=O)c4cn(-c5ncccn5)nc4CCF)C[C@@H]32)nc(-c2ccc(F)cc2)c1]

Step 1: benzyl (2-(2-(((1R,5S,6s)-3-(3-(2-fluoroethyl)-1-(pyrimidin-2-yl)-1H-pyrazole-4-carbonyl)-3-azabicyclo[3.1.0]hexan-6-yl)oxy)-6-(4-fluorophenyl)pyridin-4-yl)propan-2-yl)carbamate To a solution of 3-(2-fluoroethyl)-1-(pyrimidin-2-yl)-1H-pyrazole-4-carboxylic acid (Int. W-02, 0.020 g, 0.085 mmol), benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 39 mg, 0.085 mmol) and N-methylimidazole (24 mg, 0.30 mmol) in DMF (5.0 mL) was added chloro-N,N,N',N'-tetramethylformamidinium hexafluorophosphate (29 mg, 0.10 mmol). The mixture was stirred at 25° C. for 1 h, diluted with water (10 mL), and extracted with EtOAc (30 mL×3). The combined organic extracts were washed with brine (20 mL×3), dried over anhydrous sodium sulfate, filtered, and concentrated under reduced pressure. The mixture was subjected to prep-TLC (EtOAc) to afford the title compound.

Step 2: ((1R,5S,6s)-6-((4-(2-aminopropan-2-yl)-6-(4-fluorophenyl)pyridin-2-yl)oxy)-3-azabicyclo[3.1.0]hexan-3-yl)(3-(2-fluoroethyl)-1-(pyrimidin-2-yl)-1H-pyrazol-4-yl)methanone A mixture of benzyl (2-(2-(((1R,5S,6s)-3-(3-(2-fluoroethyl)-1-(pyrimidin-2-yl)-1H-pyrazole-4-carbonyl)-3-azabicyclo[3.1.0]hexan-6-yl)oxy)-6-(4-fluorophenyl)pyridin-4-yl)propan-2-yl)carbamate (35 mg, 0.051 mmol) in HCl (12 M aqueous, 1.0 mL) was stirred at 80° C. for 10 min. The mixture was cooled to rt and subjected to reverse phase HPLC (19-39% MeCN/water with 0.01% TFA modifier) to afford the title compound. MS m/z $(M+H)^+$: calculated 546.2, observed 546.2. $^1H$ NMR (400 MHz, $CD_3OD$) δ 8.97 (s, 1H), 8.86 (d, J=4.8 Hz, 2H), 8.16-8.11 (m, 2H), 7.60 (d, J=1.6 Hz, 1H), 7.47 (t, J=4.8 Hz, 1H), 7.21-7.15 (m, 2H), 6.80 (d, J=1.2 Hz, 1H), 4.84-4.65 (m, 2H), 4.31-4.18 (m, 1H), 4.05-3.97 (m, 3H), 3.75-3.65 (m, 1H), 3.47-3.33 (m, 1H), 3.30-3.14 (m, 1H), 2.11-2.03 (m, 2H), 1.75 (s, 6H) ppm.

Example 132

((1R,5S,6s)-6-((4-(2-aminopropan-2-yl)-6-(4-fluorophenyl)pyridin-2-yl)oxy)-3-azabicyclo[3.1.0]hexan-3-yl)(3-(2,2-difluoroethyl)-1-(pyrimidin-2-yl)-1H-pyrazol-4-yl)methanone

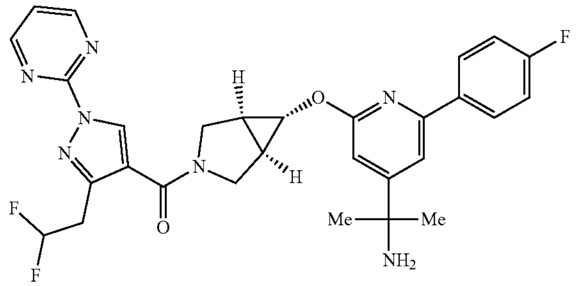 [SMILES: CC(C)(N)c1cc(O[C@H]2[C@@H]3CN(C(=O)c4cn(-c5ncccn5)nc4CC(F)F)C[C@@H]32)nc(-c2ccc(F)cc2)c1]

Step 1: benzyl (2-(2-(((1R,5S,6s)-3-(3-(2,2-difluoroethyl)-1-(pyrimidin-2-yl)-1H-pyrazole-4-carbonyl)-3-azabicyclo[3.1.0]hexan-6-yl)oxy)-6-(4-fluorophenyl)pyridin-4-yl)propan-2-yl)carbamate A solution of 3-(2,2-difluoroethyl)-1-(pyrimidin-2-yl)-1H-pyrazole-4-carboxylic acid (Int. W-03, 0.030 g, 0.12 mmol), DIPEA (0.10 mL, 0.35 mmol), benzyl (2-(2-(((1R,5S,6s)-3-azabicyclo[3.1.0]hexan-6-yl)oxy)-6-(4-fluorophenyl)pyridin-4-yl)propan-2-yl)carbamate (Int. H-02, 55 mg, 0.12 mmol) and PyBOP (0.18 g, 0.35 mmol) in DMF (3.0 mL) was stirred at rt for 1 h, diluted with water (10 mL), and extracted with EtOAc (20 mL×3). The combined organic extracts were washed with brine (20 mL×3), dried over anhydrous sodium sulfate, filtered, and concentrated under reduced pressure. The mixture was subjected to prep-TLC (EtOAc) to afford the title compound.

Step 2: ((1R,5S,6s)-6-((4-(2-aminopropan-2-yl)-6-(4-fluorophenyl)pyridin-2-yl)oxy)-3-azabicyclo[3.1.0]hexan-3-yl)(3-(2,2-difluoroethyl)-1-(pyrimidin-2-yl)-1H-pyrazol-4-yl)methanone A mixture of benzyl (2-(2-(((1R,5S,6s)-3-(3-(2,2-difluoroethyl)-1-(pyrimidin-2-yl)-1H-pyrazole-4-carbonyl)-3-azabicyclo[3.1.0]hexan-6-yl)oxy)-6-(4-fluorophenyl)pyridin-4-yl)propan-2-yl)carbamate (35 mg, 0.050 mmol) in HCl (12 M aqueous, 1.0 mL) was stirred at 80° C. for 10 min. The mixture was cooled to room temperature, concentrated under reduced pressure and subjected to reverse phase HPLC (19-39% MeCN/water with 0.01% TFA modifier) to afford the title compound. MS m/z $(M+H)^+$: calculated 564.2, observed 564.2. $^1$H NMR (400 MHz, $CD_3OD$) δ 9.02 (s, 1H), 8.87 (d, J=4.8 Hz, 2H), 8.16-8.10 (m, 2H), 7.60 (d, J=1.2 Hz, 1H), 7.53-7.46 (m, 1H), 7.17 (t, J=8.8 Hz, 2H), 6.80 (d, J=1.2 Hz, 1H), 6.46-6.12 (m, 1H), 4.24 (m, 1H), 4.04 (s, 3H), 3.77-3.67 (m, 1H), 3.62-3.41 (m, 2H), 2.12-2.05 (m, 2H), 1.76 (s, 6H) ppm.

Assay Descriptions

Sample Corrections:

Wells with DMSO (final concentration of 0.4%) or a compound at a concentration at which viral replication was completely inhibited with a control compound were used as viral replication assay Min_E and Max_E controls, respectively. To set up the assay, ARF vials were thawed in a 37° C. water bath and a control compound was resuspended in assay media DMEM (Dulbecco's Modified Eagle Medium) containing 2% FBS, 100 U/ml Penicillin-Streptomycin.

Generation and Propagation of Recombinant RSV-A2-GFP Virus

GFP sequence was derived from pJTI™ R4 Dest CMV N-EmGFP pA Vector (Invitrogen) and was cloned into the intergenic sequence between wild-type RSV-A2 P and M genes using standard recombineering techniques. Recombinant RSV-A2-GFP was propagated in Hep2 cells (human cells contain HeLa marker chromosomes and were derived via HeLa contamination, ATCC CCL-23) with a Multiplicity of Infection (MOI) of 0.1. Virus was harvested 3 days after infection by collecting all culture material and then freeze-thawing the mixture for 5 min. Working virus stocks were generated by thawing frozen viral cultures in 37° C. water bath, which were centrifuged at 218 g for 15 min at 4° C. 1/10 of 10×SPG (Biological Industries 06-3061-01-5A) were added and then mixed. The supernatant was aliquoted, frozen in liquid nitrogen, and then transferred to a −80° C. freezer for storage. Virus titer was determined by automated plaque assay in HEp-2 cells following methods described previously (Wen Z. et al.; 2019).

Generating Calu-1 Assay Ready Freezedown (ARF)

Calu-1 cells were purchased from ATCC (Cat #HTB-54) and were expanded in growth media (DMEM containing 10% FBS, 100 U/ml Penicillin-Streptomycin). To make ARF, cell culture media was removed and discarded and the cell layer was briefly rinsed with PBS to remove serum. 2.5 mL of TrypLE Express solution were added and cells incubated until dislodged, to which growth media was added and the cells were resuspended by gentle pipetting. Cells were counted for concentration and viability as determined by ViCell. Cells were centrifuged at RT, 300 g for 5 minutes to pellet cells. The supernatant was gently aspirated and the pellet was flicked to loosen cells. Cells were resuspended in an appropriate volume of freezing medium (DMEM containing 10% DMSO, 10% FBS, 100 U/ml Penicillin-Streptomycin) to achieve a concentration of $5\times10^6$ cells/mL. 1 mL aliquots of the cell suspension were transferred to freezing vials. The vials were put into an upright container in a −80° C. freezer overnight before transferring vials to liquid nitrogen for storage.

RSV-A2-GFP Viral Replication Assay

Assay ready freezedown (ARF, generation described separately) Calu-1 cells (ATCC HTB-54) were used. Compound plates were prepared by dispensing compounds dissolved in DMSO into the wells of a 384 well Corning® 3985 plate with an ECHO acoustic dispenser and compounds were tested in 10-point serial 3-fold dilution. Wells with DMSO (final concentration of 0.4%) or a compound at a concentration at which viral replication was completely inhibited with a control compound were used as viral replication assay Min_E and Max_E control, respectively. To set up the assay, ARF vial(s) were thawed in a 37° C. water bath and were then resuspended into assay media (DMEM containing 2% FBS, 100 U/ml Penicillin-Streptomycin). Cells were counted using default parameters on ViCell and diluted to 20,000 cells/mL in assay media. RSV-A2-GFP virus was added to cells at 24,000 pfu/ml (MOI=1.2) and mixed by gentle inversion. 10 μL/well of 100% DMSO was dispensed as CellTiter-Glo (CTG) assay Max_E controls wells. The cells were dispensed at 50

μL/well using Bravo with 50 μL filtered tips into compound plates. Plates were covered with MicroClime lids, loaded with 7.5 mL of assay media to minimize evaporation, and were incubated at 37° C. and 5% $CO_2$ for 96 hrs. Following incubation, distinct, GFP-expressing cells were counted using an Acumen imaging system with appropriate settings. A same-well CTG assay was performed by adding 10 μL/well reconstituted CellTiter-Glo reagent (Promega G7573) and plates were read on PerkinElmer Envision according to manufacturer's instructions. Raw data were loaded and analyzed in ActivityBase. Antiviral IC50 and cytotoxicity CC50 values were determined using a 4 parameter logistic fit based on the Levenberg-Marquardt algorithm. Model: 205-4 Parameter Logistic.

Generation and Propagation of hMPV-GFP Virus

GFP expressing rgHMPV #3 p3 was generated in Dr. Buchholz's lab (Biacchesi S. et al., *J Virol.* 2007 June; 81(11): 6057-6067) and propagated in VERO cells (ATCC Cat #CCL-81) with a Multiplicity of Infection (MOI) of 0.1. Virus was harvested 4 days after infection by collecting cultured material and was freeze-thaw cycled in liquid nitrogen twice. Working virus stocks were generated from thawing frozen samples in 37° C. water bath, which were centrifuged at 218 g for 15 min at 4° C. 1/10 of 10×SPG (Biological Industries 06-3061-01-5A) were added and then mixed. The supernatant was aliquoted, frozen in liquid nitrogen, and then transferred to a −80° C. freezer for storage. Virus titer was determined by performing titration test in 96-well plates and calculate approximate virus titer using GFP event/well data.

hMPV-GFP Viral Replication Assay

Compound plates were prepared by dispensing compounds dissolved in DMSO into wells of a 384 well Corning 3985 polystyrene flat clear bottom optical imaging microplate (202.5 nL/well) using an ECHO acoustic dispenser. Each compound was tested in 10-point serial 3-fold dilution (typical final concentrations: 40,300 nM-2 nM). Wells with DMSO (final concentration of 0.4%) or a compound at a concentration at which viral replication was completely inhibited relative to a control compound were used as viral replication assay Min_E and Max_E control, respectively. Continuous culture of VERO cells was maintained in complete culture media (OptiMEM supplemented with 2 mM GlutaMAX™ and 100 U/ml Penicillin-Streptomycin). To set up the assay, VERO cells were trypsinized with 0.25% Trypsin-EDTA until cells were dislodged, then cells were re-suspended with 1 mL FBS. Cells were spun down at 300 g for 5 minutes and cells were washed twice with culture media and counted using default parameters on ViCell. Cells were then diluted to 100,000 cells/mL (5,000 cells/50 μL) in complete culture media+TrypLE Select (80 μL/mL). hMPV-GFP virus was added to cells at 125,000 pfu/mL (MOI=1.25) and were mixed by gentle inversion. 10 μL/well of 100% DMSO was dispensed to CellTiter-Glo (CTG) assay Max_E controls wells. Cells were dispensed at 50 μL/well using Bravo and 50 μL filtered tips into compound plates. Plates were covered with MicroClime lids and loaded with 7.5 mL of assay media to minimize evaporation. Plates were lightly shaken for 10 minutes at room temperature and then incubated at 37° C. and 5% $CO_2$ for 48 hrs. Following incubation, distinct GFP-expressing cells were counted using an Acumen imaging system with appropriate settings. A same-well CTG assay was performed by adding 10 μL/well reconstituted CellTiter-Glo reagent (Promega G7573) and plates were read on PerkinElmer Envision according to manufacturer's instructions. Raw data were loaded and analyzed in ActivityBase. Antiviral IC50 and cytotoxicity CC50 values were determined using a 4 parameter logistic fit based on the Levenberg-Marquardt algorithm. Model: 205-4 Parameter Logistic.

References: Wen Z, Citron M, Bett A J, Espeseth A S, Vora K A, Zhang L, DiStefano D J. Development and application of a higher throughput RSV plaque assay by immunofluorescent imaging. *J Virol Methods.* 2019 January; 263:88-95. doi: 10.1016/j.jviromet.2018.10.022. Epub 2018 Oct. 28. PMD: 30381239.

Biacchesi S, Murphy B R, Collins P L, Buchholz U J. Frequent frameshift and point mutations in the SH gene of human metapneumovirus passaged in vitro. *J Virol.* 2007 June; 81(11):6057-67. doi: 10.1128/JVL.00128-07. Epub 2007 Mar. 21. PMID: 17376897; PMCID: MC 1900297.

Assay Data

The $EC_{50}$ of each compound is listed in Table I and $EC_{50}$ ranges are as follows: A≤0.010 μM; B>0.010 μM to ≤0.10 μM; C>0.10 μM; ND=Not Determined.

TABLE I

Summary of Activities for RSV

| EX. NO. | RSV $EC_{50}$ |
|---|---|
| 1A | C |
| 1B | A |
| 2 | B |
| 3 | A |
| 4 | B |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |

TABLE I-continued

Summary of Activities for RSV

| EX. NO. | RSV $EC_{50}$ |
|---|---|
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | B |
| 76 | B |
| 77 | A |
| 78 | B |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96A | A |
| 96B | A |
| 97 | A |
| 98 | A |
| 99 | A |
| 100 | A |
| 101 | A |
| 102 | A |
| 103A | A |
| 103B | A |
| 104A | A |
| 104B | A |
| 105A | A |
| 105B | A |
| 106A | A |
| 106B | A |
| 107A | A |
| 107B | A |
| 108A | A |
| 108B | A |
| 109A | A |
| 109B | A |
| 110A | A |
| 110B | A |
| 111A | A |
| 111B | A |
| 112 | A |
| 113A | A |
| 113B | A |
| 114 | A |
| 115 | A |
| 116A | A |

TABLE I-continued

Summary of Activities for RSV

| EX. NO. | RSV $EC_{50}$ |
|---|---|
| 116B | A |
| 117A | A |
| 117B | A |
| 118A | A |
| 118B | A |
| 119 | A |
| 120 | A |
| 121 | A |
| 122 | A |
| 123 | A |
| 124 | A |
| 125 | A |
| 126 | A |
| 127A | A |
| 127B | A |
| 128A | A |
| 128B | A |
| 129A | A |
| 129B | A |
| 129C | A |
| 129D | A |
| 130 | A |
| 131 | A |
| 132 | A |

The $EC_{50}$ of each compound is listed in Table II and $EC_{50}$ ranges are as follows: A≤0.010 μM; B>0.010 μM-≤0.10 IM; C>0.10 μM; ND=Not Determined.

TABLE II

Summary of Activities for hMPV

| EX. NO. | hMPV $EC_{50}$ |
|---|---|
| 1A | C |
| 1B | C |
| 2 | C |
| 3 | C |
| 4 | C |
| 5 | C |
| 6 | C |
| 7 | C |
| 8 | B |
| 9 | C |
| 10 | B |
| 11 | C |
| 12 | C |
| 13 | B |
| 14 | B |
| 15 | ND |
| 16 | B |
| 17 | B |
| 18 | B |
| 19 | A |
| 20 | C |
| 21 | ND |
| 22 | C |
| 23 | C |
| 24 | B |
| 25 | B |
| 26 | B |
| 27 | B |
| 28 | B |
| 29 | B |
| 30 | B |
| 31 | B |
| 32 | C |
| 33 | C |
| 34 | C |
| 35 | C |
| 36 | B |
| 37 | B |
| 38 | B |

TABLE II-continued

| Summary of Activities for hMPV | |
|---|---|
| EX. NO. | hMPV $EC_{50}$ |
| 39 | B |
| 40 | C |
| 41 | C |
| 42 | B |
| 43 | C |
| 44 | B |
| 45 | C |
| 46 | C |
| 47 | C |
| 48 | C |
| 49 | B |
| 50 | B |
| 51 | C |
| 52 | C |
| 53 | C |
| 54 | C |
| 55 | C |
| 56 | C |
| 57 | C |
| 58 | B |
| 59 | B |
| 60 | B |
| 61 | C |
| 62 | C |
| 63 | C |
| 64 | C |
| 65 | C |
| 66 | C |
| 67 | C |
| 68 | C |
| 69 | C |
| 70 | C |
| 71 | C |
| 72 | C |
| 73 | C |
| 74 | ND |
| 75 | C |
| 76 | C |
| 77 | C |
| 78 | C |
| 79 | C |
| 80 | B |
| 81 | B |
| 82 | B |
| 83 | C |
| 84 | C |
| 85 | B |
| 86 | B |
| 87 | C |
| 88 | C |
| 89 | C |
| 90 | C |
| 91 | C |
| 92 | C |
| 93 | C |
| 94 | C |
| 95 | C |
| 96A | C |
| 96B | C |
| 97 | B |
| 98 | C |
| 99 | C |
| 100 | C |
| 101 | C |
| 102 | C |
| 103A | B |
| 103B | B |
| 104A | C |
| 104B | C |
| 105A | C |
| 105B | B |
| 106A | C |
| 106B | B |
| 107A | C |
| 107B | C |
| 108A | C |

TABLE II-continued

| Summary of Activities for hMPV | |
|---|---|
| EX. NO. | hMPV $EC_{50}$ |
| 108B | C |
| 109A | C |
| 109B | B |
| 110A | B |
| 110B | C |
| 111A | C |
| 111B | B |
| 112 | C |
| 113A | C |
| 113B | C |
| 114 | C |
| 115 | C |
| 116A | C |
| 116B | C |
| 117A | C |
| 117B | C |
| 118A | C |
| 118B | C |
| 119 | C |
| 120 | C |
| 121 | C |
| 122 | C |
| 123 | C |
| 124 | C |
| 125 | C |
| 126 | C |
| 127A | C |
| 127B | C |
| 128A | C |
| 128B | C |
| 129A | C |
| 129B | C |
| 129C | C |
| 129D | C |
| 130 | C |
| 131 | C |
| 132 | C |

What is claimed is:

1. A compound of Formula I, (I)

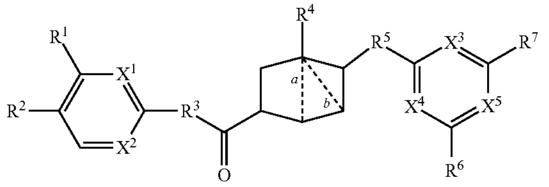

or a pharmaceutically acceptable salt thereof, wherein:

$X^1$ and $X^2$ are each independently selected from —CH and N;

$R^1$ and $R^2$ are each independently selected from H, halo and $C_{1-6}$ alkyl;

$R^3$ is a 5-member aromatic heterocyclyl ring comprised of:

(1) three carbon atoms and (i) two of N, (ii) N and NH, or (iii) N and one of S or O, or (2) two carbon atoms and (i) three of N, (ii) two of N and one of NH, or (iii) two of N and one of S or O, wherein the heterocyclyl ring is unsubstituted or substituted with 1, 2 or 3 substituents, as valence will allow, independently selected at each occurrence from:

(a) halo, (b) $—NH_2$, (c) $—C_{3-6}$cycloalkyl, (d) —$C_{1-6}$alkyl unsubstituted or substituted with 1 to 6 substituents independently selected at each occurrence from halo, dihalo, —OH, —$NH_2$, and triazole, and (e) —$OC_{1-6}$alkyl unsubstituted or substituted with 1 to 6 substituents independently selected at each occurrence from halo, —OH and —$NH_2$;

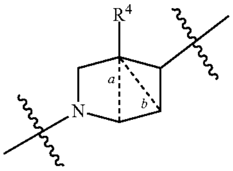

represents a bicyclic ring that is:

(i)

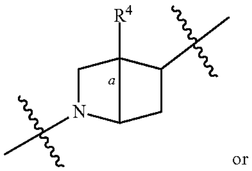

or 2-azabicyclo[2.2.0]hexane (ii)

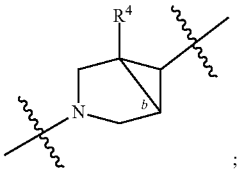

;

3-azabicyclo[3.1.0]hexane $R^4$ is —H, halo or —$C_{1-6}$alkyl;

$R^5$ is —O— or —NH—;

one of $X^3$, $X^4$ and $X^5$ is N and the others are each CH; or one of $X^3$ and $X^4$ is N, and $X^5$ is a $C_1$alkyl unsubstituted or substituted with a halo;

$R^6$ is selected from —$C_{1-6}$alkyl unsubstituted or substituted with 1 to 6 substituents independently selected at each occurrence from halo, —OH and —$NH_2$ and

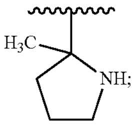

and $R^7$ is selected from:

(1) phenyl unsubstituted or substituted with 1 to 5 substituents independently selected at each occurrence from:

(a) halo, (b) —CN, (c) —$C_{1-6}$alkyl unsubstituted or substituted with 1 to 6 substituents independently selected at each occurrence from halo and —OH;

(d) —$OC_{1-6}$alkyl, unsubstituted or substituted with 1 to 6 substituents independently selected at each occurrence from halo and —OH, and (e) —$C_{3-6}$cycloalkyl unsubstituted or substituted with 1 to 5 substituents independently selected at each occurrence from halo, —OH, —$C_{1-3}$alkyl and —$OC_{1-3}$alkyl;

(2) pyridinyl, unsubstituted or substituted with 1, 2 or 3 substituents independently selected at each occurrence from (i) halo, (ii) CN, (iii) —$CH_2F$, —$CHF_2$, —$CF_3$ and —$C(CH_3)F_2$;

(3) piperidinyl, substituted with 1, 2, or 3 substituents independently selected from —H, —$C_{1-3}$alkyl and —$CF_3$;

(4)

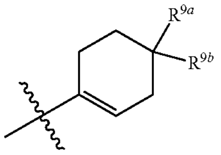

and

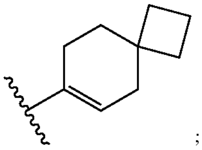

;

wherein $R^{9a}$ and $R^{9b}$ are each selected from —H, —$C_{1-3}$alkyl and —$CF_3$;

(5) A bicyclic ring system selected from:

(a)

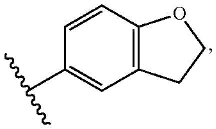

(b)

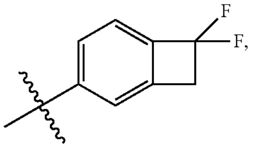

(c)

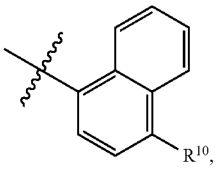

(d)

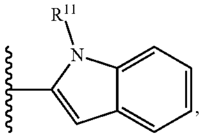

(e)

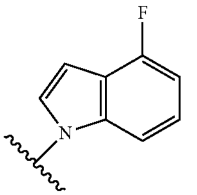

and

-continued (f)

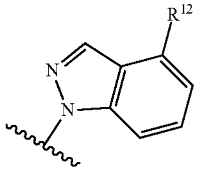

wherein $R^{10}$, $R^{11}$ and $R^{12}$ are independently selected at each occurrence from —H, —$C_{1-3}$alkyl, —$CF_3$, and 1, 2 or 3 of halo;

(6)

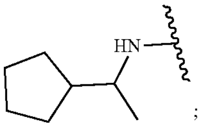 [SMILES: *NC(C)C1CCCC1]

;

and (7)

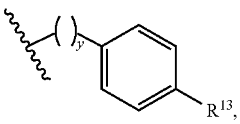

wherein $R^{13}$ is independently selected from —H and halo, and y is 1, 2 or 3.

2. The compound of claim 1, or a pharmaceutically acceptable salt thereof, wherein:

$X^1$ and $X^2$ are each independently selected from —CH and N;

$R^1$ and $R^2$ are each independently selected from H, halo and $C_{1-6}$ alkyl;

$R^3$ is a 5-member aromatic heterocyclyl ring comprised of:

(1) three carbon atoms and (i) two of N, (ii) N and NH, or (iii) N and one of S or O, or (2) two carbon atoms and (i) three of N, (ii) two of N and one of NH, or (iii) two of N and one of S or O, wherein the heterocyclyl ring is unsubstituted or substituted with 1, 2 or 3 substituents, as valence will allow, independently selected at each occurrence from:

(a) halo, (b) —$NH_2$, (c) —$C_{3-6}$cycloalkyl, (d) —$C_{1-6}$alkyl unsubstituted or substituted with 1 to 6 substituents independently selected at each occurrence from halo, —OH, and —$NH_2$, and (e) —$OC_{1-6}$alkyl unsubstituted or substituted with 1 to 6 substituents independently selected at each occurrence from halo, —OH and —$NH_2$;

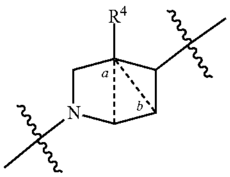

represents a bicyclic ring that is:

(i)

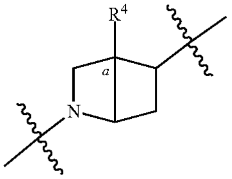

or 2-azabicyclo[2.2.0]hexane (ii)

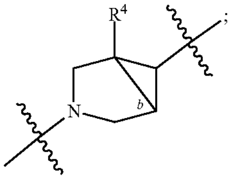

3-azabicyclo[3.1.0]hexane $R^4$ is —H, halo or —$C_{1-6}$alkyl;

$R^5$ is —O— or —NH—;

one of $X^3$, $X^4$ and $X^5$ is N and the others are each CH;

$R^6$ is selected from —$C_{1-6}$alkyl unsubstituted or substituted with 1 to 6 substituents independently selected at each occurrence from halo, —OH and —$NH_2$ and

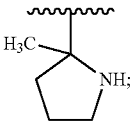

and $R^7$ is selected from:

(1) phenyl unsubstituted or substituted with 1 to 5 substituents independently selected at each occurrence from:

(a) halo, (b) —CN, (c) —$C_{1-6}$alkyl unsubstituted or substituted with 1 to 6 substituents independently selected at each occurrence from halo and —OH;

(d) —$OC_{1-6}$alkyl, unsubstituted or substituted with 1 to 6 substituents independently selected at each occurrence from halo and —OH, and (e) —$C_{3-6}$cycloalkyl unsubstituted or substituted with 1 to 5 substituents independently selected at each occurrence from halo, —OH, —$C_{1-3}$alkyl and —$OC_{1-3}$alkyl;

(2) pyridinyl, unsubstituted or substituted with 1, 2 or 3 substituents independently selected at each occurrence from (i) halo, (ii) CN, and (ii) —$CH_2F$, —$CHF_2$, —$CF_3$ and —$C(CH_3)F_2$;

(3)

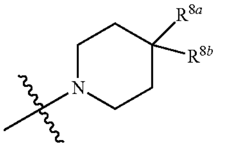

wherein $R^{8a}$ and $R^{8b}$ are each selected from —H, —$C_{1-3}$alkyl and —$CF_3$;

(4)

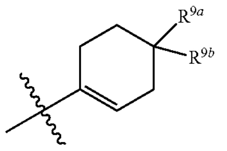

and

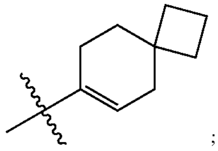

;

and wherein $R^{9a}$ and $R^{9b}$ are each selected from —H, —$C_{1-3}$alkyl and —$CF_3$;

(5) a bicyclic ring system selected from:

(a)

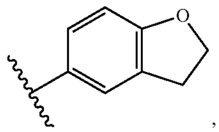

, (b)

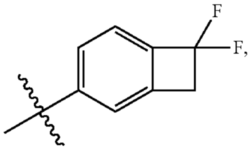

(c)

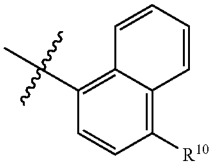

(d)

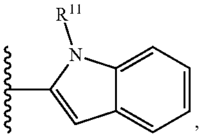

, (e)

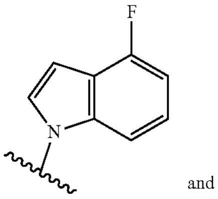

and (f)

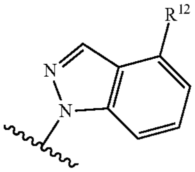

wherein $R^{10}$, $R^{11}$ and $R^{12}$ are independently selected at each occurrence from —H, —$C_{1-3}$alkyl, —$CF_3$, and 1, 2 or 3 of halo.

3. The compound of claim 1, or a pharmaceutically acceptable salt thereof, wherein: (i) $X^1$ and $X^2$ are each N, (ii) $X^1$ is N and $X^2$ is —CH, or (iii) $X^1$ and $X^2$ are each —CH.

4. The compound of claim 1, or a pharmaceutically acceptable salt thereof, wherein: $R^1$ and $R^2$ are each independently selected from —H, halo and $C_{1-3}$alkyl.

5. The compound of claim 1, or a pharmaceutically acceptable salt thereof, wherein: $R^1$ and $R^2$ are each independently selected from —H, —F, —Cl and $C_{1-3}$alkyl.

6. The compound of claim 1, or a pharmaceutically acceptable salt thereof, wherein $R^3$ is selected from:

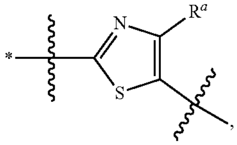

,

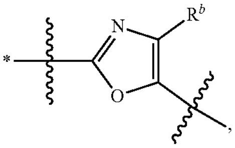

,

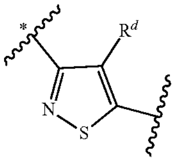

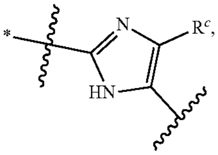

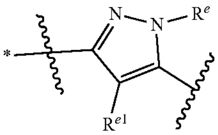

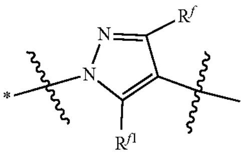

and

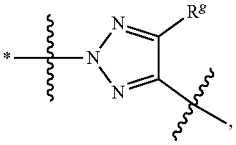

, wherein * is the point of attachment to

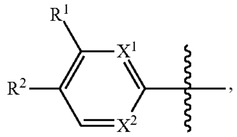

, and each of $R^a$, $R^b$, $R^c$, $R^d$, $R^e$, $R^{e1}$, $R^f$, $R^{f1}$ and $R^g$ is independently selected from:

(a) —H, (b) halo, (c) —$NH_2$, (d) —$C_{3-6}$cycloalkyl, (e) —$C_{1-6}$alkyl unsubstituted or substituted with 1 to 6 substituents independently selected at each occurrence from halo, dihalo, —OH, —$NH_2$, and triazole, and (f) —$OC_{1-6}$alkyl unsubstituted or substituted with 1 to 6 substituents independently selected at each occurrence from halo, —OH and —$NH_2$.

7. The compound of claim 1, or a pharmaceutically acceptable salt thereof, wherein each of $R^a$, $R^b$, $R^c$, $R^d$, $R^e$, $R^{e1}$, $R^f$, $R^{f1}$ and $R^g$ is independently selected from: (a) —H, (b) —F and —Cl, (c) —$NH_2$, (d) -cyclopropyl, (e) —$C_{1-3}$ alkyl unsubstituted or substituted with 1, 2 or 3 substituents independently selected at each occurrence from F, —Cl, —OH, and —$NH_2$, and (f) —$OC_{1-3}$alkyl unsubstituted or substituted with 1, 2 or 3 substituents independently selected at each occurrence from —F, —Cl, —OH, and —$NH_2$.

8. The compound of claim 1, or a pharmaceutically acceptable salt thereof, wherein:

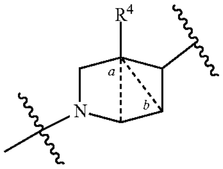

is

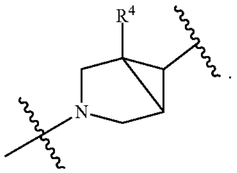

9. The compound of claim 1, or a pharmaceutically acceptable salt thereof, wherein:

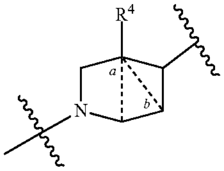

is

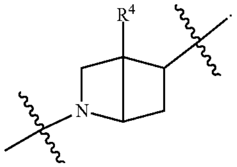

10. The compound of claim 1, or a pharmaceutically acceptable salt thereof, wherein $R^4$ is selected from —H, halo and —$C_{1-3}$alkyl.

11. The compound of claim 1, or a pharmaceutically acceptable salt thereof, wherein $R^5$ is —O—.

12. The compound of claim 1, or a pharmaceutically acceptable salt thereof, wherein $R^5$ is —NH—.

13. The compound of claim 1, or a pharmaceutically acceptable salt thereof, wherein $X^3$ is N, and $X^4$ and $X^5$ are each CH; $X^4$ is N, and $X^3$ and $X^5$ are each CH; $X^5$ is N and $X^3$ and $X^4$ are each CH; or $X^3$ is N, $X^4$ is CH, and $X^5$ is CF or CCl.

14. The compound of claim 1, or a pharmaceutically acceptable salt thereof, wherein $R^6$ is —$C_{1-6}$alkyl unsubstituted or substituted with 1, 2 or 3 substituents independently selected at each occurrence from halo, —OH, —$NH_2$, and

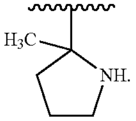

15. The compound of claim 1, or a pharmaceutically acceptable salt thereof, wherein $R^7$ is selected from:

(1) phenyl unsubstituted or substituted with 1, 2 or 3 substituents independently selected at each occurrence from:

(a) halo, (b) —CN, (c) —$C_{1-3}$alkyl unsubstituted or substituted with 1, 2 or 3 substituents independently selected at each occurrence from (i) halo and (ii) —OH, (d) —$OC_{1-3}$alkyl unsubstituted or substituted with 1, 2 or 3 substituents independently selected at each occurrence from (i) halo and (ii) —OH, (e) —$C_{3-6}$cycloalkyl unsubstituted or substituted with 1, 2 or 3 substituents independently selected at each occurrence from halo, —OH, —$C_{1-3}$alkyl and —$OC_{1-3}$alkyl;

(2) pyridinyl, unsubstituted or substituted with 1, 2 or 3 substituents independently selected at each occurrence from (i) halo, (ii) CN, (iii) —$C_{1-3}$alkyl unsubstituted or substituted with 1 to 3 of F or Cl;

(3)

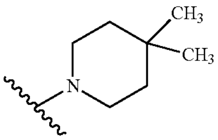

and

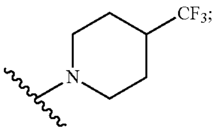

(4) unsubstituted or substituted cyclohexenyl selected from

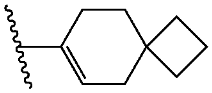

and

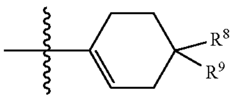

wherein $R^8$ and $R^9$ are each independently selected from —H, —$CH_3$ and —$CF_3$; and (5) a bicyclic ring system selected from:

(a)

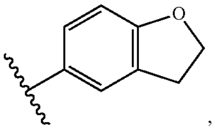

, (b)

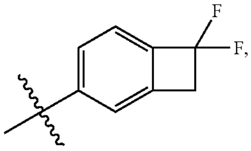

(c)

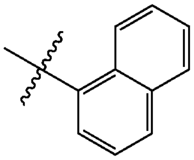

(d)

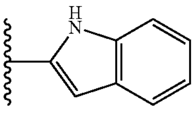

, (e)

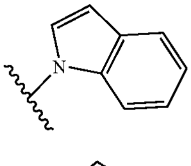

, and (f)

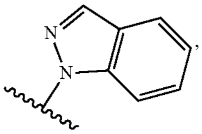

, wherein each bicyclic ring system is unsubstituted or substituted with 1, 2 or 3 substituents independently selected at each occurrence from —$C_{1-3}$alkyl and 1, 2 or 3 of halo.

16. The compound of claim 1, or a pharmaceutically acceptable salt thereof, wherein $R^7$ is:

piperidinyl, substituted with 1, 2, or 3 substituents independently selected from —$C_{1-3}$alkyl and —$CF_3$;

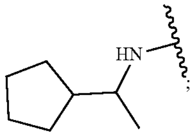

; or

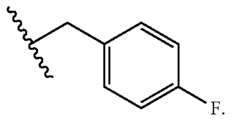

.

17. The compound of claim 1 that is:

rel-((1R,4R,5R)-5-((4-(2-aminopropan-2-yl)-6-(4-fluorophenyl)pyridin-2-yl)oxy)-2-azabicyclo[2.2.0]hexan-2-yl)(4-methyl-2-(pyrimidin-2-yl)thiazol-5-yl)methanone (enantiomer 1);

rel-((1R,4R,5R)-5-((4-(2-aminopropan-2-yl)-6-(4-fluorophenyl)pyridin-2-yl)oxy)-2-azabicyclo[2.2.0]hexan-2-yl)(4-methyl-2-(pyrimidin-2-yl)thiazol-5-yl)methanone (enantiomer 2);

rel-((1R,4R,5R)-5-((4-(2-aminopropan-2-yl)-6-(4-fluorophenyl)pyridin-2-yl)oxy)-2-azabicyclo[2.2.0]hexan-2-yl) (2-(pyrimidin-2-yl)thiazol-5-yl)methanone (enantiomer 2);

rel-((1R,4R,5R)-5-((4-(2-aminopropan-2-yl)-6-(4-fluorophenyl)pyridin-2-yl)oxy)-2-azabicyclo[2.2.0]hexan-2-yl) (4-ethyl-2-(pyrimidin-2-yl)thiazol-5-yl)methanone (enantiomer 2);

rel-((1R,4R,5R)-5-((4-(2-aminopropan-2-yl)-6-(4-fluorophenyl)pyridin-2-yl)oxy)-2-azabicyclo[2.2.0]hexan-2-yl)(1-methyl-3-(pyrimidin-2-yl)-1H-pyrazol-5-yl) methanone (enantiomer 2);

rel-((1R,4R,5R)-5-((4-(2-aminopropan-2-yl)-6-(4-fluorophenyl)pyridin-2-yl)oxy)-2-azabicyclo[2.2.0]hexan-2-yl)(3-ethyl-1-(pyrimidin-2-yl)-1H-pyrazol-4-yl)methanone (enantiomer 2):

rel-((1R,4R,5R)-5-((4-(2-aminopropan-2-yl)-6-(4-fluorophenyl)pyridin-2-yl)oxy)-2-azabicyclo[2.2.0]hexan-2-yl)(3-cyclopropyl-1-(pyrimidin-2-yl)-1H-pyrazol-4-yl) methanone (enantiomer 2);

((1R,5S,6s)-6-((4-(2-aminopropan-2-yl)-6-(4-fluorophenyl)pyridin-2-yl)amino)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl) (4-methyl-2-(pyrimidin-2-yl)thiazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl) (2-(pyrimidin-2-yl)thiazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl) (4-ethyl-2-(pyrimidin-2-yl)thiazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl) (2-(pyrimidin-2-yl)-4-(trifluoromethyl) thiazol-5-yl) methanone;

((1R,5S,6s)-6-((4-(2-aminopropan-2-yl)-6-(4-fluorophenyl)pyridin-2-yl)oxy)-3-azabicyclo[3.1.0]hexan-3-yl) (4-methyl-2-(pyridin-2-yl)thiazol-5-yl)methanone;

((1R,5S,6s)-6-((4-(2-aminopropan-2-yl)-6-(3,4,5-trifluorophenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(2,3,4-trifluorophenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(3,4-difluorophenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(3-fluorophenyl)pyridin-2-yl)oxy)-3-azabicyclo[3.1.0]hexan-3-yl) (4-methyl-2-(pyrimidin-2-yl)thiazol-5-yl)methanone;

((1R,5S,6s)-6-((4-(2-aminopropan-2-yl)-6-(3-chloro-4-fluorophenyl)pyridin-2-yl)oxy)-3-azabicyclo[3.1.0] hexan-3-yl)(4-methyl-2-(pyrimidin-2-yl)thiazol-5-yl) methanone;

((1R,5S,6s)-6-((4-(2-aminopropan-2-yl)-6-(4-chloro-3-fluorophenyl)pyridin-2-yl)oxy)-3-azabicyclo[3.1.0] hexan-3-yl)(4-methyl-2-(pyrimidin-2-yl)thiazol-5-yl) methanone;

((1R,5S,6s)-6-((4-(2-aminopropan-2-yl)-6-(4-chlorophenyl)pyridin-2-yl)oxy)-3-azabicyclo[3.1.0]hexan-3-yl) (4-methyl-2-(pyrimidin-2-yl)thiazol-5-yl)methanone;

((1R,5S,6s)-6-((4-(2-aminopropan-2-yl)-6-phenylpyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(p-tolyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(4-cyclopropylphenyl)pyridin-2-yl)oxy)-3-azabicyclo[3.1.0] hexan-3-yl)(4-methyl-2-(pyrimidin-2-yl)thiazol-5-yl) methanone;

4-(4-(2-aminopropan-2-yl)-6-(((1R,5S,6s)-3-(4-methyl-2-(pyrimidin-2-yl)thiazole-5-carbonyl)-3-azabicyclo [3.1.0]hexan-6-yl)oxy)pyridin-2-yl)benzonitrile;

((1R,5S,6s)-6-((4-(2-aminopropan-2-yl)-6-(4-(difluoromethoxy)phenyl) pyridin-2-yl)oxy)-3-azabicyclo [3.1.0]hexan-3-yl)(4-methyl-2-(pyrimidin-2-yl)thiazol-5-yl)methanone;

((1R,5S,6s)-6-((4-(2-aminopropan-2-yl)-6-(4-(difluoromethyl)phenyl)pyridin-2-yl)oxy)-3-azabicyclo[3.1.0] hexan-3-yl)(4-methyl-2-(pyrimidin-2-yl)thiazol-5-yl) methanone;

((1R,5S,6s)-6-((4-(2-aminopropan-2-yl)-6-(4-(1,1-difluoroethyl)phenyl)pyridin-2-yl)oxy)-3-azabicyclo[3.1.0] hexan-3-yl)(4-methyl-2-(pyrimidin-2-yl)thiazol-5-yl) methanone;

((1R,5S,6s)-6-((4-(2-aminopropan-2-yl)-6-(4-(trifluoromethyl)phenyl)pyridin-2-yl)oxy)-3-azabicyclo [3.1.0]hexan-3-yl)(4-methyl-2-(pyrimidin-2-yl)thiazol-5-yl)methanone;

((1R,5S,6s)-6-((4-(2-aminopropan-2-yl)-6'-(trifluoromethyl)-[2,3'-bipyridin]-6-yl)oxy)-3-azabicyclo[3.1.0] hexan-3-yl)(4-methyl-2-(pyrimidin-2-yl)thiazol-5-yl) methanone;

((1R,5S,6s)-6-((4-(2-aminopropan-2-yl)-6-(3-chloro-4-(trifluoromethyl)phenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(2-chloro-4-(trifluoromethyl)phenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(2,3-difluoro-4-(trifluoromethyl)phenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(3,4-dimethylphenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(2,4-dimethylphenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(2,3-dihydrobenzofuran-5-yl) pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(4-fluoro-3-methylphenyl)pyridin-2-yl)oxy)-3-azabicyclo[3.1.0]hexan-3-yl)(4-methyl-2-(pyrimidin-2-yl)thiazol-5-yl)methanone;

4-(4-(2-aminopropan-2-yl)-6-(((1R,5S,6s)-3-(4-methyl-2-(pyrimidin-2-yl)thiazole-5-carbonyl)-3-azabicyclo[3.1.0]hexan-6-yl)oxy)pyridin-2-yl)-2-fluorobenzonitrile;

((1R,5S,6s)-6-((4-(2-aminopropan-2-yl)-6-(3-fluoro-4-methylphenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(2-fluoro-4-methylphenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(4-fluoro-2-methylphenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(2-fluoro-3-methylphenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(4-fluoro-2-methoxyphenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(4-fluoronaphthalen-1-yl) pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(1H-indol-2-yl) pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(1-methyl-1H-indol-2-yl) pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(cyclohex-1-en-1-yl) pyridin-2-yl)oxy)-3-azabicyclo[3.1.0]hexan-3-yl)(4-methyl-2-(pyrimidin-2-yl)thiazol-5-yl)methanone;

rac-((1R,5S,6s)-6-((4-(2-aminopropan-2-yl)-6-(4-methylcyclohex-1-en-1-yl) pyridin-2-yl)oxy)-3-azabicyclo[3.1.0]hexan-3-yl)(4-methyl-2-(pyrimidin-2-yl)thiazol-5-yl)methanone;

rac-((1R,5S,6s)-6-((4-(2-aminopropan-2-yl)-6-(4-(trifluoromethyl)cyclohex-1-en-1-yl) pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(spiro [3.5]non-6-en-7-yl) pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(4-(difluoromethyl)-2-(pyrimidin-2-yl)thiazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-(6-fluoropyridin-2-yl)-1-methyl-1H-pyrazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(6-methylpyridin-2-yl)-1H-pyrazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(1-methyl-3-(pyrimidin-2-yl)-1H-pyrazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(4-chloro-1-methyl-3-(pyrimidin-2-yl)-1H-pyrazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(4-fluoro-1-methyl-3-(pyrimidin-2-yl)-1H-pyrazol-5-yl)methanone;

((1R,5S,6s)-6-((4-(2-aminopropan-2-yl)-6-(3,4-difluorophenyl)pyridin-2-yl)oxy)-3-azabicyclo[3.1.0]hexan-3-yl)(1-methyl-3-(pyrimidin-2-yl)-1H-pyrazol-5-yl)methanone;

((1R,5S,6s)-6-((4-(2-aminopropan-2-yl)-6-(3-chloro-4-fluorophenyl)pyridin-2-yl)oxy)-3-azabicyclo[3.1.0]hexan-3-yl)(1-methyl-3-(pyrimidin-2-yl)-1H-pyrazol-5-yl)methanone;

((1R,5S,6s)-6-((4-(2-aminopropan-2-yl)-6-(2-chloro-4-fluorophenyl)pyridin-2-yl)oxy)-3-azabicyclo[3.1.0]hexan-3-yl)(1-methyl-3-(pyrimidin-2-yl)-1H-pyrazol-5-yl)methanone;

((1R,5S,6s)-6-((4-(2-aminopropan-2-yl)-6-(4-chlorophenyl)pyridin-2-yl)oxy)-3-azabicyclo[3.1.0]hexan-3-yl)(1-methyl-3-(pyrimidin-2-yl)-1H-pyrazol-5-yl)methanone;

((1R,5S,6s)-6-((4-(2-aminopropan-2-yl)-6-(4-(trifluoromethyl)phenyl)pyridin-2-yl)oxy)-3-azabicyclo[3.1.0]hexan-3-yl)(1-methyl-3-(pyrimidin-2-yl)-1H-pyrazol-5-yl)methanone;

((1R,5S,6s)-6-((4-(2-aminopropan-2-yl)-6-(4-fluoro-1H-indol-1-yl) pyridin-2-yl)oxy)-3-azabicyclo[3.1.0]hexan-3-yl)(1-methyl-3-(pyrimidin-2-yl)-1H-pyrazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-methoxy-1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-ethyl-1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-cyclopropyl-1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-(difluoromethyl)-1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(1-(pyrimidin-2-yl)-3-(trifluoromethyl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-ethoxy-1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-(difluoromethoxy)-1-(pyrimidin-2-yl)-1H-pyrazol-4-yl)methanone;

(3-amino-1-(pyrimidin-2-yl)-1H-pyrazol-4-yl)((1R,5S,6s)-6-((4-(2-aminopropan-2-yl)-6-(4-fluorophenyl)pyridin-2-yl)oxy)-3-azabicyclo[3.1.0]hexan-3-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(1-(5-fluoropyrimidin-2-yl)-3-methyl-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-methyl-1-(4-methylpyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3,5-dimethyl-1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-methyl-1-phenyl-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(pyrimidin-2-yl)-1H-imidazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(5-methyl-2-(pyrimidin-2-yl)-2H-1,2,3-triazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-(pyrimidin-2-yl) isothiazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(4-methyl-2-(pyrimidin-2-yl) oxazol-5-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(5-fluoro-3-methyl-1-(pyrimidin-2-yl)-1H-pyrazol-4-yl)methanone;

((1R,5S,6s)-6-((4-(2-aminopropan-2-yl)-6-(3,4-difluorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(2,4,5-trifluorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(3,4,5-trifluorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(3-chloro-4-fluorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(4-chloro-3-fluorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(4-chlorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(4-(trifluoromethyl)phenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6'-(trifluoromethyl)-[2,3'-bipyridin]-6-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(2-methoxy-4-(trifluoromethyl)phenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(1H-indol-2-yl) pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(4,4-dimethylcyclohex-1-en-1-yl) pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(3,4-difluorophenyl)pyridin-2-yl)oxy)-3-azabicyclo[3.1.0]hexan-3-yl)(3-(difluoromethyl)-1-(pyrimidin-2-yl)-1H-pyrazol-4-yl)methanone;

((1R,5S,6s)-6-((4-(2-aminopropan-2-yl)-6-(3,4-difluorophenyl)pyridin-2-yl)oxy)-3-azabicyclo[3.1.0]hexan-3-yl)(1-(pyrimidin-2-yl)-3-(trifluoromethyl)-1H-pyrazol-4-yl)methanone;

((1R,5S,6s)-6-((4-(2-aminopropan-2-yl)-6-(4-(trifluoromethyl)phenyl)pyridin-2-yl)oxy)-3-azabicyclo[3.1.0]hexan-3-yl)(1-(pyrimidin-2-yl)-3-(trifluoromethyl)-1H-pyrazol-4-yl)methanone;

((1R,5S,6s)-6-((4-(2-aminopropan-2-yl)-6-(4-chloro-1H-indazol-1-yl) pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(3,4-difluorophenyl)pyridin-2-yl)oxy)-3-azabicyclo[3.1.0]hexan-3-yl)(3-(hydroxymethyl)-1-(pyrimidin-2-yl)-1H-pyrazol-4-yl)methanone;

ent-((1R,5S,6s)-6-((4-(2-aminopropan-2-yl)-6-(3,4-difluorophenyl)pyridin-2-yl)oxy)-3-azabicyclo[3.1.0]hexan-3-yl) (hydroxyethyl)-1-(pyrimidin-2-yl)-1H-pyrazol-4-yl)methanone (enantiomer 1);

ent-((1R,5S,6s)-6-((4-(2-aminopropan-2-yl)-6-(3,4-difluorophenyl)pyridin-2-yl)oxy)-3-azabicyclo[3.1.0]hexan-3-yl) (hydroxyethyl)-1-(pyrimidin-2-yl)-1H-pyrazol-4-yl)methanone (enantiomer 2);

((1R,5S,6s)-6-((4-(2-aminopropan-2-yl)-6-(2,4-difluorophenyl)pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(7,7-difluorobicyclo [4.2.0]octa-1 (6),2,4-trien-3-yl) pyridin-2-yl) oxy)-3-azabicyclo[3.1.0]hexan-3-yl)(1-methyl-3-(pyrimidin-2-yl)-1H-pyrazol-5-yl)methanone;

((1R,5S,6s)-6-((4-(2-aminopropan-2-yl)-6-(7,7-difluorobicyclo [4.2.0]octa-1 (6),2,4-trien-3-yl) pyridin-2-yl) oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-6-(4,4-dimethylpiperidin-1-yl) pyridin-2-yl)oxy)-3-azabicyclo[3.1.0] hexan-3-yl)(3-methyl-1-(pyrimidin-2-yl)-1H-pyrazol-4-yl)methanone;

((1R,5S,6s)-6-((4-(2-aminopropan-2-yl)-6-(4,4-dimethylpiperidin-1-yl) pyridin-2-yl)oxy)-3-azabicyclo[3.1.0] hexan-3-yl)(3-(difluoromethyl)-1-(pyrimidin-2-yl)-1H-pyrazol-4-yl)methanone;

((1R,5S,6s)-6-((4-(2-aminopropan-2-yl)-6-(4-(trifluoromethyl) piperidin-1-yl) pyridin-2-yl)oxy)-3-azabicyclo[3.1.0]hexan-3-yl)(3-methyl-1-(pyrimidin-2-yl)-1H-pyrazol-4-yl)methanone;

rel-((1R,5S,6s)-6-((4-(2-aminopropan-2-yl)-6-(4-fluorophenyl)pyridin-2-yl)oxy)-1-methyl-3-azabicyclo [3.1.0]hexan-3-yl)(4-methyl-2-(pyrimidin-2-yl)thiazol-5-yl)methanone (enantiomer 1);

rel-((1R,5S,6s)-6-((4-(2-aminopropan-2-yl)-6-(4-fluorophenyl)pyridin-2-yl)oxy)-1-methyl-3-azabicyclo [3.1.0]hexan-3-yl)(4-methyl-2-(pyrimidin-2-yl)thiazol-5-yl)methanone (enantiomer 2);

rel-((1R,5S,6s)-6-((4-(2-aminopropan-2-yl)-6-(4-fluorophenyl)pyridin-2-yl)oxy)-1-methyl-3-azabicyclo [3.1.0]hexan-3-yl)(1-methyl-3-(pyrimidin-2-yl)-1H-pyrazol-5-yl)methanone (enantiomer 1);

rel-((1R,5S,6s)-6-((4-(2-aminopropan-2-yl)-6-(4-fluorophenyl)pyridin-2-yl)oxy)-1-methyl-3-azabicyclo [3.1.0]hexan-3-yl)(1-methyl-3-(pyrimidin-2-yl)-1H-pyrazol-5-yl)methanone (enantiomer 2);

rel-((1R,5S,6s)-6-((4-(2-aminopropan-2-yl)-6-(3,4-difluorophenyl)pyridin-2-yl)oxy)-1-methyl-3-azabicyclo [3.1.0]hexan-3-yl)(1-methyl-3-(pyrimidin-2-yl)-1H-pyrazol-5-yl)methanone (enantiomer 1) rel-((1R,5S, 6s)-6-((4-(2-aminopropan-2-yl)-6-(3,4-difluorophenyl) pyridin-2-yl)oxy)-1-methyl-3-azabicyclo[3.1.0]hexan-3-yl)(1-methyl-3-(pyrimidin-2-yl)-1H-pyrazol-5-yl) methanone (enantiomer 2):

rel-((1R,5S,6s)-6-((4-(2-aminopropan-2-yl)-6-(3,4-difluorophenyl)pyridin-2-yl)oxy)-1-methyl-3-azabicyclo [3.1.0]hexan-3-yl)(3-methyl-1-(pyrimidin-2-yl)-1H-pyrazol-4-yl)methanone (enantiomer 1);

rel-((1R,5S,6s)-6-((4-(2-aminopropan-2-yl)-6-(3,4-difluorophenyl)pyridin-2-yl)oxy)-1-methyl-3-azabicyclo [3.1.0]hexan-3-yl)(3-methyl-1-(pyrimidin-2-yl)-1H-pyrazol-4-yl)methanone (enantiomer 2);

rel-((1R,5S,6s)-6-((4-(2-aminopropan-2-yl)-6-(4-fluorophenyl)pyridin-2-yl)oxy)-1-methyl-3-azabicyclo [3.1.0]hexan-3-yl)(3-methyl-1-(pyrimidin-2-yl)-1H-pyrazol-4-yl)methanone (enantiomer 1):

rel-((1R,5S,6s)-6-((4-(2-aminopropan-2-yl)-6-(4-fluorophenyl)pyridin-2-yl)oxy)-1-methyl-3-azabicyclo [3.1.0]hexan-3-yl)(3-methyl-1-(pyrimidin-2-yl)-1H-pyrazol-4-yl)methanone (enantiomer 2);

rel-((1R,5S,6s)-6-((4-(2-aminopropan-2-yl)-6-(2,4-difluorophenyl)pyridin-2-yl)oxy)-1-methyl-3-azabicyclo

[3.1.0]hexan-3-yl)(1-methyl-3-(pyrimidin-2-yl)-1H-pyrazol-5-yl)methanone (enantiomer 1):

rel-((1R,5S,6s)-6-((4-(2-aminopropan-2-yl)-6-(2,4-difluorophenyl)pyridin-2-yl)oxy)-1-methyl-3-azabicyclo [3.1.0]hexan-3-yl)(1-methyl-3-(pyrimidin-2-yl)-1H-pyrazol-5-yl)methanone (enantiomer 2);

rel-((1R,5S,6s)-6-((4-(2-aminopropan-2-yl)-6-(2,4-difluorophenyl)pyridin-2-yl)oxy)-1-methyl-3-azabicyclo [3.1.0]hexan-3-yl)(3-methyl-1-(pyrimidin-2-yl)-1H-pyrazol-4-yl)methanone (enantiomer 1);

rel-((1R,5S,6s)-6-((4-(2-aminopropan-2-yl)-6-(2,4-difluorophenyl)pyridin-2-yl)oxy)-1-methyl-3-azabicyclo [3.1.0]hexan-3-yl)(3-methyl-1-(pyrimidin-2-yl)-1H-pyrazol-4-yl)methanone (enantiomer 2);

rel-((1R,5S,6s)-6-((4-(2-aminopropan-2-yl)-6-(4-(trifluoromethyl)phenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 1);

rel-((1R,5S,6s)-6-((4-(2-aminopropan-2-yl)-6-(4-(trifluoromethyl)phenyl)pyridin-2-yl)oxy)-1-methyl-3-azabicyclo[3.1.0]hexan-3-yl)(1-methyl-3-(pyrimidin-2-yl)-1H-pyrazol-5-yl)methanone (enantiomer 2);

rel-((1R,5S,6s)-6-((4-(2-aminopropan-2-yl)-6-(4-(trifluoromethyl)phenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (enantiomer 1);

rel-((1R,5S,6s)-6-((4-(2-aminopropan-2-yl)-6-(4-(trifluoromethyl)phenyl)pyridin-2-yl)oxy)-1-methyl-3-azabicyclo[3.1.0]hexan-3-yl)(3-methyl-1-(pyrimidin-2-yl)-1H-pyrazol-4-yl)methanone (enantiomer 2);

ent-((1R,5S,6s)-6-((6-(4-fluorophenyl)-4-(2-methylpyrrolidin-2-yl) pyridin-2-yl)oxy)-3-azabicyclo[3.1.0] hexan-3-yl)(3-methyl-1-(pyrimidin-2-yl)-1H-pyrazol-4-yl)methanone (enantiomer 1);

ent-((1R,5S,6s)-6-((4-(2-amino-1-hydroxypropan-2-yl)-6-(4-fluorophenyl)pyridin-2-yl)oxy)-3-azabicyclo [3.1.0]hexan-3-yl)(4-methyl-2-(pyrimidin-2-yl)thiazol-5-yl)methanone (enantiomer 1);

ent-((1R,5S,6s)-6-((4-(2-amino-1-hydroxypropan-2-yl)-6-(4-fluorophenyl)pyridin-2-yl)oxy)-3-azabicyclo [3.1.0]hexan-3-yl)(4-methyl-2-(pyrimidin-2-yl)thiazol-5-yl)methanone (enantiomer 2);

((1R,5S,6s)-6-((2-(2-aminopropan-2-yl)-6-(4-fluorophenyl)pyridin-4-yl)oxy)-3-azabicyclo[3.1.0]hexan-3-yl) (4-methyl-2-(pyrimidin-2-yl)thiazol-5-yl)methanone;

((1R,5S,6s)-6-((6-(2-aminopropan-2-yl)-4-(4-fluorophenyl)pyridin-2-yl)oxy)-3-azabicyclo[3.1.0]hexan-3-yl) (4-methyl-2-(pyrimidin-2-yl)thiazol-5-yl)methanone;

ent-((1R,5S,6s)-6-((4-(2-aminobutan-2-yl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl) methanone (enantiomer 1);

ent-((1R,5S,6s)-6-((4-(2-aminobutan-2-yl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl) methanone (enantiomer 2):

ent-((1R,5S,6s)-6-((4-(1-aminopropyl)-6-(4-fluorophenyl)pyridin-2-yl)oxy)-3-azabicyclo[3.1.0]hexan-3-yl) (3-methyl-1-(pyrimidin-2-yl)-1H-pyrazol-4-yl)methanone (enantiomer 1);

ent-((1R,5S,6s)-6-((4-(1-aminopropyl)-6-(4-fluorophenyl)pyridin-2-yl)oxy)-3-azabicyclo[3.1.0]hexan-3-yl) (3-methyl-1-(pyrimidin-2-yl)-1H-pyrazol-4-yl)methanone (enantiomer 2):

ent-((1R,5S,6s)-6-((4-(1-aminopropyl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone;

ent-((1R,5S,6s)-6-((4-(1-aminopropyl)-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-5-fluoro-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-5-chloro-6-(4-fluorophenyl)pyridin-2-yl)oxy)-3-azabicyclo[3.1.0]hexan-3-yl)(3-methyl-1-(pyrimidin-2-yl)-1H-pyrazol-4-yl)methanone;

((1R,5S,6s)-6-((4-(2-aminopropan-2-yl)-5-chloro-6-(4-fluorophenyl)pyridin-2-yl)oxy)-3-azabicyclo[3.1.0]hexan-3-yl)(3-methoxy-1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-(2-fluoroethyl)-1-(pyrimidin-2-yl)-1H-pyrazol-4-yl)methanone;

((1R,5S,6s)-6-((4-(2-aminopropan-2-yl)-6-(4-fluorophenyl)pyridin-2-yl)oxy)-3-azabicyclo[3.1.0]hexan-3-yl)(3-(2,2-difluoroethyl)-1-(pyrimidin-2-yl)-1H-pyrazol-4-yl)methanone;

2-(3-((2H-1,2,3-triazol-2-yl)methyl)-4-((1R,5S,6s)-6-((4-(2-aminopropan-2-yl)-6-(4-fluorophenyl)pyridin-2-yl)oxy)-3-azabicyclo[3.1.0]hexane-3-carbonyl)-1H-pyrazol-1-yl)pyrimidin-1-ium;

ent-((1R,5S,6s)-6-((4-(2-aminopropan-2-yl)-6-(2,4,4-trimethylpiperidin-1-yl) pyridin-2-yl)oxy)-3-azabicyclo[3.1.0]hexan-3-yl)(3-methyl-1-(pyrimidin-2-yl)-1H-pyrazol-4-yl)methanone (enantiomer 1);

ent-((1R,5S,6s)-6-((4-(2-aminopropan-2-yl)-6-(2,4,4-trimethylpiperidin-1-yl) pyridin-2-yl)oxy)-3-azabicyclo[3.1.0]hexan-3-yl)(3-methyl-1-(pyrimidin-2-yl)-1H-pyrazol-4-yl)methanone (enantiomer 2);

ent-((1R,5S,6s)-6-((4-(2-aminopropan-2-yl)-6-(2-methyl-4-(trifluoromethyl) piperidin-1-yl) pyridin-2-yl)oxy)-3-azabicyclo[3.1.0]hexan-3-yl)(3-methyl-1-(pyrimidin-2-yl)-1H-pyrazol-4-yl)methanone (enantiomer 1);

ent-((1R,5S,6s)-6-((4-(2-aminopropan-2-yl)-6-(2-methyl-4-(trifluoromethyl) piperidin-1-yl) pyridin-2-yl)oxy)-3-azabicyclo[3.1.0]hexan-3-yl)(3-methyl-1-(pyrimidin-2-yl)-1H-pyrazol-4-yl)methanone (enantiomer 2);

ent-((1R,5S,6s)-6-((4-(2-aminopropan-2-yl)-6-(2-methyl-4-(trifluoromethyl) piperidin-1-yl) pyridin-2-yl)oxy)-3-azabicyclo[3.1.0]hexan-3-yl)(3-methyl-1-(pyrimidin-2-yl)-1H-pyrazol-4-yl)methanone (enantiomer 3);

ent-((1R,5S,6s)-6-((4-(2-aminopropan-2-yl)-6-(2-methyl-4-(trifluoromethyl) piperidin-1-yl) pyridin-2-yl)oxy)-3-azabicyclo[3.1.0]hexan-3-yl)(3-methyl-1-(pyrimidin-2-yl)-1H-pyrazol-4-yl)methanone (enantiomer 4);

ent-((1R,5S,6s)-6-((4-(2-aminopropan-2-yl)-6-((1-cyclopentylethyl)amino)pyridin-2-yl)oxy)-3-azabicyclo[3.1.0]hexan-3-yl)(3-methyl-1-(pyrimidin-2-yl)-1H-pyrazol-4-yl)methanone (enantiomer 1);

ent-((1R,5S,6s)-6-((4-(2-aminopropan-2-yl)-6-((1-cyclopentylethyl)amino)pyridin-2-yl)oxy)-3-azabicyclo[3.1.0]hexan-3-yl)(3-methyl-1-(pyrimidin-2-yl)-1H-pyrazol-4-yl)methanone (enantiomer 2);

((1R,5S,6s)-6-((4-(2-aminopropan-2-yl)-6-(4-(trifluoromethyl) piperidin-1-yl) pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(4,4-dimethylpiperidin-1-yl) pyridin-2-yl)oxy)-3-azabicyclo[3.1.0]hexan-3-yl)(4-methyl-2-(pyrimidin-2-yl)thiazol-5-yl)methanone;

((1R,5S,6s)-6-((4-(2-aminopropan-2-yl)-6-(4,4-dimethylpiperidin-1-yl) pyridin-2-yl)oxy)-3-azabicyclo[3.1.0]hexan-3-yl)(3-ethyl-1-(pyrimidin-2-yl)-1H-pyrazol-4-yl)methanone;

((1R,5S,6s)-6-((4-(2-aminopropan-2-yl)-6-(4,4-dimethylpiperidin-1-yl) pyridin-2-yl)oxy)-3-azabicyclo[3.1.0]hexan-3-yl)(3-methoxy-1-(pyrimidin-2-yl)-1H-pyrazol-4-yl)methanone; or ((1R,5S,6s)-6-((4-(2-aminopropan-2-yl)-6-(4-fluorobenzyl)pyridin-2-yl)oxy)-3-azabicyclo[3.1.0]hexan-3-yl)(4-methyl-2-(pyrimidin-2-yl)thiazol-5-yl)methanone, or a pharmaceutically acceptable salt thereof.

18. A pharmaceutical composition comprising an effective amount of the compound according to claim 1, or a pharmaceutically acceptable salt thereof, and a pharmaceutically acceptable carrier.

19. A method for the inhibition of the replication of hRSV in a human subject in need thereof which comprises administering to the subject an effective amount of the compound according to claim 1, or a pharmaceutically acceptable salt thereof.

20. A method for the treatment of hRSV infection in a human subject in need thereof which comprises administering to the subject an effective amount of the compound according to claim 1, or a pharmaceutically acceptable salt thereof.

21. A method for the inhibition of the replication of hMPV in a human subject in need thereof which comprises administering to the subject an effective amount of the compound according to claim 1, or a pharmaceutically acceptable salt thereof.

22. A method for the treatment of hMPV infection in a human subject in need thereof which comprises administering to the subject an effective amount of the compound according to claim 1, or a pharmaceutically acceptable salt thereof.

* * * * *